US011229660B2

(12) United States Patent
von Maltzahn et al.

(10) Patent No.: US 11,229,660 B2
(45) Date of Patent: Jan. 25, 2022

(54) GLYCAN THERAPEUTICS AND METHOD OF TREATING CONDITIONS ASSOCIATED WITH TMAO

(71) Applicant: Kaleido Biosciences, Inc., Lexington, MA (US)

(72) Inventors: Geoffrey A. von Maltzahn, Boston, MA (US); Jared Silverman, Brookline, MA (US); Yvonne J. Yamanaka, Cambridge, MA (US); John Miles Milwid, Cambridge, MA (US); John M. Geremia, Watertown, MA (US)

(73) Assignee: Kaleido Biosciences, Inc., Lexington, MA (US)

( * ) Notice: Subject to any disclaimer, the term of this patent is extended or adjusted under 35 U.S.C. 154(b) by 0 days.

(21) Appl. No.: 16/883,107

(22) Filed: May 26, 2020

(65) Prior Publication Data
US 2021/0113596 A1 Apr. 22, 2021

Related U.S. Application Data

(63) Continuation of application No. 16/395,929, filed on Apr. 26, 2019, now Pat. No. 10,702,542, which is a continuation of application No. 16/126,873, filed on Sep. 10, 2018, now abandoned, which is a continuation of application No. 15/866,152, filed on Jan. 9, 2018, now abandoned, which is a continuation of application No. 15/286,382, filed on Oct. 5, 2016, now Pat. No. 9,901,595, which is a continuation of application No. 15/017,396, filed on Feb. 5, 2016, now Pat. No. 9,492,473, which is a continuation of application No. PCT/US2016/013305, filed on Jan. 13, 2016.

(Continued)

(51) Int. Cl.
| | |
|---|---|
| *A61K 31/702* | (2006.01) |
| *A61K 45/06* | (2006.01) |
| *A61K 31/716* | (2006.01) |
| *A61K 31/733* | (2006.01) |
| *A61P 1/00* | (2006.01) |
| *A61K 31/09* | (2006.01) |
| *A61K 31/11* | (2006.01) |
| *A61K 31/12* | (2006.01) |
| *A61K 31/165* | (2006.01) |
| *A61K 31/34* | (2006.01) |
| *A61K 31/353* | (2006.01) |
| *A61K 31/365* | (2006.01) |
| *A61K 31/366* | (2006.01) |
| *A61K 31/7034* | (2006.01) |
| *A61K 31/7048* | (2006.01) |
| *A61K 31/706* | (2006.01) |
| *A61K 31/715* | (2006.01) |
| *A23L 33/10* | (2016.01) |
| *A23P 10/00* | (2016.01) |
| *A61K 31/7004* | (2006.01) |
| *A61K 31/7016* | (2006.01) |
| *A61K 35/741* | (2015.01) |
| *A61K 35/00* | (2006.01) |

(52) U.S. Cl.
CPC ............ *A61K 31/702* (2013.01); *A23L 33/10* (2016.08); *A23P 10/00* (2016.08); *A61K 31/09* (2013.01); *A61K 31/11* (2013.01); *A61K 31/12* (2013.01); *A61K 31/165* (2013.01); *A61K 31/34* (2013.01); *A61K 31/353* (2013.01); *A61K 31/365* (2013.01); *A61K 31/366* (2013.01); *A61K 31/7004* (2013.01); *A61K 31/706* (2013.01); *A61K 31/7016* (2013.01); *A61K 31/7034* (2013.01); *A61K 31/7048* (2013.01); *A61K 31/715* (2013.01); *A61K 31/716* (2013.01); *A61K 31/733* (2013.01); *A61K 35/741* (2013.01); *A61K 45/06* (2013.01); *A61P 1/00* (2018.01); *A23V 2002/00* (2013.01); *A61K 2035/115* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2,027,904 | A | 1/1936 | Farber |
| 2,436,967 | A | 3/1948 | Leuck |

(Continued)

FOREIGN PATENT DOCUMENTS

| | | |
|---|---|---|
| EP | 1634599 A1 | 3/2006 |
| EP | 1887017 A1 | 2/2008 |

(Continued)

OTHER PUBLICATIONS

He, Z. et al. Fish Oil is More Potent than Flaxseed Oil in Modulating Gut Microbiota and Reducing TMAO Exacerbated Atherogenesis. J of Agricultural and Food Chemistry 67(49)13635-47 Dec. 2019. (Year: 2019).*
Extended European Search Report for Application No. EP 15819734. 3, dated Feb. 7, 2018.
Extended European Search Report for Application No. EP 16743841. 5, dated Jul. 13, 2018.
Extended European Search Report for Application No. EP 16743842. 3, dated Jul. 9, 2018.

(Continued)

*Primary Examiner* — Ralph J Gitomer
(74) *Attorney, Agent, or Firm* — Wolf, Greenfield & Sacks, P.C.

(57) ABSTRACT

Preparations of glycan therapeutics, pharmaceutical compositions and medical foods thereof, optionally comprising micronutrients, polyphenols, prebiotics, probiotics, or other agents are provided and methods of making same. Also provided are methods of using said gycan therapeutics, e.g. for the modulation of human gastrointestinal microbiota and to treat dysbioses.

11 Claims, 21 Drawing Sheets

Related U.S. Application Data

(60) Provisional application No. 62/238,110, filed on Oct. 6, 2015, provisional application No. 62/238,112, filed on Oct. 6, 2015, provisional application No. 62/216,993, filed on Sep. 10, 2015, provisional application No. 62/216,995, filed on Sep. 10, 2015, provisional application No. 62/216,997, filed on Sep. 10, 2015, provisional application No. 62/217,002, filed on Sep. 10, 2015, provisional application No. 62/152,017, filed on Apr. 23, 2015, provisional application No. 62/152,016, filed on Apr. 23, 2015, provisional application No. 62/152,011, filed on Apr. 23, 2015, provisional application No. 62/152,007, filed on Apr. 23, 2015, provisional application No. 62/152,005, filed on Apr. 23, 2015, provisional application No. 62/108,039, filed on Jan. 26, 2015.

(56) References Cited

U.S. PATENT DOCUMENTS

| | | |
|---|---|---|
| 2,719,179 A | 9/1955 | Mora |
| 3,766,165 A | 10/1973 | Rennhard |
| 3,876,794 A | 4/1975 | Rennhard |
| 3,973,049 A | 8/1976 | Furda et al. |
| 4,965,354 A | 10/1990 | Yanaki et al. |
| 5,424,418 A | 6/1995 | Duflot |
| 5,580,762 A | 12/1996 | Karube et al. |
| 5,645,647 A | 7/1997 | Guzek et al. |
| 5,843,922 A | 12/1998 | Whistler et al. |
| 6,475,552 B1 | 11/2002 | Shah et al. |
| 6,559,302 B1 | 5/2003 | Shah et al. |
| 6,677,142 B1 | 1/2004 | Weissmuller et al. |
| 7,608,291 B2 | 10/2009 | Baillon et al. |
| 7,615,365 B2 | 11/2009 | Caimi et al. |
| 8,057,840 B2 | 11/2011 | Harrison et al. |
| 8,227,446 B2 | 7/2012 | Klinman et al. |
| 8,466,242 B2 | 6/2013 | Geremia et al. |
| 8,476,388 B2 | 7/2013 | Geremia et al. |
| 8,741,376 B2 | 6/2014 | Broekaert et al. |
| 8,993,039 B2 | 3/2015 | Harrison et al. |
| 9,079,171 B2 | 7/2015 | Geremia et al. |
| 9,205,418 B2 | 12/2015 | Geremia et al. |
| 9,238,845 B2 | 1/2016 | Baynes et al. |
| 9,492,473 B2 | 11/2016 | von Maltzahn et al. |
| 9,512,239 B2 | 12/2016 | Naeye et al. |
| 9,757,403 B2 | 9/2017 | Maltzahn et al. |
| 9,783,619 B2 | 10/2017 | Bureau et al. |
| 10,314,853 B2 | 6/2019 | von Maltzahn et al. |
| 10,702,542 B2 * | 7/2020 | von Maltzahn ........ A61K 31/12 |
| 10,881,676 B2 | 1/2021 | Von Maltzahn et al. |
| 2004/0220389 A1 | 11/2004 | Buchwald et al. |
| 2004/0235789 A1 * | 11/2004 | Day ...................... A61P 43/00 514/54 |
| 2005/0004070 A1 | 1/2005 | Stahl et al. |
| 2005/0075311 A1 | 4/2005 | Lane |
| 2006/0008574 A1 | 1/2006 | Begli et al. |
| 2006/0014717 A1 | 1/2006 | Angstrom et al. |
| 2006/0051812 A1 | 3/2006 | Helin et al. |
| 2006/0127448 A1 | 6/2006 | Carlson et al. |
| 2007/0036840 A1 | 2/2007 | Tuduri et al. |
| 2007/0048432 A1 | 3/2007 | Holzgraefe et al. |
| 2007/0148728 A1 | 6/2007 | Johnson et al. |
| 2007/0249524 A1 | 10/2007 | Dieckgraefe |
| 2008/0051573 A1 | 2/2008 | Hirth et al. |
| 2009/0098240 A1 | 4/2009 | Mills et al. |
| 2009/0304852 A1 | 12/2009 | Hopkins et al. |
| 2012/0220740 A1 | 8/2012 | Geremia et al. |
| 2013/0216693 A1 | 8/2013 | Harrison et al. |
| 2014/0060522 A1 | 3/2014 | Baynes et al. |
| 2014/0187474 A1 | 7/2014 | Sonnenburg |
| 2014/0234912 A1 | 8/2014 | Dekany et al. |
| 2015/0087616 A1 | 3/2015 | Ritter et al. |
| 2015/0202607 A1 | 7/2015 | Geremia et al. |
| 2015/0238948 A1 | 8/2015 | Geremia |
| 2015/0352133 A1 | 12/2015 | Jennewein |
| 2016/0007642 A1 | 1/2016 | Geremia et al. |
| 2016/0015065 A1 | 1/2016 | Sumner et al. |
| 2016/0032038 A1 | 2/2016 | Baynes et al. |
| 2016/0122447 A1 | 5/2016 | Geremia et al. |
| 2016/0366909 A1 | 12/2016 | Geremia et al. |
| 2017/0151268 A1 | 6/2017 | von Maltzahn et al. |
| 2017/0151269 A1 | 6/2017 | von Maltzahn et al. |
| 2019/0209600 A1 | 7/2019 | Gubler |
| 2020/0093845 A1 | 3/2020 | von Maltzahn et al. |

FOREIGN PATENT DOCUMENTS

| | | | |
|---|---|---|---|
| EP | | 2138048 A1 | 12/2009 |
| EP | | 2401925 A1 | 1/2012 |
| EP | | 2666788 A1 | 11/2013 |
| WO | WO 2004/052121 A1 | | 6/2004 |
| WO | WO 2005/003329 A1 | | 1/2005 |
| WO | WO 2006/030100 A1 | | 3/2006 |
| WO | WO 2006/041930 A2 | | 4/2006 |
| WO | WO 2007/010084 A2 | | 1/2007 |
| WO | WO 2007/050656 A2 | | 5/2007 |
| WO | WO 2007/117175 A1 | | 10/2007 |
| WO | WO 2008/037839 A1 | | 4/2008 |
| WO | WO 2008/156354 A1 | | 12/2008 |
| WO | WO 2009/082214 A1 | | 7/2009 |
| WO | WO 2010/105207 A1 | | 9/2010 |
| WO | WO 2010/136742 A1 | | 12/2010 |
| WO | WO 2011/008086 A1 | | 1/2011 |
| WO | WO 2011/016866 A1 | | 2/2011 |
| WO | WO 2014/031956 A1 | | 2/2014 |
| WO | WO 2014/145276 A1 | | 9/2014 |
| WO | WO 2015/153841 A1 | | 10/2015 |
| WO | WO 2016/007778 A1 | | 1/2016 |
| WO | WO 2016/122884 A1 | | 8/2016 |
| WO | WO 2016/122885 A1 | | 8/2016 |
| WO | WO 2016/122887 A1 | | 8/2016 |
| WO | WO 2016/122889 A1 | | 8/2016 |
| WO | WO 2016/172657 A2 | | 10/2016 |
| WO | WO 2016/172658 A2 | | 10/2016 |
| WO | WO 2017/083520 A1 | | 5/2017 |

OTHER PUBLICATIONS

Extended European Search Report for Application No. EP 16743843.1, dated Jun. 6, 2018.
Extended European Search Report for Application No. EP 17206409.9, dated Jun. 21, 2018.
International Search Report and Written Opinion for Application No. PCT/US2015/039795, dated Oct. 7, 2015.
International Search Report and Written Opinion for Application No. PCT/US2016/013265, dated Mar. 1, 2016.
International Search Report and Written Opinion for Application No. PCT/US2016/013271, dated Mar. 11, 2016.
International Search Report and Written Opinion for Application No. PCT/US2016/013280, dated Mar. 21, 2016.
International Search Report and Written Opinion for Application No. PCT/US2016/013305, dated Apr. 22, 2016.
International Preliminary Report on Patentability for Application No. PCT/US2016/013305, dated Aug. 10, 2017.
International Search Report and Written Opinion for Application No. PCT/US2016/029082, dated Oct. 14, 2016.
International Search Report and Written Opinion for Application No. PCT/US2016/029083, dated Oct. 14, 2016.
Adamberg et al., Degradation of fructans and production of propionic acid by Bacteroides thetaiomicron are enhanced by the shortage of amino acids. Front Nutr. 2014;1(21). 10 pages.
Aida et al., Mushroom as a potential source of prebiotics: a review. Trends in Food Science & Technology. 2009:567-75.
Alam et al., Efficacy of Partially Hydrolyzed Guar Gum-Added Oral Rehydration Solution in the Treatment of Severe Cholera in Adults. Digestion. 2008;78:24-29.
Beards et al., Bacterial, SCFA and gas profiles a range of food ingredients following in vitro fermentation by human colonic microbiota. Anaerobe. 2010;16:420-25.

(56) References Cited

OTHER PUBLICATIONS

Belknap et al., The effects of psyllium hydrophilic mucilloid on diarrhea in enterally fed patients. Heart & Lung. 1997;26(3):229-37.

Bergstrom et al., Defective Intestinal Mucin type O Glycosylation Causes Spontaneous Colitis Associated Cancer in Mice. Gastroenterology. Apr. 5, 2016.

Bier et al., Generally Recognized as Safe (GRAS) Determination for the Addition of Polydextrose to Infant Formula as a Prebiotic Ingredient in Combination with Galactooligosaccharides. US FDA, GRAS Notice, dated Aug. 2007.

Boler et al., Digestive physiological outcomes related to poly dextrose and soluble maize fibre consumption by healthy adult men. Br J Nutr. 2011;106:1864-71.

Casellas et al., Oral oligofructose-enriched inulin supplementation in acute ulcerative colitis is well tolerated and associated with lowered faecal calprotectin. Aliment Pharmacol Ther. 2007;25:1061-67.

Chen et al., Comparative Effects of Cellulose and Soluble Fibers (Pectin, Konjac Glucomannan, Inulin) on Fecal Water Toxicity toward Caco-2 Cells, Fecal Baceria Enzymes, Bile Acid, and Short-Chain Fatty Acids. J Agric Food Chem. 2010;58:10277-81.

Clemente et al., The Impact of the Gut Microbiota on Human Health: An Integrative View. Cell. 2012; 148(6): 1258-70.

Court In et al., Dietary Inclusion of Wheat Bran Arabinoxylooligosaccharides Induces Beneficial Nutritional Effects in Chickens. Cer. Chem. 2008;85(5):607-613.

Courun et al., Effects of xylooligosaccharides (XOS), arabinoxylooligosaccharides (AXOS), and soluble arabinoxylan on gut baceria of chickens; XOS and AXOS stimulate bifidobacteria. J Sci of Food Agric. 2008;88:2517-22.

Cummings et al., Carbohydrate terminology and classification. Eur J Clin Nutr. Dec. 2007;61 Suppl 1:S5-18. doi: 10.1038/sj.ejcn.1602936.

Deng et al., Effect of dietary fiber on intestinal barrier function of 5-FU stressed rats. Res Exp Med. 1999;199:111-19.

Dua et al., Characterization of lacto-N-hexaose and two fucosylated derivatives from human milk by high-performance liquid chromatography and proton NMR spectroscopy. J Chromatogr. Jun. 28, 1985;328:259-69. doi: 10.1016/s0021-9673(01)87396-9.

Duggan et al., Protective nutrients and functional foods for the gastrointestinal tract. Am J Clin Nutr. 2002;75:789-808.

Dutton et al., The Constitution of a Synthetic Xylan. Canadian Journal of Chemistry. 1962;40(8):1479-83.

Fasina et al., Comparative efficacy of a yeast product and bacitracin methylene disalicylate in enhancing early growth and intestinal maturation in broiler chicks from breeder hens of different ages. Poult Sci. 2011;90:1067-73.

Fischer et al., The gel-forming polysaccharide of psyllium husk (*Plantago ovata Forsk*). Carbohydrate Research. 2004;339:2009-17.

Fuhrer et al., Milk sialyllactose influences colitis in mice through selective intestinal bacterial colonization. J Exp Med. 2010;207(13):2843-54.

Gomez et al., Purification, Characterization, and Prebiotic Properties of Pectic Oligosaccharides from Orange Peel Wastes. J Ag Food Chem. 2014;62:9769-82.

Guerin-Deremaux et al., Effects of a soluble dietary fibre NUTRIOSE® on colonic fermentation and excretion rates in rats. Nutr Res Pract. Dec. 2010;4(6):470-6. doi: 10.4162/nrp.2010.4.6.470. Epub Dec. 28, 2010.

Hernot et al., In Vitro Fermentation Profiles, Gas Production Rates and Microbiota Modulation as Affected by Certain Fructans, Galactoologosaccharides, and Polydextrose. J Ag Food Chem. 2009;57:1354-61.

Holscher et al., Studied effects of agave inulin supplementation on fecal microbiota; saw changes in abundance of actinobacteria, bifidobacteria, and desulfo vibrio; also saw effects on fermentataion products (SCFAs). J Nutr. 2015;145:2025-32.

Hopkins et al., Nondigestible Oligosaccharides enhance Bacterial Colonization Resistance against Clostridium difficile In Vitro. App Environ Micro. 2003;69(4): 1920-27.

Islek et al., The role of Bifidobacterium lactis B94 plus inulin in the treatment of acute infectious diarrhea in children. Turk J Gastroenterol. 2014;25:628-33.

Kau et al., Human nutrition, the gut microbiome, and immune system: envisioning the future. Nature. 2011;474:327-336.

Kellow et al., Metabolic benefits of dietary prebiotics in human subjects: a systematic review of randomised controlled trials. Br J Nutr. 2014;111:1147-61.

Koropatkin et al., How glycan metabolism shapes the human gut microbiota. Nat Rev Microbiol. 2012;10:323-35.

Lewis et al., Effect of the Prebiotic Oligofructose on Relapse of Clostridium difficile—Associated Diarrhea: A Randomized, Controlled Study. Clin Gastroenterol and Hepatol. 2005;3:442-8.

Lin et al., Irinotecan (CPT-11) Chemotherapy Alters Intestinal Microbiota in Tumour Bearing Rats. PLoS One. 2012;7(7):e39764. 8 pages.

Louis et al., Diversity of human colonic butyrate-producing bacteria; inulin caused increases in Faecalbacterium prausnitzii; studied abundance of butyrate producing bacteria. Env Microbiol. 2010;12(2):304-14.

Louis et al., Diversity, metabolism and microbial ecology of butyrate producing bacteria from human large intestine; some mention of prebiotics affecting SCFA and taxa levels. FEMS Microbiol Lett. 2009;294:1-8.

Louis et al., How to Manipulate the Microbiota: Prebiotics. Microbiota of the Human Body, Advances in Experimental Medicine and Biology. 2016;9:119-142.

Louis et al., Review on effects of diet on gut bacterial metabolism; changes in oligofructose lead to shifts in species compositions of gut bacteria; inulin and FOS selectively stimulate bifido and lactobacilli; dietary fibers have effect on bacterial growth and subsequent SCFA production. J Appl Micrbiol. 2007;102:1197-1208.

Marlett et al., A Poorly Fermented Gel from Psyllium Seed Husk Increases Excreta Moisture and Bile Acid Excretion in Rats. J Nutr. 2002;132:2638-2643.

Mora et al., Synthetic Polysaccharides. V. Polymerization of Various Aldoses. J Am Chem Soc. 1960;83:3418-21.

Nakamura et al., Suppressive effect of partially hydrolyzed guar gum on transitory diarrhea induced by ingestion of maltitol and lactitol in healthy humans. Eur J Clin Nutr. 2007;61:1086-93.

Neyrink et al., Prebiotic Effects of Wheat Arabinoxylan Related to the Increase in Bifidobacteria, Roseburia and Bateroides/Prevotella in Diet-Induced Obese Mice. PLoS One. 2011;6(6):e20944. 12 pages.

Prisciandaro et al., Probiotic factors partially improve parameters of 5-fluorouracil-induced intestinal mucositis in rats. Cancer Biol & Ther. 2011;11(7):671-77.

Röytiö et al., The fermentation of polydextrose in the large intestine and its beneficial effects. Benef Micrbiol. 2014;5(3):305-313.

Saku et al., Effects of poly dextrose on serum lipids, lipoproteins, and apolipoproteins in healthy subjects. Clin Ther. 1991;13(2):254-58. Abstract Only.

Salonen et al., Impact of diet and individual variation on intestinal microbiota composition and fermentation products in obese men. The ISME J. 214;8:2218-30.

Sanz et al., Influence of Glycosidic Linkages and Molecular Weight on the Fermntation of Maltose-Based Oligosaccharides by Human Gut Bacteria. J Agric Food Chem. 2006;54:9779-84.

Schley et al., The immune-enhancing effects of dietary fibres and prebiotics. Br J Nutr. 2002;87(Suppl 2):S221-S230.

Scott et al., Prebiotic stimulation of human colonic butyrate-producing bacteria and bifidobacteria, in vitro. FEMS Microbiol Ecol. 2014;87:30-40.

Sharon, Carbohydrates as Future Anti-Adhesion Drugs for Infectious Diseases. Biochimica et Biophysica. 2006;1760(4):527-537.

Sheu et al., Effects of xylooligosaccharides on type 2 diabetes; looked at SCFA levels; mention XOS effect of Bifido populations. J Nutr Sci Vitaminol. 2008;54:396-401.

Simpson et al., Review article: dietary fibre-microbiota interactions. Alimentary Pharmacology and Therapeutics. 2015;42:158-79.

(56) References Cited

OTHER PUBLICATIONS

Smiiowilz et al., Breast Milk Oligosaccharides: Structure-Function Relationships in the Neonate. Annu Rev Nutr. 2014;34:143-69.
Synytsya et al., Glucans from fruit bodies of cultivated mushrooms *Pleurotus osteatus* and *Pleurous eryngii*: Structure and potential prebiotic activity. Carbohydrate Polymers. 2009:548-556.
Tomlin et al., A Comparative study of the effects on colon function caused by feeding ispaghula husk and polydextrose. Aliment Pharamcol Ther. 1988;2(6):513-19.
Van Den Abbeele et al., Butyrate-producing Clostridium cluster XIVa species specifically colonize muchins in an in vitro gut model. The ISME Journal. 2013;7:949-61.
Wang et al., Preparation and structural characterization of polymannose synthesized by phosphoric acid catalyzation under microwave irradation. Carbohydrate Polymers. 2015;121:355-361.
Wang et al., Rapid microwave-assisted synthesis of polydextrose and identification of structure and function. Carbohydrate Polymers. 2014;113:225-230.
Winfree et al., Effects of Dietary Protein and Energy on Growth, Feed Conversion Efficiency and Body Composition of Tilapia aurea. J Nutr. 1981;111:1001-12.
Wu et al., Diminution of the gut resistome after a gut microbiota-targeted dietary intervention in obese children. Nat Sci Rep. 2016;6(Article 24030). 9 pages.

\* cited by examiner

GLYCAN THERAPEUTICS AND METHOD OF TREATING CONDITIONS ASSOCIATED WITH TMAO

CLAIM OF PRIORITY

This application is a continuation of U.S. application Ser. No. 16/395,929, filed Apr. 26, 2019, which is a continuation of U.S. application Ser. No. 16/126,873, filed Sep. 10, 2018, which is a continuation of U.S. application Ser. No. 15/866, 152, filed Jan. 9, 2018, which is a continuation of U.S. Pat. No. 9,901,595, filed Oct. 5, 2016, which is a continuation of U.S. Pat. No. 9,492,473, filed Feb. 5, 2016, which is a continuation of International Application No. PCT/US2016/013305, filed Jan. 13, 2016, which claims priority to U.S. Application No. 62/108,039, filed Jan. 26, 2015; U.S. Application No. 62/152,016, filed Apr. 23, 2015; U.S. Application No. 62/152,005, filed Apr. 23, 2015; U.S. Application No. 62/152,007, filed Apr. 23, 2015; U.S. Application No. 62/152,011, filed Apr. 23, 2015; U.S. Application No. 62/152,017, filed Apr. 23, 2015; U.S. Application No. 62/216,995, filed Sep. 10, 2015; U.S. Application No. 62/216,997, filed Sep. 10, 2015; U.S. Application No. 62/217,002, filed Sep. 10, 2015; U.S. Application No. 62/216,993, filed Sep. 10, 2015; U.S. Application No. 62/238,112, filed Oct. 6, 2015; and U.S. Application No. 62/238,110, filed Oct. 6, 2015. The disclosure of each of the foregoing is incorporated herein by reference in its entirety.

BACKGROUND

The microbiota of humans is complex, and varies by individual depending on genetics, age, sex, stress, nutrition and diet. The microbiota perform many activities and may influence the physiology of the host. Changing the numbers and species of gut microbiota can alter community function and interaction with the host. A limited number of probiotic bacteria is known in the art, and some association with health benefits documented when taken by humans. Some foods are considered 'prebiotic' foods that contain substances that may promote the growth of certain bacteria that are thought to be beneficial to the human host. The results of clinical tests with these substances are conflicted with respect to their efficacy, and their influence on human health is generally described as being modest. Thus, there is a need for novel therapeutic inputs that can stimulate beneficial microbiota shifts and improve human health.

SUMMARY OF THE INVENTION

In one aspect, the present invention features methods of modulating the abundance of a bacterial taxa in a human subject's gastrointestinal microbiota, the method comprising administering to the human subject a pharmaceutical composition comprising a glycan therapeutic preparation in an amount effective to modulate the abundance of the bacterial taxa, wherein i) the glycan therapeutic preparation comprises a mixture of branched glycans, wherein the average degree of branching (DB, branching points per residue) of the glycans in the preparation is at least 0.01 (e.g., at least 0.05, or at least 0.1), ii) at least 50% of the glycans in the preparation have a degree of polymerization (DP) of at least 3 and less than 30 glycan units, and iii) the ratio of alpha- to beta-glycosidic bonds present in the glycans of the preparation is between about 1:1 to about 5:1 overall. In some embodiments, the bacterial taxa comprises at least a first and a second bacterial taxa.

In some embodiments, the preparation comprises branched oligosaccharides. In some embodiments, the average degree of branching in the preparation (DB) is at least 0.05 (e.g., at least 0.1).

In some embodiments, at least one, at least two, at least three, at least four, or more of the glycosidic bonds independently comprise a 1→2 glycosidic bond, a 1→3 glycosidic bond, a 1→4 glycosidic bond, or a 1→6 glycosidic bond. In some embodiments, one or more, two or more, or three or more glycosidic bonds are present in both alpha and beta configuration.

In some embodiments, a glycan unit comprises at least one, at least two, at least three, or more of a monosaccharide selected from the group of a tetrose, a pentose, a hexose, and a heptose. In some embodiments, a glycan unit comprises at least one, at least two, at least three, or more of a monosaccharide selected from the group of glucose, galactose, arabinose, mannose, fructose, xylose, fucose, and rhamnose.

In some embodiments, at least a plurality of the glycans, e.g., at least 10, 20, 30 40, 50, 60, 70, 80, 90, 95, or 99% (by weight or number), or substantially all, of the glycans in the preparation, do not comprise more than a preselected reference level, of a repeating unit of glycan units, e.g., a repeating unit of 2, 3, 4 or more glycan units. In an embodiment, the preselected reference level is 10, 20, 30, 40, 50, or 60% of the total glycan units in a glycan. By way of example, in an embodiment, a glycan made up of 20 saccharide monomers, less than 50% of those 20 monomers are repeating units of a 2 or 3 glycan repeat.

In some embodiments, the glycan therapeutic preparation is synthetic and not isolated from a natural oligosaccharide or polysaccharide source.

In some embodiments, the abundance of the bacterial taxa (e.g., of each of a first and a second bacterial taxa) in the human subject's gastrointestinal microbiota is modulated by at least about 5%, 10%, 25% 50%, 75%, 100%, 250%, 500%, 750%, or by at least 1000%. In some embodiments, the modulation comprises an increase or a decrease in the abundance of the bacterial taxa (e.g., of each of a first and a second bacterial taxa) in the human subject's gastrointestinal microbiota.

In some embodiments, the bacterial taxa (e.g., a first and a second bacterial taxa) comprises a commensal bacterial taxa. In other embodiments, the bacterial taxa (e.g., a first and a second bacterial taxa) comprises a pathogenic bacterial taxa.

In some embodiments, the bacterial taxa (e.g., a first and a second bacterial taxa) comprises a genus selected from the group of *Akkermansia, Alistipes, Anaerofilum, Bacteroides, Bilophila, Blautia, Bifidobacterium, Butyrivibrio, Campylobacter, Candidatus, Citrobacter, Clostridium, Collinsella, Coprococcus, Desulfovibrio, Dialister, Dorea, Enterobacter, Enterococcus, Escherichia, Eubacterium, Faecalibacterium, Fusobacterium, Haemophilus, Klebsiella, Lachnospira, Lactobacillus, Odoribacter, Oscillospira, Parabacteroides, Peptococcus, Peptostreptococcus, Phascolarctobacterium, Porphyromonas, Portiera, Prevotella, Providencia, Pseudomonas, Roseburia, Ruminococcus, Salmonella, Shigella, Staphylococcus, Streptococcus, Subdoligranulum, Vibrio,* and *Yersinia*. In some embodiments, the bacterial taxa (e.g., a first and a second bacterial taxa) comprises a genus selected from the group of *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus,* and *Enterococcus*. In some embodiments, the bacterial taxa (e.g., a first and a second bacterial taxa) comprises a genus selected from the group of *Akkermansia, Bacteroides, Bifidobacterium, Lactobacillus,* and *Parabacteroides.* In some embodiments, the bacterial taxa (e.g., a first and a second bacterial taxa) comprises a genus selected from the group of *Akkermansia* and *Blautia.*

In some embodiments, the bacterial taxa (e.g., a first and a second bacterial taxa) comprises a taxa predominant in the small intestine or large intestine. In some embodiments, the bacterial taxa (e.g., a first and a second bacterial taxa) predominant in the small intestine comprises a genus selected from the group of *Achromobacter, Agrobacterium, Blautia, Burkholderia, Coprococcus, Cryocola, Enterococcus, Eubacterium, Holdemania, Lactococcus, Mycobacterium, Pseudoramibacter, Ralstonia, Sphingomonas, Streptococcus,* and *Turicibacter.* In some embodiments, the bacterial taxa (e.g., a first and a second bacterial taxa) predominant in the large intestine comprises a genus selected from the group of *Anaerotruncus, Akkermansia, Bacteroides, Bilophila, Butyricimonas, Odoribacter, Parabacteroides, Phascolarctobacterium, Prevotella,* and *Ruminococcus.*

In some embodiments, the pharmaceutical composition further comprises a polyphenol preparation. In some embodiments, the polyphenol preparation comprises a plant polyphenol isolated from a plant source material. In some embodiments, the plant source material comprises blueberry, cranberry, grape, peach, plum, pomegranate, soy, red wine, black tea, or green tea.

In some embodiments, the modulating the abundance of a bacterial taxa (e.g., a first and a second bacterial taxa) treats a dysbiosis, e.g., a dysbiosis described herein.

In another aspect, the present invention features a method of reducing a drug- or treatment-induced symptom in a human subject, comprising administering to the human subject a glycan therapeutic preparation in an amount effective to reduce a symptom induced by a drug or treatment, wherein i) the glycan therapeutic preparation comprises a mixture of branched glycans, wherein the average degree of branching (DB) of the glycans in the preparation is at least 0.01 (e.g., at least 0.05, or at least 0.1), ii) at least 50% of the glycans in the preparation have a degree of polymerization (DP) of at least 3 and less than 30 glycan units, and iii) the ratio of alpha- to beta-glycosidic bonds present in the glycans of the preparation is between about 1:1 to about 5:1 overall.

In some embodiments, the drug- or treatment-induced symptom is selected from the group of bloating, diarrhea, vomiting, nausea, and constipation. In some embodiments, the drug- or treatment-induced is diarrhea. In some embodiments, the drug- or treatment-induced symptom is constipation.

In some embodiments, the composition reduces drug-induced symptoms and the composition is administered prior to, concomitant with, or after administration of the drug. In some embodiments, the drug is an anti-diabetic drug, an immune-suppressive drug, an antimicrobial drug, a chemotherapeutic drug, an anti-psychotic drug, a proton pump inhibitor drug, or a non-steroid anti-inflammatory drug (NSAID). In some embodiments, the drug is selected from the group of ciprofloxacin, clindamycin, amoxicillin-clavulanate, cefixime, ephalosporins, fluoroquinolones, azithromycin, clarithromycin, erythromycin, tetracycline, azithromycin, irinotecan (camptosar), 5-fluorouracil, leucovorin, oxaliplatin, bortezomib, imatinib, lenalidomide, imbruvica, ipilimumab, pertuzumab, capecitabine, docetaxel, lapatinib, erlotinib, carmustine, etoposide, aracytine, melphalan, cytarabine, daunorubicine, amsacrine, mitoxantrone, olanzapine, ranitidine, famotidine, cimetidine, omeprazole, sucralfate, esomeprazole, naproxen, diclofenac, indomethacin, ibuprofen, ketoprofen, piroxicam, celecoxib, nimesulid, aspirin, metformin, paroxetine, valproic acid, and clozapine.

In some embodiments, the composition reduces treatment-induced symptoms and the treatment comprises radiation treatment or surgery.

In some embodiments, the drug- or treatment-induced symptom is exhibited by the subject during a treatment regimen. In some embodiments, the reducing the one or more symptom increases compliance by the subject to the treatment regimen. In some embodiments, the reducing the one or more symptom increases the subject's tolerance to a higher dose of the drug to be administered during the treatment regimen.

In another aspect, the present invention features a method for modulating microbial diversity in a human subject's gastrointestinal tract, the composition comprising a glycan therapeutic preparation in an amount effective to modulate the microbial diversity, wherein i) the glycan therapeutic preparation comprises a mixture of branched glycans, wherein the average degree of branching (DB, branching points per residue) of the glycans in the preparation is at least 0.01 (e.g., at least 0.05, or at least 0.1), ii) at least 50% of the glycans in the preparation have a degree of polymerization (DP) of at least 3 and less than 30 glycan units; and iii) the ratio of alpha- to beta-glycosidic bonds present in the glycans of the preparation is between about 1:1 to about 5:1 overall. In some embodiments, the microbial diversity comprises bacterial diversity. In some embodiments, the modulating comprises an increase or a decrease in microbial diversity.

In some embodiments, the microbial diversity is determined (e.g., measured) by or expressed through use of the Shannon Diversity Index. In some embodiments, the Shannon Diversity is increased or decreased by at least about 5%. In some embodiments, the Shannon Diversity is increased or decreased by at least about 15%. In some embodiments, the Shannon Diversity is increased or decreased by at least about 0.3 log-fold. In some embodiments, Shannon Diversity is increased or decreased by at least about 0.6 log-fold. In some embodiments, Shannon Diversity is increased or decreased by at least about 1 log-fold.

In some embodiments, the abundance of at least one bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus,* and *Enterococcus* is modulated. In some embodiments, the abundance of at least one bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus,* and *Enterococcus* is increased by at least about 5%.

In some embodiments, the abundance of at least two bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus,* and *Enterococcus* is modulated. In some embodiments, the abundance of at least two bacterial taxa selected from the group of genus *Prevotella, Akkermansia, Bacteroides, Clostridium* (Erysipelotrichaceae), *Clostridium* (Clostridiaceae), *Bifidobacterium,*

*Aggregatibacter, Clostridium* (Peptostreptococcaveae), *Parabacteroides, Lactobacillus,* and *Enterococcus* is increased by at least about 5%.

In some embodiments, the abundance of at least one bacterial taxa selected from the group of genus *Akkermansia, Bacteroides, Bifidobacterium, Lactobacillus,* and *Parabacteroides* is modulated. In some embodiments, the abundance of at least two bacterial taxa selected from the group of genus *Akkermansia, Bacteroides, Bifidobacterium, Lactobacillus,* and *Parabacteroides* is modulated. In some embodiments, the abundance of at least one bacterial taxa selected from the group of genus *Akkermansia* and *Blautia* is modulated. In some embodiments, the abundance of both of the bacterial genera *Akkermansia* and *Blautia* is modulated. In some embodiments, the modulating the microbial diversity treats a dysbiosis.

In another aspect, the present invention features a method of treating a human subject in need thereof, the method comprising: a) identifying a human subject in need of treatment for dysbiosis, and b) administering to the human subject a pharmaceutical composition comprising a glycan therapeutic preparation in an amount effective to treat the dysbiosis, wherein i) the glycan therapeutic preparation comprises a mixture of branched glycans, wherein the average degree of branching (DB) of the glycans in the preparation is at least 0.01 (e.g., at least 0.05, or at least 0.1), ii) at least 50% of the glycans in the preparation have a degree of polymerization (DP) of at least 3 and less than 30 glycan units, and iii) the ratio of alpha- to beta-glycosidic bonds present in the glycans of the preparation is between about 1:1 to about 5:1 overall.

In some embodiments, the human subject has an infectious disease, disorder or condition. In some embodiments, the infectious disease, disorder or condition is selected from the group of *Clostridium difficile* infection (CDI); Vancomycin-resistant enterococci (VRE) infection, infectious colitis, or *C. difficile* colitis. In some embodiments, the infectious disease, disorder or condition is diarrhea selected from the group of *Clostridium difficile* associated diarrhea (CDAD), antibiotic-associated diarrhea (AAD), antibiotic-induced diarrhea, travelers' diarrhea (TD), pediatric diarrhea, and (acute) infectious diarrhea.

In some embodiments, the human subject has a metabolic disease, disorder or condition. In some embodiments, the metabolic disease, disorder or condition is selected from the group of obesity, (insulin resistance) pre-diabetes, type II diabetes, high fasting blood sugar (hyperglycemia), and metabolic syndrome. In some embodiments, the metabolic disease, disorder or condition is a cardiovascular risk factor selected from the group of high blood cholesterol, high LDL, high blood pressure (hypertension), high triglyceride levels, low HDL.

In some embodiments, the human subject has an inflammatory disease, disorder or condition. In some embodiments, the inflammatory disease, disorder or condition is selected from the group of inflammatory bowel disease (IBD), ulcerative colitis (UC), Crohn's disease (CD), intestinal inflammation, and microscopic colitis. In some embodiments, the inflammatory disease, disorder or condition is selected from the group of irritable bowel syndrome (IBS), constipation, diarrhea, indigestion, and non-ulcer dyspepsia.

In some embodiments, the human subject has an autoimmune disease, disorder, or condition. In some embodiments, the autoimmune disease, disorder or condition is selected from the group of autoimmune arthritis, type I diabetes, multiple sclerosis, and psoriasis. In some embodiments, the human subject has an allergy. In some embodiments, the allergy comprises asthma or atopic dermatitis.

In some embodiments, the human subject has a neurological disease, disorder, or condition. In some embodiments, the neurological disease, disorder or condition is selected from the group of autism, hyperammonemia, and hepatic encephalopathy.

In some embodiments, treating further comprises administering a second drug or pharmaceutical agent. In some embodiments, the second drug or pharmaceutical agent is a standard-of-care drug or agent. In some embodiments, the treatment effects of the pharmaceutical composition comprising a glycan therapeutic preparation and the second drug or pharmaceutical agent are additive. In some embodiments, the treatment effects of the pharmaceutical composition comprising a glycan therapeutic preparation and the second drug or pharmaceutical agent are synergistic.

In some embodiments, the composition is administered daily. In some embodiments, the composition is administered each day for a predetermined number of days (the treatment period). In some embodiments, the treatment period comprises between about 1 day and about 30 days. In some embodiments, the treatment period comprises between about 1 month and about 6 months. In some embodiments, the subject is administered the composition for a single treatment period. In some embodiments, the subject is administered the composition for more than one treatment period.

In some embodiments, by treating the dysbiosis the disease of the human subject is treated.

In another aspect, the present invention features a method of modulating a functional pathway of the microbiota of a human subject's gastrointestinal tract, the composition comprising a glycan therapeutic preparation in an amount effective to modulate the functional pathway, wherein i) the glycan therapeutic preparation comprises a mixture of branched glycans, wherein the average degree of branching (DB) of the glycans in the preparation is at least 0.01 (e.g., at least 0.05, or at least 0.1); ii) at least 50% of the glycans in the preparation have a degree of polymerization (DP) of at least 3 and less than 30 glycan units; and iii) the ratio of alpha- to beta-glycosidic bonds present in the glycans of the preparation is between about 1:1 to about 5:1 overall.

In some embodiments, the functional pathway modulates the production of an anti-microbial agent, a secondary bile acid, a short-chain fatty acid, a siderophore, or a metabolite listed in Table 2 by the microbiota. In some embodiments, the antimicrobial agent comprises a bacteriocin or hydrogen peroxide. In some embodiments, the short-chain fatty acid comprises formate, butyrate, acetate, propionate, or valerate. In some embodiments, the metabolite comprises 2-hydroxyisobutyrate, 3-hydroxyisovalerate, 3-methylcrotonylglycine, 3-methylcrotonylglycine, allantoin, betaine, formate, mannitol, p-cresol glucuronide, phenylacetylglycine, sarcosine, taurine, acetic acid, acetylaldehyde, ascorbic acid, butanedione, butyric acid, deoxycholic acid, ethylphenyl sulfate, formic acid, indole, isobutyric acid, isovaleric acid, propionic acid, serotonin, succinic acid, succinate, TMAO, tryptophan, valeric acid, ursodeoxycholic acid, lactate, lactic acid, or hydrogen peroxide.

In some embodiments, the functional pathway modulates the level of an inflammatory or immunomodulatory cytokine in the human subject. In some embodiments, the inflammatory and immunomodulatory cytokine comprises interleukin-1α (IL-1α), IL-1β, IL-2, IL-4, IL-6, IL-8, IL-10, IL-12, IL-13, IL-17A, IL-17F, IL-22, IL-23, tumor necrosis factor (TNF), chemokine (C-C motif) ligand 5 (CCL5, also known as RANTES), transforming growth factor beta (TGF-β), or interferon gamma (IFN-γ).

In some embodiments, the functional pathway increases the level of a short-chain fatty acid in the subject. In some embodiments, the increase in the short-chain fatty acid induces the generation of regulatory T (Treg) cells by the subject. In some embodiments, the increase in the short-chain fatty acid reduces the permeability of the intestinal or plasma endotoxin level in the subject. In some embodiments, the increase of a short-chain fatty acid reduces the inflammatory response of the subject. In some embodiments, the short-chain fatty acid is produced by at least one bacterial species of the Ruminocaccaceae and/or Lachnospiraceae family.

In some embodiments, the subject is obese.

In another aspect, the present invention features a method of preventing a relapse of a *Clostridium difficile* infection in a human subject previously administered a drug for the treatment of a *C. difficile* infection, the method comprising administering a glycan therapeutic preparation in an amount effective to prevent the relapse, wherein i) the glycan therapeutic preparation comprises a mixture of branched glycans, wherein the average degree of branching (DB) of the glycans in the preparation is at least 0.01 (e.g., at least 0.05, or at least 0.1); ii) at least 50% of the glycans in the preparation have a degree of polymerization (DP) of at least 3 and less than 30 glycan units; and iii) the ratio of alpha- to beta-glycosidic bonds present in the glycans is between about 1:1 to about 5:1 overall.

In some embodiments, the relapse comprises the recurrence of one or more symptoms associated with a *C. difficile* infection. In some embodiments, the relapse occurs during or after a first-line or standard of care drug treatment regimen.

In some embodiments, the drug for the treatment of a *C. difficile* infection is an antibiotic. In some embodiments, the antibiotic is selected from the group of vancomycin, metronidazole, and fidaxomicin. In some embodiments, the composition is administered concurrently or after administration of the drug for the treatment of a *C. difficile* infection.

In some embodiments, the composition is administered in combination with a second drug or treatment. In some embodiments, the second drug or treatment comprises an antibiotic. In some embodiments, the antibiotic is selected from the group of vancomycin, metronidazole, and fidaxomicin.

In some embodiments, administration of the composition results in a reduction of the severity of a symptom associated with a *C. difficile* infection in the subject but does not eliminate the population of *C. difficile* in the subject. In some embodiments, administration of the composition results in a reduction of the severity of a symptom associated with a *C. difficile* infection in the subject but does not change the level of the population of *C. difficile* in the subject.

In another aspect, the present invention features a method of making a pharmaceutical composition, the method comprising a) providing a preparation comprising a mixture of synthetic glycans, b) acquiring a value for one or more of the following characteristics of the preparation, c) the degree of polymerization (DP), d) the average degree of branching (DB), e) the ratio of alpha-glycosidic to beta-glycosidic bonds, and f) formulating the preparation as a pharmaceutical composition if one or more of the following criteria are met: i) at least 50% of the glycans in the preparation have a DP of at least 3 and less than 30 glycan units, ii) the average degree of branching (DB) of the glycans in the preparation is at least 0.01 (e.g., at least 0.05, or at least 0.1), iii) the ratio of alpha- to beta-glycosidic bonds present in the glycans of the preparation is between about 1:1 to about 5:1 overall.

In some embodiments, the method further comprises a) acquiring a value for any one or both additional characteristics of the preparation: i) the identity of the glycan units, ii) the ratio of glycan units, and b) formulating the preparation as a pharmaceutical composition if: iii) the glycan unit ratio in the preparation is about the same as the ratio of the glycan unit input.

In some embodiments, the method further comprises: b) acquiring a value for any one or both additional characteristics of the preparation: iv) the level of bacterial growth, in media supplemented with the preparation, of commensal strains selected from the group consisting of *Bacteroides caccae* ATCC 43185, *Prevotella copri* DSM 18205, *Bacteroides thetaiotamicron* ATCC 29741, *Bacteroides cellulosilyticus* DSM 14838, *Clostridium scindens* ATCC 35704, *Ruminococcus obeum* ATCC 29714, *Clostridium nexile* ATCC 27757, and *Parabacteroides distasonis* ATCC 8503, v) the level of bacterial growth, in media supplemented with the preparation, of pathogenic strains selected from the group consisting of *Clostridium difficile* ATCC BAA-1382, *Clostridium difficile* ATCC 43255, *Enterococcus faecium* ATCC 700221, and *Salmonella enterica* ATCC 27869, and c) formulating the preparation as a pharmaceutical composition if one or both of the following criteria are met: vi) promotion by the media supplemented with the preparation of growth of at least 5 commensal strains, vii) promotion by the media supplemented with the preparation of growth of no more than 2 pathogenic strain. In some embodiments, step (b) may be performed prior to, concurrently with, another step in the process.

In some embodiments, the step of formulating the preparation as a pharmaceutical composition comprises one or more of: i) removing unwanted constituents from the preparation, ii) reducing the volume of the preparation, iii) sterilizing the preparation, iv) admixing the preparation with a pharmaceutically acceptable excipient or carrier, v) admixing the preparation with a second drug or pharmaceutical agent, vi) formulating the preparation into a aqueous solution or syrup, vii) formulating the preparation into a tablet or pill, and viii) formulating the preparation into a capsule.

In some embodiments, the step of formulating the preparation as a pharmaceutical composition comprises one or more of ix) packaging the preparation, x) labeling the packaged preparation, and xi) selling or offering for sale the packaged and labeled preparation.

In another aspect, the present invention features a method of making a pharmaceutical composition, the method comprising: (i) providing a therapeutic glycan preparation comprising at least one glycan unit selected from the group consisting of glucose, galactose, fucose, xylose, arabinose, rhamnose, and mannose, (ii) determining if a preselected NMR peak or group of NMR peaks is associated with the glycan preparation, and (iii) if the preselected peak or group of peaks is present, formulating the preparation as a pharmaceutical composition.

In some embodiments, the peak is a 1H-13C HSQC NMR peak. In some embodiments, determining comprises acquiring a value for the identity of an 1H-13C HSQC peak or group of peaks associated with the preparation, and if a preselected peak is present, formulating the preparation as a pharmaceutical composition.

In some embodiments, i) for glycans comprising glucose, the peaks comprise at least one 1H-13C HSQC peak selected from 5.42, 92.5; 5.21, 92.8; 5.18, 93.9; 5.08, 97.0; 5.36, 98.4; 5.34, 99.8; 5.38, 100.3; 4.95, 98.6; 4.62, 96.6; 4.70, 103.6; 4.49, 103.4 1H shift (ppm) and 13C shift (ppm) or a corresponding peak; ii) for glycans comprising galactose, the peaks comprise at least one 1H-13C HSQC peak selected from 5.37, 92.9; 5.24, 93.1; 5.14, 96.0; 4.96, 99.3; 5.31, 98.7; 5.39, 101.4; 5.00, 101.8; 4.80, 101.3; 4.63, 97.0; 4.56, 97.2; 4.53, 103.1; 4.43, 104.1 1H shift (ppm) and 13C shift (ppm) or a corresponding peak; iii) for glycans comprising fucose, the peaks comprise at least one 1H-13C HSQC peak selected from 5.18, 92.9; 5.33, 92.4; 5.04, 96.3; 4.90, 99.7; 4.52, 97.0; 4.39, 103.6 1H shift (ppm) and 13C shift (ppm) or a corresponding peak; iv) for glycans comprising xylose, the peaks comprise at least one 1H-13C HSQC peak selected from 5.18, 93.0; 5.10, 94.3; 5.34, 98.2; 5.31, 99.6; 5.11, 100.8; 4.91, 99.4; 4.56, 97.3; 4.64, 104.2; 4.54, 103.4; 4.44, 102.6; 4.44, 104.1 1H shift (ppm) and 13C shift (ppm) or a corresponding peak; v) for glycans comprising arabinose, the peaks comprise at least one 1H-13C HSQC peak selected from 5.22, 93.2; 5.13, 93.2; 5.29, 96.0; 5.26, 97.2; 5.12, 96.6; 5.18, 99.6; 5.06, 99.2; 4.99, 100.0; 5.26, 101.9; 5.06, 102.1; 4.55, 97.4; 4.54, 105.2; 4.50, 105.5; 4.38, 103.9 1H shift (ppm) and 13C shift (ppm) or a corresponding peak; vi) for glycans comprising rhamnose, the peaks comprise at least one 1H-13C HSQC peak selected from 5.21, 93.2; 5.10, 94.5; 4.85, 94.1; 5.01, 95.8; 5.35, 100.5; 5.15, 102.2; 5.04, 102.9; 4.78, 97.9; 4.71, 99.0; 4.72, 101.0 1H shift (ppm) and 13C shift (ppm) or a corresponding peak; vii) for glycans comprising mannose, the peaks comprise at least one 1H-13C HSQC peak selected from 5.37, 93.0; 5.16, 94.6; 4.88, 94.2; 5.39, 101.7; 5.24, 101.9; 5.13, 102.8; 5.03, 102.7; 5.24, 105.6; 5.09, 108.0; 4.88, 94.2; 4.89, 100.0; 4.70, 101.1 1H shift (ppm) and 13C shift (ppm) or a corresponding peak.

In some embodiments, i) for glycans comprising glucose, the peaks comprise at least two, at least three, at least four, or more 1H-13C HSQC peaks selected from 5.42, 92.5; 5.21, 92.8; 5.18, 93.9; 5.08, 97.0; 5.36, 98.4; 5.34, 99.8; 5.38, 100.3; 4.95, 98.6; 4.62, 96.6; 4.70, 103.6; 4.49, 103.4 1H shift (ppm) and 13C shift (ppm) or a corresponding peak; ii) for glycans comprising galactose, the peaks comprise at least two, at least three, at least four, or more 1H-13C HSQC peaks selected from 5.37, 92.9; 5.24, 93.1; 5.14, 96.0; 4.96, 99.3; 5.31, 98.7; 5.39, 101.4; 5.00, 101.8; 4.80, 101.3; 4.63, 97.0; 4.56, 97.2; 4.53, 103.1; 4.43, 104.1 1H shift (ppm) and 13C shift (ppm) or a corresponding peak; iii) for glycans comprising fucose, the peaks comprise at least two, at least three, at least four, or more 1H-13C HSQC peaks selected from 5.18, 92.9; 5.33, 92.4; 5.04, 96.3; 4.90, 99.7; 4.52, 97.0; 4.39, 103.6 1H shift (ppm) and 13C shift (ppm) or a corresponding peak; iv) for glycans comprising xylose, the peaks comprise at least two, at least three, at least four, or more 1H-13C HSQC peaks selected from 5.18, 93.0; 5.10, 94.3; 5.34, 98.2; 5.31, 99.6; 5.11, 100.8; 4.91, 99.4; 4.56, 97.3; 4.64, 104.2; 4.54, 103.4; 4.44, 102.6; 4.44, 104.1 1H shift (ppm) and 13C shift (ppm) or a corresponding peak; v) for glycans comprising arabinose, the peaks comprise at least two, at least three, at least four, or more 1H-13C HSQC peaks selected from 5.22, 93.2; 5.13, 93.2; 5.29, 96.0; 5.26, 97.2; 5.12, 96.6; 5.18, 99.6; 5.06, 99.2; 4.99, 100.0; 5.26, 101.9; 5.06, 102.1; 4.55, 97.4; 4.54, 105.2; 4.50, 105.5; 4.38, 103.9 1H shift (ppm) and 13C shift (ppm) or a corresponding peak; vi) for glycans comprising rhamnose, the peaks comprise at least two, at least three, at least four, or more 1H-13C HSQC peaks selected from 5.21, 93.2; 5.10, 94.5; 4.85, 94.1; 5.01, 95.8; 5.35, 100.5; 5.15, 102.2; 5.04, 102.9; 4.78, 97.9; 4.71, 99.0; 4.72, 101.0 1H shift (ppm) and 13C shift (ppm) or a corresponding peak; vii) for glycans comprising mannose, the peaks comprise at least two, at least three, at least four, or more 1H-13C HSQC peaks selected from 5.37, 93.0; 5.16, 94.6; 4.88, 94.2; 5.39, 101.7; 5.24, 101.9; 5.13, 102.8; 5.03, 102.7; 5.24, 105.6; 5.09, 108.0; 4.88, 94.2; 4.89, 100.0; 4.70, 101.1 1H shift (ppm) and 13C shift (ppm) or a corresponding peak.

In another aspect, the present invention features a pharmaceutical composition comprising a therapeutic glycan preparation comprising a mixture of branched glycans, wherein the average degree of branching (DB) is at least 0.01, wherein i) at least 50% of the glycans in the preparation have a degree of polymerization (DP) of at least 3 and less than 30 glycan units, ii) the glycan preparation comprises both alpha- and beta-glycosidic bonds, iii) at least one of the glycosidic bonds present in the glycans of the preparation comprise a 1→2 glycosidic bond, a 1→3 glycosidic bond, a 1→4 glycosidic bond, or a 1→6 glycosidic bond, and iv) the ratio of alpha- to beta-glycosidic bonds present in the glycans of the preparation is between about 1:1 to about 5:1.

In some embodiments, at least one, at least two, at least three, at least four, or more of the glycosidic bonds independently comprise a 1→2 glycosidic bond, a 1→3 glycosidic bond, a 1→4 glycosidic bond, or a 1→6 glycosidic bond. In some embodiments, one or more, two or more, or three or more glycosidic bonds are present in both alpha and beta configuration.

In some embodiments, a glycan unit comprises at least one, at least two, at least three, or more of a monosaccharide selected from the group of a tetrose, a pentose, a hexose, and a heptose. In some embodiments, a glycan unit comprises at least one, at least two, at least three, or more of a monosaccharide selected from the group of glucose, galactose, arabinose, mannose, fructose, xylose, fucose, and rhamnose.

In some embodiments, at least a plurality of the glycans, e.g., at least 10, 20, 30 40, 50, 60, 70, 80, 90, 95, or 99% (by weight or number), or substantially all, of the glycans in the preparation, do not comprise more than a preselected reference level, of a repeating unit of glycan units, e.g., a repeating unit of 2, 3, 4 or more glycan units. In an embodiment, the preselected reference level is 10, 20, 30, 40, 50, or 60% of the total glycan units in a glycan. By way of example, in an embodiment, a glycan made up of 20 saccharide monomers, less than 50% of those 20 monomers are repeating units of a 2 or 3 glycan repeat.

In some embodiments, the glycan therapeutic preparation is synthetic and not isolated from a natural oligosaccharide or polysaccharide source.

In some embodiments, the composition further comprises a polyphenol preparation. In some embodiments, the composition further comprises a preparation of probiotic bacteria. In some embodiments, the composition further comprises a drug or therapeutic agent. In some embodiments, the composition further comprises a pharmaceutically acceptable excipient.

In some embodiments, the composition is formulated as a unit-dosage form. In some embodiments, the unit-dosage form is formulated for oral delivery. In some embodiments, the unit-dosage form is formulated to dissolve in an aqueous solution and is orally administered as a beverage, syrup, solution, or suspension.

In some embodiments, the unit-dosage form is formulated as a delayed release or time controlled system. In some embodiments, the unit-dosage form is formulated to release the therapeutic glycan preparation in a specific region of the GI tract. In some embodiments, the specific region of the GI tract comprises the stomach, small intestine, large intestine, or colon.

In some embodiments, the composition modulates the abundance of a bacterial genus present in the GI tract. In some embodiments, the composition modulates the abundance of a bacterial genus present in one or both of the small intestine or large intestine. In some embodiments, the composition modulates the abundance of a bacterial genus predominant in the small intestine selected from the group of genus *Achromobacter, Agrobacterium, Blautia, Burkholderia, Coprococcus, Cryocola, Enterococcus, Eubacterium, Holdemania, Lactococcus, Mycobacterium, Pseudoramibacter, Ralstonia, Sphingomonas, Streptococcus,* and *Turicibacter*. In some embodiments, the composition modulates the abundance of a bacterial genus predominant in the large intestine selected from the group of genus *Anaerotruncus, Akkermansia, Bacteroides, Bilophila, Butyricimonas, Odoribacter, Parabacteroides, Phascolarctobacterium, Prevotella,* and *Ruminococcus*.

In some embodiments, the unit-dosage form comprises about 0.1 mL to about 5 mL of the therapeutic glycan preparation, is formulated for oral delivery, and is formulated to release the therapeutic glycan preparation in a specific region of the GI tract. In some embodiments, the unit-dosage form comprises about 0.1 mg to about 100 mg of the therapeutic glycan preparation, is formulated for oral delivery, and is formulated to release the therapeutic glycan preparation in a specific region of the GI tract.

In some embodiments, the unit-dosage form comprises about 0.1 mL to about 5 mL of the therapeutic glycan preparation, is formulated for oral delivery, and the composition modulates the abundance of a bacterial genus selected from the group of *Bacteroides, Butyricimonas, Odoribacter, Parabacteroides, Prevotella, Anaerotruncus, Phascolarctobacterium, Ruminococcus, Bilophila, Akkermansia, Cryocola, Mycobacterium, Enterococcus, Lactococcus, Streptococcus, Turicibacter, Blautia, Coprococcus, Holdemania, Pseudoramibacter, Eubacterium, Agrobacterium, Sphingomonas, Achromobacter, Burkholderia,* and *Ralstonia*.

In some embodiments, the unit-dosage form comprises about 0.1 mg to about 100 mg of the therapeutic glycan preparation, is formulated for oral delivery, and the composition modulates the abundance of a bacterial genus selected from the group of *Bacteroides, Butyricimonas, Odoribacter, Parabacteroides, Prevotella, Anaerotruncus, Phascolarctobacterium, Ruminococcus, Bilophila, Akkermansia, Cryocola, Mycobacterium, Enterococcus, Lactococcus, Streptococcus, Turicibacter, Blautia, Coprococcus, Holdemania, Pseudoramibacter, Eubacterium, Agrobacterium, Sphingomonas, Achromobacter, Burkholderia,* and *Ralstonia*.

In some embodiments, the present invention features a pharmaceutical kit comprising a) a glycan therapeutic preparation in an amount effective to modulate the abundance of the bacterial taxa, wherein i) the glycan therapeutic preparation comprises a mixture of branched glycans, wherein the average degree of branching (DB) of the glycans in the preparation is at least 0.01; ii) at least 50% of the glycans in the preparation have a degree of polymerization (DP) of at least 3 and less than 30 glycan units; and iii) the ratio of alpha- to beta-glycosidic bonds present in the glycans of the preparation is between about 1:1 to about 5:1, b) at least a second constituent selected from the group of a preparation of polyphenols, a preparation of probiotic bacteria, a drug or therapeutic agent, and a dietary component, c) instructional material, and d) packaging.

In another aspect, the present invention features a pharmaceutical composition comprising a therapeutic glycan preparation comprising at least one glycan unit selected from the group of: glucose, galactose, fucose, xylose, arabinose, rhamnose, and mannose, wherein the preparation comprises a glycan unit associated with one or more of the following 1H-13C HSQC peaks: i) for glycans comprising glucose, the peaks comprise at least one of an 1H-13C HSQC peak selected from 5.42, 92.5; 5.21, 92.8; 5.18, 93.9; 5.08, 97.0; 5.36, 98.4; 5.34, 99.8; 5.38, 100.3; 4.95, 98.6; 4.62, 96.6; 4.70, 103.6; 4.49, 103.4 1H shift (ppm) and 13C shift (ppm) or a corresponding peak; ii) for glycans comprising galactose, the peaks comprise at least one of an 1H-13C HSQC peak selected from 5.37, 92.9; 5.24, 93.1; 5.14, 96.0; 4.96, 99.3; 5.31, 98.7; 5.39, 101.4; 5.00, 101.8; 4.80, 101.3; 4.63, 97.0; 4.56, 97.2; 4.53, 103.1; 4.43, 104.1 1H shift (ppm) and 13C shift (ppm) or a corresponding peak; iii) for glycans comprising fucose, the peaks comprise at least one of an 1H-13C HSQC peak selected from 5.18, 92.9; 5.33, 92.4; 5.04, 96.3; 4.90, 99.7; 4.52, 97.0; 4.39, 103.6 1H shift (ppm) and 13C shift (ppm) or a corresponding peak; iv) for glycans comprising xylose, the peaks comprise at least one of an 1H-13C HSQC peak selected from 5.18, 93.0; 5.10, 94.3; 5.34, 98.2; 5.31, 99.6; 5.11, 100.8; 4.91, 99.4; 4.56, 97.3; 4.64, 104.2; 4.54, 103.4; 4.44, 102.6; 4.44, 104.1 1H shift (ppm) and 13C shift (ppm) or a corresponding peak; v) for glycans comprising arabinose, the peaks comprise at least one of an 1H-13C HSQC peak selected from 5.22, 93.2; 5.13, 93.2; 5.29, 96.0; 5.26, 97.2; 5.12, 96.6; 5.18, 99.6; 5.06, 99.2; 4.99, 100.0; 5.26, 101.9; 5.06, 102.1; 4.55, 97.4; 4.54, 105.2; 4.50, 105.5; 4.38, 103.9 1H shift (ppm) and 13C shift (ppm) or a corresponding peak; vi) for glycans comprising rhamnose, the peaks comprise at least one of an 1H-13C HSQC peak selected from 5.21, 93.2; 5.10, 94.5; 4.85, 94.1; 5.01, 95.8; 5.35, 100.5; 5.15, 102.2; 5.04, 102.9; 4.78, 97.9; 4.71, 99.0; 4.72, 101.0 1H shift (ppm) and 13C shift (ppm) or a corresponding peak; vii) for glycans comprising mannose, the peaks comprise at least one of an 1H-13C HSQC peak selected from 5.37, 93.0; 5.16, 94.6; 4.88, 94.2; 5.39, 101.7; 5.24, 101.9; 5.13, 102.8; 5.03, 102.7; 5.24, 105.6; 5.09, 108.0; 4.88, 94.2; 4.89, 100.0; 4.70, 101.1 1H shift (ppm) and 13C shift (ppm) or a corresponding peak.

In some embodiments, the pharmaceutical composition comprises a therapeutic glycan preparation comprising at least one glycan unit selected from the group of: glucose, galactose, fucose, xylose, arabinose, rhamnose, and mannose, wherein the preparation comprises a glycan unit associated with two or more of the following 1H-13C HSQC peaks: i) for glycans comprising glucose, the peaks comprise at least two, at least three, at least four, or more 1H-13C HSQC peaks selected from 5.42, 92.5; 5.21, 92.8; 5.18, 93.9; 5.08, 97.0; 5.36, 98.4; 5.34, 99.8; 5.38, 100.3; 4.95, 98.6; 4.62, 96.6; 4.70, 103.6; 4.49, 103.4 1H shift (ppm) and 13C shift (ppm) or a corresponding peak; ii) for glycans comprising galactose, the peaks comprise at least two, at least three, at least four, or more 1H-13C HSQC peaks selected from 5.37, 92.9; 5.24, 93.1; 5.14, 96.0; 4.96, 99.3; 5.31, 98.7; 5.39, 101.4; 5.00, 101.8; 4.80, 101.3; 4.63, 97.0; 4.56, 97.2; 4.53, 103.1; 4.43, 104.1 1H shift (ppm) and 13C shift (ppm) or a corresponding peak; iii) for glycans comprising fucose, the peaks comprise at least two, at least three, at least four, or more 1H-13C HSQC peaks selected from 5.18, 92.9; 5.33, 92.4; 5.04, 96.3; 4.90, 99.7; 4.52, 97.0; 4.39, 103.6 1H shift (ppm) and 13C shift (ppm) or a corresponding peak; iv) for glycans comprising xylose, the peaks comprise at least two, at least three, at least four, or more 1H-13C HSQC peaks selected from 5.18, 93.0; 5.10, 94.3; 5.34, 98.2; 5.31, 99.6; 5.11, 100.8; 4.91, 99.4; 4.56, 97.3; 4.64, 104.2; 4.54, 103.4; 4.44, 102.6; 4.44, 104.1 1H shift (ppm) and 13C shift (ppm) or a corresponding peak; v) for glycans comprising arabinose, the peaks comprise at least two, at least three, at least four, or more 1H-13C HSQC peaks selected from 5.22, 93.2; 5.13, 93.2; 5.29, 96.0; 5.26, 97.2; 5.12, 96.6; 5.18, 99.6; 5.06, 99.2; 4.99, 100.0; 5.26, 101.9; 5.06, 102.1; 4.55, 97.4; 4.54, 105.2; 4.50, 105.5; 4.38, 103.9 1H shift (ppm) and 13C shift (ppm) or a corresponding peak; vi) for glycans comprising rhamnose, the peaks comprise at least two, at least three, at least four, or more 1H-13C HSQC peaks selected from 5.21, 93.2; 5.10, 94.5; 4.85, 94.1; 5.01, 95.8; 5.35, 100.5; 5.15, 102.2; 5.04, 102.9; 4.78, 97.9; 4.71, 99.0; 4.72, 101.0 1H shift (ppm) and 13C shift (ppm) or a corresponding peak; vii) for glycans comprising mannose, the peaks comprise at least two, at least three, at least four, or more 1H-13C HSQC peaks selected from 5.37, 93.0; 5.16, 94.6; 4.88, 94.2; 5.39, 101.7; 5.24, 101.9; 5.13, 102.8; 5.03, 102.7; 5.24, 105.6; 5.09, 108.0; 4.88, 94.2; 4.89, 100.0; 4.70, 101.1 1H shift (ppm) and 13C shift (ppm) or a corresponding peak.

In another aspect, the present invention features a pharmaceutical composition for use in modulating the abundance of a bacterial taxa in a human subject's gastrointestinal microbiota, the composition comprising a glycan therapeutic preparation in an amount effective to modulate the abundance of the bacterial taxa, wherein i) the glycan therapeutic preparation comprises a mixture of branched glycans, wherein the average degree of branching (DB, branching points per residue) of the glycans in the preparation is at least 0.01 (e.g., at least 0.05, or at least 0.1), ii) at least 50% of the glycans in the preparation have a degree of polymerization (DP) of at least 3 and less than 30 glycan units, and iii) the ratio of alpha- to beta-glycosidic bonds present in the glycans of the preparation is between about 1:1 to about 5:1 overall. In some embodiments, the bacterial taxa comprises at least a first and a second bacterial taxa.

In some embodiments, the preparation comprises branched oligosaccharides. In some embodiments, the average degree of branching in the preparation (DB) is at least 0.05 (e.g., at least 0.1).

In some embodiments, at least one, at least two, at least three, at least four, or more of the glycosidic bonds independently comprise a 1→2 glycosidic bond, a 1→3 glycosidic bond, a 1→4 glycosidic bond, or a 1→6 glycosidic bond. In some embodiments, one or more, two or more, or three or more glycosidic bonds are present in both alpha and beta configuration.

In some embodiments, a glycan unit comprises at least one, at least two, at least three, or more of a monosaccharide selected from the group of a tetrose, a pentose, a hexose, and a heptose. In some embodiments, a glycan unit comprises at least one, at least two, at least three, or more of a monosaccharide selected from the group of glucose, galactose, arabinose, mannose, fructose, xylose, fucose, and rhamnose.

In some embodiments, at least a plurality of the glycans, e.g., at least 10, 20, 30 40, 50, 60, 70, 80, 90, 95, or 99% (by weight or number), or substantially all, of the glycans in the preparation, do not comprise more than a preselected reference level, of a repeating unit of glycan units, e.g., a repeating unit of 2, 3, 4 or more glycan units. In an embodiment, the preselected reference level is 10, 20, 30, 40, 50, or 60% of the total glycan units in a glycan. By way of example, in an embodiment, a glycan made up of 20 saccharide monomers, less than 50% of those 20 monomers are repeating units of a 2 or 3 glycan repeat.

In some embodiments, the glycan therapeutic preparation is synthetic and not isolated from a natural oligosaccharide or polysaccharide source.

In some embodiments, the abundance of the bacterial taxa (e.g., of each of a first and a second bacterial taxa) in the human subject's gastrointestinal microbiota is modulated by at least about 5%, 10%, 25% 50%, 75%, 100%, 250%, 500%, 750%, or by at least 1000%. In some embodiments, the modulation comprises an increase or a decrease in the abundance of the bacterial taxa (e.g., of each of a first and a second bacterial taxa) in the human subject's gastrointestinal microbiota.

In some embodiments, the bacterial taxa (e.g., a first and a second bacterial taxa) comprises a commensal bacterial taxa. In other embodiments, the bacterial taxa (e.g., a first and a second bacterial taxa) comprises a pathogenic bacterial taxa.

In some embodiments, the bacterial taxa (e.g., a first and a second bacterial taxa) comprises a genus selected from the group of *Akkermansia, Alistipes, Anaerofilum, Bacteroides, Bilophila, Blautia, Bifidobacterium, Butyrivibrio, Campylobacter, Candidatus, Citrobacter, Clostridium, Collinsella, Coprococcus, Desulfovibrio, Dialister, Dorea, Enterobacter, Enterococcus, Escherichia, Eubacterium, Faecalibacterium, Fusobacterium, Haemophilus, Klebsiella, Lachnospira, Lactobacillus, Odoribacter, Oscillospira, Parabacteroides, Peptococcus, Peptostreptococcus, Phascolarctobacterium, Porphyromonas, Portiera, Prevotella, Providencia, Pseudomonas, Roseburia, Ruminococcus, Salmonella, Shigella, Staphylococcus, Streptococcus, Subdoligranulum, Vibrio*, and *Yersinia*. In some embodiments, the bacterial taxa (e.g., a first and a second bacterial taxa) comprises a genus selected from the group of *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus*. In some embodiments, the bacterial taxa (e.g., a first and a second bacterial taxa) comprises a genus selected from the group of *Akkermansia, Bacteroides, Bifidobacterium, Lactobacillus*, and *Parabacteroides*. In some embodiments, the bacterial taxa (e.g., a first and a second bacterial taxa) comprises a genus selected from the group of *Akkermansia* and *Blautia*.

In some embodiments, the bacterial taxa (e.g., a first and a second bacterial taxa) comprises a taxa predominant in the small intestine or large intestine. In some embodiments, the bacterial taxa (e.g., a first and a second bacterial taxa) predominant in the small intestine comprises a genus selected from the group of *Achromobacter, Agrobacterium, Blautia, Burkholderia, Coprococcus, Cryocola, Enterococcus, Eubacterium, Holdemania, Lactococcus, Mycobacterium, Pseudoramibacter, Ralstonia, Sphingomonas, Streptococcus*, and *Turicibacter*. In some embodiments, the bacterial taxa (e.g., a first and a second bacterial taxa) predominant in the large intestine comprises a genus selected from the group of *Anaerotruncus, Akkermansia, Bacteroides, Bilophila, Butyricimonas, Odoribacter, Parabacteroides, Phascolarctobacterium, Prevotella*, and *Ruminococcus*.

In some embodiments, the pharmaceutical composition further comprises a polyphenol preparation. In some embodiments, the polyphenol preparation comprises a plant polyphenol isolated from a plant source material. In some embodiments, the plant source material comprises blueberry, cranberry, grape, peach, plum, pomegranate, soy, red wine, black tea, or green tea.

In some embodiments, the modulating the abundance of a bacterial taxa (e.g., a first and a second bacterial taxa) treats a dysbiosis, e.g., a dysbiosis described herein.

In another aspect, the present invention features a pharmaceutical composition for use in reducing a drug- or treatment-induced symptom in a human subject, comprising administering to the human subject a glycan therapeutic preparation in an amount effective to reduce a symptom induced by a drug or treatment, wherein i) the glycan therapeutic preparation comprises a mixture of branched glycans, wherein the average degree of branching (DB) of the glycans in the preparation is at least 0.01 (e.g., at least 0.05, or at least 0.1), ii) at least 50% of the glycans in the preparation have a degree of polymerization (DP) of at least 3 and less than 30 glycan units, and iii) the ratio of alpha- to beta-glycosidic bonds present in the glycans of the preparation is between about 1:1 to about 5:1 overall.

In some embodiments, the drug- or treatment-induced symptom is selected from the group of bloating, diarrhea, vomiting, nausea, and constipation. In some embodiments, the drug- or treatment-induced is diarrhea. In some embodiments, the drug- or treatment-induced symptom is constipation.

In some embodiments, the composition reduces drug-induced symptoms and the composition is administered prior to, concomitant with, or after administration of the drug. In some embodiments, the drug is an anti-diabetic drug, an immune-suppressive drug, an antimicrobial drug, a chemotherapeutic drug, an anti-psychotic drug, a proton pump inhibitor drug, or a non-steroid anti-inflammatory drug (NSAID). In some embodiments, the drug is selected from the group of ciprofloxacin, clindamycin, amoxicillin-clavulanate, cefixime, ephalosporins, fluoroquinolones, azithromycin, clarithromycin, erythromycin, tetracycline, azithromycin, irinotecan (camptosar), 5-fluorouracil, leucovorin, oxaliplatin, bortezomib, imatinib, lenalidomide, imbruvica, ipilimumab, pertuzumab, capecitabine, docetaxel, lapatinib, erlotinib, carmustine, etoposide, aracytine, melphalan, cytarabine, daunorubicine, amsacrine, mitoxantrone, olanzapine, ranitidine, famotidine, cimetidine, omeprazole, sucralfate, esomeprazole, naproxen, diclofenac, indomethacin, ibuprofen, ketoprofen, piroxicam, celecoxib, nimesulid, aspirin, metformin, paroxetine, valproic acid, and clozapine.

In some embodiments, the composition reduces treatment-induced symptoms and the treatment comprises radiation treatment or surgery.

In some embodiments, the drug- or treatment-induced symptom is exhibited by the subject during a treatment regimen. In some embodiments, the reducing the one or more symptom increases compliance by the subject to the treatment regimen. In some embodiments, the reducing the one or more symptom increases the subject's tolerance to a higher dose of the drug to be administered during the treatment regimen.

In another aspect, the present invention features a pharmaceutical composition for use in modulating microbial diversity in a human subject's gastrointestinal tract, the composition comprising a glycan therapeutic preparation in an amount effective to modulate the microbial diversity, wherein i) the glycan therapeutic preparation comprises a mixture of branched glycans, wherein the average degree of branching (DB, branching points per residue) of the glycans in the preparation is at least 0.01 (e.g., at least 0.05, or at least 0.1), ii) at least 50% of the glycans in the preparation have a degree of polymerization (DP) of at least 3 and less than 30 glycan units; and iii) the ratio of alpha- to beta-glycosidic bonds present in the glycans of the preparation is between about 1:1 to about 5:1 overall. In some embodiments, the microbial diversity comprises bacterial diversity.

In some embodiments, the modulating comprises an increase or a decrease in microbial diversity.

In some embodiments, the microbial diversity is determined (e.g., measured) by or expressed through use of the Shannon Diversity Index. In some embodiments, the Shannon Diversity is increased or decreased by at least about 5%. In some embodiments, the Shannon Diversity is increased or decreased by at least about 15%. In some embodiments, the Shannon Diversity is increased or decreased by at least about 0.3 log-fold. In some embodiments, Shannon Diversity is increased or decreased by at least about 0.6 log-fold. In some embodiments, Shannon Diversity is increased or decreased by at least about 1 log-fold.

In some embodiments, the abundance of at least one bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus* is modulated. In some embodiments, the abundance of at least one bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus* is increased by at least about 5%.

In some embodiments, the abundance of at least two bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus* is modulated. In some embodiments, the abundance of at least two bacterial taxa selected from the group of genus *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus* is increased by at least about 5%.

In some embodiments, the abundance of at least one bacterial taxa selected from the group of genus *Akkermansia, Bacteroides, Bifidobacterium, Lactobacillus*, and *Parabacteroides* is modulated. In some embodiments, the abundance of at least two bacterial taxa selected from the group of genus *Akkermansia, Bacteroides, Bifidobacterium, Lactobacillus*, and *Parabacteroides* is modulated. In some embodiments, the abundance of at least one bacterial taxa selected from the group of genus *Akkermansia* and *Blautia* is modulated. In some embodiments, the abundance of both of the bacterial genera *Akkermansia* and *Blautia* is modulated. In some embodiments, the modulating the microbial diversity treats a dysbiosis.

In another aspect, the present invention features a pharmaceutical composition for use in treating a human subject in need thereof, the treating comprising: a) identifying a human subject in need of treatment for dysbiosis, and b) administering to the human subject a pharmaceutical composition comprising a glycan therapeutic preparation in an amount effective to treat the dysbiosis, wherein i) the glycan therapeutic preparation comprises a mixture of branched glycans, wherein the average degree of branching (DB) of the glycans in the preparation is at least 0.01 (e.g., at least 0.05, or at least 0.1), ii) at least 50% of the glycans in the preparation have a degree of polymerization (DP) of at least 3 and less than 30 glycan units, and iii) the ratio of alpha- to beta-glycosidic bonds present in the glycans of the preparation is between about 1:1 to about 5:1 overall.

In some embodiments, the human subject has an infectious disease, disorder or condition. In some embodiments, the infectious disease, disorder or condition is selected from the group of *Clostridium difficile* infection (CDI); Vancomycin-resistant enterococci (VRE) infection, infectious colitis, or *C. difficile* colitis. In some embodiments, the infectious disease, disorder or condition is diarrhea selected from the group of *Clostridium difficile* associated diarrhea (CDAD), antibiotic-associated diarrhea (AAD), antibiotic-induced diarrhea, travelers' diarrhea (TD), pediatric diarrhea, and (acute) infectious diarrhea.

In some embodiments, the human subject has a metabolic disease, disorder or condition. In some embodiments, the metabolic disease, disorder or condition is selected from the group of obesity, (insulin resistance) pre-diabetes, type II diabetes, high fasting blood sugar (hyperglycemia), and metabolic syndrome. In some embodiments, the metabolic disease, disorder or condition is a cardiovascular risk factor selected from the group of high blood cholesterol, high LDL, high blood pressure (hypertension), high triglyceride levels, low HDL.

In some embodiments, the human subject has an inflammatory disease, disorder or condition. In some embodiments, the inflammatory disease, disorder or condition is selected from the group of inflammatory bowel disease (IBD), ulcerative colitis (UC), Crohn's disease (CD), intestinal inflammation, and microscopic colitis. In some embodiments, the inflammatory disease, disorder or condition is selected from the group of irritable bowel syndrome (IBS), constipation, diarrhea, indigestion, and non-ulcer dyspepsia.

In some embodiments, the human subject has an autoimmune disease, disorder, or condition. In some embodiments, the autoimmune disease, disorder or condition is selected from the group of autoimmune arthritis, type I diabetes, multiple sclerosis, and psoriasis. In some embodiments, the human subject has an allergy. In some embodiments, the allergy comprises asthma or atopic dermatitis.

In some embodiments, the human subject has a neurological disease, disorder, or condition. In some embodiments, the neurological disease, disorder or condition is selected from the group of autism, hyperammonemia, and hepatic encephalopathy.

In some embodiments, treating further comprises administering a second drug or pharmaceutical agent. In some embodiments, the second drug or pharmaceutical agent is a standard-of-care drug or agent. In some embodiments, the treatment effects of the pharmaceutical composition comprising a glycan therapeutic preparation and the second drug or pharmaceutical agent are additive. In some embodiments, the treatment effects of the pharmaceutical composition comprising a glycan therapeutic preparation and the second drug or pharmaceutical agent are synergistic.

In some embodiments, the composition is administered daily. In some embodiments, the composition is administered each day for a predetermined number of days (the treatment period). In some embodiments, the treatment period comprises between about 1 day and about 30 days. In some embodiments, the treatment period comprises between about 1 month and about 6 months. In some embodiments, the subject is administered the composition for a single treatment period. In some embodiments, the subject is administered the composition for more than one treatment period.

In some embodiments, by treating the dysbiosis the disease of the human subject is treated.

In another aspect, the present invention features a pharmaceutical composition for use in modulating a functional pathway of the microbiota of a human subject's gastrointestinal tract, the composition comprising a glycan therapeutic preparation in an amount effective to modulate the functional pathway, wherein i) the glycan therapeutic preparation comprises a mixture of branched glycans, wherein the average degree of branching (DB) of the glycans in the preparation is at least 0.01 (e.g., at least 0.05, or at least 0.1); ii) at least 50% of the glycans in the preparation have a degree of polymerization (DP) of at least 3 and less than 30 glycan units; and iii) the ratio of alpha- to beta-glycosidic bonds present in the glycans of the preparation is between about 1:1 to about 5:1 overall.

In some embodiments, the functional pathway modulates the production of an anti-microbial agent, a secondary bile acid, a short-chain fatty acid, a siderophore, or a metabolite listed in Table 2 by the microbiota. In some embodiments, the antimicrobial agent comprises a bacteriocin or hydrogen peroxide. In some embodiments, the short-chain fatty acid comprises formate, butyrate, acetate, propionate, or valerate. In some embodiments, the metabolite comprises 2-hydroxyisobutyrate, 3-hydroxyisovalerate, 3-methylcrotonylglycine, 3-methylcrotonylglycine, allantoin, betaine, formate, mannitol, p-cresol glucuronide, phenylacetylglycine, sarcosine, taurine, acetic acid, acetylaldehyde, ascorbic acid, butanedione, butyric acid, deoxycholic acid, ethylphenyl sulfate, formic acid, indole, isobutyric acid, isovaleric acid, propionic acid, serotonin, succinic acid, succinate, TMAO, tryptophan, valeric acid, ursodeoxycholic acid, lactate, lactic acid, or hydrogen peroxide.

In some embodiments, the functional pathway modulates the level of an inflammatory or immunomodulatory cytokine in the human subject. In some embodiments, the inflammatory and immunomodulatory cytokine comprises interleukin-1α (IL-1α), IL-1β, IL-2, IL-4, IL-6, IL-8, IL-10, IL-12, IL-13, IL-17A, IL-17F, IL-22, IL-23, tumor necrosis factor (TNF), chemokine (C-C motif) ligand 5 (CCL5, also known as RANTES), transforming growth factor beta (TGF-β), or interferon gamma (IFN-γ).

In some embodiments, the functional pathway increases the level of a short-chain fatty acid in the subject. In some embodiments, the increase in the short-chain fatty acid induces the generation of regulatory T (Treg) cells by the subject. In some embodiments, the increase in the short-chain fatty acid reduces the permeability of the intestinal or plasma endotoxin level in the subject. In some embodiments, the increase of a short-chain fatty acid reduces the inflammatory response of the subject. In some embodiments, the short-chain fatty acid is produced by at least one bacterial species of the Ruminocaccaceae and/or Lachnospiraceae family.

In some embodiments, the subject is obese.

In another aspect, the present invention features a pharmaceutical composition for use in preventing a relapse of a *Clostridium difficile* infection in a human subject previously administered a drug for the treatment of a *C. difficile* infection, the composition comprising a glycan therapeutic preparation in an amount effective to prevent the relapse, wherein i) the glycan therapeutic preparation comprises a mixture of branched glycans, wherein the average degree of branching (DB) of the glycans in the preparation is at least 0.01 (e.g., at least 0.05, or at least 0.1); ii) at least 50% of the glycans in the preparation have a degree of polymerization (DP) of at least 3 and less than 30 glycan units; and iii) the ratio of alpha- to beta-glycosidic bonds present in the glycans is between about 1:1 to about 5:1 overall.

In some embodiments, the relapse comprises the recurrence of one or more symptoms associated with a *C. difficile* infection. In some embodiments, the relapse occurs during or after a first-line or standard of care drug treatment regimen.

In some embodiments, the drug for the treatment of a *C. difficile* infection is an antibiotic. In some embodiments, the antibiotic is selected from the group of vancomycin, metronidazole, and fidaxomicin. In some embodiments, the composition is administered concurrently or after administration of the drug for the treatment of a *C. difficile* infection.

In some embodiments, the composition is administered in combination with a second drug or treatment. In some embodiments, the second drug or treatment comprises an antibiotic. In some embodiments, the antibiotic is selected from the group of vancomycin, metronidazole, and fidaxomicin.

In some embodiments, administration of the composition results in a reduction of the severity of a symptom associated with a *C. difficile* infection in the subject but does not eliminate the population of *C. difficile* in the subject. In some embodiments, administration of the composition results in a reduction of the severity of a symptom associated with a *C. difficile* infection in the subject but does not change the level of the population of *C. difficile* in the subject

BRIEF DESCRIPTION OF THE DRAWINGS

FIG. 17A), man52glu29gal19 (1%; FIG. 17B) and water (both plots) as described in Example 14. The slopes of the glu100- and man52glu29gal19-treated groups were significantly different than the slope of the water-treated mice (P<0.001; linear mixed-effects model with significant interaction between study day and weight change; Regression lines are shown with shading representing +/− standard error of the slope). Individual animal % weight changes are plotted (triangles or circles).

DETAILED DESCRIPTION OF THE INVENTION

Figure 1:
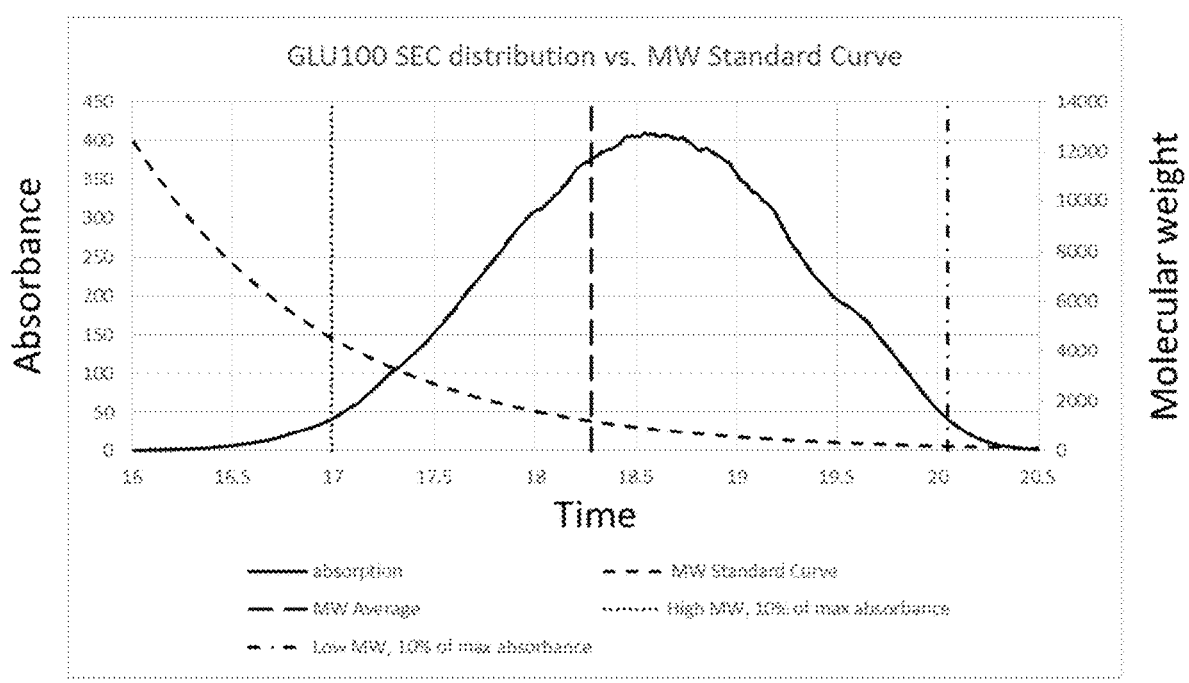
FIG. 1. A representative SEC curve between 16 and 20.5 minutes of a glu100 sample showing the average MW and the MW at 10% of maximum absorption on both the leading and trailing edges of the curve.

In humans the gastrointestinal microbiota is largely stable when the host is in good health; however, the ecosystem of the gastrointestinal microbiota varies depending on host age, disease, including infections with pathogens, stress, diet, and pharmaceutical treatments and can enter a state of dysbiosis. The invention relates to preparations of glycan therapeutics and pharmaceutical compositions thereof (and medical foods or dietary supplements thereof), and related methods, which have been found to be effective to treat dysbiosis. The preparations of glycan therapeutics and pharmaceutical compositions described herein surprisingly have a therapeutic effect on a number of diseases, disorders or pathological conditions, which may be associated with dysbiosis. While not wishing to be bound by theory, it is believed that preparations of glycan therapeutics and pharmaceutical compositions described herein work by modulating microbial organisms within a human host's gastrointestinal (GI) tract to cause a desired physiological effect, such as improving health, in the host. The glycan therapeutics can be selectively digested by certain microbial constituents thereby inducing specific changes in the GI tract, both in the composition and/or activity (e.g. function) of the microbiota that confer benefits upon host well-being and health. The glycan therapeutics can act as tailored, finely tuned modulators for the resident or acquired microbiota, e.g., enhancing or restoring the growth of beneficial bacteria and/or suppressing the growth of pathogenic microbes or microbes that are associated with a disease or condition.

The glycan therapeutics described herein can mediate shifts in the abundance of important taxa of the gastrointestinal microbiota (and associated functional or genomic shifts), and methods are provided by which glycan therapeutics can alter the composition or function of the gastrointestinal microbiota. In some embodiments, the microbial shifts allow multiple important microbiota properties to be introduced, modulated, increased, decreased, or stimulated. In some embodiments, the modulation includes alterations in i) ecosystem resilience to disturbance (or dysbioses), ii) microbiota diversity, iii) metabolite production, iv) pathobiont and pathogen colonization, and v) altered effects on host metabolic, immune, and other functions or any combination thereof.

Described herein are methods, compositions, and kits useful for the treatment and/or prevention of dysbiosis and diseases possibly associated with a dysbiosis of the gastrointestinal microbiota and/or the reduction of symptoms thereof in a subject in need thereof, and for improving overall health of the host. Further described herein are dosage forms for glycan therapeutics. In some embodiments, the dosage forms are formulated for specific delivery to specific regions of the GI tract, such as, e.g., the small or large intestine. Administration of the pharmaceutical compositions, medical foods or dietary supplements comprising preparations of glycan therapeutics may treat or prevent dysiosis, e.g., conditions in which a beneficial bacterial microbiota is disturbed and in which the microbiota exhibit a dysbiosis. In some embodiments, the disturbance can be ameliorated by the use of the glycan therapeutics described herein so that improved physiological growth and function of both the beneficial microbiota and the host can be achieved. Such treatment or prevention may occur directly, e.g., a glycan therapeutic described herein may cause displacement of a pathogenic microbe with a non-pathogenic microbe or increase the growth of beneficial or commensal microbes, or it may occur indirectly, e.g., a glycan therapeutic described herein may affect metabolism or other functions of the microbiota, thus modulating host physiology, e.g., through the effect of one or more downstream metabolic products. Administration of glycan therapeutics described herein may improve the overall health of the host and may restore a healthy equilibrium in a selected niche, such as the GI tract, by influencing one or more members of the microbial community.

Generation of Glycan Therapeutic Preparations

Preparations comprising a plurality of glycans such as oligo- and polysaccharide mixtures can be generated using a non-enzymatic catalyst, e.g., the polymeric catalyst described in U.S. Pat. No. 8,466,242, which is incorporated herein by reference in its entirety, or by other suitable methods. Methods to prepare the polymeric and solid-supported catalysts described herein can be found in WO 2014/031956, which is hereby incorporated by reference herein. The glycans generated, e.g., by using the catalyst, can be structurally much more diverse glycans than those produced by enzymatic reactions.

Provided are also methods for generating the preparations of glycans (e.g. oligo- or polysaccharide compounds) described herein, by: a) providing one or more mono- or disaccharide glycan unit, or a combination thereof, b) contacting the mono- or disaccharides with any of the polymeric catalysts described herein and a suitable solvent (such as, e.g. water or a non-aqueous solvent) for a period of time sufficient to produce a polymerized species population (with a desired average degree of polymerization); and c) isolating and/or recovering at least a portion of the polymerized glycan preparation.

In some embodiments, preparations of glycans (e.g. oligo- or polysaccharides) are polymolecular. In some embodiments, preparations of glycans (e.g. oligo- or polysaccharides) are polymolecular and polydisperse. For example, the glycan therapeutic preparations comprise a mixture of distinct oligosaccharide species (e.g. of different degree of polymerization and degree of branching and different alpha-to-beta glycosidic bond ratios). In some embodiments, the glycan therapeutic preparations comprise a plurality of distinct species (e.g. oligosaccharides) and may consist of $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, or more species in various proportions to each other. Herein described are the average properties of the glycan therapeutic preparations, such as degree of polymerization, degree of branching, alpha- and beta-glycosidic bond ratios, etc.

Figure 6A:
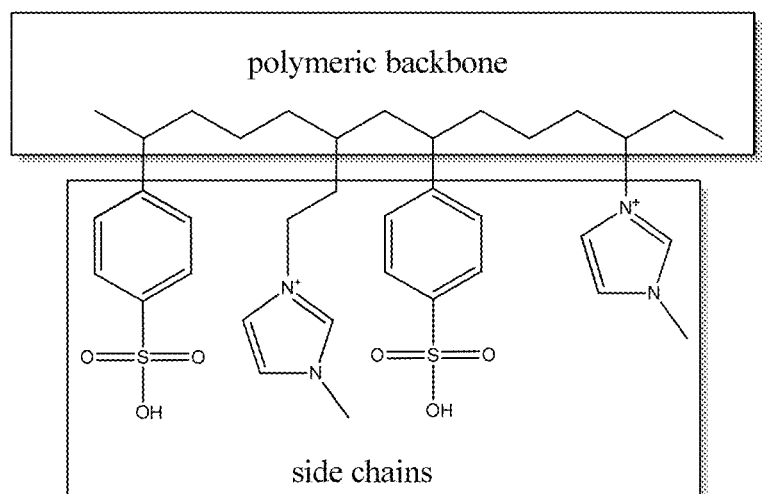
FIGS. 6A-6B. A portion of an exemplary catalyst with a polymeric backbone and side chains is illustrated in FIG. 6A. A portion of an exemplary catalyst, in which a side chain with the acidic group is connected to the polymeric backbone by a linker and in which a side chain with the cationic group is connected directly to the polymeric backbone is illustrated in FIG. 6B.
Figure 6B:
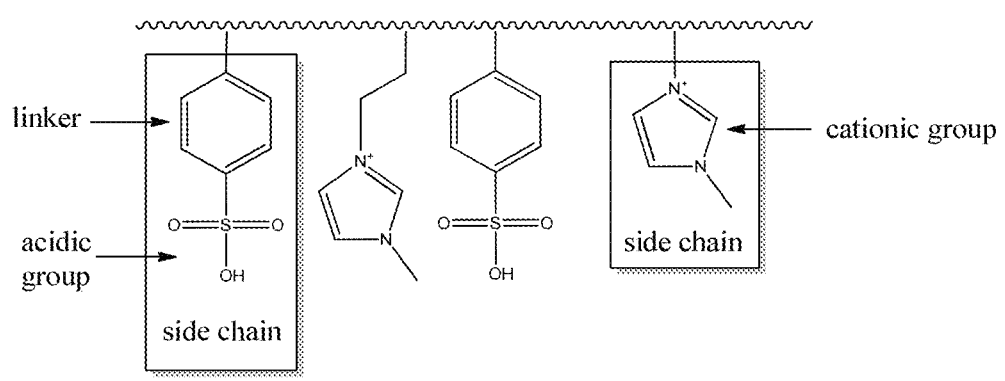

In certain embodiments, the starting material (comprising the glycan units) is contacted with a polymer catalyst under conditions that promote the formation of one or more glycosidic bond between glycan units, thereby producing a preparation of glycans. In some embodiments, the glycan unit is a monosaccharide. Suitable polymer catalysts comprise acidic monomers and ionic monomers that are connected to form a polymeric backbone, wherein each acidic monomer has at least one Bronsted-Lowry acid, and each ionic monomer independently has at least one nitrogen-containing cationic group or phosphorous-containing cationic group. In some embodiments, each acidic monomer of the polymer catalyst may have one Bronsted-Lowry acid, and optionally the Bronsted-Lowry acids are distinct. In some embodiments, each ionic monomer of the polymer catalyst has one nitrogen-containing cationic group or phosphorous-containing cationic group. In some embodiments, at least one ionic monomer of the polymer catalyst has two nitrogen-containing cationic groups or phosphorous-containing cationic groups. A schematic outlining the general functional groups is shown in FIGS. 6A and 6B.

In certain embodiments, synthesis of the glycans (e.g. oligo- or polysaccharides) using the polymeric catalyst is carried out in an aqueous environment. One suitable aqueous solvent is water, which may be obtained from various sources. Generally, water sources with lower concentrations of ionic species are preferable, as such ionic species may reduce the effectiveness of the polymeric catalyst. In some embodiments where the aqueous solvent is water, the water has less than 10% of ionic species (e.g., salts of sodium, phosphorous, ammonium, magnesium).

Generally, the polymeric catalyst and the glycan units are introduced into an interior chamber of a reactor, either concurrently or sequentially. Glycan (e.g. oligo- or polysaccharides) synthesis can be performed in a batch process or a continuous process. For example, in one embodiment, glycan synthesis is performed in a batch process, where the contents of the reactor are continuously mixed or blended, and all or a substantial amount of the products of the reaction are removed (e.g. isolated and/or recovered). In one variation, glycan synthesis is performed in a batch process, where the contents of the reactor are initially intermingled or mixed but no further physical mixing is performed. In another variation, glycan synthesis is performed in a batch process, wherein once further mixing of the contents, or periodic mixing of the contents of the reactor, is performed (e.g., at one or more times per hour), all or a substantial amount of the products of the reaction are removed (e.g. isolated and/or recovered) after a certain period of time.

In other embodiments, glycan (e.g. oligo- or polysaccharide) synthesis is performed in a continuous process, where the contents flow through the reactor with an average continuous flow rate but with no explicit mixing. After introduction of the polymeric catalyst and glycan units into the reactor, the contents of the reactor are continuously or periodically mixed or blended, and after a period of time, less than all of the products of the reaction are removed (e.g. isolated and/or recovered). In one variation, glycan synthesis is performed in a continuous process, where the mixture containing the catalyst and glycan units is not actively mixed. Additionally, mixing of catalyst and the glycan units may occur as a result of the redistribution of polymeric catalysts settling by gravity, or the non-active mixing that occurs as the material flows through a continuous reactor.

In some embodiments of the method, the starting material for the polymerization reaction is one or more glycan unit selected from one or more monosaccharides, one or more disaccharides, or a combination thereof. In some embodiments of the method, the starting material for the polymerization reaction is one or more glycan unit selected from a furanose sugar and a pyranose sugar. In some embodiments of the method, the starting material for the polymerization reaction is one or more glycan unit selected from a tetrose, a pentose, a hexose, or a heptose. In some embodiments of the method, the starting material for the polymerization reaction is one or more glycan unit selected from a glucose, a galactose, an arabinose, a mannose, a fructose, a xylose, a fucose, and a rhamnose, all optionally in either their L- or D-form, in alpha or beta configuration (for dimers), and/or a deoxy-form, where applicable, and any combination thereof. In some embodiments, the glycan units are substituted or derivatized with one or more of an acetate ester, sulfate half-ester, phosphate ester, or a pyruvyl cyclic acetal group, or have been otherwise derivatized at, e.g., at one or more hydroxyl groups.

The glycan units used in the methods described herein may include one or more sugars. In some embodiments, the one or more sugars are selected from monosaccharides, disaccharides, and trisaccharides, or any mixtures thereof. In some embodiments, the one or more sugars are monosaccharides, such as one or more C5 or C6 monosaccharides. In some embodiments, the one or more sugars are C5 monosaccharides. In other embodiments, the one or more sugars are C6 monosaccharides.

In some embodiments of the method, the starting material for the polymerization reaction is one or more glycan unit selected from amino sugars, deoxy sugars, imino sugars, sugar acids, short-chained fatty acids, and sugar alcohols to produce hybrid glycans.

In some embodiments, the starting material for the polymerization reaction is one or more glycan unit selected from monosaccharides and other carbohydrates including, but not limited to glycolaldehyde, glyceraldehyde, dihydroxyacetone, erythrose, threose, erythulose, arabinose, lyxose, ribose, xylose, ribulose, xylulose, allose, altrose, galactose, glucose, gulose, idose, mannose, talose, fructose, psicose, sorbose, tagatose, fucose, fuculose, rhamnose, mannoheptulose, sedoheptulose, neuraminic acid, N-acetylneuraminic acid, N-acetylgalactosamine, N-acetylglucosamine, fructosamine, galactosamine, glucosamine, sorbitol, glycerol, erythritol, threitol, arabitol, xylitol, mannitol, sorbitol, galactitol, fucitol, and lactic acid.

In some embodiments, the starting material for the polymerization reaction is one or more glycan unit selected from disaccharides and other carbohydrates including, but not limited to acarviosin, N-acetyllactosamine, allolactose, cellobiose, chitobiose, glactose-alpha-1,3-galactose, gentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralose, sucrose, sucrose acetate isobutyrate, sucrose octaacetate, trehalose, turanose, vicianose, and xylobiose.

In some embodiments, the starting material for the polymerization reaction is one or more glycan unit selected from an amino sugar, a deoxy sugar, an imino sugar, a sugar acid, a short-chained fatty acid, and a sugar alcohol.

In some embodiments, the glycan unit may exist as a salt (e.g., a pharmaceutically acceptable salt), such as, e.g., a hydrochlorate, hydroiodate, hydrobromate, phosphate, sulfate, methanesulfate, acetate, formate, tartrate, malate, citrate, succinate, lactate, gluconate, pyruvate, fumarate, propionate, aspartate, glutamate, benzoate, ascorbate salt.

Suitable glycan units include amino sugars, such as, e.g. acarbose, N-acetylemannosamine, N-acetylmuramic acid, N-acetylneuraminic acid, N-acetyletalosaminuronic acid, arabinopyranosyl-N-methyl-N-nitrosourea, D-fructose-L-histidine, N-glycolyneuraminic acid, ketosamine, kidamycin, mannosamine, 1B-methylseleno-N-acetyl-D-galactosamine, muramic acid, muramyl dipeptide, phosphoribosylamine, PUGNAc, sialyl-Lewis A, sialyl-Lewis X, validamycin, voglibose, N-acetylgalactosamine, N-acetylglucosamine, aspartylglucosamine, bacillithiol, daunosamine, desosamine, fructosamine, galactosamine, glucosamine, meglumine, and perosamine.

Suitable glycan units include deoxy sugars, such as, e.g. 1-5-ahydroglucitol, cladinose, colitose, 2-deoxy-D-glucose, 3-deoxyglucasone, deoxyribose, dideoxynucleotide, digitalose, fludeooxyglucose, sarmentose, and sulfoquinovose.

Suitable glycan units include imino sugars, such as, e.g. castanospermine, 1-deoxynojirimycin, iminosugar, miglitol, miglustat, and swainsonine.

Suitable glycan units include sugar acids, such as, e.g. N-acetylneuraminic acid, N-acetyltalosamnuronic acid, aldaric acid, aldonic acid, 3-deoxy-D-manno-oct-2-ulosonic acid, glucuronic acid, glucosaminuronic acid, glyceric acid, N-glycolylneuraminic acid, iduronic acid, isosaccharinic acid, pangamic acid, sialic acid, threonic acid, ulosonic acid, uronic acid, xylonic acid, gluconic acid, ascorbic acid, ketodeoxyoctulosonic acid, galacturonic acid, galactosaminuronic acid, mannuronic acid, mannosaminuronic acid, tartaric acid, mucic acid, saccharic acid, lactic acid, oxalic acid, succinic acid, hexanoic acid, fumaric acid, maleic acid, butyric acid, citric acid, glucosaminic acid, malic acid, succinamic acid, sebacic acid, and capric acid.

Suitable glycan units include short chained fatty acids, such as, e.g., formic acid, acetic acid, propionic acid, butryic acid, isobutyric acid, valeric acid, and isovaleric acid.

Suitable glycan units include sugar alcohols, such as, e.g., methanol, ethylene glycol, glycerol, erythritol, threitol, arabitol, ribitol, xylitol, mannitol, sorbitol, galactitol, iditol, volemitol, fucitol, inositol, maltotritol, maltotetraitol, and polyglycitol.

The glycan units (e.g. sugars) used in the methods described herein may be obtained from any commercially known sources, or produced according to any methods known in the art.

Reaction Conditions

In some embodiments, the glycan unit and catalyst (e.g., polymeric catalyst or solid-supported catalyst) are allowed to react for at least 1 hour, at least 2 hours, at least 3 hours, at least 4 hours, at least 6 hours, at least 8 hours, at least 16 hours, at least 24 hours, at least 36 hours, or at least 48 hours; or between 1-24 hours, between 2-12 hours, between 3-6 hours, between 1-96 hours, between 12-72 hours, or between 12-48 hours.

In some embodiments, the degree of polymerization of the one or more oligosaccharides produced according to the methods described herein can be regulated by the reaction time. For example, in some embodiments, the degree of polymerization of the one or more oligosaccharides is increased by increasing the reaction time, while in other embodiments, the degree of polymerization of the one or more oligosaccharides is decreased by decreasing the reaction time.

Reaction Temperature

In some embodiments, the reaction temperature is maintained in the range of about 25° C. to about 150° C. In certain embodiments, the temperature is from about 30° C. to about 125° C., about 60° C. to about 120° C., about 80° C. to about 115° C., about 90° C. to about 110° C., about 95° C. to about 105° C., or about 100° C. to 110° C.

Amount of Glycan Units

The amount of the glycan unit used in the methods described herein relative to the amount solvent used may affect the rate of reaction and yield. The amount of the glycan unit used may be characterized by the dry solids content. In certain embodiments, dry solids content refers to the total solids of a slurry as a percentage on a dry weight basis. In some embodiments, the dry solids content of the glycan unit is between about 5 wt % to about 95 wt %, between about 10 wt % to about 80 wt %, between about 15 wt %, to about 75 wt %, or between about 15 wt %, to about 50 wt %.

Amount of Catalyst

The amount of the catalyst used in the methods described herein may depend on several factors including, for example, the selection of the type of glycan unit, the concentration of the glycan unit, and the reaction conditions (e.g., temperature, time, and pH). In some embodiments, the weight ratio of the catalyst to the glycan unit is about 0.01 g/g to about 50 g/g, about 0.01 g/g to about 5 g/g, about 0.05 g/g to about 1.0 g/g, about 0.05 g/g to about 0.5 g/g, about 0.05 g/g to about 0.2 g/g, or about 0.1 g/g to about 0.2 g/g.

Solvent

In certain embodiments, the methods of using the catalyst are carried out in an aqueous environment. One suitable aqueous solvent is water, which may be obtained from various sources. Generally, water sources with lower concentrations of ionic species (e.g., salts of sodium, phosphorous, ammonium, or magnesium) are preferable, as such ionic species may reduce effectiveness of the catalyst. In some embodiments where the aqueous solvent is water, the water has a resistivity of at least 0.1 megaohm-centimeters, of at least 1 megaohm-centimeters, of at least 2 megaohm-centimeters, of at least 5 megaohm-centimeters, or of at least 10 megaohm-centimeters.

Water Content

Moreover, as the dehydration reaction of the methods progresses, water is produced with each coupling of the one or more glycan units. In certain embodiments, the methods described herein may further include monitoring the amount of water present in the reaction mixture and/or the ratio of water to monomer or catalyst over a period of time. In some embodiments, the method further includes removing at least a portion of water produced in the reaction mixture (e.g., by removing at least about any of 10%, 20%, 30%, 40%, 50%, 60%, 70%, 80%, 90%, 95%, 97%, 99%, or 100%, such as by vacuum filtration). It should be understood, however, that the amount of water to monomer may be adjusted based on the reaction conditions and specific catalyst used.

Any method known in the art may be used to remove water in the reaction mixture, including, for example, by vacuum filtration, vacuum distillation, heating, and/or evaporation. In some embodiments, the method comprises including water in the reaction mixture.

In some aspects, provided herein are methods of producing an oligosaccharide composition, by: combining a glycan unit and a catalyst having acidic and ionic moieties to form a reaction mixture, wherein water is produced in the reaction mixture; and removing at least a portion of the water produced in the reaction mixture. In certain variations, at least a portion of water is removed to maintain a water content in the reaction mixture of less than 99%, less than 90%, less than 80%, less than 70%, less than 60%, less than 50%, less than 40%, less than 30%, less than 20%, less than 10%, less than 5%, or less than 1% by weight.

In some embodiments, the degree of polymerization of the one or more oligosaccharides produced according to the methods described herein can be regulated by adjusting or controlling the concentration of water present in the reaction mixture. For example, in some embodiments, the degree of polymerization of the one or more oligosaccharides is increased by decreasing the water concentration, while in other embodiments, the degree of polymerization of the one or more oligosaccharides is decreased by increasing the water concentration. In some embodiments, the water content of the reaction is adjusted during the reaction to regulate the degree of polymerization of the one or more oligosaccharides produced.

In one example, to a round bottom flask equipped with an overhead stirrer and a jacketed short-path condenser one or more mono-, dimer-, trimer or other oligosaccharides may be added along with 1-50% (1-10%, 1-20%, 1-30%, 1-40%, 1-60%, 1-70%) by dry weight of one or more of the catalysts described herein. Water or another compatible solvent (0.1-5 equiv, 1-5 equiv, 1-4 equiv, 0.1-4 equiv) may be added to the dry mixture and the slurry can be combined at slow speed (e.g. 10-100 rpm, 50-200 rpm, 100-200 rpm) using a paddle sized to match the contours of the selected round bottom flask as closely as possible. The mixture is heated to 70-180° C. (70-160° C., 75-165° C., 80-160° C.) under 10-1000 mbar vacuum pressure. The reaction may be stirred for 30 minutes to 6 hours, constantly removing water from the reaction. Reaction progress can be monitored by HPLC. The solid mass obtained by the process can be dissolved in a volume of water sufficient to create a solution of approximately 50 Brix (grams sugar per 100 g solution). Once dissolution is complete, the solid catalyst can be removed by filtration and the oligomer solution can be concentrated to approximately 50-75 Brix, e.g., by rotary evaporation. Optionally, an organic solvent can be used and water immiscible solvents can be removed by biphasic extraction and water miscible solvents can be removed, e.g., by rotary evaporation concomitant to the concentration step.

Additional Processing Steps

Optionally, the preparation may undergo additional processing steps. Additional processing steps may include, for example, purification steps. Purification steps may include, for example, separation, dilution, concentration, filtration, desalting or ion-exchange, chromatographic separation, or decolorization, or any combination thereof.

Decolorization

In some embodiments, the methods described herein further include a decolorization step. The one or more oligosaccharides produced may undergo a decolorization step using any method known in the art, including, for example, treatment with an absorbent, activated carbon, chromatography (e.g., using ion exchange resin), hydrogenation, and/or filtration (e.g., microfiltration).

In certain embodiments, the one or more oligosaccharides produced are contacted with a color-absorbing material at a particular temperature, at a particular concentration, and/or for a particular duration of time. In some embodiments, the mass of the color absorbing species contacted with the one or more oligosaccharides is less than 50% of the mass of the one or more oligosaccharides, less than 35% of the mass of the one or more oligosaccharides, less than 20% of the mass of the one or more oligosaccharides, less than 10% of the mass of the one or more oligosaccharides, less than 5% of the mass of the one or more oligosaccharides, less than 2% of the mass of the one or more oligosaccharides, or less than 1% of the mass of the one or more oligosaccharides.

In some embodiments, the one or more oligosaccharides are contacted with a color absorbing material. In certain embodiments, the one or more oligosaccharides are contacted with a color absorbing material for less than 10 hours, less than 5 hours, less than 1 hour, or less than 30 minutes. In a particular embodiment, the one or more oligosaccharides are contacted with a color absorbing material for 1 hour.

In certain embodiments, the one or more oligosaccharides are contacted with a color absorbing material at a temperature from 20 to 100 degrees Celsius, 30 to 80 degrees Celsius, 40 to 80 degrees Celsius, or 40 to 65 degrees Celsius. In a particular embodiment, the one or more oligosaccharides are contacted with a color absorbing material at a temperature of 50 degrees Celsius.

In certain embodiments, the color absorbing material is activated carbon. In one embodiment, the color absorbing material is powdered activated carbon. In other embodiments, the color absorbing material is an ion exchange resin. In one embodiment, the color absorbing material is a strong base cationic exchange resin in a chloride form. In another embodiment, the color absorbing material is cross-linked polystyrene. In yet another embodiment, the color absorbing material is cross-linked polyacrylate. In certain embodiments, the color absorbing material is Amberlite FPA91, Amberlite FPA98, Dowex 22, Dowex Marathon MSA, or Dowex Optipore SD-2.

Ion-Exchange/De-Salting (Demineralization)

In some embodiments, the one or more oligosaccharides produced are contacted with a material to remove salts, minerals, and/or other ionic species. In certain embodiments, the one or more oligosaccharides are flowed through an anionic/cationic exchange column pair. In one embodiment, the anionic exchange column contains a weak base exchange resin in a hydroxide form and the cationic exchange column contains a strong acid exchange resin in a protonated form.

Separation and Concentration

In some embodiments, the methods described herein further include isolating the one or more oligosaccharides produced. In certain variations, isolating the one or more oligosaccharides comprises separating at least a portion of the one or more oligosaccharides from at least a portion of the catalyst, using any method known in the art, including, for example, centrifugation, filtration (e.g., vacuum filtration, membrane filtration), and gravity settling. In some embodiments, isolating the one or more oligosaccharides comprises separating at least a portion of the one or more oligosaccharides from at least a portion of any unreacted sugar, using any method known in the art, including, for example, filtration (e.g., membrane filtration), chromatography (e.g., chromatographic fractionation), differential solubility, and centrifugation (e.g., differential centrifugation).

In some embodiments, the methods described herein further include a concentration step. For example, in some embodiments, the isolated oligosaccharides undergo evaporation (e.g., vacuum evaporation) to produce a concentrated oligosaccharide composition. In other embodiments, the isolated oligosaccharides undergo a spray drying step to produce an oligosaccharide powder. In certain embodiments, the isolated oligosaccharides undergo both an evaporation step and a spray drying step.

Water Content

Moreover, as the dehydration reaction of the methods progresses, water is produced with each coupling of the one or more sugars. In certain embodiments, the methods described herein may further include monitoring the amount of water present in the reaction mixture and/or the ratio of water to sugar or catalyst over a period of time. In some embodiments, the method further includes removing at least a portion of water produced in the reaction mixture (e.g., by removing at least about any of 10%, 20%, 30%, 40%, 50%, 60%, 70%, 80%, 90%, 95%, 97%, 99%, or 100%, such as by vacuum filtration). It should be understood, however, that the amount of water to sugar may be adjusted based on the reaction conditions and specific catalyst used.

Any method known in the art may be used to remove water in the reaction mixture, including, for example, by vacuum filtration, vacuum distillation, heating, and/or evaporation. In some embodiments, the method comprises including water in the reaction mixture.

In some aspects, provided herein are methods of producing an oligosaccharide composition, by: combining a glycan unit and a catalyst having acidic and ionic moieties to form a reaction mixture, wherein water is produced in the reaction mixture; and removing at least a portion of the water produced in the reaction mixture. In certain variations, at least a portion of water is removed to maintain a water content in the reaction mixture of less than 99%, less than 90%, less than 80%, less than 70%, less than 60%, less than 50%, less than 40%, less than 30%, less than 20%, less than 10%, less than 5%, or less than 1% by weight.

In some embodiments, the degree of polymerization of the one or more oligosaccharides produced according to the methods described herein can be regulated by adjusting or controlling the concentration of water present in the reaction mixture. For example, in some embodiments, the degree of polymerization of the one or more oligosaccharides is increased by decreasing the water concentration, while in other embodiments, the degree of polymerization of the one or more oligosaccharides is decreased by increasing the water concentration. In some embodiments, the water content of the reaction is adjusted during the reaction to regulate the degree of polymerization of the one or more oligosaccharides produced.

Fractionation

In some embodiments, the methods described herein further include a fractionation step. Oligo- or polysaccharides prepared and purified may be subsequently separated by molecular weight using any method known in the art, including, for example, high-performance liquid chromatography, adsorption/desorption (e.g. low-pressure activated carbon chromatography), or filtration (for example, ultrafiltration or diafiltration). In certain embodiments, prepared and purified glycans are separated into pools representing 60%, 65%, 70%, 75%, 80%, 85%, 90%, 95%, 97%, 98%, or greater than 98% short (about DP1-2), medium (about DP3-10), long (about DP11-18), or very long (about DP>18) species.

In certain embodiments, prepared glycans are fractionated by adsorption onto a carbonaceous material and subsequent desorption of fractions by washing the material with mixtures of an organic solvent in water at a concentration of 1%, 5%, 10%, 20%, 50%, or 100%. In one embodiment, the adsorption material is activated charcoal. In another embodiment, the adsorption material is a mixture of activated charcoal and a bulking agent such as diatomaceous earth or Celite 545 in 5%, 10%, 20%, 30%, 40%, or 50% portion by volume or weight.

In further embodiments, prepared glycans are separated by passage through a high-performance liquid chromatography system. In certain variations, prepared glycans are separated by ion-affinity chromatography, hydrophilic interaction chromatography, or size-exclusion chromatography including gel-permeation and gel-filtration.

In other embodiments, low molecular weight materials are removed by filtration methods. In certain variations, low molecular weight materials may be removed by dialysis, ultrafiltration, diafiltration, or tangential flow filtration. In certain embodiments, the filtration is performed in static dialysis tube apparatus. In other embodiments, the filtration is performed in a dynamic flow filtration system. In other embodiments, the filtration is performed in centrifugal force-driven filtration cartridges.

Characteristics of Glycan Therapeutic Preparations

The glycan therapeutics described herein may comprise oligosaccharides and/or polysaccharides. In some embodiments, the glycan therapeutics comprise homo-oligo- or polysaccharides (or homoglycans), wherein all the monosaccharides in a polysaccharide are of the same type. Glycan therapeutics comprising homopolysaccharides can include monosaccharides bonded together via a single or multiple glycosidic bond types.

In some embodiments, the glycan therapeutics comprise hetero-oligo- or polysaccharides (or heteroglycans), wherein more than one type of monosaccharide is present. Glycan therapeutics comprising heteropolysaccharides can include distinct types of monosaccharides bonded together via a single or multiple glycosidic bond types.

Monosaccharides are the building blocks of disaccharides (such as sucrose and lactose) and polysaccharides (such as cellulose and starch). The glycan therapeutics may comprise a single type of monosaccharide (referred to as homopolymers or homoglycans) or a mixture (referred to as heteropolymers or heteroglycans). An oligosaccharide is a saccharide polymer containing a small number (typically two to nine) of glycan units (in this case, monosaccharides).

For example, fructo-oligosaccharides (FOS), which are found in many vegetables, consist of short chains of fructose molecules, some of which are terminated with a glucose molecule. Galactooligosaccharides (GOS), which also occur naturally, consist of short chains of galactose molecules. These compounds can be only partially digested by humans. Oligosaccharides are primarily produced from the breakdown of natural polymers such as starch or inulin, from direct extractions out of natural substances, such as soybean, or from chemical or enzymatic syntheses.

Polysaccharides are polymeric carbohydrate molecules composed of long chains of glycan units bound together by linkages, such as, e.g. glycosidic linkages. Polysaccharides contain more than ten glycan units (in this case, monosaccharides). Naturally occurring polysaccharides may have a general formula of $C_x(H_2O)_y$, where x is usually a large number, e.g. between 10 and 2500. In some embodiments, hydrolysis may be used to generate the constituent monosaccharides or oligosaccharides that are suitable to produce the glycans described herein. Glycan units, such as e.g. monosaccharides, may exist in many different forms, for example, conformers, cyclic forms, acyclic forms, stereoisomers, tautomers, anomers, and isomers.

In some embodiments, glycan therapeutic preparations (e.g. oligo- or polysaccharides) are created that are polydisperse, exhibiting a range of degrees of polymerization. Optionally, the preparations may be fractionated, e.g. representing 60%, 65%, 70%, 75%, 80%, 85%, 90%, 95%, 97%, 98%, or greater than 98% short (about DP1-2), medium (about DP3-10), long (about DP11-18), or very long (about DP>18) species.

In one embodiment, a polydisperse, fractionated glycan therapeutic preparation is provided comprising at least 85%, 90%, or at least 95% medium-length species with a DP of about 3-10. In one embodiment, a polydisperse, fractionated glycan therapeutic preparation is provided comprising at least 85%, 90%, or at least 95% long-length species with a DP of about 11-18. In one embodiment, a polydisperse, fractionated glycan therapeutic preparation is provided comprising at least 85%, 90%, or at least 95% very long-length species with a DP of about 18-30. In some embodiments, the medium, long and very long fractionated preparations comprise an alpha- to beta-glycosidic bond ratio from 0.8:1 to 5:1 or from 1:1 to 4:1. In some embodiments, the fractionated preparations have an average degree of branching of between about 0.01 and about 0.2 or between about 0.05 and 0.1.

In some embodiments, methods are provided using the disclosed polymeric catalyst to control the molecular weight distribution of the glycans. For example, a majority, e.g. about 55%, 60%, 65%, 70%, 75%, 80%, 85%, 90%, 95%, or about 97% of the glycan therapeutic preparation has a DP of between 2 and 25, between 3 and 25, between 4 and 25, between 5 and 25, between 6 and 25, between 7 and 25, between 8 and 25, between 9 and 25, between 10 and 25, between 2 and 30, between 3 and 30, between 4 and 30, between 5 and 30, between 6 and 30, between 7 and 30, between 8 and 30, between 9 and 30, or between 10 and 30.

In one embodiment, the glycan therapeutic preparation has a degree of polymerization (DP) of at least 3 and less than 30 glycan units.

In some embodiments, about 55%, 60%, 65%, 70%, 75%, 80%, 85%, 90%, 95%, or about 97% of the glycan therapeutic preparation has a DP of at least 5 and less than 30 glycan units. In some embodiments, about 55%, 60%, 65%, 70%, 75%, 80%, 85%, 90%, 95%, or about 97% of the glycan therapeutic preparation has a DP of at least 8 and less than 30 glycan units. In some embodiments, about 55%, 60%, 65%, 70%, 75%, 80%, 85%, 90%, 95%, or about 97% of the glycan therapeutic preparation has a DP of at least 10 and less than 30 glycan units. In some embodiments, about 55%, 60%, 65%, 70%, 75%, 80%, 85%, 90%, 95%, or about 97% of the glycan therapeutic preparation has a DP of between 3, 4, 5, 6, 7, 8 and 10, 11, 12, 13, 14, 15, 16, 17, 18, 19, 20 glycan units. In some embodiments, about 55%, 60%, 65%, 70%, 75%, 80%, 85%, 90%, 95%, or about 97% of the glycan therapeutic preparation has a DP of between 10, 11, 12, 13, 14, 15, 16, 17, 18, 19 and 20, 21, 22, 23, 24, 25, 26, 27, 28, 29, 30 glycan units. In some embodiments, about 55%, 60%, 65%, 70%, 75%, 80%, 85%, 90%, 95%, or about 97% of the glycan therapeutic preparation has a DP of between 3, 4, 5, 6, 7, 8, 9, 10 and 20, 21, 22, 23, 24, 25, 26, 27, 28 glycan units.

In some embodiments, the glycan therapeutic preparation has a degree of polymerization (DP) distribution after combining the one or more glycan units (e.g. sugars) with the polymeric catalyst (e.g., at 2, 3, 4, 8, 12, 24, or 48 hours after combining the one or more glycan units (e.g. sugars) with the catalyst) is: DP2=0%-40%, such as less than 40%, less than 30%, less than 20%, less than 10%, less than 5%, or less than 2%; or 10%-30% or 15%-25%; DP3=0%-20%, such as less than 15%, less than 10%, less than 5%; or 5%-15%; and DP4+=greater than 15%, greater than 20%, greater than 30%, greater than 40%, greater than 50%; or 15%-75%, 20%-40% or 25%-35%.

The yield of conversion for the one or more glycan units (e.g. sugars) in the methods described herein can be determined by any suitable method known in the art, including, for example, high performance liquid chromatography (HPLC). In some embodiments, the yield of conversion to a glycan therapeutic preparation with DP>1 after combining the one or more glycan units with the catalyst (e.g., at 2, 3, 4, 8, 12, 24, or 48 hours after combining the one or more glycan units with the catalyst) is greater than about 50% (e.g., greater than about 55%, 60%, 65%, 70%, 75%, 80%, 85%, 90%, 95%, or 98%). In some embodiments, the yield of conversion to a glycan therapeutic preparation with >DP2 after combining the one or more glycan units with the catalyst (e.g., at 2, 3, 4, 8, 12, 24, or 48 hours after combining the one or more glycan units with the catalyst) is greater than 30% (e.g., greater than 35%, 40%, 45%, 50%, 55%. 60%, 65%, 70%, 75%, 80%, 85%, 90%, 95%, or 98%).

In one embodiment, about 55%, 60%, 65%, 70%, 75%, 80%, 85%, 90%, 95%, or about 97% of the glycan therapeutic preparation has a DP of at least 2. In one embodiment, about 55%, 60%, 65%, 70%, 75%, 80%, 85%, 90%, 95%, or about 97% of the glycan therapeutic preparation has a DP of at least 3.

In some embodiments, glycan therapeutic preparations are provided, wherein at least 5%, 10%, 15%, 20%, 25%, 30%, 35%, 40%, 45%, 50%, 55%, 60%, 65%, 70%, 75%, 80%, 85%, 90%, 95%, 97%, 98%, 99%, 99.8%, or at least 99.9% or even 100% of the glycan therapeutic preparation has a degree of polymerization (DP) of at least 2, 3, 4, 5, 6, 7, 8, 9, 10, 11, or at least 12 glycan units and less than 75, 70, 65, 60, 55, 50, 45, 40, 35, 30, 25, 20, 19, 18, 17, 16, or less than 15 glycan units.

In some embodiments, glycan therapeutic preparations are provided, wherein at least 5%, 10%, 15%, 20%, 25%, 30%, 35%, 40%, 45%, 50%, 55%, 60%, 65%, 70%, 75%, 80%, 85%, 90%, 95%, 97%, 98%, 99%, 99.8%, or at least 99.9% or even 100% of the glycan therapeutic preparation has a degree of polymerization (DP) of at least 5 and less than 30 glycan units, at least 8 and less than 30 glycan units.

In some embodiments, about 55%, 60%, 65%, 70%, 75%, 80%, 85%, 90%, 95%, or about 97% of the glycan therapeutic preparation has an average degree of polymerization (DP) of about DP5, DP6, DP7, DP8, DP9, DP10, DP11, or DP12.

In some embodiments, glycan therapeutic preparations are provided wherein at least 50%, 60%, 70%, or 80% of the glycan therapeutic preparation has a degree of polymerization of at least 3 and less than 30 glycan units, or of at least 5 and less than 25 glycan units. In some embodiments, the average DP of the glycan therapeutic preparation is between about DP7 and DP9 or between about DP6 and DP10. In some embodiments, these glycan therapeutic preparations comprise an alpha- to beta-glycosidic bond ratio from 0.8:1 to 5:1 or from 1:1 to 4:1. In some embodiments, the fractionated preparations have an average degree of branching of between about 0.01 and about 0.2 or between about 0.05 and 0.1.

In some embodiments, about 55%, 60%, 65%, 70%, 75%, 80%, 85%, 90%, 95%, or about 97% of the glycan therapeutic preparation has an average molecular weight of about 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800 g/mol and less than 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and 5000 g/mol.

In some embodiments, the glycan preparations (e.g. oligo- or polysaccharides) range in structure from linear to highly branched. Unbranched glycans may contain only alpha linkages or only beta linkages. Unbranched glycans may contain at least one alpha and at least one beta linkage. Branched glycans may contain at least one glycan unit being linked via an alpha or a beta glycosidic bond so as to form a branch. The branching rate or degree of branching (DB) may vary, such that about every $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, $25^{th}$, $30^{th}$, $35^{th}$, $40^{th}$, $45^{th}$, $50^{th}$, $60^{th}$, or $70^{th}$ unit comprises at least one branching point. For example, animal glycogen contains a branching point approximately every 10 units.

In some embodiments, preparations of glycan therapeutics are provided, wherein the preparation comprises a mixture of branched glycans, wherein the average degree of branching (DB, branching points per residue) is 0, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 0.95, 0.99, 1, or 2. In some embodiments, preparations of glycan therapeutics are provided, wherein the average degree of branching is at least 0.01, 0.05, 0.1, 0.2, 0.3, or at least 0.4. In some embodiments, preparations of glycan therapeutics are provided, wherein the average degree of branching is between about 0.01 and 0.1, 0.01 and 0.2, 0.01 and 0.3, 0.01 and 0.4, or 0.01 and 0.5. In some embodiments, preparations of glycan therapeutics are provided, wherein the average degree of branching is not 0. In some embodiments, preparations of glycan therapeutics are provided, wherein the average degree of branching is not between at least 0.1 and less than 0.4 or at least 0.2 and less than 0.4. In some embodiments, the preparations of glycan therapeutics comprise linear glycans. In some embodiments, the preparations of glycan therapeutics comprise glycans that exhibit a branched or branch-on-branch structure.

In some embodiments, preparations of glycan therapeutics are provided wherein the average degree of branching (DB) is not 0, but is at least 0.01, 0.05, 0.1, or at least 0.2, or ranges between about 0.01 and about 0.2 or between about 0.05 and 0.1.

Some glycans comprise oligosaccharides which have a reducing end and a non-reducing end, whether or not the saccharide at the reducing end is in fact a reducing sugar. In accordance with accepted nomenclature, most oligosaccharides are depicted herein with the non-reducing end on the left and the reducing end on the right. Most oligosaccharides described herein are described with the name or abbreviation for the non-reducing saccharide (e.g., Gal or D-Gal), preceded or followed by the configuration of the glycosidic bond (alpha or beta), the ring bond, the ring position of the reducing saccharide involved in the bond, and then the name or abbreviation of the reducing saccharide (e.g., Glc or D-Glc). The linkage (e.g., glycosidic linkage, galactosidic linkage, glucosidic linkage, etc.) between two sugar units can be expressed, for example, as 1,4, 1→4, or (1-4), used interchangeably herein. Each saccharide can be in the cyclic form (e.g. pyranose or furanose form). For example, lactose is a disaccharide composed of cyclic forms of galactose and glucose joined by a beta (1-4) linkage where the acetal oxygen bridge is in the beta orientation.

Linkages between the individual glycan units found in preparations of glycan therapeutics may include alpha 1→2, alpha 1→3, alpha 1→4, alpha 1→6, alpha 2→1, alpha 2→3, alpha 2→4, alpha 2→6, beta 1→2, beta 1→3, beta 1→4, beta 1→6, beta 2→1, beta 2→3, beta 2→4, and beta 2→6.

In some embodiments, the glycan therapeutic preparations comprise only alpha linkages. In some embodiments, the glycan therapeutics comprise only beta linkages. In some embodiments, the glycan therapeutics comprise mixtures of alpha and beta linkages. In some embodiments, the alpha:beta glycosidic bond ratio in a preparation is about 0.1:1, 0.2:1, 0.3:1, 0.4:1, 0.5:1, 0.6:1, 0.7:1, 0.8:1, 0.9:1, 1:1, 1.2:1, 1.5:1, 1.7:1, 2:1, 2.2:1, 2.5:1, 2.7:1, 3:1, 4:1, 5:1, 6:1, 7:1, 8:1, 9:1, or about 10:1.

In some embodiments, the glycan therapeutic preparation comprises both alpha- and beta-glycosidic bonds selected from the group consisting of 1→2 glycosidic bond, a 1→3 glycosidic bond, a 1→4 glycosidic bond, a 1→5 glycosidic bond and a 1→6 glycosidic bond. In some embodiments, the glycan therapeutic preparation comprises at least two or at least three alpha and beta 1→2 glycosidic bonds, alpha and beta 1→3 glycosidic bonds, alpha and beta 1→4 glycosidic bonds, alpha and beta 1→5 glycosidic bonds, and/or alpha and beta 1→6 glycosidic bonds. In some embodiments, the glycan therapeutic preparations comprise and alpha:beta glycosidic bond ratio in a preparation of about 0.8:1, 1:1, 2:1, 3:1, 4:1 or 5:1, or it ranges from about 0.8:1 to about 5:1 or from about 1:1 to about 4:1.

In some embodiments, the preparations of glycan therapeutics (e.g. oligosaccharides and polysaccharides) comprises a desired mixture of glycan units with alpha- or beta configuration, e.g. the preparation of glycan therapeutics comprises a desired ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 of alpha- to beta-configuration or beta- to alpha-configuration.

In some embodiments, the preparations of glycan therapeutics (e.g. oligosaccharides and polysaccharides) comprises substantially all alpha- or beta configured glycan units, optionally comprising about 1%, 2%, 3%, 4% 5%, 6%, 7%, 8%, 9%, 10%, 11%, 12%, 13%, 14%, 15%, 16%, 17%, 18%, 19%, or 20% of the respective other configuration.

In some embodiments, the preparations of glycan therapeutics comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% glycans with alpha glycosidic bonds. In some embodiments, the preparations of glycan therapeutics comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% glycans with beta glycosidic bonds. In some embodiments, preparations of glycan therapeutics are provided, wherein at least 10%, 15%, 20%, 25%, 30%, 35%, 40%, 45%, 50%, 55%, 60%, 65%, 70%, 75%, 80%, or at least 85% of glycans with glycosidic bonds that are alpha glycosidic bonds, at least 10%, 15%, 20%, 25%, 30%, 35%, 40%, 45%, 50%, 55%, 60%, 65%, 70%, 75%, 80%, or at least 85% of glycans with glycosidic bonds that are beta glycosidic bonds, and wherein the percentage of alpha and beta glycosidic bonds does not exceed 100%.

In some embodiments, preparations of glycan therapeutics are provided, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% of glycan glycosidic bonds are one or more of: 1→2 glycosidic bonds, 1→3 glycosidic bonds, 1→4 glycosidic bonds, and 1→6 glycosidic bonds. In some embodiments, preparations of glycan therapeutics are provided, wherein at least 1%, 2%, 3%, 4%, 5%, 6%, 7%, 8%, 9%, 10%, 15%, at least 20%, or 25% each of glycan glycosidic bonds are 1→2, 1→3, 1→4, and 1→6 glycosidic bonds. Optionally, the preparations of glycan therapeutics further comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, or at least 85% of glycan glycosidic bonds that are selected from the group consisting of: alpha 2→1, alpha 2→3, alpha 2→4, alpha 2→6, beta 2→1, beta 2→3, beta 2→4, and beta 2→6, glycosidic bonds.

In some embodiments, the preparations of glycan therapeutics comprise glycans with at least two glycosidic bonds selected from the group consisting of alpha 1→2 and alpha 1→3, alpha 1→2 and alpha 1→4, alpha 1→2 and alpha 1→6, alpha 1→2 and beta 1→2, alpha 1→2 and beta 1→3, alpha 1→2 and beta 1→4, alpha 1→2 and beta 1→6, alpha 1→3 and alpha 1→4, alpha 1→3 and alpha 1→6, alpha 1→3 and beta 1→2, alpha 1→3 and beta 1→3, alpha 1→3 and beta 1→4, alpha 1→3 and beta 1→6, alpha 1→4 and alpha 1→6, alpha 1→4 and beta 1→2, alpha 1→4 and beta 1→3, alpha 1→4 and beta 1→4, alpha 1→4 and beta 1→6, alpha 1→6 and beta 1→2, alpha 1→6 and beta 1→3, alpha 1→6 and beta 1→4, alpha 1→6 and beta 1→6, beta 1→2 and beta 1→3, beta 1→2 and beta 1→4, beta 1→2 and beta 1→6, beta 1→3 and beta 1→4, beta 1→3 and beta 1→6, and beta 1→4 and beta 1→6.

For preparations comprising branched glycan therapeutics (e.g. those with a DB of 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 0.95, 0.99, 1, or 2) comprising a side chain, which can be the same or a different side chain, the side chain may be attached via one or more beta and alpha linkages, such as (1-2), (1-3), (1-4), (1-6), (2-3), (2-6) or other suitable linkages to the main chain.

In some embodiments, preparations of glycan therapeutics are provided, wherein at least one glycan unit is a sugar in L-form. In some embodiments, preparations of glycans are provided, wherein at least one glycan unit is a sugar in D-form. In some embodiments, preparations of glycans are provided, wherein the glycan units are sugars in L- or D-form as they naturally occur or are more common (e.g. D-glucose, D-xylose, L-arabinose).

In some embodiments, the preparation of glycan therapeutics (e.g. oligosaccharides and polysaccharides) comprises a desired mixture of L- and D-forms of glycan units, e.g. of a desired ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 L- to D-forms or D- to L-forms.

In some embodiments, the preparation of glycan therapeutics comprises glycans with substantially all L- or D-forms of glycan units, optionally comprising about 1%, 2%, 3%, 4% 5%, 6%, 7%, 8%, 9%, 10%, 11%, 12%, 13%, 14%, 15%, 16%, 17%, 18%, 19%, or 20% of the respective other form.

In some embodiments, preparations of glycan therapeutics are provided, wherein at least one glycan unit is a tetrose, a pentose, a hexose, or a heptose. Optionally, the glycan units involved in the formation of the glycans (e.g. a mixture of branched oligosaccharides or polysaccharides) of the glycan therapeutic preparation are varied. Examples of monosaccharide glycan units include hexoses, such as glucose, galactose, and fructose, and pentoses, such as xylose. Monosaccharides generally have the chemical formula: $C_x(H_2O)_y$, where conventionally $x \geq 3$. Monosaccharides can be classified by the number x of carbon atoms they contain, for example: diose (2) triose (3) tetrose (4), pentose (5), hexose (6), and heptose (7). The monosaccharide glycan units may exist in an acyclic (open-chain) form. Open-chain monosaccharides with same molecular graph may exist as two or more stereoisomers. The monosaccharides may also exist in a cyclic form through a nucleophilic addition reaction between the carbonyl group and one of the hydroxyls of the same molecule. The reaction creates a ring of carbon atoms closed by one bridging oxygen atom. In these cyclic forms, the ring usually has 5 (furanoses) or 6 atoms (pyranoses).

In some embodiments, the preparation of glycan therapeutics (e.g. oligosaccharides and polysaccharides) comprises a desired mixture of different monosaccharide glycan units, such as a mixture of a diose (2), a triose (3), tetrose (4), pentose (5), hexose (6), or heptose (7), in any desired ratio, e.g. for any two glycan units: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150, etc., for any three glycan units:1:1:1, 1:2:1, 1:3:1, 1:4:1, 1:5:1, 1:6:1, 1:7:1, 1:8:1, 1:9:1, 1:10:1, 1:12:1, 1:14:1, 1:16:1, 1:18:1, 1:20:1, 1:1:2, 1:2:2, 1:3:2, 1:4:2, 1:5:2, 1:6:2, 1:7:2, 1:8:2, 1:9:2, 1:10:2, 1:1:3, 1:2:3, 1:3:3, 1:4:3, 1:5:3, 1:6:3, 1:7:3, 1:8:3, 1:9:3, 1:10:3, 1:1:4, 1:2:4, 1:3:4, 1:4:4, 1:5:4, 1:6:4, 1:7:4, 1:8:4, 1:9:4, 1:10:4, 1:1:5, 1:2:5, 1:3:5, 1:4:5, 1:5:5, 1:6:5, 1:7:5, 1:8:5, 1:9:5, 1:10:5, etc., for any four glycan units: 1:1:1:1, 1:2:2:1, 1:3:2:1, 1:4:2:1, 1:5:2:1, 1:6:2:1, 1:7:2:1, 1:8:2:1, 1:9:2:1, 1:10:2:1, 1:1:1:2, 1:2:2:2, 1:3:2:2, 1:4:2:2, 1:5:2:2, 1:6:2:2, 1:7:2:2, 1:8:2:2, 1:9:2:2, 1:10:2:2, etc., for any five glycan units: 1:1:1:1:1, 1:2:2:1:1, etc., for any six glycan units: 1:1:1:1:1:1, 1:1:1:1:1:2, etc., for any seven glycan units: 1:1:1:1:1:1:1, 1:1:1:1:1:1:2, etc., and so on.

In some embodiments, the preparation of glycan therapeutics comprises a desired mixture of two, three, four or five different glycan units, such as a mixture of, e.g., i) one or more glycan units selected from monosaccharides, selected from glucose, a galactose, an arabinose, a mannose, a fructose, a xylose, a fucose, and a rhamnose; ii) one or more glycan units selected from disaccharides selected from acarviosin, n-acetyllactosamine, allolactose, cellobiose, chitobiose, glactose-alpha-1,3-galactose, gentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralose, sucrose, sucrose acetate isobutyrate, sucrose octaacetate, trehalose, turanose, vicianose, and xylobiose; iii) one or more glycan units selected from amino sugars selected from acarbose, N-acetylemannosamine, N-acetylmuramic acid, N-acetylnueraminic acid, N-acetyletalosaminuronic acid, arabinopyranosyl-N-methyl-N-nitrosourea, D-fructose-L-histidine, N-glycolyneuraminic acid, ketosamine, kidamycin, mannosamine, 1B-methylseleno-N-acetyl-D-galactosamine, muramic acid, muramyl dipeptide, phosphoribosylamine, PUGNAc, sialyl-Lewis A, sialyl-Lewis X, validamycin, voglibose, N-acetylgalactosamine, N-acetylglucosamine, aspartylglucosamine, bacillithiol, daunosamine, desosamine, fructosamine, galactosamine, glucosamine, meglumine, and perosamine; iv) one or more glycan units selected from deoxy sugars selected from 1-5-ahydroglucitol, cladinose, colitose, 2-deoxy-D-glucose, 3-deoxyglucasone, deoxyribose, dideoxynucleotide, digitalose, fludeooxyglucose, sarmentose, and sulfoquinovose; v) one or more glycan units selected from imino sugars selected from castanospermine, 1-deoxynojirimycin, iminosugar, miglitol, miglustat, and swainsonine; one or more glycan units selected from sugar acids selected from N-acetylneuraminic acid, N-acetyltalosamnuronic acid, aldaric acid, aldonic acid, 3-deoxy-D-manno-oct-2-ulosonic acid, glucuronic acid, glucosaminuronic acid, glyceric acid, N-glycolylneuraminic acid, iduronic acid, isosaccharinic acid, pangamic acid, sialic acid, threonic acid, ulosonic acid, uronic acid, xylonic acid, gluconic acid, ascorbic acid, ketodeoxyoctulosonic acid, galacturonic acid, galactosaminuronic acid, mannuronic acid, mannosaminuronic acid, tartaric acid, mucic acid, saccharic acid, lactic acid, oxalic acid, succinic acid, hexanoic acid, fumaric acid, maleic acid, butyric acid, citric acid, glucosaminic acid, malic acid, succinamic acid, sebacic acid, and capric acid; vi) one or more glycan units selected from short-chain fatty acids selected from formic acid, acetic acid, propionic acid, butryic acid, isobutyric acid, valeric acid, and isovaleric acid; and vii) one or more glycan units selected from sugar alcohols selected from methanol, ethylene glycol, glycerol, erythritol, threitol, arabitol, ribitol, xylitol, mannitol, sorbitol, galactitol, iditol, volemitol, fucitol, inositol, maltotritol, maltotetraitol, and polyglycitol.

In some embodiments, the preparation of glycan therapeutics comprises a glycan unit or plurality of glycan units present in a salt form (e.g., a pharmaceutically acceptable salt form), such as, e.g., a hydrochlorate, hydroiodate, hydrobromate, phosphate, sulfate, methanesulfate, acetate, formate, tartrate, malate, citrate, succinate, lactate, gluconate, pyruvate, fumarate, propionate, aspartate, glutamate, benzoate, ascorbate salt.

Exemplary glycans are described by a three-letter code representing the monomeric sugar component followed by a number out of one hundred reflecting the percentage of the material that monomer constitutes. Thus, 'glu100' is ascribed to a glycan generated from a 100% D-glucose (glycan unit) input and 'glu50gal50' is ascribed to a glycan generated from 50% D-glucose and 50% D-galactose (glycan units) input or, alternatively from a lactose dimer (glycan unit) input. As used herein: xyl=D-xylose; ara=L-arabinose; gal=D-galactose; glu=D-glucose; rha=L-rhamnose; fuc=L-fucose; man=D-mannose; sor=D-sorbitol; gly=D-glycerol; neu=NAc-neuraminic acid.

In some embodiments, the preparation of glycan therapeutics comprises one glycan unit A selected from i) to vii) above, wherein glycan unit A comprises 100% of the glycan unit input. For example, in some embodiments, the glycan therapeutic preparation is selected from the homo-glycans xyl100, rha100, ara100, gal100, glu100, and man100. In some embodiments, the glycan therapeutic preparation is selected from the homo-glycans fuc100 and fru100.

In some embodiments, the preparation of glycan therapeutics comprises a mixture of two glycan units A and B selected independently from i) to vii) above, wherein A and B may be selected from the same or a different group i) to vii) and wherein A and B may be selected in any desired ratio (e.g. anywhere from 1-99% A and 99-1% B, not exceeding 100%).

For example, in some embodiments, the glycan therapeutic preparation is selected from the hetero-glycans ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10.

In some embodiments, the preparation of glycan therapeutics comprises a mixture of three glycan units A, B and C selected independently from i) to vii) above, wherein A, B and C may be selected from the same or a different group i) to vii) and wherein A, B and C may be selected in any desired ratio (e.g. anywhere from 1-99% A, 1-99% B, 1-99% C, not exceeding 100%).

For example, in some embodiments, the glycan therapeutic preparation is selected from the hetero-glycans xyl75glu12gal12, xyl33glu33gal33, glu33gal33fuc33, man52glu29gal19, and the hybrid glycan glu33gal33neu33.

In some embodiments, the preparation of glycan therapeutics comprises a mixture of four glycan units A, B, C and D selected independently from i) to vii) above, wherein A, B, C and D may be selected from the same or a different group i) to vii) and wherein A, B, C and D may be selected in any desired ratio (e.g. anywhere from 1-99% A, 1-99% B, 1-99% C, 1-99% D, not exceeding 100%).

In some embodiments, the preparation of glycan therapeutics comprises a mixture of five glycan units A, B, C, D and E selected independently from i) to vii) above, wherein A, B, C, D and E may be selected from the same or a different group i) to vii) and wherein A, B, C, D and E may be selected in any desired ratio (e.g. anywhere from 1-99% A, 1-99% B, 1-99% C, 1-99% D, 1-99% E, not exceeding 100%).

In some embodiments, preparations of glycan therapeutics are provided, wherein at least one glycan unit is selected from the group consisting of a glucose, a galactose, an arabinose, a mannose, a fructose, a xylose, a fucose, and a rhamnose.

In some embodiments, the preparation of glycan therapeutics (e.g. oligosaccharides and polysaccharides) comprises a desired mixture of two different monosaccharide glycan units, such as a mixture of, e.g., glucose and galactose, glucose and arabinose, glucose and mannose, glucose and fructose, glucose and xylose, glucose and fucose, glucose and rhamnose, galactose and arabinose, galactose and mannose, galactose and fructose, galactose and xylose, galactose and fucose, and galactose and rhamnose, arabinose and mannose, arabinose and fructose, arabinose and xylose, arabinose and fucose, and arabinose and rhamnose, mannose and fructose, mannose and xylose, mannose and fucose, and mannose and rhamnose, fructose and xylose, fructose and fucose, and fructose and rhamnose, xylose and fucose, xylose and rhamnose, and fucose and rhamnose, e.g. a in a ratio of 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, or 1:100 or the reverse ratio thereof.

In some embodiments, the preparation of glycan therapeutics (e.g. oligosaccharides and polysaccharides) comprises a desired mixture of three different monosaccharide glycan units, such as a mixture of, e.g. for glucose-containing glycan-therapeutic preparations, glucose, galactose and arabinose; glucose, galactose and mannose; glucose, galactose and fructose; glucose, galactose and xylose; glucose, galactose and fucose, glucose, galactose and rhamnose; glucose, arabinose, and mannose; glucose, arabinose and fructose; glucose, arabinose and xylose; glucose, arabinose and fucose; glucose, arabinose and rhamnose; glucose, mannose and fructose; glucose, mannose and xylose; glucose, mannose and fucose; glucose, mannose rhamnose; glucose, fructose and xylose; glucose, fructose and fucose; glucose, fructose and rhamnose; glucose, fucose and rhamnose, e.g. a in a ratio of 1:1:1, 1:2:1, 1:3:1, 1:4:1, 1:5:1, 1:6:1, 1:7:1, 1:8:1, 1:9:1, 1:10:1, 1:12:1, 1:14:1, 1:16:1, 1:18:1, 1:20:1, 1:1:2, 1:2:2, 1:3:2, 1:4:2, 1:5:2, 1:6:2, 1:7:2, 1:8:2, 1:9:2, 1:10:2, 1:1:3, 1:2:3, 1:3:3, 1:4:3, 1:5:3, 1:6:3, 1:7:3, 1:8:3, 1:9:3, 1:10:3, 1:1:4, 1:2:4, 1:3:4, 1:4:4, 1:5:4, 1:6:4, 1:7:4, 1:8:4, 1:9:4, 1:10:4, 1:1:5, 1:2:5, 1:3:5, 1:4:5, 1:5:5, 1:6:5, 1:7:5, 1:8:5, 1:9:5, 1:10:5, etc.

In some embodiments, the preparation of glycan therapeutics (e.g. oligosaccharides and polysaccharides) comprises substantially all diose (2) monosaccharide units, optionally comprising 1%, 2%, 3%, 4% 5%, 6%, 7%, 8%, 9%, 10%, 11%, 12%, 13%, 14%, 15%, 16%, 17%, 18%, 19%, or 20% of a triose (3) tetrose (4), pentose (5), hexose (6), or heptose (7), or any combination thereof.

In some embodiments, the preparation of glycan therapeutics (e.g. oligosaccharides and polysaccharides) comprises substantially all triose (3) monosaccharide units, optionally comprising 1%, 2%, 3%, 4% 5%, 6%, 7%, 8%, 9%, 10%, 11%, 12%, 13%, 14%, 15%, 16%, 17%, 18%, 19%, or 20% of a diose (2), tetrose (4), pentose (5), hexose (6), or heptose (7), or any combination thereof.

In some embodiments, the preparation of glycan therapeutics (e.g. oligosaccharides and polysaccharides) comprises substantially all of tetrose (4) monosaccharide units, optionally comprising 1%, 2%, 3%, 4% 5%, 6%, 7%, 8%, 9%, 10%, 11%, 12%, 13%, 14%, 15%, 16%, 17%, 18%, 19%, or 20% of a diose (2), triose (3), pentose (5), hexose (6), or heptose (7), or any combination thereof.

In some embodiments, the preparation of glycan therapeutics (e.g. oligosaccharides and polysaccharides) comprises substantially all of pentose (5) monosaccharide units, optionally comprising 1%, 2%, 3%, 4% 5%, 6%, 7%, 8%, 9%, 10%, 11%, 12%, 13%, 14%, 15%, 16%, 17%, 18%, 19%, or 20% of a diose (2), triose (3) tetrose (4), hexose (6), or heptose (7), or any combination thereof.

In some embodiments, the preparation of glycan therapeutics (e.g. oligosaccharides and polysaccharides) comprises substantially all of hexose (6) monosaccharide units, optionally comprising 1%, 2%, 3%, 4% 5%, 6%, 7%, 8%, 9%, 10%, 11%, 12%, 13%, 14%, 15%, 16%, 17%, 18%, 19%, or 20% of a diose (2), triose (3) tetrose (4), pentose (5), or heptose (7), or any combination thereof.

In some embodiments, the preparation of glycan therapeutics (e.g. oligosaccharides and polysaccharides) comprises substantially all of heptose (7) monosaccharide units, optionally comprising 1%, 2%, 3%, 4% 5%, 6%, 7%, 8%, 9%, 10%, 11%, 12%, 13%, 14%, 15%, 16%, 17%, 18%, 19%, or 20% of a diose (2), triose (3) tetrose (4), pentose (5), or hexose (6), or any combination thereof.

In some embodiments, preparations of glycan therapeutics are provided, wherein at least one glycan unit is a furanose sugar. In some embodiments, preparations of glycans are provided, wherein at least one glycan unit is a pyranose sugar. In some embodiments, glycan therapeutics comprise mixtures of furanose and pyranose sugars. In some embodiments, the furanose: pyranose sugar ratio in a preparation is about 0.1:1, 0.2:1, 0.3:1, 0.4:1, 0.5:1, 0.6:1, 0.7:1, 0.8:1, 0.9:1, 1:1, 1.2:1, 1.5:1, 1.7:1, 2:1, 2.2:1, 2.5:1, 2.7:1, 3:1, 4:1, 5:1, 6:1, 7:1, 8:1, 9:1, or about 10:1.

In some embodiments, the preparation of glycan therapeutics (e.g. oligosaccharides and polysaccharides) comprises a desired mixture of furanose and pyranose sugars, e.g. of a desired ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 furanose to and pyranose or pyranose to furanose.

In some embodiments, the preparation of glycan therapeutics comprises substantially all furanose or pyranose sugar, optionally comprising 1%, 2%, 3%, 4% 5%, 6%, 7%, 8%, 9%, 10%, 11%, 12%, 13%, 14%, 15%, 16%, 17%, 18%, 19%, or 20% of the respective other sugar.

In some embodiments, the preparation of glycan therapeutics comprises substantially all pyranose sugar and no more than about 0.1%, 02%, 0.5%, 1%, 2%, 3%, 4%, or no more than 5% of monomeric glycan units in the preparation in furanose form. In some embodiments, no more than 3%, 2% or no more than 1% of monomeric glycan units in the preparation are in furanose form.

In some embodiments, the preparation of glycan therapeutics does not comprise N-acetylgalactosamine or N-acetylglucosamine. In some embodiments, the preparation of glycans does not comprise sialic acid. In some embodiments, the preparation of glycan therapeutics does not comprise a lipid and fatty acid. In some embodiments, the preparation of glycan therapeutics does not comprise an amino acid.

In some embodiments, the preparation of glycan therapeutics does not comprise a detectable repeating unit. In some embodiments, the preparation of glycan therapeutics does not comprise a statistically significant amount of a repeating unit. In some embodiments, the repeating unit has a DP of at least 2, 3, 4, 5, or at least 6 glycan units. For example, hyaluronan is a glycosaminoglycan with a repeating disaccharide unit consisting of two glucose derivatives, glucuronate (glucuronic acid) and N-acetylglucosamine. The glycosidic linkages are beta (1→3) and beta (1→4). Cellulose is a polymer made with repeated glucose units linked together by beta-linkages. The presence and amount of repeating units can be determined, e.g. using by total hydrolysis (e.g. to determine the proportion of glycan units), methylation analysis (e.g. to determine the distribution of bond types), and HSQC (e.g. to determine the distribution of alpha- and beta-glycosides). Statistical methods to determine significance are known by one of skill in the art.

If desired, the monosaccharide or oligosaccharide glycan units of the glycans are further substituted or derivatized, e.g., hydroxyl groups can be etherified or esterified. For example, the glycans (e.g. oligo- or polysaccharide) can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). The degree of substitution (DS, average number of hydroxyl groups per glycosyl unit) can be 1, 2, or 3, or another suitable DS. In some embodiments, 1%, 2%, 3%, 4% 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 80%, 85%, 90%, 95%, 96%, 97%, 98%, 99%, or 100% of glycan units are substituted or derivatized. In some embodiments, the degree of substitution varies between subunits, e.g., a certain percentage is not derivatized, exhibits a DS of 1, exhibits a DS of 2, or exhibits a DS of 3. Any desired mixture can be generated, e.g. 0-99% of subunits are not derivatized, 0-99% of subunits exhibit a DS of 1, 0-99% of subunits exhibit a DS of 2, and 0-99% of subunits exhibit a DS of 3, with the total making up 100%. The degree of substitution can be controlled by adjusting the average number of moles of substituent added to a glycosyl moiety (molar substitution (MS)). The distribution of substituents along the length of the glycan oligo- or polysaccharide chain can be controlled by adjusting the reaction conditions, reagent type, and extent of substitution. In some embodiments, the monomeric subunits are substituted with one or more of an acetate ester, sulfate half-ester, phosphate ester, or a pyruvyl cyclic acetal group.

The molar percentage of species with a degree of polymerization (DP) of n (denoted here as DP(n)) in a population is determined by high performance liquid chromatography (HPLC), e.g., on an Agilent 1260 BioInert series instrument equipped with a refractive index (RI) detector and a variety of columns familiar to those skilled in the art using water as the mobile phase. The columns are selected from chemistries including, but not limited to, HILIC, metal coordination, and aqueous size-exclusion chromatography that best isolate the species of interest. Molar % DP(n) is determined by the formula:

$$\% DP(n) = 100 * AUC[DP(n)]/AUC[DP(\text{total})],$$

where AUC is defined as the area under the curve for the species of interest as determined by calibration to known standards. The molar percentage of glycosidic bond isomers (% alpha and % beta) are determined by nuclear magnetic resonance (NMR) spectroscopy using a variety of 2D techniques familiar to those skilled in the art. Alpha- and beta-isomers may be distinguished, e.g., by their distinct shift on the NMR spectrum and the molar percentage is determined by the formula:

$$(\text{glycosidic isomer } n) \text{ of glycosidic bonds} = 100 * AUC[\text{shift (isomer } n)]/AUC[\text{shift (isomer alpha} + \text{isomer beta})],$$

where AUC is defined as the area under the curve at a specific shift value known to represent the desired isomer n. The molar percentage of regiochemical isomers is determined in an analogous fashion using the formula:

% (regioisomer $n$) of regioisomers=100*AUC[shift (regioisomer $n$)]/AUC[shift (all regioisomers)].

The relative percentage of monomeric sugars making up the oligomeric population is determined, e.g., by total acidic digestion of the oligomeric sample followed by conversion to the alditol acetate followed by gas chromatographic (GC) analysis of the resultant monomeric solutions compared against GC of known standards. The molar percentage of monomer(n), where n can be any sugar, is determined by the formula:

% (sugar $n$)=100*AUC[sugar $n$]/AUC[total of all monomeric sugars].

In some embodiments, the solubility of the preparation of glycan therapeutics can be controlled, e.g. by selecting the charge, structure (e.g. DP, degree of branching), and/or derivatization of the glycan units.

Preparations of glycan therapeutics consisting of one type of sugar unit uniformly linked in linear chains are usually water insoluble at 23° C. even when the glycans have a low molecular weight with degrees of polymerization (DP) between 20 and 30. The degree of solubility of the glycan therapeutics can be adjusted, e.g. by the introduction of (1→6)-linkages and alternating glycosidic bonds in the glycans. The extra degrees of freedom provided by the rotation about the C-5 to C-6 bonds gives higher solution entropy values. Homoglycans with two types of sugar linkages or heteroglycans composed of two types of sugars are generally more soluble than homogeneous polymers. Ionization of linear homoglycans can add solubility, e.g. to that of gels. The viscosity of the solutions often depends on the tertiary structures of the glycans.

In some embodiments, the glycan therapeutic preparations are highly branched, e.g. have an average DB of at least 0.01, 0.05, or 0.1. In some embodiments, the glycan therapeutic preparations have an average DB of 0.1 to 0.2. The glycan therapeutic preparations comprising branched oligosaccharide are highly soluble. In some embodiments, glycan therapeutic preparations can be concentrated to at least to 55 Brix, 65 Brix, 60 Brix, 65 Brix, 70 Brix, 75 Brix, 80 Brix, or at least 85 Brix without obvious solidification or crystallization at 23° C. (final solubility limit). In some embodiments, glycan therapeutic preparations are concentrated to at least about 0.5 g/ml, 1 g/ml, 1.5 g/ml, 2 g/ml, 2.5 g/ml, 3 g/ml, 3.5 g/ml or at least 4 g/ml without obvious solidification or crystallization at 23° C. (final solubility limit).

In some embodiments, the glycan therapeutic preparations (e.g. oligosaccharides) are branched, e.g. have an average DB of at least 0.01, 0.05, or 0.1 and has a final solubility limit in water of at least about 70 Brix, 75 Brix, 80 Brix, or at least about 85 Brix at 23° C. or is at least about 1 g/ml, 2 g/ml or at least about 3 g/ml.

In some embodiments, the preparation of glycan therapeutics has a final solubility limit of at least 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 5 g/L, 10 g/L, 20 g/L, 30 g/L, 40 g/L, 50 g/L, 100 g/L, 200 g/L, 300 g/L, 400 g/L, 500 g/L, 600 g/L, 700 g/L, 800 g/L, 900 g/L, 1000 g/L in deionized water, or in a suitable buffer such as, e.g., phosphate-buffered saline, pH 7.4 or similar physiological pH) and at 20° C. In some embodiments, the preparation of glycan therapeutics is greater than 50%, greater than 60%, greater than 70%, greater than 80%, greater than 90%, greater than 95%, greater than 96%, greater than 97%, greater than 98%, greater than 99%, or greater than 99.5% soluble with no precipitation observed at a concentration of greater than 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 5 g/L, 10 g/L, 20 g/L, 30 g/L, 40 g/L, 50 g/L, 100 g/L, 200 g/L, 300 g/L, 400 g/L, 500 g/L, 600 g/L, 700 g/L, 800 g/L, 900 g/L, 1000 g/L in deionized water, or in a suitable buffer such as, e.g., phosphate-buffered saline, pH 7.4 or similar physiological pH) and at 20° C.

In some embodiments, the preparation of glycan therapeutics has a desired degree of sweetness. For example, sucrose (table sugar) is the prototype of a sweet substance. Sucrose in solution has a sweetness perception rating of 1, and other substances are rated relative to this (e.g., fructose, is rated at 1.7 times the sweetness of sucrose). In some embodiments, the sweetness of the preparation of glycan therapeutics ranges from 0.1 to 500,000 relative to sucrose. In some embodiments, the relative sweetness is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 25000, 50000, 75000, 100000, 150000, 200000, 250000, 300000, 350000, 40000, 450000, 500000, or more than 500,000 relative to sucrose (with sucrose scored as one). In some embodiments, the preparation of glycan therapeutics is mildly sweet, or both sweet and bitter.

In some embodiments, the preparation of glycan therapeutics, e.g. a preparation that is substantially DP2+ or DP3+ (e.g. at least 80%, 90%, or at least 95%, or a fractionated preparation of DP2+ or DP3+), is substantially imperceptible as sweet and the relative sweetness is about 0, 0.0001, 0.001, 0.005, 0.01, 0.05, 0.1, 0.2, 0.3, 0.4, 0.5, 0.6, 0.7, or about 0.8 relative to sucrose (with sucrose scored as one).

Identification and Characterization of Glycan Therapeutic Preparations

If desired, the glycan therapeutic preparations can be characterized. For example, preparations of glycan therapeutics that have been identified in one or more in vitro or in vivo assays to increase growth of health promoting bacteria or that suppress the growth of microbial pathogens may be further characterized by any method known in the art and by the methods described herein. Suitable methods are further described in the Examples.

For glycan therapeutic preparations, the monomeric building blocks (e.g. the monosaccharide or glycan unit composition), the anomeric configuration of side chains, the presence and location of substituent groups, degree of polymerization/molecular weight and the linkage pattern can be identified by standard methods known in the art, such as, e.g. methylation analysis, reductive cleavage, hydrolysis, GC-MS (gas chromatography-mass spectrometry), MALDI-MS (Matrix-assisted laser desorption/ionization-mass spectrometry), ESI-MS (Electrospray ionization-mass spectrometry), HPLC (High-Performance Liquid chromatography with ultraviolet or refractive index detection), HPAEC-PAD (High-Performance Anion-Exchange chromatography with Pulsed Amperometric Detection), CE (capillary electrophoresis), IR (infra red)/Raman spectroscopy, and NMR (Nuclear magnetic resonance) spectroscopy techniques. For polymers of crystalline consistency, the crystal structure can be solved using, e.g., solid-state NMR, FT-IR (Fourier transform infrared spectroscopy), and WAXS (wide-angle X-ray scattering). The DP, DP distribution, and polydispersity can be determined by, e.g., viscosimetry and SEC (SEC-HPLC, high performance size-exclusion chromatography). Alien groups, end groups and substituents can be identified, e.g., using SEC with labeling, aqueous analytics, MALDI-MS, FT-IR, and NMR. To identify the monomeric components of the glycans methods such as, e.g. acid-catalyzed hydrolysis, HPLC (high performance liquid chromatography) or GLC (gas-liquid chromatography) (after conversion to alditol acetates) may be used. To determine the linkages present in the glycans, in one example, the polysaccharide is methylated with methyl iodide and strong base in DMSO, hydrolysis is performed, a reduction to partially methylated alditols is achieved, an acetylation to methylated alditol acetates is performed, and the analysis is carried out by GLC/MS (gas-liquid chromatography coupled with mass spectrometry). In some embodiments, to determine the polysaccharide sequence a partial depolymerization is carried out using an acid or enzymes to determine the structures. Possible structures of the polysaccharide are compared to those of the hydrolytic oligomers, and it is determined which one of the possible structures could produce the oligomers. To identify the anomeric configuration, in one example, the intact polysaccharide or a preparation of oligosaccharides are subjected to enzymatic analysis, e.g. they are contacted with an enzyme that is specific for a particular type of linkage, e.g., β-galactosidase, or α-glucosidase, etc., and NMR may be used to analyze the products.

For example, the distribution of (or average) degree of polymerization (DP) of a glycan therapeutic preparation may be measured by injecting a sample with a concentration of, e.g., 10-100 mg/mL onto an Agilent 1260 BioPure HPLC (or similar) equipped with a 7.8×300 mm BioRad Aminex HPX-42A column (or similar) and RI detector as described, e.g., in Gómez et al. (Purification, Characterization, and Prebiotic Properties of Pectic Oligosaccharides from Orange Peel Wastes, J Agric Food Chem, 2014, 62:9769). Alternatively, a sample with a concentration may be injected into a Dionex ICS5000 HPLC (or similar) equipped with a 4×250 mm Dionex CarboPac PA1 column (or similar) and PAD detector as described, e.g., in Holck et al., (Feruloylated and nonferuloylated arabino-oligosaccharides from sugar beet pectin selectively stimulate the growth of bifidobacterium spp. in human fecal in vitro fermentations, Journal of Agricultural and Food Chemistry, 2011, 59(12), 6511-6519). Integration of the resulting spectrum compared against a standard solution of oligomers allows determination of the average DP.

Distribution of molecular weights can be measured, e.g, by MALDI mass spectrometry. Oligosaccharide concentration can be measured with a Mettler-Toledo sugar refractometer (or similar) with the final value adjusted against a standardized curve to account for refractive differences between monomers and oligomers.

Distribution of glycoside regiochemistry can be characterized, e.g., by a variety of 2D-NMR techniques including COSY, HMBC, HSQC, DEPT, and TOCSY analysis using standard pulse sequences and a Bruker 500 MHz spectrometer. Peaks can be assigned by correlation to the spectra of naturally occurring polysaccharides with known regiochemistry.

In some embodiments, the relative peak assignment of a sample is dependent on a number of factors including, but not limited to, the concentration and purity of the sample, the identity and quality of the solvent (e.g., the isotopically labeled solvent), and the pulse sequence utilized. As such, in embodiments, the relative peak assignment of, for example, a glycan comprising glucose may vary (e.g., by about 0.01 ppm, about 0.02 ppm, or about 0.05 ppm) when the NMR spectrum is obtained in similar conditions due to said factors. In these instances as used herein, the terms "corresponding peak" or "corresponding peaks" refer to NMR peaks associated with the same sample but that vary (e.g., by about 0.01 ppm, about 0.02 ppm, or about 0.05 ppm) due to factors including, for example, the concentration and purity of the sample, the identity and quality of the isotopically labeled solvent, and the pulse sequence utilized.

Monomeric compositions of oligomers may be measured, e.g., by the complete hydrolysis method in which a known amount of oligomer is dissolved into a strong acid at elevated temperature and allowed sufficient time for total hydrolysis to occur. The concentration of individual monomers may then be measured by the HPLC or GC methods described herein and known in the art to achieve relative abundance measurements as in Holck et al. Absolute amounts can be measured by spiking the HPLC sample with a known amount of detector active standard selected to prevent overlap with any of the critical signals.

The degree of branching in any given population may be measured by the methylation analysis method established, e.g, by Hakomori (J. Biochem. (Tokyo), 1964, 55, 205). With these data, identification of potential repeat units may be established by combining data from the total hydrolysis, average DP, and methylation analysis and comparing them against the DEPT NMR spectrum. Correlation of the number of anomeric carbon signals to these data indicates if a regular repeat unit is required to satisfy the collected data as demonstrated, e.g., in Harding, et al. (Carbohydr. Res. 2005, 340, 1107).

Preparation of glycan therapeutics (e.g. those comprising monosaccharide or disaccharide glycan units such as glucose, galactose, fucose, xylose, arabinose, rhamnose, and mannose) may be identified using one, two, three, or four of the following parameters: a) the presence of 2, 3, 4, 5, 6, 7 or more (e.g. at least 4 or 5) diagnostic anomeric NMR peaks each representing a different glycosidic bond type, b) an alpha- to beta-bond ratio between about 0.8 to 1 and about 5 to 1 (e.g. between about 1:1 and 4:1, commonly favoring the alpha bond type), c) at least 2 or at least 3 different glycoside regiochemistries from the list of 1,2-; 1,3-; 1,4-; and 1,6-substituted and at least 2 or at least 3 different glycoside regiochemistries from list of 1,2,3-; 1,2,4-; 1,2,6-; 1,3,4-; 1,3,6-; and 1,4,6-substituted, and d) a DP distribution in which at least 50%, 60%, 70% or at least 80% of the individual species have a DP of at least 2, at least 3, between 3 and 30 or between 5 and 25. In some embodiments, glycan therapeutics represent a unique structural class distinct from naturally occurring oligosaccharides. In some embodiments, glycan therapeutic preparations have novel average properties (e.g., DP, DB, alpha:beta glycosidic bond ratio) that are distinct from naturally occurring preparations of oligosaccharides. These structural features may be quantitated by the methods described herein. The glycan therapeutic preparations described herein have at least one, two, three, four, or at least five of the following characteristics:

(i) a distribution of molecular weights ranging, e.g. from about DP3 to about DP30 or from about DP5 to about DP25 that may be identified by quantitative mass spectrometry measurements, SEC-HPLC, IAC-HPLC, or IEC-HPLC;

(ii) a significant proportion of both alpha and beta bonds, with bond ratios, e.g., ranging from 0.8:1, 1:1, 2:1, 3:1, 4:1, to 5:1 (generally favoring the alpha stereochemistry) that may be identified by a variety of NMR techniques including the HSQC pulse sequence which allows explicit discrimination and quantitation of signals from alpha and beta glycosides. The presence of both alpha- and beta-glycosidic bonds in the observed ratios (see Table 6, showing the presence of a large proportion of both alpha and beta bonds across the single and multi-sugar glycans tested) in glycan therapeutic preparation of some embodiments, is distinct from preparations of naturally occurring oligo- or polysaccharides which generally favor one primary glycosidic stereochemistry and optionally comprise only a relatively small portion of the opposing stereochemistry;

(iii) presence of at least one, two, three or four glycoside regiochemistries that may be identified either by a fingerprint NMR process or by the permethylation branching identification developed by Hakomori, et al. In some embodiments, glycan therapeutic preparations have at least 0.1%, 0.2%, 0.5%, 1%, 2%, 3%, 4%, 5%, 6%, 7%, 8%, 9%, or at least 10% of one, two, three or four of the 1,2-; 1,3-; 1,4-, and 1,6-glycoside bond types. In some embodiments, glycan therapeutic preparations have at least 0.1%, 0.2%, 0.5%, 1%, 2%, 3%, 4%, 5%, 6%, 7%, 8%, 9%, or at least 10% of two of the 1,2-; 1,3-; 1,4-, and 1,6-glycoside bond types. In some embodiments, glycan therapeutic preparations have at least 0.1%, 0.2%, 0.5%, 1%, 2%, 3%, 4%, 5%, 6%, 7%, 8%, 9%, or at least 10% of three of the 1,2-; 1,3-; 1,4-, and 1,6-glycoside bond types. In some embodiments, glycan therapeutic preparations have at least 0.1%, 0.2%, 0.5%, 1%, 2%, 3%, 4%, 5%, 6%, 7%, 8%, 9%, or at least 10% of all four of the 1,2-; 1,3-; 1,4-, and 1,6-glycoside bond types. In some embodiments, the glycan therapeutic preparation additionally comprises at least 0.1%, 0.2%, 0.5%, 1%, 2%, 3%, 4% or at least 5% of branched bond types. In some embodiments, the glycan therapeutic preparation comprises at least 0.1%, 0.2%, 0.5%, 1%, 2%, 3%, 4% or at least 5% of at least one, two, or at least three branched bond types including but not limited to 1,3,6-; 1,4,6-; or 1,2,4-glycosides. In some embodiments, the glycan therapeutic preparation comprises at least two branched bond types of 1,3,6-; 1,4,6-; or 1,2,4-glycosides. In some embodiments, the glycan therapeutic preparation comprises at least 0.1%, 0.2%, 0.5%, 1%, 2%, 3%, 4% or at least 5% of three branched bond types of 1,3,6-; 1,4,6-; or 1,2,4-glycosides. Sugars that do not have a hydroxyl group at a given position X will not will not have the 1,X-bond type, e.g. fucose (6-dehydroxy-galactose) will not have 1,6-glycosidic bonds but will have 1,2-; 1,3-; and 1,4-glycosidic bonds. In some embodiments, the glycan therapeutic preparation comprises at least 0.1%, 02%, 0.5%, 1%, 2%, or at least 3% of monomeric glycan units in furanose form. The presence of a large number of glycoside regiochemistries and branching (see FIG. 4A, FIG. 4B, and FIG. 4C for 3 exemplary glycans) in glycan therapeutic preparation of some embodiments, is distinct from preparations of naturally occurring oligo- or polysaccharides which generally favor specific bond architectures. Although all of these regiochemistries are known to occur in oligosaccharides of natural sources, preparations of naturally sourced oligosaccharide do not comprise the number and complexity of regiochemistries that are exhibited by glycan therapeutic preparations of some embodiments.

Figure 5:
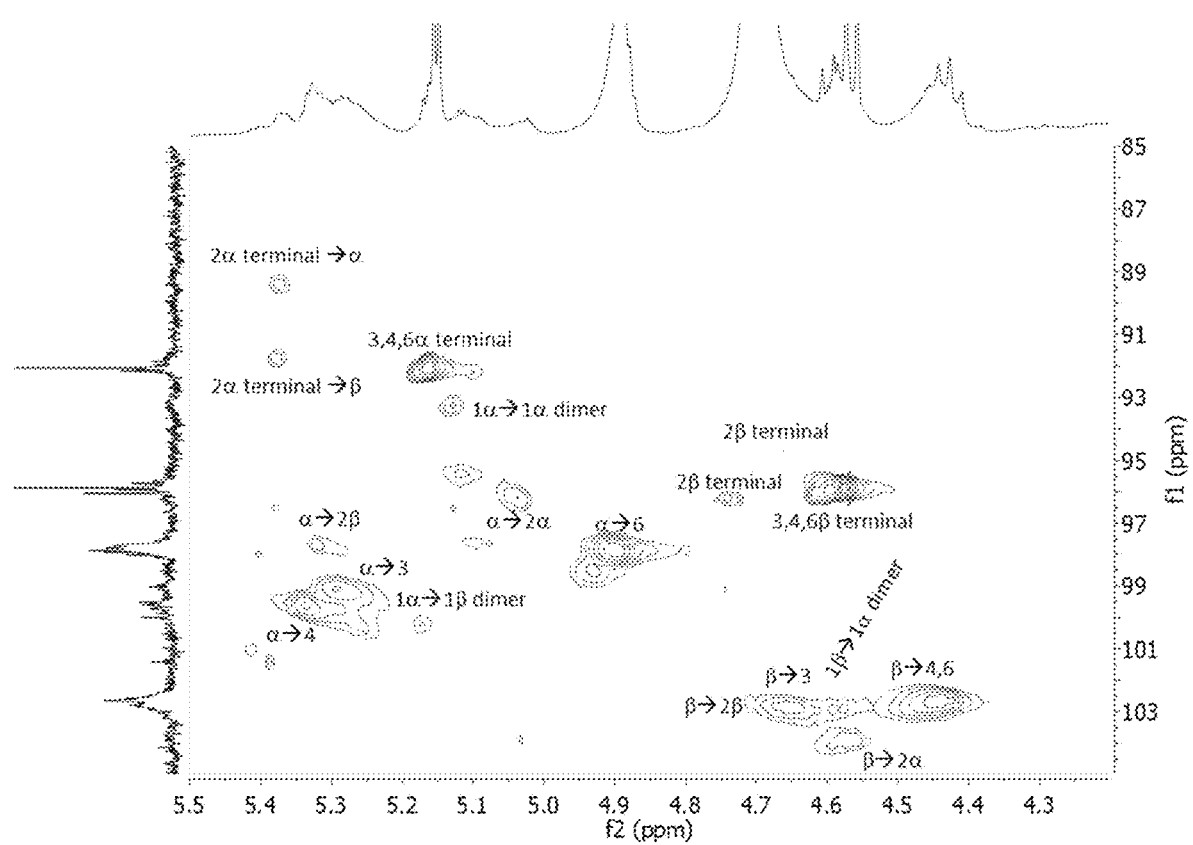
FIG. 5. A representative partial assignment of the peaks in the anomeric region of a glu100 sample $^1$H-$^{13}$C HSQC spectrum showing the separation between alpha and beta isomers in the $^1$H axis, with alpha isomers downfield ($^1$H>4.8 ppm in this case) and beta isomers upfield ($^1$H<4.8 ppm in this case). In addition, terminal and internal sugars can be distinguished in the $^{13}$C axis with terminal sugars upfield ($^{13}$C<94 ppm for alpha and $^{13}$C<100 ppm for beta in this case) and internal sugars downfield ($^{13}$C>94 ppm for alpha and $^{13}$C>100 ppm for beta in this case).

(iv) a distribution of glycosidic bonds that represents at least 50%, 60%, 70%, 80% or at least 90% of all possible combinations of regio- and stereochemistries. Individually, the regiochemical distribution can be determined by branching analysis and the stereochemical distribution can be determined by NMR. The HSQC-NMR. In some embodiments, the glycan therapeutic preparations exhibit a diversity of peaks in the anomeric region that are associated with a multiplicative combination of both regiochemistry and stereochemistry. In some embodiments, the glycan therapeutic preparation comprises at least two or at least three of alpha-1,2-; alpha-1,3-; alpha-1,4-; and alpha-1,6-glycosides and at least two, or at least three of beta-1,2-; beta-1,3-; beta-1,4-; and beta-1,6-glycosides. In some embodiments, the glycan therapeutic preparation comprises all four of alpha-1,2-; alpha-1,3-; alpha-1,4-; and alpha-1,6-glycosides and all four of beta-1,2-; beta-1,3-; beta-1,4-; and beta-1,6-glycosides. As an exemplar, HSQC of a glu100 preparation shows that the preparation contains all alpha-1,2-; alpha-1,3-; alpha-1,4-; and alpha-1,6-glycosides as well as all beta-1,2-; beta-1,3-; beta-1,4-; and beta-1,6-glycosides. Sugars that do not have a hydroxyl group at a given position X will not will not have the 1,X-bond type, e.g. fucose (6-dehydroxy-galactose) will not have 1,6-glycosidic bonds but will have 1,2-; 1,3-; and 1,4-glycosidic bonds;

(v) a unique HSQC "fingerprint" that is the result of the additive nature of the HSQC pulse sequence. For any given glycan, the HSQC spectra allow the identification of peaks that are unique to specific regio- and stereochemical bond arrangement. For example, FIG. 5 shows a partial assignment of the spectra of a glu100 preparation demonstrating how these peaks may be used to identify specific glycosidic regio- and stereochemistries. Component glycan units (e.g. sugars) within a glycan demonstrate spin-isolation in the HSQC pulse sequence and the HSQC spectrum of any glycan consisting of multiple sugars is the sum of peaks of its individual sugars. Glycan unit constituents (e.g. monomers) can be identified by an HSQC spectrum that shows 4, 5, 6 or more of the peaks listed in Table 7 for each of its component glycan units (e.g. sugars). The spectra in FIGS. 3A-3C exemplify this by comparing the spectra of preparations of glu100, gal100, and glu50gal50.

Pharmaceutical Compositions, Medical Foods, and Unit Dosage Forms

Provided herein are also methods of producing pharmaceutical compositions comprising a glycan therapeutic preparation that meets one or more, two or more, three or more or four or more of the characteristics of the preparations described herein (including criteria (i)-(v) above). In particular, methods include providing a glycan therapeutic preparation and acquiring the value(s) for one or more, two or more, or three or more characteristics of the preparation, including, e.g., i) the degree of polymerization (DP), ii) the average degree of branching (DB, branching points per residue), iii) the ratio of alpha-glycosidic to beta-glycosidic bonds, iv) the identity of the glycan units, and v) the ratio of glycan units, and producing a pharmaceutical composition comprising a glycan therapeutic preparation if the desired or predetermined criteria of the preparation are met within a desired range of deviation.

Methods for formulating the glycan therapeutic preparation into a pharmaceutical composition, medical food or dietary supplement are known in the art and may include one or more, two or more, three or more, or four or more of the following steps: (i) formulating the preparation into drug product, (ii) packaging the preparation, (iii) labeling the packaged preparation, and (iv) selling or offering for sale the packaged and labeled preparation. Formulating the glycan therapeutic preparation into a drug product is known in the art and may include one or more, two or more, three or more, or four or more of the following steps: (i) removing unwanted constituents from the preparation, (ii) reducing the volume of the preparation, (iii) sterilizing the preparation, (iv) admixing the preparation with a pharmaceutically acceptable excipient or carrier, (v) admixing the preparation with a second drug or pharmaceutical agent, (vi) formulating the preparation into a suitable consistency, such as, e.g., aqueous diluted solution, a syrup or a solid, (vii) formulating the preparation into a suitable dosage form, e.g. into a tablet, pill or capsule.

In some embodiments, the glycan therapeutic preparation undergoes further processing to produce either glycan therapeutic syrup or powder. For example, in one variation, the glycan therapeutic preparation is concentrated to form a syrup. Any suitable methods known in the art to concentrate a solution may be used, such as the use of a vacuum evaporator. In another variation, the glycan therapeutic preparation is spray dried to form a powder. Any suitable methods known in the art to spray dry a solution to form a powder may be used.

Provided herein are pharmaceutical compositions, medical foods and dietary supplements comprising glycan therapeutic preparations. Optionally, the pharmaceutical compositions, medical foods and dietary supplements comprising glycan therapeutic preparations further comprise a second agent, e.g., a prebiotic substance and/or a probiotic bacterium. In some embodiments, the pharmaceutical compositions and medical foods and dietary supplements comprising glycan therapeutic preparations further comprise a micronutrient. In some embodiments, the pharmaceutical compositions and medical foods and dietary supplements comprising glycan therapeutic preparations do not contain a prebiotic substance. In some embodiments, the pharmaceutical compositions and medical foods and dietary supplements comprising glycan therapeutic preparations do not contain a probiotic bacterium. Further, optionally, the pharmaceutical compositions and medical foods and dietary supplements comprising glycan therapeutic preparations comprise one or more excipients or carriers, including diluents, binders, disintegrants, dispersants, lubricants, glidants, stabilizers, surfactants, flavoring agents, and colorants.

In some embodiments, the pharmaceutical compositions or medical foods and dietary supplements comprise a glycan therapeutic preparation of glu100, ara100, xyl100, gal100, glu50gal50, gal75xyl25, ara50gal50, man62glu38, ara50xyl50, man52glu29gal19, or glu33gal33fuc33.

In some embodiments, the pharmaceutical compositions or medical foods and dietary supplements comprise a glycan therapeutic preparation of glu100, ara100, xyl100, glu50gal50, man52glu29gal19, or glu33gal33fuc33.

In some embodiments, the pharmaceutical compositions or medical foods and dietary supplements comprise a glycan therapeutic preparation of glu100 and man52glu29gal19.

In some embodiments, pharmaceutical compositions and medical foods and dietary supplements comprising glycan therapeutic preparations (and kits comprising same) comprise one or more micronutrient. In some embodiments, the micronutrient is selected from the group consisting of a trace mineral, choline, a vitamin, and a polyphenol.

In some embodiments, the micronutrient is a trace metal. Trace minerals suitable as a micronutrient include, but are not limited to, boron, cobalt, chromium, calcium, copper, fluoride, iodine, iron, magnesium, manganese, molybdenum, selenium, and zinc.

In some embodiments, the micronutrient is a vitamin. Vitamins suitable as a micronutrient include, but are not limited to, Vitamin B complex, Vitamin B1 (thiamin), Vitamin B2 (riboflavin), Vitamin B3 (niacin), Vitamin B5 (pantothenic acid), Vitamin B6 group (pyridoxine, pyridoxal, pyridoxamine), Vitamin B7 (biotin), Vitamin B8 (ergadenylic acid), Vitamin B9 (folic acid), Vitamin B12 (cyanocobalamin), Choline, Vitamin A (retinol), Vitamin C (ascorbic acid), Vitamin D, Vitamin E (tocopherol), Vitamin K, carotenoids (alpha carotene, beta carotene, cryptoxanthin, lutein, lycopene) and zeaxanthin.

In some embodiments, the micronutrient is a polyphenol. Polyphenols are chemical compounds or molecules that are characterized by having at least one aromatic ring with one or more hydroxyl groups. In some embodiments, the polyphenol is a synthetic polyphenol or a naturally occurring polyphenol. In some embodiments, the polyphenol is a naturally occurring polyphenol and is derived from plant source material.

In some embodiments, the polyphenol is a flavonoid or catechin. In some embodiments, the flavonoid or catechin is selected from anthocyanins, chalcones, dihydrochalcones, dihydroflavonols, flavanols, flavanones, flavones, flavonols and isoflavonoids. In some embodiments, the polyphenol is a lignan.

In some embodiments, the polyphenol is selected from alkylmethoxyphenols, alkylphenols, curcuminoids, furanocoumarins, hydroxybenzaldehydes, hydroxybenzoketones, hydroxycinnamaldehydes, hydroxycoumarins, hydroxyphenylpropenes, methoxyphenols, naphtoquinones, phenolic terpenes, and tyrosols. In some embodiments, the polyphenol is a tannin or tannic acid.

In some embodiments, the polyphenol is selected from hydroxybenzoic acids, hydroxycinnamic acids, hydroxyphenylacetic acids, hydroxyphenylpropanoic acids, and hydroxyphenylpentanoic acids. In some embodiments, the polyphenol is a stilbene.

In some embodiments, the polyphenol is any one of the polyphenols listed in Table 5.

Further, if desired, the pharmaceutical compositions and medical foods and dietary supplements comprising glycan therapeutic preparations may comprise therapeutically active agents, prebiotic substances and/or probiotic bacteria. Alternatively or in addition, therapeutically active agents, prebiotic substances and/or probiotic bacteria may be administered separately (e.g. prior to, concurrent with or after administration of the glycan therapeutics) and not as a part of the pharmaceutical composition or medical food or dietary supplement (e.g. as a co-formulation) of glycan therapeutics. In some embodiments, pharmaceutical compositions or medical foods or dietary supplements comprising preparations of glycan therapeutics are administered in combination with a recommended or prescribed diet, e.g. a diet that is rich in probiotic and/or prebiotic-containing foods, such as it may be determined by a physician or other healthcare professional. Therapeutically active agents, prebiotic substances and/or probiotic bacteria may be administered to modulate the gut microbiome of the subject. In some embodiments, the combined effect (e.g. on the number or intensity of the microbial, genomic or functional shifts) is additive. In other embodiments, the combined effect (e.g. on the number or intensity of the microbial, genomic or functional shifts) is synergistic.

In some embodiments, the pharmaceutical compositions and medical foods and dietary supplements comprising glycan therapeutic preparations described herein further comprise a prebiotic substance or preparation thereof.

In some embodiments, prebiotics may be administered to a subject receiving the pharmaceutical compositions or medical foods or dietary supplements comprising glycan therapeutic preparations described herein. Prebiotics are non-digestible substances that when consumed may provide a beneficial physiological effect on the host by selectively stimulating the favorable growth or activity of a limited number of indigenous bacteria in the gut (Gibson G R, Roberfroid M B. Dietary modulation of the human colonic microbiota: introducing the concept of prebiotics. J Nutr. 1995 June; 125(6):1401-12.). A prebiotic such as a dietary fiber or prebiotic oligosaccharide (e.g. crystalline cellulose, wheat bran, oat bran, corn fiber, soy fiber, beet fiber and the like) may further encourage the growth of probiotic and/or commensal bacteria in the gut by providing a fermentable dose of carbohydrates to the bacteria and increase the levels of those microbial populations (e.g. lactobacilli and bifidobacteria) in the gastrointestinal tract.

Prebiotics include, but are not limited to, various galactans and carbohydrate based gums, such as psyllium, guar, carrageen, gellan, lactulose, and konjac. In some embodiments, the prebiotic is one or more of galactooligosaccharides (GOS), lactulose, raffinose, stachyose, lactosucrose, fructo-oligosaccharides (FOS, e.g. oligofructose or oligofructan), inulin, isomalto-oligosaccharide, xylo-oligosaccharides (XOS), paratinose oligosaccharide, isomaltose oligosaccharides (IMOS), transgalactosylated oligosaccharides (e.g. transgalacto-oligosaccharides), transgalactosylate disaccharides, soybean oligosaccharides (e.g. soyoligosaccharides), chitosan oligosaccharide (chioses), gentiooligosaccharides, soy- and pectin-oligosaccharides, glucooligosaccharides, pecticoligosaccharides, palatinose polycondensates, difructose anhydride III, sorbitol, maltitol, lactitol, polyols, polydextrose, linear and branched dextrans, pullalan, hemicelluloses, reduced paratinose, cellulose, beta-glucose, beta-galactose, beta-fructose, verbascose, galactinol, xylan, inulin, chitosan, beta-glucan, guar gum, gum arabic, pectin, high sodium alginate, and lambda carrageenan, or mixtures thereof.

Prebiotics can be found in certain foods, e.g. chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso. In some embodiments, the glycan therapeutics described herein are administered to a subject in conjunction with a diet that includes foods rich in prebiotics. Suitable sources of soluble and insoluble fibers are commercially available.

In some embodiments, the pharmaceutical compositions and medical foods and dietary supplements comprising glycan therapeutic preparations further comprise a probiotic bacterium or preparation thereof, e.g., derived from bacterial cultures that are generally recognized as safe (GRAS) or known commensal or probiotic microbes. In some embodiments, to maximize the beneficial effect of endogenous commensal microbes or exogenously administered probiotic microorganisms, the pharmaceutical compositions and medical foods and dietary supplements comprising glycan therapeutic preparations are administered to stimulate the growth and/or activity of advantageous bacteria in the GI tract.

Examples of suitable probiotics include, but are not limited to, organisms classified as genera *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacillus, Bacillus, Enterococcus, Escherichia, Streptococcus, Saccharomyces, Streptomyces*, and family Christensenellaceae. Non-exclusive examples of probiotic bacteria that can be used in the methods and compositions described herein include *L. acidophilus, Lactobacillus* species, such as *L. crispatus, L. casei, L. rhamnosus, L. reuteri, L. fermentum, L. plantarum, L. sporogenes,* and *L. bulgaricus*, as well as *Bifidobacterum* species, such as *B. lactis, B. animalis, B. bifidum, B. longum, B. adolescentis*, and *B. infantis*. Yeasts, such as *Saccharomyces boulardii*, are also suitable as probiotics for administration to the gut, e.g. via oral dosage forms or foods. For example, yogurt is a product which already contains bacteria species, such as *Lactobacillus bulgaricus* and *Streptococcus thermophilus*.

Beneficial bacteria for the modulation of the gastrointestinal microbiota may include bacteria that produce organic acids (lactic & acetic acids) or that produce cytotoxic or cytostatic agents (to inhibit pathogenic growth), such as, e.g., hydrogen peroxide ($H_2O_2$) and bacteriocins. Bacteriocins are small antimicrobial peptides which can kill both closely-related bacteria, or exhibit a broader spectrum of activity (e.g., nisin).

Beneficial bacteria may include one or more of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia municiphilia, minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*. In some embodiments, the probiotic or commensal bacteria include one or more of the bacteria listed in Table 1.

The prebiotic substances and probiotic strains that may be combined with glycan therapeutics described herein to produce a composition or kit may be isolated at any level of purity by standard methods and purification can be achieved by conventional means known to those skilled in the art, such as distillation, recrystallization and chromatography. The cultivated bacteria to be used in the composition are separated from the culture broth with any method including, without limitations, centrifuging, filtration or decantation. The cells separated from the fermentation broth are optionally washed by water, saline (0.9% NaCl) or with any suitable buffer. The wet cell mass obtained may be dried by any suitable method, e.g., by lyophilization.

In some embodiments, the probiotic bacteria are lyophilized vegetative cells. In some embodiments, the preparations of spores from sporulating probiotic bacteria are used.

In one embodiment, a pharmaceutical glycan therapeutic composition further comprises a prebiotic and probiotic. In one embodiment, the pharmaceutical composition comprises probiotics whose viability has been partially attenuated (e.g. a mixture comprising 10%, 20%, 30%, 40%, 50% or more non-viable bacteria), or probiotics consisting solely of non-viable microbes. The compositions may further comprise microbial membranes and/or cell walls that have been isolated and purified from killed microbes. If desired, the probiotic organism can be incorporated into the pharmaceutical glycan therapeutic composition as a culture in water or another liquid or semisolid medium in which the probiotic remains viable. In another technique, a freeze-dried powder containing the probiotic organism may be incorporated into a particulate material or liquid or semisolid material by mixing or blending.

In some embodiments, the pharmaceutical compositions and medical foods and dietary supplements comprising glycan therapeutic preparations further comprise a second therapeutic agent or preparation thereof. In some embodiments, the therapeutic agent is an antibiotic, an antifungal agent, an antiviral agent, or an anti-inflammatory agent (e.g. a cytokine, hormone, etc.). Antibiotics include aminoglycosides, such as amikacin, gentamicin, kanamycin, neomycin, streptomycin, and tobramycin; cephalosporins, such as cefamandole, cefazolin, cephalexin, cephaloglycin, cephaloridine, cephalothin, cephapirin, and cephradine; macrolides, such as erythromycin and troleandomycin; penicillins, such as penicillin G, amoxicillin, ampicillin, carbenicillin, cloxacillin, dicloxacillin, methicillin, nafcillin, oxacillin, phenethicillin, and ticarcillin; polypeptide antibiotics, such as bacitracin, colistimethate, colistin, polymyxin B; tetracyclines, such as chlortetracycline, demeclocycline, doxycycline, methacycline, minocycline, tetracycline, and oxytetracycline; and miscellaneous antibiotics such as chloramphenicol, clindamycin, cycloserine, lincomycin, rifampin, spectinomycin, vancomycin, viomycin and metronidazole.

The glycan therapeutic preparations described herein, other therapeutically active agents, prebiotic substances, micronutrients and probiotics may be comingled or mixed in a single pharmaceutical composition or medical food or dietary supplement. In other embodiments, they may be contained in separate containers (and/or in various suitable unit dosage forms) but packaged together in one or more kits. In some embodiments, the preparations or compositions are not packaged or placed together. A physician may then administer the preparations or compositions together, e.g. prior to, concomitant with, or after one another. In some embodiments, the preparations or compositions act synergistically in modulating the microbiota in a subject, e.g., in the GI tract.

In some embodiments, a pharmaceutical composition comprises between 0.1% and 100% glycan therapeutic preparation by w/w, w/v, v/v or molar %. In another embodiment, a pharmaceutical composition comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% of glycan therapeutic preparation by w/w, w/v, v/v or molar %. In one embodiment, a pharmaceutical composition comprises about 1-90%, about 10-90%, about 20-90%, about 30-90%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 90-96%, about 93-96%, about 93-95%, about 94-98%, about 93-99%, or about 90-100% of glycan therapeutic preparation by w/w, w/v, v/v or molar %.

A pharmaceutical composition comprising a glycan therapeutic preparation can optionally comprise one or more excipients or carriers. The pharmaceutical composition can comprise from about 1% to about 90% of the one or more excipients or carriers by w/w, w/v, v/v or molar %. For example, the pharmaceutical composition can comprise about 1-90%, 1-75%, 1-60%, 1-55%, 1-50%, 1-45%, 1-40%, 1-25%, 1-15%, 1-10%, 10-90%, 10-75%, 10-60%, 10-55%, 10-50%, 10-45%, 10-40%, 10-25%, 10-15%, 15-90%, 15-75%, 15-60%, 15-55%, 15-50%, 15-45%, 15-40%, 15-25%, 25-90%, 25-75%, 25-60%, 25-55%, 25-50%, 25-45%, 25-40%, 40-90%, 40-75%, 40-60%, 40-55%, 40-50%, 40-45%, 45-90%, 45-75%, 45-60%, 45-55%, 45-50%, 50-90%, 50-75%, 50-60%, 50-55%, 55-90%, 55-75%, 55-60%, 60-90%, 60-75%, 75-90% of the one or more excipients or carriers by w/w, w/v, v/v or molar %.

Medical Food

Also provided herein are preparations of glycan therapeutics formulated as a medical food. Any glycan therapeutic preparation described herein may be formulated as a medical food as well as pharmaceutical compositions that comprise glycan therapeutic preparations.

A medical food is defined in section 5(b)(3) of the Orphan Drug Act (21 U.S.C. 360ee(b)(3)). Medical food is formulated to be consumed (oral intake) or administered enterally (e.g. feeding/nasogastric tube) under medical supervision, e.g. by a physician. It is intended for the specific dietary management of a disease or condition, such as, e.g. dysbiosis of the gastrointestinal microbiota or a GI-tract disease described herein. Medical foods as used herein do not include food that is merely recommended by a physician as part of an overall diet to manage the symptoms or reduce the risk of a disease or condition. Medical foods comprising a preparation of glycan therapeutics are foods that are synthetic (e.g., formulated and/or processed products, such as, being formulated for the partial or exclusive feeding of a patient by oral intake or enteral feeding by tube) and not naturally occurring foodstuff used in a natural state. Medical foods comprising a preparation of glycan therapeutics may represent a major component of the management of a GI tract disease or condition, e.g. the medical food may represent a partial or exclusive source of food for the subject in need of a medical food. In some embodiments, the subject has limited or impaired capacity to ingest, digest, absorb, or metabolize ordinary foodstuffs or certain nutrients. In other embodiments, the subject has other special medically determined nutrient requirements, the dietary management of which cannot be achieved by the modification of the normal diet alone. Medical foods comprising a preparation of glycan therapeutics are administered to a subject in need thereof under medical supervision (which may be active and ongoing) and usually, the subject receives instructions on the use of the medical food. Medical foods may comprise one or more food additives, color additives, GRAS excipients and other agents or substances suitable for medical foods. Medical food preparations may be nutritionally complete or incomplete formulas.

Dietary Supplements

Any glycan therapeutic preparation described herein may be formulated as a dietary supplement, e.g, for use in a method described herein.

Dietary supplements are regulated under the Dietary Supplement Health and Education Act (DSHEA) of 1994. A dietary supplement is a product taken by mouth that contains a "dietary ingredient" intended to supplement the diet. The "dietary ingredients" in these products may include, in addition to a glycan therapeutic preparation described herein, one or more of: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on their label must not represent the product as a conventional food or a sole item of a meal or diet. DSHEA requires that every supplement be labeled a dietary supplement and not as a general food.

Dosage Forms

The glycan therapeutic preparations described herein may be formulated into any suitable dosage form, e.g. for oral or enteral administration. The dosage forms described herein can be manufactured using processes that are known to those of skill in the art.

The dosage form may be a packet, such as any individual container that contains a pharmaceutical glycan therapeutic composition in the form of, e.g., a liquid (wash/rinse), a gel, a cream, an ointment, a powder, a tablet, a pill, a capsule, a depository, a single-use applicator or medical device (e.g. a syringe). For example, provided is also an article of manufacture, such as a container comprising a unit dosage form of the pharmaceutical glycan therapeutic composition, and a label containing instructions for use of such glycan therapeutic.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and/or other agents (e.g., prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

In one embodiment, a provided glycan therapeutic composition includes a softgel formulation. A softgel can contain a gelatin based shell that surrounds a liquid fill. The shell can be made of gelatin, plasticizer (e.g., glycerin and/or sorbitol), modifier, water, color, antioxidant, or flavor. The shell can be made with starch or carrageenan. The outer layer can be enteric coated. In one embodiment, a softgel formulation can include a water or oil soluble fill solution, or suspension of a composition covered by a layer of gelatin.

Solid formulations for oral use may comprise an enteric coating, which may control the location at which a glycan therapeutic composition is absorbed in the digestive system. For example, an enteric coating can be designed such that a glycan therapeutic composition does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid).

Formulations for oral use may also be presented in a liquid dosage from. Liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents. In some embodiments, liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form may comprise an effective amount of a glycan therapeutic and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for administration. Examples of such vehicles and additives can be found in Remington's Pharmaceutical Sciences, 17th edition (1985).

The pharmaceutical compositions provided herein can be in unit-dosage forms or multiple-dosage forms. A unit-dosage form, as used herein, refers to physically discrete unit suitable for administration to human in need thereof. In an embodiment, the unit-dosage form is provided in a package. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example a multiple dosage form can be provided which comprises a first dosage element comprising a composition comprising a glycan therapeutic and a second dosage element comprising a prebiotic, a therapeutic agent and/or a probiotic, which can be in a modified release form. In this example a pair of dosage elements can make a single unit dosage. In one embodiment a kit is provided comprising multiple unit dosages, wherein each unit comprises a first dosage element comprising a composition comprising a glycan therapeutic and a second dosage element comprising probiotic, a pharmaceutical agent, a prebiotic or a combination thereof, which can be in a modified release form. In another embodiment the kit further comprises a set of instructions.

In some embodiments, the unit-dosage form comprises between about 0.001 mg to about 10 g of the glycan therapeutic (e.g., a glycan therapeutic disclosed herein). For example, the unit-dosage form may comprise about 0.001 mg to about 9.5 g, about 0.005 mg to about 9 g, about 0.01 mg to about 8.5 g, about 0.05 mg to about 8 g, about 0.075 mg to about 7.5 g, about 0.1 mg to about 7 g, about 0.25 mg to about 6.5 g, about 0.5 mg to about 6 g, about 0.75 mg to about 5.5 g, about 1 mg to about 5 g, about 2.5 mg to about 4.5 g, about 5 mg to about 4 g, about 7.5 mg to about 3.5 g, about 10 mg to about 3 g, about 12.5 mg to about 2.5 g, about 15 mg to about 2 g, about 17.5 mg to about 1.5 g, about 20 mg to about 1 g, about 25 mg to about 750 mg, about 50 mg to about 500 g, or about 75 mg to about 250 mg of the glycan therapeutic.

In certain embodiments, the unit-dosage form comprises about 0.001 mg to about 100 mg, about 0.005 mg to about 75 mg, about 0.01 mg to about 50 mg, about 0.05 mg to about 25 mg, about 0.1 mg to about 10 mg, about 0.5 mg to about 7.5 mg, or about 1 mg to about 5 mg of the glycan therapeutic. In other embodiments, the unit-dosage form comprises about 1 mg to about 100 mg, about 2.5 mg to about 75 mg, about 5 mg to about 50 mg, or about 10 mg to about 25 mg of the glycan therapeutic. In other embodiments, the unit-dosage form comprises about 100 mg to about 10 g, about 250 mg to about 7.5 g, about 500 mg to about 5 g, about 750 mg to about 2.5 g, or about 1 g to about 2 g of the glycan therapeutic.

In other embodiments, the unit-dosage form comprises between about 0.001 mL to about 1000 mL of the glycan therapeutic (e.g., a glycan therapeutic disclosed herein). For example, the unit-dosage form may comprise about 0.001 mL to about 950 mL, about 0.005 mL to about 900 mL, about 0.01 mL to about 850 mL, about 0.05 mL to about 800 mL, about 0.075 mL to about 750 mL, about 0.1 mL to about 700 mL, about 0.25 mL to about 650 mL, about 0.5 mL to about 600 mL, about 0.75 mL to about 550 mL, about 1 mL to about 500 mL, about 2.5 mL to about 450 mL, about 5 mL to about 400 mL, about 7.5 mL to about 350 mL, about 10 mL to about 300 mL, about 12.5 mL to about 250 mL, about 15 mL to about 200 mL, about 17.5 mL to about 150 mL, about 20 mL to about 100 mL, or about 25 mL to about 75 mL of the glycan therapeutic.

In certain embodiments, the unit-dosage form comprises about 0.001 mL to about 10 mL, about 0.005 mL to about 7.5 mL, about 0.01 mL to about 5 mL, about 0.05 mL to about 2.5 mL, about 0.1 mL to about 1 mL, about 0.25 mL to about 1 mL, or about 0.5 mL to about 1 mL of the glycan therapeutic. In other embodiments, the unit-dosage form comprises about 0.01 mL to about 10 mL, about 0.025 mL to about 7.5 mL, about 0.05 mL to about 5 mL, or about 0.1 mL to about 2.5 mL of the glycan therapeutic. In other embodiments, the unit-dosage form comprises about 0.1 mL to about 10 mL, about 0.25 mL to about 7.5 mL, about 0.5 mL to about 5 mL, about 0.5 mL to about 2.5 mL, or about 0.5 mL to about 1 mL of the glycan therapeutic.

In some embodiments, the unit-dosage form, e.g., a tablet, capsule (e.g., a hard capsule, push-fit capsule, or soft capsule), or softgel, has a body length of between about 0.1 inches to about 1.5 inches (e.g., about 0.5 inches and about 1 inch), or about 5 mm to about 50 mm (e.g., about 10 mm to about 25 mm). In some embodiments, the unit-dosage form. e.g., a tablet, capsule (e.g., a hard capsule, push-fit capsule, or soft capsule), or softgel, has an external diameter of about 0.05 inches to about 1 inch (e.g., about 0.1 inches to about 0.5 inches), or about 1 mm to about 25 mm (e.g., about 5 mm to about 10 mm).

Each unit-dosage form of the glycan therapeutic may have a caloric value of between about 0.01 kcal and about 1000 kcal. For example, the unit-dosage form may have a caloric value of about 0.01 kcal to about 900 kcal, about 0.05 kcal to about 800 kcal, about 0.1 kcal to about 700 kcal, about 0.25 kcal to about 600 kcal, about 0.5 kcal to about 500 kcal, about 0.75 kcal to about 400 kcal, about 1 kcal to about 300 kcal, about 5 kcal to about 200 kcal, or about 10 kcal to about 100 kcal. In certain embodiments, the unit-dosage form of the glycan therapeutic has a caloric value of between 10 kcal to about 500 kcal. In other embodiments, the unit-dosage form of the glycan therapeutic has a caloric value of between 50 kcal to about 500 kcal.

In still other embodiments, the unit-dosage form may have a caloric value of about 0.001 kcal to about 100 kcal, about 0.005 kcal to about 90 kcal, about 0.01 kcal to about 80 kcal, about 0.025 kcal to about 70 kcal, about 0.05 kcal to about 60 kcal, about 0.075 kcal to about 50 kcal, about 0.1 kcal to 40 kcal, about 0.25 kcal to about 30 kcal, about 0.5 kcal to about 25 kcal, about 0.25 kcal to about 20 kcal, or about 0.1 kcal to about 10 kcal.

The unit-dosage form of the glycan therapeutic may be formulated to dissolve in an aqueous solution (e.g., water, milk, juice, and the like) and is orally administered as a beverage, syrup, solution, or suspension. For example, the unit-form dosage of the glycan therapeutic may comprise a cube, packet, lozenge, pill, tablet, capsule, candy, powder, elixir, or concentrated syrup formulated for dissolving into an aqueous solution prior to oral administration. In other embodiments, the unit-dosage form of the glycan therapeutic may comprise a cube, packet, lozenge, pill, tablet, capsule, candy, powder, elixir, or concentrated syrup formulated to dissolve in vivo, e.g., in the mouth, stomach, intestine, or colon of the subject upon oral administration.

In some embodiments, the glycan therapeutic composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy).

The dosage forms described herein can be manufactured using processes that are known to those of skill in the art. For example, for the manufacture of tablets, an effective amount of a prebiotic can be dispersed uniformly in one or more excipients or additives, for example, using high shear granulation, low shear granulation, fluid bed granulation, or by blending for direct compression. Excipients and additives include diluents, binders, disintegrants, dispersants, lubricants, glidants, stabilizers, surfactants, antiadherents, sorbents, sweeteners, and colorants, or a combination thereof. Diluents, also termed fillers, can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, alginic acid, dextrin, casein, methyl cellulose, waxes, natural and synthetic gums, e.g., acacia, tragacanth, sodium alginate, gum arabic, xantan gum, and synthetic polymers such as polymethacrylates, polyvinyl alcohols, hydroxypropylcellulose, and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses (e.g., carboxymethylcelluloses (e.g., carboxymethylcellulose (CMC), CMC-Na, CMC-Ca)), starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. Exemplary sweeteners may include stevia extract, aspartame, sucrose, alitame, saccharin, and the like. If desired, the tablets can also comprise nontoxic auxiliary substances such as pH buffering agents, preservatives, e.g., antioxidants, wetting or emulsifying agents, solubilizing agents, coating agents, flavoring agents (e.g., mint, cherry, anise, peach, apricot, licorice, raspberry, vanilla), and the like. Additional excipients and additives may include aluminum acetate, benzyl alcohol, butyl paraben, butylated hydroxy toluene, calcium disodium EDTA, calcium hydrogen phosphate dihydrate, dibasic calcium phosphate, tribasic calcium phosphate, candelilla wax, carnuba wax, castor oil hydrogenated, cetylpyridine chloride, citric acid, colloidal silicone dioxide, copolyvidone, corn starch, cysteine HCl, dimethicone, disodium hydrogen phosphate, erythrosine sodium, ethyl cellulose, gelatin, glycerin, glyceryl monooleate, glyceryl monostearate, glycine, HPMC pthalate, hydroxypropylcellulose, hydroxyl propyl methyl cellulose, hypromellose, iron oxide red or ferric oxide, iron oxide yellow, iron oxide or ferric oxide, magnesium carbonate, magnesium oxide, magnesium stearate, methionine, methacrylic acid copolymer, methyl paraben, silicified microcrystalline cellulose, mineral oil, phosphoric acid, plain calcium phosphate, anhydrous calcium phosphate, polaxamer 407, polaxamer 188, plain polaxamer, polyethylene oxide, polyoxyl40 stearate, polysorbate 80, potassium bicarbonate, potassium sorbate, potato starch, povidone, propylene glycol, propylene paraben, propyl paraben, retinyl palmitate, saccharin sodium, selenium, silica, silica gel, fumed silica, sodium benzoate, sodium carbonate, sodium citrate dihydrate, sodium crossmellose, sodium lauryl sulfate, sodium metabisulfite, sodium propionate, sodium starch, sodium starch glycolate, sodium stearyl fumarate, sorbic acid, sorbitol, sorbitan monooleate, pregelatinized starch, succinic acid, triacetin, triethyl citrate, vegetable stearin, vitamin A, vitamin E, vitamin C, or a combination thereof. The amounts of these excipients and additives can be properly selected based on their relation to other components and properties of the preparation and production method.

Immediate-release formulations of an effective amount of a glycan therapeutic composition can comprise one or more combinations of excipients that allow for a rapid release of a pharmaceutically active agent (such as from 1 minute to 1 hour after administration). Controlled-release formulations (also referred to as sustained release (SR), extended-release (ER, XR, or XL), time-release or timed-release, controlled-release (CR), or continuous-release) refer to the release of a glycan therapeutic composition from a dosage form at a particular desired point in time after the dosage form is administered to a subject.

In one embodiment a controlled release dosage form begins its release and continues that release over an extended period of time. Release can occur beginning almost immediately or can be sustained. Release can be constant, can increase or decrease over time, can be pulsed, can be continuous or intermittent, and the like. In one embodiment, a controlled release dosage refers to the release of an agent from a composition or dosage form in which the agent is released according to a desired profile over an extended period of time. In one aspect, controlled-release refers to delayed release of an agent from a composition or dosage form in which the agent is released according to a desired profile in which the release occurs after a period of time.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In a further aspect, the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a glycan therapeutic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as sodium bicarbonate, sodium carbonate, potassium bicarbonate and potassium carbonate, magnesium carbonate and the like. Reactants which evolve oxygen or other gasses and which are safe for human consumption are also included. In one embodiment citric acid and sodium bicarbonate are used.

In another aspect, the dosage form can be in a candy form (e.g., matrix), such as a lollipop or lozenge. In one embodiment an effective amount of a glycan therapeutic is dispersed within a candy matrix. In one embodiment the candy matrix comprises one or more sugars (such as dextrose or sucrose). In another embodiment the candy matrix is a sugar-free matrix. The choice of a particular candy matrix is subject to wide variation. Conventional sweeteners (e.g., sucrose), sugar alcohols suitable for use with diabetic patients (e.g., sorbitol or mannitol), or other sweeteners (e.g., sweeteners described herein) may be employed. The candy base can be very soft and fast dissolving, or can be hard and slower dissolving. Various forms will have advantages in different situations.

A candy mass composition comprising an effective amount of the glycan therapeutic can be orally administered to a subject in need thereof so that an effective amount of the glycan therapeutic will be released into the subject's mouth as the candy mass dissolves and is swallowed. A subject in need thereof includes a human adult or child.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In one embodiment, the pharmaceutical particles have a final size of 3-1000 microns, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 microns. In another embodiment the pharmaceutical particles have a final size of 10-500 microns. In another embodiment the pharmaceutical particles have a final size of 50-600 microns. In another embodiment the pharmaceutical particles have a final size of 100-800 microns.

In another aspect, the disclosure provides a method of making a unit-dosage form described herein, comprising providing a glycan therapeutic (e.g., a glycan therapeutic described herein); formulating the glycan therapeutic into a unit-dosage form (e.g., a unit-dosage form described herein), packaging the unit-dosage form, labelling the packaged unit-dosage form, and/or selling or offering for sale the packaged and labeled unit-dosage form.

The unit-dosage forms described herein may also be processed. In one embodiment, the processing comprises one or more of: processing the dosage form into a pharmaceutical composition, e.g., formulating, combining with a second component, e.g., an excipient or buffer; portioning into smaller or larger aliquots; disposing into a container, e.g., a gas or liquid tight container; packaging; associating with a label; shipping or moving to a different location. In one embodiment, the processing comprises one or more of: classifying, selecting, accepting or discarding, releasing or withholding, processing into a pharmaceutical composition, shipping, moving to a different location, formulating, labeling, packaging, releasing into commerce, or selling or offering for sale, depending on whether the predetermined threshold is met. In some embodiments, the processed dosage forms comprise a glycan therapeutic described herein.

In some embodiments, the processing comprises one or more of: processing the dosage form into a pharmaceutical composition, e.g., formulating, combining with a second component, e.g., an excipient or buffer; portioning into smaller or larger aliquots; disposing into a container, e.g., a gas or liquid tight container; packaging; associating with a label; shipping or moving to a different location. In one embodiment, the processing comprises one or more of: classifying, selecting, accepting or discarding, releasing or withholding, processing into a pharmaceutical composition, shipping, moving to a different location, formulating, labeling, packaging, releasing into commerce, or selling or offering for sale, depending on the determination. In another embodiment, an oral dosage form is provided comprising a glycan therapeutic composition, wherein the oral dosage form is a syrup. The syrup can comprise about 1%, 5%, 10%, 15%, 20%, 25%, 30%, 35%, 40%, 45%, 50%, 55%, 60%, 65%, 70%, 75%, 80%, or 85% solid. The syrup can comprise about 15%, 20%, 25%, 30%, 35%, 40%, 45%, or 50% liquid, for example, water. The solid can comprise a glycan therapeutic composition. The solid can be, for example, about 1-96%, 10-96%, 20-96%, 30-96%, 40-96%, 50-96%, 60-96%, 70-96%, 80-96%, or 90-96% glycan therapeutic composition. In another embodiment, a glycan therapeutic composition is formulated as a viscous fluid.

In one embodiment, the composition comprises a foaming component, a neutralizing component, or a water-insoluble dietary fiber. A foaming component can be at least one member selected from the group consisting of sodium hydrogencarbonate, sodium carbonate, and calcium carbonate. In one embodiment a neutralizing component can be at least one member selected from the group consisting of citric acid, L-tartaric acid, fumaric acid, L-ascorbic acid, DL-malic acid, acetic acid, lactic acid, and anhydrous citric acid. In one embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

In some embodiments, the dosage forms are formulated to release the pharmaceutical compositions comprising glycan therapeutic preparations in a specific region(s) of the GI tract, such as the small or the large intestine. In some embodiments, the dosage forms are formulated to release the pharmaceutical compositions comprising therapeutic glycan preparations in a specific region(s) of the GI tract, such as the cecum, ascending colon, transverse colon, descending colon, sigmoid colon, and/or rectum.

In some embodiments, the dosage form for the pharmaceutical glycan therapeutic compositions described herein is an enzyme-responsive delivery system. For example, trypsin responsive polymers can be made using hydrogels that are crosslinked by peptides that are degraded by trypsin. Trypsin is active in the small intestine. Trypsin-responsive delivery systems can be used to target delivery of the pharmaceutical glycan therapeutic compositions to the small intestine. In another example, enzyme-digestible hydrogels consisting of poly(vinyl pyrrolidone) crosslinked with albumin are degraded in the presence of pepsin.

In some embodiments, the dosage form for the pharmaceutical glycan therapeutic compositions described herein is a delivery device that enables prolonged retention at a specific site in the GI tract. For example, a gastroretentive delivery system enables prolonged release of the pharmaceutical glycan therapeutic compositions to the stomach. Gastroretentive delivery may be used for the pharmaceutical glycan therapeutic compositions that modulate bacteria in the stomach or in the upper small intestine.

In some embodiments, the dosage form for the pharmaceutical glycan therapeutic compositions described herein is a mucoadhesive delivery system that adheres to the mucosal surfaces of the stomach. They are typically composed of polymers with numerous hydrogen-bonding groups, e.g., cross-linked polyacrylic acids, sodium carboxymethyl cellulose, sodium alginate, carrageenan, Carbopol 934P, or thiolated polycarbophil.

In some embodiments, the dosage form for the pharmaceutical glycan therapeutic compositions described herein is an expanding delivery system that rapidly increases in size in the stomach, which slows its passage through the pylorus. Such systems include systems that unfold in the stomach. For example, geometric shapes such as tetrahedrons, rings, disks, etc. can be packed into a gelatin capsule. When the capsule dissolves, the shape unfolds. The systems can be composed of one or more erodible polymer (e.g., hydroxypropyl cellulose), one or more nonerodible polymer (e.g., polyolefins, polyamides, polyurethanes). The glycan therapeutic may then be dispersed within the polymer matrix. The retention times can be fine-tuned by the polymer blend. Alternatively, devices made out of elastic polymers that are stable in the acidic pH of the stomach but dissolve in the neutral/alkaline conditions further along the GI tract can be used. Such polymer formulations can prevent intestinal obstruction when the device exits the stomach. Supramolecular polymer gels crosslinked by hydrogen bonds between carboxyl groups may also be used, e.g. composed of poly(acryloyl 6-aminocaproic acid) (PA6ACA) and poly(methacrylic acid-co-ethyl acrylate) (EUDRAGIT L 100-55). Other systems include swellable excipients, such as collagen sponges. For example, a hydrogel matrix (e.g. a swellable core: polyvinyl pyrrolidone XL, Carbopol 934P, calcium carbonate) swells 2-50 times in the stomach. Superporous hydrogel composites swell to hundreds of times their original volume in a few minutes. Some systems exploit gas generation to achieve expansion, e.g. carbon dioxide-generating, expandable systems that are surrounded by a hydrophilic membrane.

In some embodiments, the dosage form for the pharmaceutical glycan therapeutic compositions described herein is a density-controlled delivery system. These systems are designed to either float or sink in gastric fluids, which delays their emptying from the stomach. For example, high-density systems enable the device to settle to the bottom of the stomach, below the pylorus, and thus avoid stomach emptying. Other systems are low-density/floating systems. Such devices may, e.g., comprise entrapped air in hollow chambers or may incorporate low-density materials like fats, oils, or foam powder. Low density may be achieved through swelling, e.g. hydrocolloid containing capsules dissolve upon contacting gastric fluid and the hydrocolloids swell to form a mucous body. Alternative polymers include: chitosans, sodium alginate, and glycerol monooleate matrix. Low density may be achieved through gas generation. For example, tablets loaded with carbonate and optionally citric acid generate carbon dioxide after contact with acidic aqueous media. The carbon dioxide generated is entrapped within the gelling hydrocolloid causing the system to float. Hydrocolloids include hydroxypropyl methylcellulose and Carbopol 934P.

In some embodiments, the dosage form for the pharmaceutical glycan therapeutic compositions described herein employs a design to retain a device in the small or large intestine. The location-specific nature of the device is provided by a specific triggering method, e.g. pH, enzyme, etc. These include systems designed for mucoadhesion and also microneedle pills. Microneedle pills comprise a drug reservoir spiked with microneedles that is encapsulated in a pH-responsive coating. When the pill reaches the desired location in the GI tract and the coating dissolves, the microneedles enable the pill to become stuck to the lining of the GI tract. In other embodiments, the microneedle pills comprise a capsule that consists of two chemical compartments filled with citric acid and sodium bicarbonate, respectively. As the pill dissolves in the digestive system, barriers between the two substances erode, allowing them to mix and create a chemical reaction that pushes micro-needles of saccharides through the outer layer of the capsule and into the lining of the small intestine. The saccharide needles can be filled with drugs that are delivered into nearby blood vessels as the saccharide is absorbed.

In some embodiments, the dosage form for the pharmaceutical glycan therapeutic compositions described herein employs a pH sensitive polymer coating. For example, pH-dependent polymers (bi- or tri-phasic) can be insoluble at low pH levels (e.g. acid resistance in the stomach, pH 1-2) and become increasingly soluble as pH rises, e.g. to about 5.5-6.2 in the duodenum, to about pH 5.7 in the ascending colon, to about pH 6.4 in the cecum, to about pH 6.6 in the transverse colon, to about pH 7.0 in the descending colon, to about 7.2-7.5 in the ileum, or to about pH 7.5 in the distal small intestine. In one example, TARGIT™ technology may be used for site-specific delivery of the pharmaceutical glycan therapeutic compositions in the gastrointestinal (GI) tract. The system employs pH-sensitive coatings onto injection-moulded starch capsules to target the terminal ileum and colon.

In some embodiments, the dosage form for the pharmaceutical glycan therapeutic compositions described herein is a delayed release system or time controlled release system. Such systems usually employ enteric coatings that may be combined with pH sensitive and time release functions. For example, ETP (enteric coated time-release press coated) tablets may be used that are composed of three components: a glycan therapeutic-containing core tablet (rapid release function), a press-coated, swellable hydrophobic polymer layer (e.g. hydroxypropyl cellulose layer (HPC), and a time release function. The duration of lag phase can be controlled either by weight or composition of polymer layer and an enteric coating layer (acid resistance function).

In some embodiments, the dosage form for the pharmaceutical glycan therapeutic compositions described herein employs Eudragit® enteric coatings of tablets and capsules. Other suitable synthetic polymers include: Shellac, ethyl cellulose, cellulose acetate phthalate, hydroxypropylmethyl cellulose, polyvinyl acetate phthalate and poly glutamic acid coatings, such as poly-γ-glutamic acid (γ-PGA). These coatings combine both mucoadhesive and pH-dependent release strategies. To enhance colon targeted delivery Eudragits® are methacrylic co-polymers with varying side group compositions that alter the pH at which they are soluble. For example, for Eudragit®-coated systems no significant drug release occurs in the stomach (e.g. at pH 1.4) and in the small intestine (e.g. at pH 6.3), while significant drug release can be seen at pH 7.8 in the ileocaecal region.

In some embodiments, the dosage form for the pharmaceutical glycan therapeutic compositions described herein is a microbial-triggered system, such as a polysaccharide based delivery system. Polysaccharide based delivery systems contain biodegradable and mucoadhesive polymer coatings, including coatings of chitosan and pectin. Other suitable natural polymers include, e.g., guar gum, inulin, cyclodextrin, dextran, amylase, chondrotin sulphate, and locust bean gum. These delivery systems can be used to target the glycan therapeutic to the small intestine. Coatings with naturally occurring polysaccharides like guar gum, xanthan gum, chitosan, alginates, etc. are degraded by colonic gut microbiota, e.g. enzymes such as, xylosidase, arabinosidase, galactosidase etc. For example, CODES™ technology may be used to deliver the pharmaceutical glycan therapeutic compositions. This system combines the polysaccharide coating with a pH-sensitive coating. In some embodiments, the system consists of a core tablet coated with three layers of polymer coatings: The outer coating is composed of Eudragit L. This coating gets dissolved in the duodenum and exposes the next coating. The next coating is composed of Eudragit E. This layer allows the release of lactulose present in the inner core. The lactulose gets metabolized into short chain fatty acids that lower the surrounding pH where the Eudragit E layer dissolves. The dissolving of Eudragit E results in the exposure of the glycan therapeutic. The bacteria present in the colon are responsible for the degradation of polysaccharides that are released from the core tablet. The degradation of polysaccharides may result in organic acids formation that lowers the pH of the contents surrounding the tablet.

In some embodiments, the dosage form for the pharmaceutical glycan therapeutic compositions described herein is a pressure-controlled delivery system. The system employs the fact that higher pressures are encountered in the colon than in the small intestine. For example, for ethylcellulose systems that are insoluble in water, the release of glycan therapeutics occurs following disintegration of a water-insoluble polymer capsule as a result of pressure in the lumen of the colon. The release profile may be adjusted by varying the thickness of the ethylcellulose, the capsule size and/or density of the capsule.

In some embodiments, the dosage form for the pharmaceutical glycan therapeutic compositions described herein is a pulsatile colon targeted delivery system. For example, the system can be a pulsincap system. The capsule which is employed comprises a plug that is placed in the capsule that controls the release of the glycan therapeutic. A swellable hydrogel (e.g. hydroxyl propyl methyl cellulose (HPMC), poly methyl methacrylate or polyvinyl acetate) seals the drug content. When the capsule gets in contact with a fluid the plug is pushed off from the capsule and the glycan therapeutic is released. The release profile can be controlled by varying the length and/or point of intersection of the plug with the capsule body. Another system is a port system. The capsule body is enclosed in a semi-permeable membrane. The insoluble plug consists of an osmotically active agent and the glycan therapeutic. When the capsule gets in contact with a fluid the semi-permeable membrane permits inflow of the fluid which increases pressure in the capsule body. This leads to an expelling of the plug and release of the glycan therapeutic.

In some embodiments, the dosage form for the pharmaceutical glycan therapeutic compositions described herein is an osmotically controlled colon targeted delivery system. An exemplary system, OROS-CT, consists of osmotic units (up to 5 or 6 push pull units) encapsulated in a hard gelatin capsule. The push pull units are bilayered with outer enteric impermeable membrane and inner semi-permeable membrane. The internal, central part of the push pull consists of the drug layer and push layer. The glycan therapeutic is released through the semi-permeable membrane. The capsule body enclosing the push pull units is dissolved immediately after administration. In the GI tract the enteric impermeable membrane prevents water absorption. The enteric coating is dissolved in small intestine (higher pH, >7), water enters the unit through the semi-permeable membrane causing push layer to swell and force out the glycan therapeutic.

In some embodiments, the dosage form for the pharmaceutical glycan therapeutic compositions described herein is "smart pill" which can be used to release the glycan therapeutic just before reaching the ileocecal valve.

In some embodiments, the dosage form for the pharmaceutical glycan therapeutic compositions described herein is a rectally administered formulation. For example, enemas introduce a pharmaceutical glycan therapeutic composition in liquid formulation into the rectum. The volume administered is typically less than 10 mL. Suppositories introduce a pharmaceutical glycan therapeutic composition into the rectum. Suppositories are solid dosage forms that melt or dissolve when inserted into the rectum, releasing the glycan therapeutics. Typical excipients for suppository formulations include cocoa butter, polyethylene glycols, and agar.

Generation of Polyphenols, Synthesis and Preparation of Extracts

Provided herein are pharmaceutical compositions comprising glycan therapeutic preparations and polyphenol preparations. In some embodiments, the pharmaceutical compositions comprising glycan therapeutic preparations comprise at least one polyphenol. In some embodiments, the pharmaceutical compositions comprising glycan therapeutic preparations comprise a plurality of polyphenols.

The preparations of glycan therapeutics and the preparations of polyphenols may be generated separately. For example, the preparation of glycan therapeutics may be synthesized and the preparation of polyphenols may be extracted as described herein. In another example, the preparation of glycan therapeutics may be synthesized and the preparation of polyphenols may also be synthesized as described herein. In yet another example, the preparation of glycan therapeutics may be synthesized and the preparation of polyphenols may comprise a plurality of polyphenols that was extracted from a source and a plurality that was synthesized.

In some embodiments, preparations of polyphenols are generated from extracts containing the polyphenols. In other embodiments, the preparations of polyphenols comprise polyphenols that are synthesized.

Pharmaceutical compositions and medical foods may be generated by mixing the preparation of glycan therapeutics with the preparation of polyphenols by any suitable method known in the art. In some embodiments, the preparations are mixed in a 0.000000001:1, 0.00000001:1, 0.0000001:1, 0.000005:1, 0.00001:1, 0.0001:1. 0.001:1, 0.01:1, 0.1:1, 0.5:1, 1:1, 1:2, 1:5, 1:10, 1:100, 1:1,000, 1:10,000, 1:100,000, 1:1000,000 (v/v), (w/w), (w/v) or molar ratio (glycan: polyphenol, polyphenol:glycan).

In some embodiments, the preparations of polyphenols are extracted from plants, plant parts, plant cells, or plant products. Examples of plant parts are but not limited to bark, flower, petal, stem, stalk, tuber, root, fruit, berry, seed, nut, leaf. Examples of plant products include but are not limited to pomace juice, pulp, skin, mash, paste, and slurry. Examples of plants may include but are not limited to blueberry, cranberry, grape, peach, plum, pomegranate, soy, red wine, black tea, green tea. In some embodiments, the polyphenols are extracted from multiple plants, plant parts, or plant products. In some embodiments the polyphenol extract is combined from multiple plants, plant parts, or plant products.

Polyphenols may be extracted from any suitable source, such as, e.g. foods rich in polyphenols, including, but not limited to, cloves, peppermint, star anise, cocoa powder, oregano, celery seed, black chokeberry, dark chocolate, flaxseed meal, black elderberry, chestnut, common sage, rosemary, spearmint, common thyme, lowbush blueberry, blackcurrant, capers, black olive, highbush blueberry, hazelnut, pecan nut, soy flour, plum, green olive, sweet basil, curry, powder, sweet cherry, globe artichoke heads, blackberry, roasted soybean, milk chocolate, strawberry, red chicory, red raspberry, coffee, filter, ginger, whole grain hard wheat flour, prune, almond, black grape, red onion, green chicory, common thyme, fresh, refined maize flour, soy, tempeh, whole grain rye flour, apple, spinach, shallot, lemon verbena, black tea, red wine, green tea, soy yogurt, yellow onion, soy meat, whole grain wheat flour, pure apple juice, pure pomegranate juice, extra-virgin olive oil, black bean, peach, pure blood orange juice, cumin, pure grapefruit juice, white bean, Chinese cinnamon, pure blond orange juice, broccoli, redcurrant, soy tofu, pure lemon juice, whole grain oat flour, apricot, caraway, refined rye flour, asparagus, walnut, potato, Ceylan cinnamon, parsley, nectarine, curly endive, marjoram, red lettuce, chocolate beverage with milk, quince, endive (escarole), soy milk, pure pummelo juice, rapeseed oil, pear, soybean sprout, green grape, carrot, vinegar, soy cheese, white wine, and rosé wine.

In some embodiments, polyphenols may be extracted from plant juice. In some embodiments, the plant juice is the juice of a blueberry, blackberry, raspberry, hockenberry, gooseberry, boysenberry, acai berry, baneberry, barberry, bearberry, bilberry, chokeberry, bunchberry, buffalo berry, chokecherry, cowberry, elderberry, cranberry, dew berry, currant, farkleberry, goji berry, gooseberry, grape, holly berry, huckleberry, ivy berry, june berry, juniper berry, lingonberry, logan berry, mistletoe berry, nannyberry, Oregon grape, persimmon, pokeberry, privet berry, salmonberry, strawberry, sugarberry, tayberry, thimbleberry, white mulberry, red mulberry, black mulberry, wineberry, wintergreen, yew berry, or young berry.

In some embodiments, polyphenols may be extracted from plants or plant tissue that have been modified, bred, engineered, or otherwise changed, e.g., to alter the composition or quantity of polyphenol contents. In some embodiments, the plants or plant tissue is treated, subjected to, or contacted with a polyphenol-inducing agent (e.g. a chemical agent or radiation, such as UV) prior to or after harvesting or isolating of the plant or plant tissue to induce or stimulate the production of polyphenols by the plant or plant tissue or to increase the relative amount of polyphenols in the plant or plant tissue, when e.g. compared to a non-treated plant or tissue or a plant or tissue that has not been subjected to or contacted with the polyphenol-inducing agent.

In some embodiments, the pharmaceutical compositions of glycan therapeutics comprise preparations of polyphenols that can be extracted by any method known in the art. For example, the extraction method may comprise one or more of the following steps: i) drying the source; ii) milling, grinding, crushing, blending, or otherwise homogenizing the source; iii) extracting the polyphenols from the source, e.g. using a solvent.

The source material may optionally be pretreated with enzymes or treated with enzymes during extraction. Examples of enzymes include but are not limited to pectinolytic and cell-wall polysaccharide degrading enzymes.

The solvent may be any suitable solvent known in the art. For example, the solvent can be an organic solvent, such as but not limited to, methanol, ethanol, acetone, and ethyl acetate optionally an aqueous solvent (comprising water). If desired, the solvent may include organic acids, such as but not limited to trifluoroacetic acid, formic acid, acetic acid, citric acid, hydrochloric acid, tartaric acid, sulfuric acid, or phosphoric acid. The solvent may be a mixture of an organic solvent and an acid in any suitable ratio. The solvent may include supercritical $CO_2$.

The extraction may be carried out between 0 and 100° C. Extraction methods include: maceration and soxhlet extraction, rotary evaporation, microwave-assisted extraction, ultrasound-assisted extraction, subcritical water extraction, supercritical fluid extraction, pressurized fluid extraction, pressured liquid extraction, and accelerated solvent extraction.

In some embodiments, the extraction may be performed multiple times upon the same source material. If desired, multiple extractions from the source material may be combined. In other embodiments, multiple extractions from different source materials may be combined.

Purification and fractionation of the polyphenol extract may be accomplished by any suitable method known in the art, including, but not limited to: i) sequential extraction or liquid-liquid partitioning, ii) solid phase extraction, iii) countercurrent chromatography, and iv) centrifugation. For sequential extraction, the crude extract may be washed with non-polar solvents to remove lipids. Examples of non-polar solvents are but not limited to hexane, dichloromethane, and chloroform. For solid phase extraction, the crude extract may be washed over a solid phase binding substrate to separate polyphenols substituents and/or remove sugars. In some embodiments, water-soluble constituents such as sugar and organic acids are removed with acidified water. Examples of solid phase binding substrates are but not limited to C18, Amberlite XAD-2, XAD-7, XAD-16, Oasis HLB, Silica-based C8, copolymer-based HLB, PH, ENV+, RP-C18, Toyopearl, LH-20, polyamide resin, and MCX. If desired, the polyphenols may be further fractionated by adjusting the eluent solvent and solvent pH. Examples of eluents include but are not limited to ethanol, methanol, acetone, and water, and any combination thereof. In some embodiments, phenolic acids are eluted with water. In some embodiments, nonpolymeric phenols are eluted with acidified ethyl acetate. In some embodiments, polymeric phenols are eluted with a combination of water, acetone, ethanol, and/or methanol. In some embodiments, procyanidins are eluted with acetone and water.

As one example, proanthocyanidins may be isolated from grape berry skins. Grape skins can be collected after the juice is squeezed from the grape berries and removed. A suitable solvent, e.g. an acetone/water mixture may be used to extract polyphenols from the grape berry skins. The solvent is then removed. Aqueous phase extraction may be carried out, e.g. with cloroform and the extracts can optionally be freeze dried. The resulting powder may be purified using adsorption chromatography. The proanthocyanidins can be washed and eluted with a solvent (e.g. methanol, acetone) and trifluoroacetic acid. The solvent is removed and the acqueous phase optionally freeze dried to generate proanthocyanidin powders.

Various methods can be used to characterize the resulting proanthocyanidin mixtures. Acid-catalysis in the presence of excess phloroglucinol may be used to determine subunit composition, conversion yield, and mean degree of polymerization. Mass distribution of polyphenols is determined with mass spectrometry. The mass spectrometry method consists of dissolution of polyphenols in a suitable solvent (e.g. methanol/acetonitrile) and infusion into the electrosprayer. Gel permeation chromatography can provide spectra of eluting peaks and is run with two columns in series (for example, TSKgel G3000 Hxl particle size 6 um followed by G2500 Hxl particle size 5 um, both 300×7.8 mm i.d.), carried out under isocratic conditions with the mobile phase as dimethylformamide Pigmented proanthocyanidins can be characterized with UV-Vis spectrophotometry. Finally, elemental analysis for C, H, and N can be done by loading powder sample into a tin cup and running analysis using an elemental analyzer, such as, e.g., a Carlo Erba EZ 1108.

In some embodiments, the compositions described herein comprise synthetic polyphenols. Polyphenols may not only be derived from suitable plant sources (e.g. plant extracts) but can be synthesized. Polyphenols may be synthesized via a suitable combination of chemical, biochemical, or biotechnological methods known in the art. In some embodiments, the polyphenols are extracted from natural sources and subsequently modified via chemical, biochemical, or biotechnological methods. In some embodiments, the synthesized or modified polyphenol chemical structures are not found in nature. Examples of chemical modifications include but are not limited to methylation, hydroxylation, prenylation, glycosylation, dimzerization, polymerization. Examples of glycosylation include but are not limited to glucosides, galactosides, arabinosides, rhamnosides.

Methods for chemical synthesis of polyphenols are known in the art and are described, e.g., in Quideau S et al. "Plant Polyphenols: Chemical Properties, Biological Activities, and Synthesis", Angewandte Chemie 2011, 50, 586-621. In some embodiments, the polyphenols are synthesized or modified via biotechnological methods, e.g. using enzymes to catalyze suitable reactions. The reactions may occur within cells (e.g. in bacteria, yeast, plant cells) or in extracts or lysates in or obtained from e.g. from bacteria, yeast, or plant cells. In some embodiments, specific enzymes are isolated and used in suitable buffer systems and under suitable reaction conditions. Methods for biotechnological synthesis of polyphenols are known in the art and are described, e.g., in Cress B et al. "Isoflavonoid Production By Genetically Engineered Microorganisms", Natural Products. Springer-Verlag Berlin Heidelberg, 2013. 1647-1681; Trantas E A et al. "When Plants Produce Not Enough Or At All: Metabolic Engineering Of Flavonoids In Microbial Hosts", Frontiers in Plant Science 2015, 6.

Polyphenols may be quantified or measured by any suitable method. In some embodiments, known concentrations of a reference standard (e.g. a polyphenol or plurality of polyphenols) are used for comparison in a measurement. In some embodiments, total polyphenols are quantified via the Folin-Denis method, Folin-Ciocalteau method, permanganate titration, colorimetry with iron salts, HPLC, precipitation of substrates, or electromagnetic absorbance.

In some embodiments, polyphenol classes are quantified. For example, anthocyanins may be quantified using electromagnetic absorbance between wavelength 490 and 550 nM at one or multiple pH. Proanthocyanidins can be quantified using coloriometric methods, substrate precipitation, or protein binding assays, or a combination thereof. In another example, tannins can be quantified using potassium iodide, rhodanine, or sodium nitrite, or protein binding assays, or a combination thereof. In some embodiments, gas chromatography is used for the separation and quantification of polyphenols or a plurality of polyphenols. If desired, the polyphenols may be modified prior to gas chromatography, e.g. to make the polyphenols more volatile.

Alternatively or in addition, the polyphenols are quantified via HPLC, optionally using various solid supports and mobile phases. Polyphenols may also be quantified via mass spectrometry (MS). In some embodiments, the polyphenols are quantified with HPLC-MS optionally using various solid supports and mobile phases. In some embodiments, the antioxidant capacity of polyphenols is measured. For example, the antioxidant capacity of polyphenols can be measured via Trolox equivalent antioxidant capacity assay, oxygen radical absorbance capacity assay, total radical-trapping antioxidant parameter assay, ferric ion reducing antioxidant power assay, cupric ion reducing antioxidant capacity assay, or a combination thereof.

Other methods for phenolic extraction, purification, analysis and quantification are known in the art and are described, e.g., in Dai J. and Mumper R J, "Plant Phenolics: Extraction, Analysis and Their Antioxidant and Anticancer Properties", Molecules 2010, 15(10), 7313-7352.

In some embodiments, polyphenols can be extracted and/or concentrated using proteins from various sources and optionally varying the pH, e.g., described in Raskin et al., U.S. patent publication No. 20140328997.

In some embodiments, the yield of extracted polyphenols is μg/kg source material. In some embodiments, the yield of extracted polyphenols is mg/kg source material. In some embodiments the yield of extracted polyphenols is g/kg source material.

In some embodiments, the preparation of polyphenols includes flavonoids. In some embodiments, the flavonoids are anthocyanins, anthocyanidins, chalcones, dihydrochalcones, dihydroflavonols, flavanols, flavan-3-ols, flavanones, flavones, flavonols, isoflavonoids, proanthocyanidins, condensed tannins, non-hydrolyzable tannins. In some embodiments the flavonoids are monomers. In some embodiments the flavonoids are dimers. In some embodiments the flavonoids are polymers. In some embodiments the flavonoids are chemically modified. Examples of chemical modifications are but not limited to methylation, hydroxylation, prenylation, glycosylation. Examples of glycosylation are but not limited to glucosides, galactosides, arabinosides, rhamnosides.

In some embodiments, the preparation of polyphenols includes hydrolyzable tanins, phlorotannins, lignans, alkymethoxyphenols, alkyphenols, curcumoids, furanocoumarins, hydroxybenzaldehydes, hydroxybenzoketones, hydroxycinnamaldehyde, hydroxycoumarins, hydroxyphenylpropenes, methoxyphenols, naphtoquinones, phenolic terpenes, tyrosols, arbutin, catechol, pyrocatechol, resorcinol, coumestrol, phenol, phlorin, pyrogallol, phloroglucinol, salvianolic acid, hydroxybenzoic acid, hydroxycinnamic acid, hydroxyphenylacetic acid, hydroxyphenylpropanic acid, hydroxyphenylpentanoic acid, stilbenes. In some embodiments the polyphenols are monomers. In some embodiments the polyphenols are dimers. In some embodiments the polyphenols are polymers. In some embodiments the polyphenols are chemically modified. Examples of chemical modifications are but not limited to methylation, hydroxylation, prenylation, glycosylation. Examples of glycosylation are but not limited to glucosides, galactosides, arabinosides, rhamnosides.

In some embodiments, the extracts comprise a plurality of one or more (e.g. 2, 3, 4, 5, 6, 7, 8, 9, 10, 15, 20, 30, 40, 50, 60, 70, 80, 90, 100 or more) polyphenols listed in Table 5. In some embodiments, the pharmaceutical compositions comprising glycan therapeutics described herein comprise a plurality of one or more (e.g. 2, 3, 4, 5, 6, 7, 8, 9, 10, 15, 20, 30, 40, 50, 60, 70, 80, 90, 100 or more) polyphenols listed in Table 5.

Kits

Kits also are contemplated. For example, a kit can comprise unit dosage forms of the pharmaceutical glycan therapeutic composition, and a package insert containing instructions for use of the glycan therapeutic in treatment of a gastrointestinal disorder or condition. The kits include a pharmaceutical glycan therapeutic composition in suitable packaging for use by a subject in need thereof. Any of the compositions described herein can be packaged in the form of a kit. A kit can contain an amount of a pharmaceutical glycan therapeutic composition (optionally additionally comprising a prebiotic substance, a probiotic bacterium, and/or a second therapeutic agent) sufficient for an entire course of treatment, or for a portion of a course of treatment. Doses of a pharmaceutical glycan therapeutic composition can be individually packaged, or the pharmaceutical glycan therapeutic composition can be provided in bulk, or combinations thereof. Thus, in one embodiment, a kit provides, in suitable packaging, individual doses of a glycan therapeutic composition that correspond to dosing points in a treatment regimen, wherein the doses are packaged in one or more packets.

In one embodiment, the pharmaceutical glycan therapeutic composition can be provided in bulk in a single container, or in two, three, four, five, or more than five containers. For example, \each container may contain enough of a pharmaceutical glycan therapeutic composition for a particular week of a treatment program that runs for a month. If more than one bulk container is provided, the bulk containers can be suitably packaged together to provide sufficient pharmaceutical glycan therapeutic composition for all or a portion of a treatment period. The container or containers can be labeled with a label indicating information useful to the subject in need thereof or the physician performing the treatment protocol, such as, e.g. dosing schedules.

The pharmaceutical glycan therapeutic composition can be packaged with other suitable substances, such as probiotic bacteria, prebiotic substances or other substances, as described herein. The other substance or substances can be packaged separately from the pharmaceutical glycan therapeutic composition, or mixed with the pharmaceutical glycan therapeutic composition, or combinations thereof. Thus, in one embodiment, kits include a dosage form containing all the ingredients intended to be used in a course of treatment or a portion of a course of treatment, e.g., a pharmaceutical glycan therapeutic composition and optionally buffers, excipients, etc., a probiotic, prebiotic or a therapeutic agent. In one embodiment, a pharmaceutical glycan therapeutic composition is packaged in one package or set of packages, and additional components, such as probiotic bacteria, prebiotics, and therapeutic agents are packaged separately from the pharmaceutical glycan therapeutic composition.

Kits can further include written materials, such as instructions, expected results, testimonials, explanations, warnings, clinical data, information for health professionals, and the like. In one embodiment, the kits contain a label or other information indicating that the kit is only for use under the direction of a health professional. The container can further include scoops, syringes, bottles, cups, applicators or other measuring or serving devices.

Methods of Modulating Microbial Taxa, Genomic and Functional States of the Microbiome Provided herein are method for modulating the abundance of bacterial taxa (e.g. 1, 2, 3, 4, 5 or more taxa) in a human subject's gastrointestinal microbiota. These methods include administering to the human subject a pharmaceutical composition comprising a glycan therapeutic preparation in an amount effective to modulate the abundance of the taxa. The abundance of a bacterial taxa may increase relatively to other taxa (or relative from one point in time to another) when the glycan therapeutic is administered and the increase can be at least a 5%, 10%, 25% 50%, 75%, 100%, 250%, 500%, 750% increase or at least a 1000% increase. The abundance of a bacterial taxa may also decrease relative to other taxa (or relative from one point in time to another) when the glycan therapeutic is administered and the decrease can be at least a 5%, 10%, 25% 50%, 75%, 85%, 90%, 95%, 96%, 97%, 98%, 99% decrease, or at least a 99.9% decrease. In some embodiments, a dysbiosis has shifted the microbiota and has increased one or more non-desired taxa and/or increased one or more desired taxa. Administration of the glycan therapeutic can modulate the abundance of the desired and/or non-desired bacterial taxa in the subject's gastrointestinal microbiota, thereby treating the dysbiosis.

In some embodiments, the glycan therapeutic is capable of modulating (e.g. increasing or decreasing) the growth of one or more bacterium, such as, e.g., those that belong to genera *Bacteroides, Odoribacter, Parabacteroides, Alistipes, Blautia, Clostridium, Coprococcus, Dorea, Eubacterium, Lachnospira, Roseburia, Ruminococcus, Faecalibacterium, Oscillospira*, and *Subdoligranulum* which can be found in the GI tract. In some embodiments, the glycan therapeutic is capable of modulating (e.g. increasing or decreasing) the growth of one or more bacterium, such as, e.g., those that are thought to be associated with a healthy gastrointestinal state, such as, for example, one or more of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*.

In some embodiments, the glycan therapeutic is capable of modulating (e.g. increasing or decreasing) the growth of at least two bacterial taxa selected from *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus*. Exemplary glycan therapeutics include glu100, ara100, glu50gal50, and glu33gal33fuc33, In some embodiments, the glycan therapeutic is capable of modulating the growth of the two bacterial taxa: *Akkermensia* and *Blautia*. An exemplary glycan therapeutic is xyl100.

In some embodiments, the glycan therapeutics drive selective changes in both the composition and activity (or function) of the gastrointestinal microbiota, thereby conferring health benefits upon the host. In some embodiments, the glycan therapeutic is a selective substrate for one or a limited number of potentially beneficial bacteria that reside in the GI tract, stimulating their growth and/or metabolic activity. In some embodiments, the glycan therapeutic is capable of altering the composition of gastrointestinal microbiota to a composition higher or lower in specific bacteria. In some embodiments, the glycan therapeutic selectively stimulates the growth and/or selective activity of gastrointestinal bacteria associated with health and well-being. In one example, the glycan therapeutic compositions described herein decrease the abundance or relative number or density of a pathogenic bacterium.

The relationship between microbiota and their host is not merely commensal (a non-harmful coexistence), but in many cases a symbiotic relationship. Though subjects can survive without microbiota, the microorganisms perform a variety of useful functions, such as fermenting unused energy substrates, training the immune system, preventing growth of pathogenic bacteria, regulating the development of the gut, producing vitamins for the host (such as biotin and vitamins) (See, e.g., Dominguez-Bello M G and Blaser M J, 2008 Microbes Infect, 10(9): 1072-1076). Common gastrointestinal bacterial taxa include genera *Bacteroides, Odoribacter, Parabacteroides, Alistipes, Blautia, Clostridium, Coprococcus, Dorea, Eubacterium, Lachnospira, Roseburia, Ruminococcus, Faecalibacterium, Oscillospira,* and *Subdoligranulum*. Some bacterial genera and species are thought to be associated with a healthy state of the GI tract, such as, e.g., the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus,* and *Streptococcus,* and/or the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius,* and *Streptococcus thermophilus*.

However, in certain conditions, pathogenic species and pathobionts which are capable of causing disease, e.g. by inducing an infection and/or inflammation and/or bacteria associated with a disease state without necessarily being a causative agent, are present in the niche. In some embodiments, disease-associated bacteria, pathobionts or pathogens that may be modulated by the glycan therapeutics described herein are selected from the group consisting of the genera *Bilophila, Campylobacter, Candidatus, Citrobacter, Clostridium, Collinsella, Desulfovibrio, Enterobacter, Enterococcus, Escherichia, Fusobacterium, Haemophilus, Klebsiella, Lachnospiraceae, Peptostreptococcus, Porphyromonas, Portiera, Providencia, Pseudomonas, Salmonella, Shigella, Staphylococcus, Streptococcus, Vibrio,* and *Yersinia*.

In some embodiments, disease-associated bacteria, pathobionts or pathogens that may be modulated by the glycan therapeutics described herein are selected from the group consisting of the species *Bilophila wadsworthia, Campylobacter jejuni, Citrobacter farmer, Clostridium difficile, Clostridium perfringens, Clostridium tetani, Collinsella aerofaciens, Enterobacter hormaechei, Enterococcus faecalis, Enterococcus faecium, Escherichia coli, Fusobacterium varium, Fusobacterium nucleatum, Haemophilus parainfluenzae, Klebsiella pneumonia, Peptostreptococcus stomatis, Porphyromonas asaccharolytica, Pseudomonas aeruginosa, Salmonella bongori, Salmonella enteric, Shigella boydii, Shigella dysenteriae, Shigella flexneri, Shigella sonnei, Staphylococcus aureus, Streptococcus infantarius, Vibrio cholera,* and *Yersinia enterocolitica*.

In some embodiments, disease-associated bacteria, pathobionts or pathogens that may be modulated by the glycan therapeutics described herein may reside predominantly in one or more specific regions of the GI tract.

For example, the following disease-associated bacteria, pathobionts and pathogens reside predominantly in the large intestine (colon): *Listeria, Entamoeba histolytica, Balantidium coli, Basidiobolus ranarum, Trypanosoma cruzi, Clostridium botulinum, Fasciola hepatica, Histoplasma capsulatum, Rotavirus, Schistosoma mansoni, Schistosoma japonicum,* and *Schistosoma mekongi, Shigella, Brachyspira aalborgi, Serpulina pilosicoli, Trichuris trichiura,* and *Yersinia enterocolitica*.

The following disease-associated bacteria, pathobionts and pathogens reside predominantly in the small intestine: *Vibrio, Yersinia enterocolitica, Yersinia pseudotuberculosis, Clostridium perfringens, Capillaria philippinensis, Cryptosporidium parvum, Cyclospora cayetanensis* and CMV virus.

The following disease-associated bacteria, pathobionts and pathogens reside predominantly in the large and small intestine: *Campylobacter* and *Salmonella*.

In another example, the following disease-associated bacteria, pathobionts and pathogens reside predominantly in the stomach: CMV virus, *Bacillus anthracis, Candida, Cryptosporidium,* EBV (Epstein-Barr virus), *Giardia lamblia, Helicobacter pylori, Helicobacter felis, Helicobacter fennelliae, Helicobacter cinaedi, Mycobacterium avium,* Herpes varicella zoster, *Histoplasma,* and *Toxoplasma*.

A healthy microbial community protects the host, e.g., by enhancing the intestinal barrier, by competitive exclusion of potential pathogens or disease-associated bacteria, and by growth inhibition of bacterial pathogens and disease-associated bacteria. A healthy bacterial community may exert direct antibacterial effects on pathogens and disease-associated bacteria through production of antibacterial substances, including bacteriocins and acid (Cotter P D, et al. 2005 Nat Rev, 3:777-788; Servin A L, 2004 FEMS Microbiol Rev, 28: 405-440). The antibacterial substances exert their effects alone or synergistically to inhibit the growth of pathogens or disease-associated bacteria. A healthy bacterial community may decrease adhesion of both pathogens and their toxins to gastrointestinal lining.

In some embodiments, the glycan therapeutic modulates (e.g. increases or decreases) the growth of one or more bacterial taxa residing in the GI tract, such as, e.g., those that belong to genera *Bacteroides, Odoribacter, Parabacteroides, Alistipes, Blautia, Clostridium, Coprococcus, Dorea, Eubacterium, Lachnospira, Roseburia, Ruminococcus, Faecalibacterium, Oscillospira,* and *Subdoligranulum* which can be found in the GI tract. In some embodiments, the glycan therapeutic modulates (e.g. increases or decreases) the growth of one or more bacterial taxa, such as those that are thought to be associated with a healthy gastrointestinal state, e.g., one or more of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus,* and *Streptococcus,* and/or one or more of the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius,* and *Streptococcus thermophilus*. In some embodiments, the glycan therapeutic modulates (e.g. increases or decreases) the growth of one or more bacterial taxa, such as taxa of the phylum Verrucomicrobia, e.g., those of the genus *Akkermansia*.

In some embodiments, modulates (e.g. increases or decreases) the growth of one or more bacterial taxa predominantly residing in the small intestine. For example, the glycan therapeutic modulates one or more (2, 3, 4, 5, 6, 7, 8, 9, 10 or more) bacterial taxa that reside predominantly in the small intestine, such as, e.g. Actinobacteria, Firmicutes (Bacilli, Clostridia), and Proteobacteria (Alphaproteobacteria, Betaproteobacteria). In some embodiments, the glycan therapeutic modulates one or more (2, 3, 4, 5, 6, 7, 8, 9, 10 or more) bacterial taxa that reside predominantly in the small intestine selected from the genera: *Cryocola, Mycobacterium, Enterococcus, Lactococcus, Streptococcus, Turicibacter, Blautia, Coprococcus, Holdemania, Pseudoramibacter Eubacterium, Agrobacterium, Sphingomonas, Achromobacter, Burkholderia*, and *Ralstonia*.

In some embodiments, the glycan therapeutic modulates (e.g. increases or decreases) the growth of one or more bacterial taxa predominantly residing in the large intestine. For example, the glycan therapeutic modulates one or more (2, 3, 4, 5, 6, 7, 8, 9, 10 or more) bacterial taxa that reside predominantly in the large intestine, such as, e.g. Bacteroidetes, Firmicutes (Clostridia), Verrucomicrobia, and Proteobacteria (Deltaproteobacteria). In some embodiments, the glycan therapeutic modulates one or more (2, 3, 4, 5, 6, 7, 8, 9, 10 or more) bacterial taxa that reside predominantly in the large intestine selected from the genera: *Bacteroides, Butyricimonas, Odoribacter, Parabacteroides, Prevotella, Anaerotruncus, Phascolarctobacterium, Ruminococcus, Bilophila*, and *Akkermansia*.

In some embodiments, the glycan therapeutic modulates (e.g. increases or decreases) the growth of one or more bacterial taxa predominantly residing in the cecum, such as, e.g. Actinobacteria, *Bacteroides*, Bacilli, Clostridia, Mollicutes, Alpha Proteobacteria, and Verrucomicrobia.

In some embodiments, the glycan therapeutic modulates (e.g. increases or decreases) the growth of one or more bacterial taxa predominantly residing in the ascending colon, such as, e.g. Actinobacteria, *Bacteroides*, Bacilli, Clostridia, Fusobacteria, Beta Proteobacteria, Delta/Epsilon Proteobacteria, Gamma Proteobacteria, and Verrucomicrobia.

In some embodiments, the glycan therapeutic modulates (e.g. increases or decreases) the growth of one or more bacterial taxa predominantly residing in the traverse colon, such as, e.g. Actinobacteria, *Bacteroides*, Clostridia, Mollicutes, Fusobacteria, and Gamma Proteobacteria.

In some embodiments, the glycan therapeutic modulates (e.g. increases or decreases) the growth of one or more bacterial taxa predominantly residing in the descending colon, such as, e.g. *Bacteroides*, Clostridia, Mollicutes, Fusobacteria, Delta/Epsilon Proteobacteria and Verrucomicrobia.

In some embodiments, the glycan therapeutic modulates (e.g. increases or decreases) the growth of one or more bacterial taxa predominantly residing in the sigmoid colon, such as, e.g. Actinobacteria, *Bacteroides*, Bacilli, Clostridia, Mollicutes, Alpha Proteobacteria, Beta Proteobacteria, and Verrucomicrobia.

In some embodiments, the glycan therapeutic modulates (e.g. increases or decreases) the growth of one or more bacterial taxa predominantly residing in the rectum, such as, e.g. *Bacteroides*, Clostridia, Mollicutes, Alpha Proteobacteria, Gamma Proteobacteria, and Verrucomicrobia.

In some embodiments, the glycan therapeutics modulate (e.g. stimulate/increase or suppress/decrease) the growth of one or more (e.g. 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 150, 200, or more than 200) endogenous commensal microbial taxa or exogenously administered probiotic bacterial taxa of various genera including, e.g. *Alistipes, Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Odoribacter, Oscillospira, Parabacteroides, Phascolarctobacterium, Peptococcus, Peptostreptococcus, Prevotella, Roseburia, Ruminococcus*, and *Streptococcus* and *Subdoligranulum*.

In some embodiments, the glycan therapeutics modulate (e.g. stimulate/increase or suppress/decrease) the growth of one or more (e.g. 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 150, 200, or more than 200) endogenous commensal or symbiotic microbial taxa or exogenously administered probiotic bacterial taxa of various genera including, but not limited to, bacterial taxa selected from the group consisting of genera *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus* and of the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus* thought to be associated with gastrointestinal health may be modulated by the glycan therapeutics described herein.

In some embodiments, the glycan therapeutics modulate (e.g. substantially increase or substantially decrease) the growth (and the total number) of (or substantially increase or substantially decrease the relative representation in the total gastrointestinal community) of one or more of (e.g. 1, 2, 3, 4, 5, 6, 7, 8, 9, 10, 11, 12, 13, 14, 15, 16, 17, 18, 19, 20, 25, 30, 35, 40, 45, 50, or more than 50) the genus, species, or phylogenetic clade listed in Table 1. Table 1 provides a genus level list of microbial constituents of the GI tract.

In some embodiments, the glycan therapeutics substantially increase the growth, e.g. the total number or the relative representation in the total gastrointestinal community, the community of the large intestine or the community of the small intestine of one or more of (e.g. 1, 2, 3, 4, 5, 6, 7, 8, 9, 10, 11, 12, 13, 14, 15, 16, 17, 18, 19, 20, 25, 30, 35, 40, 45, 50, or more than 50) of the OTU, genus, species, or phylogenetic clade listed in Table 1, 3, and 4.

In some embodiments, the glycan therapeutics substantially decrease the growth, e.g. the total number or the relative representation in the total gastrointestinal community, the community of the large intestine or the community of the small intestine of one or more of (e.g. 1, 2, 3, 4, 5, 6, 7, 8, 9, 10, 11, 12, 13, 14, 15, 16, 17, 18, 19, 20, 25, 30, 35, 40, 45, 50, or more than 50) of the OTU, genus, species, or phylogenetic clade listed in Table 1, 3, and 4.

In some embodiments, the glycan therapeutics substantially increase and decrease the growth, e.g. the total number or the relative representation in the total gastrointestinal community, the community of the large intestine or the community of the small intestine of one or more of (e.g. 1, 2, 3, 4, 5, 6, 7, 8, 9, 10, 11, 12, 13, 14, 15, 16, 17, 18, 19, 20, 25, 30, 35, 40, 45, 50, or more than 50) of the OTU, genus, species, or phylogenetic clade listed in Table 1, 3, and 4.

In some embodiments, provided herein are glycan therapeutics that are substrates only for a selected group bacteria that are capable of utilizing the glycan therapeutic as a food source. The breakdown of the glycan therapeutic then exerts beneficial effects on the health of the host. The beneficial health effects are due to a selective stimulation of the growth and/or biological activity of a selected number of microbial genera, species, or strains in the gastrointestinal microbiota that are capable of utilizing the glycan therapeutic as a food source and confer health benefits to the host. The effects of the glycan therapeutic, in certain embodiments, are due to selective stimulation of the growth of the beneficial bacteria in the GI tract. Such increases and decreases in the abundance of certain taxa may be sufficient to "normalize" the resident microbiota, e.g. to reinstate a healthy state or equilibrium. Increase or decrease is with respect to the ratio present in the human subject prior to ingestion of the pharmaceutical glycan therapeutic composition, or to a control group not taking the pharmaceutical glycan therapeutic composition. The prebiotic index (PI) can be used as a proxy for effects of the glycan therapeutics described herein. PI relates to the sum of: (Bifidobacteria/total bacteria)+(Lactobacilli/total bacteria)−(*Bacteroides*/total bacteria)−(Clostridia/total bacteria), (see Palframan et al, 2003, Lett Appl Microbiol 37:281-284). In some embodiments, the ratio of *Eubacterium* rectale/total bacteria may also be considered. *Eubacterium* rectale produces butyrate which is advantageous for the gut barrier in adults.

For example, the stimulation of growth of certain bacterial taxa may reduce the pH of the colon, increase the production of short chain fatty acids, prevent the proliferation and adhesion of pathogenic microorganisms (barrier effect), increase the metabolism of potentially carcinogenic aminated compounds, and/or increase the production of vitamins.

In some embodiments, provided herein are glycan therapeutics that can be digested by the microbiota (e.g. by carbohydrate fermentation) without certain side effects or with a substantial reduction of symptoms of fermentation, such as increased gas formation that may cause flatulence, discomfort, and/or bloating.

In certain embodiments, the ratio of certain bacterial taxa or their relative abundance may be shifted. Such shifts may be measured with respect to the ratio present in the subject prior to administration of the pharmaceutical glycan therapeutic composition, or to a control group not taking the pharmaceutical glycan therapeutic composition.

In some embodiments, the glycan therapeutic is a selective substrate for one or a limited number of potentially beneficial bacterial taxa that reside in the GI tract, stimulating their growth and/or metabolic activity. In some embodiments, the glycan therapeutic is capable of altering the composition of gastrointestinal microbiota to a composition higher or lower in specific bacterial taxa. In some embodiments, the glycan therapeutic selectively stimulates the growth and/or selective activity of gastrointestinal bacterial taxa associated with health and well-being.

Methods are provided that comprise administering to a subject in need thereof a pharmaceutical glycan therapeutic composition in an amount effective to modulate microbial diversity. In some embodiments, administration of the glycan therapeutic modulates (e.g. increases or decreases) microbial diversity in the GI tract (or specifically in the large intestine or the small intestine) of a human subject. The diversity may increase or decrease when an effective amount of the glycan therapeutic is administered.

In some embodiments, the glycan therapeutic increases diversity. In some embodiments, the glycan therapeutic decreases diversity. Exemplary glycan therapeutics that modulate microbial diversity include glu100, ara100, xyl100, glu50gal50, and glu33gal33fuc33.

In some embodiments, a dysbiosis has shifted the microbiota and has increased or decreased the microbial diversity such that a disturbed state is reached. Administration of the glycan therapeutic can modulate the microbial diversity, thereby treating the dysbiosis. In some embodiments, the microbial diversity is decreased and the abundance of one or more, two or more, three or more, or four or more bacterial taxa is increased, including *Akkermansia, Blautia, Bacteroides, Bifidobacterium Lactobacillus*, and *Parabacteroides*.

Microbial diversity can be measured by any suitable method known in the art, including analysis of 16S rDNA sequences described herein. Diversity can be expressed, e.g. using the Shannon Diversity index (Shannon entropy), number of observed OTUs, Chao1 index, etc. In some embodiments, the glycan therapeutics modulate (e.g. increase or decrease) diversity within a microbial community, e.g. that of the GI tract, which may be expressed using Shannon entropy as a measure.

In some embodiments, the glycan therapeutics increase microbial diversity and associated Shannon entropy by 0.0001%, 0.0005%, 0.001%, 0.005%, 0.01%, 0.05%, 0.1%, 0.5%, 1%, 5%, 10%, 50%, 100%, 500%, 1000%, 5000%, or 10000%. In some embodiments, the glycan therapeutics increase microbial diversity and associated Shannon entropy by (log) 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or more. In some embodiments, the glycan therapeutics decrease microbial diversity and associated Shannon entropy by 0.0001%, 0.0005%, 0.001%, 0.005%, 0.01%, 0.05%, 0.1%, 0.5%, 1%, 5%, 10%, 20%, 30%, 40%, 50%, 60%, 70%, 80%, 90%, or 99% or more. In some embodiments, the glycan therapeutics decrease microbial diversity and associated Shannon entropy by (log) 1-fold, 2-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or more.

In some embodiments, the glycan therapeutics increase microbial diversity and associated Shannon entropy by at least 1%, 2%, 3%, 4%, 5%, 10%, 15% 20%, 25%, 30%, 35%, 40%, 45%, or by at least 50%.

In some embodiments, the glycan therapeutics increase microbial diversity and associated Shannon entropy by at least (log) 0.2-fold, 0.3-fold, 0.4-fold, 0.5-fold, 0.8-fold, 1-fold, 1.2-fold, 1.5-fold, 1.8-fold, or at least 2-fold.

In some embodiments, the glycan therapeutics decrease microbial diversity and associated Shannon entropy by at least 1%, 2%, 3%, 4%, 5%, 10%, 15% 20%, 25%, 30%, 35%, 40%, 45%, 50%, 55%, 60%, 65%, 70%, or by at least 75%.

In some embodiments, the glycan therapeutics decrease microbial diversity and associated Shannon entropy by at least (log) 0.2-fold, 0.3-fold, 0.4-fold, 0.5-fold, 0.8-fold, 1-fold, 1.2-fold, 1.5-fold, 1.8-fold, 2-fold, 3-fold, 4-fold, or at least 5-fold.

Some methods described herein include the administration of glycan therapeutics to modulate the host's immune functions and intestinal epithelial cell functions. The glycan therapeutics may upregulate the immune function, e.g. to improve the ability of the host to fight infections, while downregulation of immune function may prevent the onset of allergy or intestinal inflammation. Modulated beneficial bacteria may stimulate intestinal epithelial cell responses, including restitution of damaged epithelial barrier, production of antibacterial substances and cell-protective proteins, and blocking of cytokine-induced intestinal epithelial cell apoptosis.

Bacteria can elicit both pro- and anti-inflammatory responses from host (mammalian) cells, and different bacterial species can elicit different host responses. In one embodiment, glycan therapeutics are used to alter the bacterial population to elicit a desired host response. The host response may be modulated via direct interactions with the bacterial population or via indirect interactions via secreted or shed bacterial products (e.g., short-chain fatty acids). Glycan therapeutics may alter the bacterial population such that the bacterial population, upon either direct or indirect interaction with host cells, stimulates the production of antimicrobial peptides (AMPs), or modulates (i.e., increases or decreases the production of) inflammatory and immunomodulatory cytokines including interleukin-1α (IL-1α), IL-1β, IL-2, IL-4, IL-6, IL-8, IL-10, IL-12, IL-13, IL-17A, IL-17F, IL-22, IL-23, tumor necrosis factor (TNF), chemokine (C-C motif) ligand 5 (CCL5, also known as RANTES), transforming growth factor beta (TGF-β), interferon gamma (IFN-γ), or modulates other innate or adaptive immune responses.

In some embodiments, the inflammatory state of the GI tract is modulated by oral administration of a glycan therapeutic. In some embodiments, bacterial fermentation of glycan therapeutics in the gut produces short-chain fatty acids (SCFAs). SCFAs produced by the gut microbiota serve as energy sources for colonic epithelial cells and are thought to contribute to the maintenance of gut barrier function, which in turn limits plasma endotoxin levels and prevents systemic inflammation (Cani et al., Changes in gut microbiota control inflammation in obese mice through a mechanism involving GLP-2-driven improvement of gut permeability, Gut, 2009, 58:1091). In addition, SCFAs promote the generation of regulatory T (Treg) cells, and are thought to play a role in limiting inflammatory responses (Arpaia et al., Metabolites produced by commensal bacteria promote peripheral regulatory T-cell generation, Nature, 2013, 504: 451). In some embodiments, glycan therapeutics are administered to induce systemic effects, e.g. of SCFAs and other microbially produced immunomodulatory molecules or metabolites to modulate the inflammatory state of distal sites.

The glycan therapeutics when administered to a subject in an effective amount may modulate the production of one or more microbial metabolites, such as those listed in Table 2. In some embodiments, glycan therapeutics when administered to a subject in an effective amount may modulate (e.g. increase or decrease) one or more of the following microbial metabolites: formic acid, acetic acid, propionic acid, butyric acid, isobutyric acid, valeric acid, isovaleric acid, ascorbic acid, lactic acid, tryptophan, serotonin, and/or indole. In some embodiments, glycan therapeutics when administered to a subject in an effective amount may modulate (e.g. increase or decrease) one or more of the following microbial metabolites: succinic acid, trimethylamine (TMA), TMAO (trimethylamine N-oxide), deoxy cholic acid, ethyphenyl sulfate, acetaldehyde, hydrogen peroxide, and/or butanedione. In some embodiments, a substantial increase or decrease in a metabolite may be detected. In some embodiments, the glycan therapeutic is digested by the gut microbiota (e.g. Clostridia), resulting, e.g., in the release of short-chain fatty acids such as butyrate, acetate, and propionate, which may act immunomodulatory (e.g. anti-inflammatory) and other metabolites (e.g. bile acids, and lactate) that may confer beneficial health effects on the host.

The glycan therapeutics when administered to a subject in an effective amount may modulate one or more host pathways. Short chain fatty acids (SCFAs) are bacterial metabolites produced in the gut by commensal bacteria including members of the families Ruminocaccaceae and Lachnospiraceae (Vital M, Howe A C, Tiedje J M. 2014. Revealing the bacterial butyrate synthesis pathways by analyzing (meta)genomic data. mBio 5(2):e00889-14. doi:10.1128/mBio.00889-14). SCFAs modulate a number of human immunological factors; for example, treatment with propionate, a SCFA, in mice or in vitro increased expression of Foxp3, a T cell regulatory factor, and IL-10, an anti-inflammatory cytokine, in colonic regulatory T cells. Additionally, exposure to SCFAs has been shown to increase frequency and number of colonic regulatory T cells (cTregs) and CD4+ T cells in germ-free mice (Smith P M et al. 2013. The microbial metabolites, short chain fatty acids, regulate colonic Treg cell homeostasis. Science; 341(6145). SCFAs promote gut barrier function by affecting mucin production and gastrointestinal peptide LL-37, and SCFAs additionally modulate inflammation by suppressing NF-kB and the production of inflammatory cytokines such as IL-6 and TNF-α (Kim C H et al. 2014. Gut Microbiota-Derived Short-Chain Fatty Acids, T Cells, and Inflammation. Immune Network 14(6):277-288). In some embodiments, glycan therapeutics when administered in an effective amount modulate bacterial species that produce SCFAs, such as, e.g., those of the Ruminocaccaeae family and/or Lachnospiraceae family. In some embodiments, the glycan therapeutics modulate host immunity and inflammation. For example, in the in vitro assay of Example 8, growth of ROB.74, a member of the Ruminocaccaeae family, was supported by 13 out of 15 glycans, and growth of CSC.32 and CNE.31, members of the Lachnospiraceae family, were supported by 6 and 7 out of 15 glycans, respectively.

In some embodiments, method of modulating a functional pathway of the microbiota of the gastrointestinal tract are provided. The methods include administering to the human subject a pharmaceutical composition comprising a glycan therapeutic preparation in an amount effective to modulate the functional pathway. In some embodiments, the functional pathway modulates the production of anti-microbial agent, a secondary bile acid, a short-chain fatty acid, a siderophore or a metabolite listed in Table 2 by the microbiota. In some embodiments, the short chain fatty acid is produced by one or more bacterial member of the Ruminocaccaceae and/or Lachnospiraceae family. In some embodiments, the subject is obese.

In some embodiments, the pharmaceutical glycan therapeutic compositions comprise one or more polyphenols. The glycan therapeutic preparation and the one or more polyphenols in the pharmaceutical composition can have additive or synergistic effects.

In some embodiments, the polyphenols are capable of modulating one or more bacterial constituents in the GI tract (e.g. for polyphenols from cranberry extract: Anhê F F et al. et al. "A polyphenol-rich cranberry extract protects from diet-induced obesity, insulin resistance and intestinal inflammation in association with increased *Akkermansia* spp. population in the gut microbiota of mice." Gut. 2014; for blueberry extract: Guglielmetti S et al. "Differential modulation of human intestinal bifidobacterium populations after consumption of a wild blueberry (*Vaccinium angustifolium*) drink. J Agric Food Chem. 2013; 61(34):8134-40; Lacombe A et al. "Phytochemicals in lowbush wild blueberry inactivate *Escherichia coli* O157:H7 by damaging its cell membrane." Foodborne Pathog Dis. 2013; 10(11): 944-50; for grape extracts: Choy Y Y et al. "Phenolic metabolites and substantial microbiome changes in pig feces by ingesting grape seed proanthocyanidins." Food Funct. 2014; 5(9):

2298-308; Roopchand D E et al. "Dietary polyphenols promote growth of the gut bacterium *Akkermansia muciniphila* and attenuate high fat diet-induced metabolic syndrome." Diabetes. 2015; for peach and plum extract: Noratto G D et al. "Carbohydrate-free peach (*Prunus persica*) and plum (*Prunus domestica*) juice affects fecal microbial ecology in an obese animal model." PLoS One. 2014; 9(7): e101723; for red wine and black tea: Kemperman R A, Gross G, Mondot S, et al. Impact of polyphenols from black tea and red wine/grape juice on a gut model microbiome. Food Res Int. 2013, 53(2):659-69; for soy (legume): Rafii F "The role of colonic bacteria in the metabolism of the natural isoflavone daidzin to equol." Metabolites. 2015 Jan. 14:56-73).

In some embodiments, the pharmaceutical composition comprising the glycan therapeutic preparation and the polyphenol preparation modulates (e.g. increases or decreases) the growth of one or more bacterial taxa, such as bacteria of the phylum Verrucomicrobia, e.g., those of the genus *Akkermansia*. In some embodiments, the pharmaceutical composition comprising the glycan therapeutic preparation and the polyphenol preparation increases the abundance of bacteria of the phylum Verrucomicrobia, including the genus *Akkermansia*

In some embodiments, polyphenols in the compositions have antioxidant functions. In some embodiments, polyphenols in the compositions have anti-bacterial functions. In some embodiments, the antioxidant and/or anti-bacterial function of the polyphenols in the composition modulates the abundance of one or more bacteria residing in the GI tract.

In some embodiments, the pharmaceutical glycan therapeutic composition comprises polyphenols that act as antimicrobials, e.g., by inhibiting the growth of subsets of species, such as, e.g. pathogens or pathobionts. (Puupponen-Pimiä R et al. "Antimicrobial properties of phenolic compounds from berries." 2001. Journal of Applied Microbiology 90: 494-507; Puupponen-Pimiä R et al. "Berry phenolics selectively inhibit the growth of intestinal pathogens." 2005. Journal of Applied Microbiology 98: 991-1000).

In some embodiments, polyphenols in the composition are a selective substrate for one or more bacterial taxa that reside in the GI tract, (e.g., Selma M V et al. "Interaction between Phenolics and Gut Microbiota: Role in Human Health." 2009. Journal of Agricultural and Food Chemistry 57: 6485-6501; Déprez S et al. "Polymeric Proanthocyanidins Are Catabolized by Human Colonic Microflora into Low-Molecular-Weight Phenolic Acids." 2000. The Journal of Nutrition 131: 2733-2738; Tzounis X et al. "Flavanol monomer-induced changes to the human faecal microflora." 2007. The British Journal of Nutrition 99: 782-792; Kutschera M et al. "Isolation of catechin-converting human intestinal bacteria." 2011. Journal of Applied Microbiology 111: 165-175; Schneider H et al. "Anaerobic transformation of quercetin-3-glucoside by bacteria from the human intestinal tract." 1999. Archives of Microbiology 171: 81-91; Hein E M et al. "Deconjugation and Degradation of Flavonol Glycosides by Pig Cecal Microbiota Characterized by Fluorescence in Situ Hybridization (FISH)." 2008. Journal of Agricultural and Food Chemistry 56: 2281-2290).

Methods of Screening a Plurality of Glycan Therapeutic Preparations

In order to characterize the effects of the glycan therapeutics, provided is an in vitro microplate-based screening system that demonstrates the efficacy of the glycan therapeutic preparation, including the ability to inhibit (or antagonize/suppress) the growth of certain microbial constituents and the ability to promote (or increase) the growth of other microbial constituents. These methods provide novel glycan therapeutic preparations that are able to improve the health of the gastrointestinal microbiome and/or promote health of the subject. In some embodiments, the screening methods include: i) providing a plurality of preparations of glycan therapeutics, ii) subjecting the preparation to one or more screen, iii) selecting a preparation of glycan therapeutics based on the screens, and optionally iv) isolating the selected preparation of glycan therapeutics. A suitable single strain screening method is described in the Examples. Other suitable screens are known to one of ordinary skill and any necessary experimental parameters may be adjusted with only routine experimentation.

In some embodiments, glycan therapeutics promote the growth of bacterial strains that are able to significantly reduce the rate of pathogen growth and/or capable of partially or fully restoring a bacterial community that is associated with a healthy GI tract.

In some embodiments, glycan therapeutics are provided that promote the growth of beneficial bacteria. Exemplary glycans are listed in Table 8. In some embodiments, commensal growth-promoting glycan therapeutic include gal100, glu100, xyl100, ara100, ara50gal50, ara50xyl50, gal75xyl25, glu50gal50, man62glu38, glu33gal33fuc33 and man52glu29gal19.

In some embodiments, glycan therapeutics are provided that do not promote the growth of pathogenic bacteria but promote the growth of beneficial bacteria. Exemplary glycans are listed in Table 9. In some embodiments, commensal-selective glycan therapeutic (e.g. a glycan therapeutic that preferentially promotes the growth of commensal bacteria over the growth of pathogenic bacteria) include gal100, glu100, xyl100, ara50gal50, and ara50xyl50.

In some embodiments, methods are provided that include selecting a glycan therapeutic for further processing (e.g. formulating it into a pharmaceutical composition) or further testing (e.g. analyzing additional characteristics) using a single strain screen. For example, the glycan therapeutic may be tested for promoting growth in media supplemented with the preparation of commensal strains selected from the group consisting of *Bacteroides caccae* ATCC 43185, *Prevotella copri* DSM 18205, *Bacteroides thetaiotaomicron* ATCC 29741, *Bacteroides cellulosilyticus* DSM 14838, *Clostridium scindens* ATCC 35704, *Ruminococcus obeum* ATCC 29714, *Clostridium nexile* ATCC 27757, and *Parabacteroides distasonis* ATCC 8503. Alternatively or in addition, the glycan therapeutic may be tested for promoting growth in media supplemented with the preparation of pathogenic strains selected from the group consisting of *Clostridium difficile* ATCC BAA-1382, *Clostridium difficile* ATCC 43255, *Enterococcus faecium* ATCC 700221, and *Salmonella enterica* ATCC 27869. A glycan therapeutic may be selected for further processing or testing if one or both of the following criteria are met: i) the glycan therapeutic promotes the growth of at least 4, 5, or at least 6 commensal strains, and ii) the glycan therapeutic promotes the growth of no more than 3, 2, 1 or no more than 0 pathogenic strains.

The effect of the glycan therapeutics on bacterial growth can also be tested in other in vitro assays and using laboratory animal models. The bacteria can be collected from samples taken from the niche of interest (e.g. a stool sample containing feces) and propagated by methods known in the art. Competitive in vitro growth assays may then be performed using conditions that are suitable for growth of bacteria from the niche of interest, e.g. conditions that may mimic the natural environment of the niche, e.g. the GI tract or a subset thereof, such as the large and small intestine. Such conditions include, but are not limited to aerobic, anaerobic, low/high/neutral pH, physiological temperature (e.g. human body temperature), etc.

In some embodiments, in vivo assays are performed to detect the effect of the glycan therapeutic on bacterial growth in the GI tract. In order to determine whether the glycan therapeutic preparation modulates the microbial populations in the GI tract of a subject, a laboratory animal model, such as a mouse model of human disease, can be used. The microbiota of the mice can be evaluated and characterized. Qualitative assessments can be accomplished using 16S rRNA profiling of the microbial community in the GI tract of normal mice. It can also be accomplished by full genome sequencing, whole genome shotgun sequencing (WGS), or traditional microbiological techniques. Quantitative assessments can be conducted using quantitative PCR (qPCR) or by using traditional microbiological techniques and counting colony formation. Optionally, the mice can receive an antibiotic treatment to mimic the condition of a disturbed gastrointestinal microbiota in which the GI microbiota exhibit a dysbiosis. It is known that antibiotic treatment can decrease the taxonomic richness, diversity, and evenness of gut communities, including a reduction of abundance of a significant number of bacterial taxa. (Dethlefsen et al., The pervasive effects of an antibiotic on the human gut microbiota, as revealed by deep 16S rRNA sequencing, PLoS Biology 6(11):3280 (2008)).

Various effects of glycan therapeutics (e.g. to assess modulation of bacterial taxa, modulation of microbial diversity, modulation of drug-induced symptoms, and therapeutic effects (e.g. assessing the modulation of disease-associated phenotypes)), can be assessed in suitable animal models for a certain disease, such as, e.g., a DSS-colitis mouse model (e.g. to assess diseases, disorders or conditions associated with an inflammation or drug-induced damage), a diet-induced obesity mouse model (e.g. to assess metabolic diseases, disorders or conditions) and a *C. difficile* infection mouse model (e.g. to assess diseases, disorders or conditions associated with an infection or drug-induced damage), and wild-type mouse models subjected to, e.g., drug-treatments (e.g. antibiotic regimen, cancer drug regimen, etc.) or diet-changes, such as, e.g. zero-fiber diet, low-fiber diets, normal chow diet, high-fat diet, etc. to assess various states of the microbiota of the gastrointestinal tract.

In some embodiments, the screening methods are carried out using a suitable laboratory animal model. For example, a preparation of glycan therapeutics may be administered to a laboratory animal and after a period of time a sample is taken from the laboratory animal's GI tract and analyzed for growth of bacterial taxa. The laboratory animal may, if desired, be contacted with pathogens or other bacteria to facilitate colonization of the animal prior to or concurrent with administration of the glycan therapeutic. In some embodiments, a preparation of glycan therapeutics is selected that is capable of modulating (e.g. increasing or decreasing) the growth of at least 1, 2, 3, 4, 5, 6, 7, 8, 9, 10, 15, or at least 20 bacterial taxa in the laboratory animal.

In one embodiment, the animal model is a *C. difficile* mouse model and the glycan therapeutic is capable of modulating one or more of *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus,* and *Enterococcus*. In one embodiment, the animal model is a zero-fiber and normal chow wild-type mouse model and the glycan therapeutic is capable of modulating *Akkermansia* and *Blautia*. In some embodiments, the therapeutic glycan is xyl100, glu100, glu33gal33fuc33, glu50gal50, or ara100.

In some embodiments, the screen is an in vitro assay in which one or more bacterial taxa are grown in a growth medium and the growth is monitored in the presence of the glycan therapeutics and compared to growth in the absence of the glycan therapeutics. Any practical number of bacterial taxa may be grown in the medium, such as, e.g., 1, 2, 3, 4, 5, 6, 7, 8, 9, 10, 15, 20, 30, 40, or 50 taxa. In some embodiments, a preparation of glycan therapeutics is selected that modulates (e.g. increases or decreases) the growth of at least 1, 2, 3, 4, 5, 6, 7, 8, 9, 10, 15, or at least 20 bacterial taxa. In one embodiment, the screen is a single strain assay and the glycan therapeutic is selected from those listed in Table 8 modifying at least 5, 6, 7, or 8 strains of Table 8.

In some embodiments, the growth of one or more bacterium is increased by at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 100%, 110%, 120%, 130%, 140%, 150%, 160%, 170%, 180%, 190%, 200%, 250%, 300%, 350%, 400%, 450%, 500%, 600%, 700%, 800%, 900%, or by at least 1000% after 1 hour, 6 hours, 12 hours, 18 hours, 24 hours, 48 hours or 72 hours of contacting.

In other embodiments, the growth of one or more bacterium is decreased by at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or by at least 99.9% after 1 hour, 6 hours, 12 hours, 18 hours, 24 hours, 48 hours or 72 hours of contacting.

In some embodiments, the glycan therapeutic also modulates the concentration of one or more microbial metabolite selected from the group consisting of the metabolites listed in Table 2. In some embodiments, the metabolite concentration is increased by at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 100%, 110%, 120%, 130%, 140%, 150%, 160%, 170%, 180%, 190%, 200%, 250%, 300%, 350%, 400%, 450%, 500%, 600%, 700%, 800%, 900%, or by at least 1000% after 1 hour, 6 hours, 12 hours, 18 hours, 24 hours, 48 hours or 72 hours of contacting. In other embodiments, the metabolite concentration is decreased by at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or by at least 99.9% after 1 hour, 6 hours, 12 hours, 18 hours, 24 hours, 48 hours or 72 hours of contacting.

Digestibility is a parameter that can be ascertained for the glycan therapeutics described herein. In some embodiments, glycan therapeutics disclosed herein are screened to assess their digestibility. Digestibility of glycan therapeutics can be assessed by any suitable method known in the art. In some embodiments, digestibility is assessed by a physiologically relevant in vitro digestion reaction. Samples at different stages of the digestion can be analyzed by standard glycan techniques known in the art and described herein. By monitoring the amount of intact glycan therapeutics observed over time, the half-life of digestion can be calculated. Suitable assays can be used to assess comparative digestibility (e.g., against a benchmark glycan) or to assess absolute digestibility.

Digestibility of a glycan therapeutic is a function of the number or representation of hydrolysable glycosidic bonds in the glycan species of the preparation. Enzymes that are capable of hydrolyzing glycosidic bonds usually are specific to a particular bond, stereochemistry, and a subunit composition. Certain types of hydrolyzable bonds, e.g., alpha 1,4; alpha 1,6, alpha 1,2; and alpha 1,6 glycosidic linkages are recognized by specific microbial enzymes (e.g. alpha-glucosidase, cyclomaltodextrinase, neopullunanase, glucanotransferase, trehalohydrolase, and the like) and are not substrates for mammalian enzymes. Digestibility of glycans depends on many factors, including, e.g., the degree of polymerization, the degree of branching, the type of glycosidic linkages, position of the linkages, anomeric configuration (e.g. L- or D-configuration, alpha/beta configuration) of the glycan unit(s) (e.g. monosaccharide), and the glycan unit composition. For example, furanosides are generally more susceptible to hydrolysis than pyranosides. Deoxy sugars are generally more acid labile than non-deoxy sugars. Uronic acids are generally less susceptible to hydrolysis than non-uronic monosaccharides. Branching protects against digestion by human enzymes, and it is generally observed that the larger the molecule, the lesser the fermentation speed (digestibility) in the colon. These characteristics generally promote indigestibility by human glycosidases and can promote selective fermentation or digestion by the microbiota.

In some embodiments, pharmaceutical glycan therapeutic compositions that are administered orally and that reach the gut comprise a mixture of a plurality of glycan species with a desired degree of digestibility in the gut (or specific regions of the gut) of the host. In some embodiments, the glycan therapeutic is non-digestible to mammalian enzymes and can only be hydrolyzed by microbial enzymes. In some embodiments, the glycan therapeutic cannot be metabolized by a human and is only metabolizable (or fermentable) by the human's microbiota.

Different microbial taxa have different hydrolyzing enzymes. In some embodiments, the glycan therapeutic is fermentable in an in vitro single strain digestibility assay by one, two, three, four, five or more commensal bacterial species, e.g. *Bacteroides caccae* ATCC 43185, *Prevotella copri* DSM 18205, *Bacteroides thetaiotamicron* ATCC 29741, *Bacteroides cellulosilyticus* DSM 14838, *Clostridium scindens* ATCC 35704, *Ruminococcus obeum* ATCC 29714, *Clostridium nexile* ATCC 27757, and *Parabacteroides distasonis* ATCC 8503. In some embodiments, the glycan therapeutic is non-fermentable in an in vitro single strain digestibility assay by one, two, three, four, five or more pathogenic species, e.g., of *Clostridium difficile* ATCC BAA-1382, *Clostridium difficile* ATCC 43255, *Enterococcus faecium* ATCC 700221, and *Salmonella enterica* ATCC 27869. In some embodiments, the glycan therapeutic is non-fermentable by a specific bacterial taxa in a single strain in vitro digestibility assay (e.g. at least 70%, 80%, 90%, 95% or 98% of the glycan preparation is non-fermentable) but is fermentable by the taxa in vivo in a suitable bacterial niche of the host (e.g. the GI tract or a specific region thereof, such as the colon or intestine). In some embodiments, the bacterial taxa include *Akkermansia, Bacteroides, Bifidobacterium, Lactobacillus*, and *Parabacteroides*. Fermentability can be measured, e.g., by monitoring growth of the bacterial taxa in vitro or in vivo.

In some embodiments, hydrolysis of glycosidic bonds are catalyzed by an enzyme and the rate of catalysis can be measured by any suitable means known in the art and the rate can be compared to that of another enzyme. A high rate of hydrolysis, transfer of glycan units, and/or modification of glycan units may suggest that the bond is a suitable substrate of the enzyme. Ease of hydrolysis can be expressed by a high rate of catalytic reaction. Other bonds are incompatible with an enzyme or a set of enzymes and they are difficult to hydrolyze. In some embodiments, the digestibility (expressed as half-life) is 30 minutes or less, 20 minutes or less, 15 minutes or less, 10 minutes or less, 5 minutes or less, 4 minutes or less, 3 minutes or less, 2 minutes or less or 1 minute or less. In some embodiments, the digestibility (expressed as half-life) is 30 minutes or more, 45 minutes or more, 1 hour or more, 2 hours or more, 3 hours or more, 4 hours or more, 5 hours or more, or 10 hours or more. In some embodiments, the preparation of glycan therapeutics comprises less than 1%, 2%, 3%, 4%, 5%, 6%, 7%, 8%, 9%, 10%, 12%, 14%, 16%, 18%, 20%, 30%, 40%, or less than 50% bonds that are hydrolyzable by a mammalian amylase enzyme. Digestibility may also be assessed by gastric digestion half-life.

Identification of Bacterial Constituents

In some embodiments, the pharmaceutical glycan therapeutic compositions described herein are administered to a subject to increase the growth of beneficial bacteria and/or to decrease the growth of pathogens in the GI tract. In some embodiments, the microbial community is shifted by the glycan therapeutic toward that of a healthy state. The microbial changes occurring in the GI tract can be analyzed using any number of methods known in the art and described herein.

As one quantitative method for determining whether a glycan therapeutic preparation results in a shift of the population of bacteria in the GI tract, quantitative PCR (qPCR) can be performed. Genomic DNA can be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions, or by other standard methods known to those skilled in the art.

In some embodiments, qPCR can be conducted using HotMasterMix (5PRIME, Gaithersburg, Md.) and primers specific for certain (e.g. beneficial or desired) bacteria and may be conducted on a MicroAmp® Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (BioRad, Hercules, Calif.), with fluorescent readings of the FAM and ROX channels. The Cq value for each well on the FAM channel is determined by the CFX Manager™ software version 2.1. The $\log_{10}$ (cfu/ml) of each experimental sample is calculated by inputting a given sample's Cq value into linear regression model generated from the standard curve comparing the Cq values of the standard curve wells to the known $\log_{10}$ (cfu/ml) of those samples. The skilled artisan may employ alternative qPCR modes.

In some embodiments, the microbial constituents are identified by characterizing the DNA sequence of microbial 16S small subunit ribosomal RNA gene (16S rRNA gene). 16S rRNA gene is approximately 1,500 nucleotides in length, and in general is highly conserved across organisms, but contain specific variable and hypervariable regions (V1-V9) that harbor sufficient nucleotide diversity to differentiate species- and strain-level taxa of most organisms. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10): 4801-4805 (1978)).

Composition of a microbial community can be deduced by sequencing full 16S rRNA gene, or at least one of the V1, V2, V3, V4, V5, V6, V7, V8, and V9 regions of this gene or by sequencing of any combination of variable regions from this gene (e.g. V1-3 or V3-5). In one embodiment, the V1, V2, and V3 regions are used to characterize a microbiota. In another embodiment, the V3, V4, and V5 regions are used to characterize a microbiota. In another embodiment, the V4 region is used to characterize a microbiota.

Sequences that are at least 97% identical to each other are grouped into Operational Taxonomic Units (OTUs). OTUs that contain sequences with 97% similarity correspond to approximately species level taxa. At least one representative sequence from each OTU is chosen, and is used to obtain a taxonomic assignment for an OTU by comparison to a reference database of highly curated 16S rRNA gene sequences (such as Greengenes or SILVA databases). Relationship between OTUs in a microbial community could be deduces by constructing a phylogenetic tree from representative sequences from each OTU.

Using known techniques, in order to determine the full 16S sequence or the sequence of any variable region of the 16S sequence, genomic DNA is extracted from a bacterial sample, the 16S rRNA (full region or specific variable regions) amplified using polymerase chain reaction (PCR), the PCR products are cleaned, and nucleotide sequences delineated to determine the genetic composition of 16S rRNA gene or a variable region of the gene. If full 16S sequencing is performed, the sequencing method used may be, but is not limited to, Sanger sequencing. If one or more variable regions is used, such as the V4 region, the sequencing can be, but is not limited to being performed using the Sanger method or using a next-generation sequencing method, such as an Illumina method. Primers designed to anneal to conserved regions of 16S rRNA genes (e.g., the 515F and 805R primers for amplification of the V4 region) could contain unique barcode sequences to allow characterizing multiple microbial communities simultaneously.

As another method to identify microbial composition is characterization of nucleotide markers or genes, in particular highly conserved genes (e.g., "house-keeping" genes), or a combination thereof, or whole genome shotgun sequence (WGS). Using defined methods, DNA extracted from a bacterial sample will have specific genomic regions amplified using PCR and sequenced to determine the nucleotide sequence of the amplified products. In the WGS method, extracted DNA will be fragmented into pieces of various lengths (from 300 to about 40,000 nucleotides) and directly sequenced without amplification. Sequence data can be generated using any sequencing technology including, but not limited to Sanger, Illumina, 454 Life Sciences, Ion Torrent, ABI, Pacific Biosciences, and/or Oxford Nanopore.

In addition to the 16S rRNA gene, a selected set of genes that are known to be marker genes for a given species or taxonomic group is analyzed to assess the composition of a microbial community. These genes are alternatively assayed using a PCR-based screening strategy. For example, various strains of pathogenic *Escherichia coli* are distinguished using genes that encode heat-labile (LTI, LTIIa, and LTIIb) and heat-stable (STI and STII) toxins, verotoxin types 1, 2, and 2e (VT1, VT2, and VT2e, respectively), cytotoxic necrotizing factors (CNF1 and CNF2), attaching and effacing mechanisms (eaeA), enteroaggregative mechanisms (Eagg), and enteroinvasive mechanisms (Einv). The optimal genes to utilize to determine the taxonomic composition of a microbial community by use of marker genes are familiar to one with ordinary skill in the art of sequence based taxonomic identification.

Sequencing libraries for microbial whole-genome sequencing (WGS) may be prepared from bacterial genomic DNA. For genomic DNA that has been isolated from a human or laboratory animal sample, the DNA may optionally enriched for bacterial DNA using commercially available kits, for example, the NEBNext Microbiome DNA Enrichment Kit (New England Biolabs, Ipswich, Mass.) or other enrichment kit. Sequencing libraries may be prepared from the genomic DNA using commercially available kits as well, such as the Nextera Mate-Pair Sample Preparation Kit, TruSeq DNA PCR-Free or TruSeq Nano DNA, or the Nextera XT Sample Preparation Kit (Illumina, San Diego, Calif.) according to the manufacturer's instructions. Alternatively, libraries can be prepared using other kits compatible with the Illumina sequencing platform, such as the NEBNext DNA Library Construction Kit (New England Biolabs, Ipswich, Mass.). Libraries may then be sequenced using standard sequencing technology including, but not limited to, a MiSeq, HiSeq or NextSeq sequencer (Illumina, San Diego, Calif.). Alternatively, a whole-genome shotgun fragment library prepared using standard methods in the art. For example, the shotgun fragment library could be constructed using the GS FLX Titanium Rapid Library Preparation Kit (454 Life Sciences, Branford, Conn.), amplified using a GS FLX Titanium emPCR Kit (454 Life Sciences, Branford, Conn.), and sequenced following standard 454 pyrosequencing protocols on a 454 sequencer (454 Life Sciences, Branford, Conn.). Bacterial RNA may be isolated from microbial cultures or samples that contain bacteria by commercially available kits, such as the RiboPure Bacterial RNA Purification Kit (Life Technologies, Carlsbad, Calif.). Another method for isolation of bacterial RNA may involve enrichment of mRNA in purified samples of bacterial RNA through remove of tRNA. Alternatively, RNA may be converted to cDNA, which used to generate sequencing libraries using standard methods such as the Nextera XT Sample Preparation Kit (Illumina, San Diego, Calif.).

Nucleic acid sequences are analyzed to define taxonomic assignments using sequence similarity and phylogenetic placement methods or a combination of the two strategies. A similar approach is used to annotate protein names, protein function, transcription factor names, and any other classification schema for nucleic acid sequences. Sequence similarity based methods include BLAST, BLASTx, tBLASTn, tBLASTx, RDP-classifier, DNAclust, RapSearch2, DIAMOND, USEARCH, and various implementations of these algorithms such as QIIME or Mothur. These methods map a sequence read to a reference database and select the best match. Common databases include KEGG, MetaCyc, NCBI non-redundant database, Greengenes, RDP, and Silva for taxonomic assignments. For functional assignments, reads are mapped to various functional databases such as COG, KEGG, BioCyc, MetaCyc, and the Carbohydrate-Active Enzymes (CAZy) database. Microbial clades are assigned using software including MetaPhlAn.

Proteomic Analysis of Microbial Populations

Preparations of glycan therapeutics may be selected based on their ability to increase the expression of microbial proteins associated with healthy states or to decrease the expression of microbial proteins associated with diseased states. Proteomic analysis of microbial populations can be performed following protocols known to one skilled in the art (e.g., Cordwell, Exploring and exploiting bacterial proteomes, Methods in Molecular Biology, 2004, 266:115). To identify differentially expressed proteins (for example, to identify changes in protein expression upon treatment of microbial populations with glycan therapeutics), proteomic analysis can be performed as described, e.g., in Juste et al. (Bacterial protein signals are associated with Crohn's disease, Gut, 2014, 63:1566). For example, the protein is isolated from the microbial lysates of two samples (for example, an untreated microbial population and a population that has been treated with glycan therapeutics). Each protein sample is labeled (e.g., with a fluorescent dye, e.g., Cy3 or Cy5 CyDye DIGE Fluor minimal dye, GE Healthcare) and analyzed by two-dimensional differential gel electrophoresis (2D-DIGE). Gels are stained and protein spots identified as being significantly different between the two samples are excised, digested, and analyzed by liquid chromatography-tandem mass spectrometry (LC-MS/MS). X!TandemPipeline (http://pappso.inra.fr/bioinfo/xtandempipeline/) can be used to identify differentially expressed proteins.

Preparations of glycan therapeutics may also be selected for administration to a human subject based on their effect on the presence of microbial fermentation products. For example, preparations of glycan therapeutics can be selected for their ability to induce or promote growth of bacteria that produce short chain fatty acids such as propionate (propionic acid), acetate, and/or butyrate (butyric acid). Similarly, preparations of glycan therapeutics can be selected for their ability to induce or promote growth of bacteria that produce lactic acid, which can modulate the growth of other bacteria by producing an acidic environment. Such analysis may also be used to pair probiotic bacteria with glycan therapeutics such that the glycan therapeutic is a substrate for the production of the desired fermentation products.

The metabolites that are present in fresh or spent culture media or in biological samples collected from humans may be determined using methods described herein. Unbiased methods that may be used to determine the relative concentration of metabolites in a sample and are known to one skilled in the art, such as gas or liquid chromatography combined with mass spectrometry or $^1$H-NMR. These measurements may be validated by running metabolite standards through the same analytical systems.

In the case of gas chromatography-mass spectrometry (GC-MS) or liquid-chromatography-mass spectrometry (LC-MS) analysis, polar metabolites and fatty acids could be extracted using monophasic or biphasic systems of organic solvents and an aqueous sample and derivatized (Fendt et al., Reductive glutamine metabolism is a function of the α-ketoglutarate to citrate ratio in cells, Nat Commun, 2013, 4:2236; Fendt et al., Metformin decreases glucose oxidation and increases the dependency of prostate cancer cells on reductive glutamine metabolism, Cancer Res, 2013, 73:4429; Metallo et al., Reductive glutamine metabolism by IDH1 mediates lipogenesis under hypoxia, Nature, 2011, 481:380). An exemplary protocol for derivatization of polar metabolites involves formation of methoxime-tBDMS derivatives through incubation of the metabolites with 2% methoxylamine hydrochloride in pyridine followed by addition of N-tert-butyldimethylsilyl-N-methyltrifluoroacetamide (MTBSTFA) with 1% tert-butyldimethylchlorosilane (t-BDMCS). Non-polar fractions, including triacylglycerides and phospholipids, may be saponified to free fatty acids and esterified to form fatty acid methyl esters, for example, either by incubation with 2% $H_2SO_4$ in methanol or by using Methyl-8 reagent (Thermo Scientific). Derivatized samples may then be analyzed by GC-MS using standard LC-MS methods, for example, a DB-35MS column (30 m×0.25 mm i.d.×0.25 µm, Agilent J&W Scientific) installed on a gas chromatograph (GC) interfaced with an mass spectrometer (MS). Mass isotopomer distributions may be determined by integrating metabolite ion fragments and corrected for natural abundance using standard algorithms, such as those adapted from Fernandez et al. (Fernandez et al., Correction of 13C mass isotopomer distributions for natural stable isotope abundance, J Mass Spectrom, 1996, 31:255). In the case of liquid chromatography-mass spectrometry (LC-MS), polar metabolites may be analyzed using a standard benchtop LC-MS/MS equipped with a column, such as a SeQuant ZIC-pHILIC Polymeric column (2.1×150 mm; EMD Millipore). Exemplary mobile phases used for separation could include buffers and organic solvents adjusted to a specific pH value.

In combination or in the alternative, extracted samples may be analyzed by $^1$H-nuclear magnetic resonance ($^1$H-NMR). Samples may be combined with isotopically enriched solvents such as D2O, optionally in the presence of a buffered solution (e.g., $Na_2HPO_4$, $NaH_2PO_4$ in $D_2O$, pH 7.4). Samples may also be supplemented with a reference standard for calibration and chemical shift determination (e.g., 5 mM 2,2-dimethyl-2-silapentane-5-sulfonate sodium salt (DSS-$d_6$, Isotec, USA)). Prior to analysis, the solution may be filtered or centrifuged to remove any sediment or precipitates, and then transferred to a suitable NMR tube or vessel for analysis (e.g., a 5 mm NMR tube). $^1$H-NMR spectra may be acquired on a standard NMR spectrometer, such as an Avance II+500 Bruker spectrometer (500 MHz) (Bruker, DE), equipped with a 5 mm QXI-Z C/N/P probehead) and analyzed with spectra integration software (such as Chenomx NMR Suite 7.1; Chenomx Inc., Edmonton, AB). (Duarte et al., $^1$H-NMR protocol for exometabolome analysis of cultured mammalian cells, Methods Mol Biol, 2014:237-47). Alternatively, $^1$H-NMR may be performed following other published protocols known in the art (Chassaing et al., Lack of soluble fiber drives diet-induced adiposity in mice, Am J Physiol Gastrointest Liver Physiol, 2015; Bal et al., Comparison of Storage Conditions for Human Vaginal Microbiome Studies, PLoS ONE, 2012: e36934).

Methods of Treatment

Provided herein are methods for treating a human subject. These methods, in some embodiments, include one or both of i) identifying a human subject having or suspected of having a dysbiosis of the gastrointestinal microbiota, and ii) administering to the human subject a pharmaceutical composition comprising a glycan therapeutic preparation in an amount effective to treat the dysbiosis.

The pharmaceutical glycan therapeutic compositions described herein are suitable for administration to humans in need thereof. In certain embodiments, the subject is a human that has one or more symptoms of a dysbiosis of the gastrointestinal microbiota, including but not limited to overgrowth of an undesired pathogen or one or more undesired bacterial taxa, reduced representation of key health-associated bacterial taxa, reduced or increased diversity of microbial species compared to a healthy individual, or reduced overall abundance of beneficial bacteria.

In some embodiments, the glycan therapeutics are beneficial in the treatment of various diseases, disorders or conditions. Such disease, disorders or conditions may be associated with a dysbiosis of the microbiota. Disturbances in beneficial microbiota can occur due to a variety of factors (e.g. genetic or environmental) including, but not limited to, use of antibiotics, chemotherapeutics and other dysbiosis-inducing drugs or treatments (e.g. radiation treatment), pathogen infection, pathobiont activity, miscalibrated caloric intake (e.g. high-fat, high-sugar), miscalibrated (non-digestible) fiber intake (e.g. low or zero fiber), host factors (e.g. host genetic alterations), and similar.

In some embodiments, the disease, disorder or condition is associated with a dysbiosis of the gastrointestinal microbiota. In some embodiments, by treating the dysbiosis the disease, disorder or condition is treated.

Symptoms that may be associated with a dysbiosis of the gastrointestinal microbiota and/or with a gastrointestinal disease, disorder or condition include, but are not limited to gas, heartburn, stomach upset, bloating, flatulence, diarrhea, abdominal pain, cramping, nausea, and vomiting. Minor digestive problems related to the GI also include occasional bloating, diarrhea, constipation, gas, or stomach upset.

Infectious Diseases

In some embodiments, administration of the glycan therapeutic reduces infection. In some embodiments, a subject is identified to be suitable for treatment if the subject has or is suspected of having a disease, disorder or condition including: gastrointestinal infectious diseases including *Clostridium difficile* infection (CDI); Vancomycin-resistant enterococci (VRE) infection, infectious colitis, and *C. difficile* colitis; mycoses, such as, e.g., *Candida albicans* infection, *Campylobacter jejuni* infection, *Helicobacter pylori* infection; diarrhea, such as, e.g., *Clostridium difficile* associated diarrhea (CDAD), antibiotic-associated diarrhea (AAD), antibiotic-induced diarrhea, travellers' diarrhea (TD), pediatric diarrhea, (acute) infectious diarrhea, colon and liver cancers, ameboma; necrotizing enterocolitis (NEC), and small intestine bacterial overgrowth (SIBO); indigestion or non-ulcer dyspepsia; anal fissures, perianal abscess and anal fistula; diverticulosis or diverticulitis; peptic ulcers; and gastroenteritis.

In one embodiment, the subject being identified to be suitable for treatment with a glycan therapeutic has or is suspected of having a *Clostridium difficile* infection (CDI); a Vancomycin-resistant enterococci (VRE) infection, infectious colitis, or *C. difficile* colitis.

In one embodiment, the subject being identified to be suitable for treatment with a glycan therapeutic has or is suspected of having mycoses, such as, e.g., *Candida albicans* infection, *Campylobacter jejuni* infection, or *Helicobacter pylori* infection.

In some embodiments, the GI tract infection is a bacterial or viral infection, such as an infection with, e.g., VRE, *C. difficile*, *Escherichia coli*, *Salmonella*, *Shigella*, *Campylobacter*, *Vibrio cholera*, *Clostridium perfringes*, *Bacillus cereus*, *Vibrio parahemolyticus*, *Yersinia enterocolitica*, *Helicobacter pylori*, rotavirus, or norovirus.

In some embodiments, the GI tract infection is a fungal infection, such as an infection with, e.g., *Candida*, *Aspergillus*, *Mucor*, *Cryptococcus*, *Histoplasma*, or *Coccidioides*.

In some embodiments, the GI tract infection is a protozoal infection, such as an infection with, e.g., *Entamoeba histolytica*, *Giardia lamblia*, *Cryptosporidium parvum*.

In one embodiment, the subject being identified to be suitable for treatment with a glycan therapeutic has or is suspected of having diarrhea, such as, e.g., *Clostridium difficile* associated diarrhea (CDAD), antibiotic-associated diarrhea (AAD), antibiotic-induced diarrhea, travellers' diarrhea (TD), pediatric diarrhea, or (acute) infectious diarrhea.

In one embodiment, the subject being identified to be suitable for treatment with a glycan therapeutic has or is suspected of having necrotizing enterocolitis (NEC); gastroenteritis; small intestine bacterial overgrowth (SIBO) or similar disease, disorder or condition associated with a GI tract infection.

In one embodiment, the subject being identified to be suitable for treatment with a glycan therapeutic has or is suspected of having colon cancer, liver cancer, ameboma; indigestion or non-ulcer dyspepsia; anal fissures, perianal abscess and anal fistula; diverticulosis or diverticulitis; peptic ulcer or similar disease, disorder or condition associated with structural alterations of the GI tract.

In some embodiments, subjects with *Clostridium difficile* infection (CDI)-induced colitis may be treated according to the methods provided herein. Subjects with CDI-induced colitis may present with watery diarrhea, cramping, abdominal pain, anorexia, malaise, fever, dehydration, lower abdominal tenderness, and/or rebound tenderness. The presence of *C. difficile* in the stool of patients can be tested by stool culture, glutamate dehydrogenase enzyme immunoassay, PCR assay to detect genes for *C. difficile* toxins, stool cytotoxin assay, or enzyme immunoassay for *C. difficile* toxins A and B. Patient populations include subjects with primary CDI, subjects with recurrent CDI, subjects with different severities of CDI-associated diarrhea (mild, moderate, severe), and subjects at risk for CDI due to the presence of risk factors such as antibiotics treatment, broad-spectrum antibiotics treatment, residence in a hospital or long-term care facility, gastrointestinal tract surgery, diseases of the colon, a weakened immune system, chemotherapy, advanced age, kidney disease, or use of proton-pump inhibitors. Standard-of-care treatments for CDI include antibiotics such as metronidazole, fidaxomicin, or vancomycin. Treatments may also include probiotics, fecal transplant, and fluids to prevent dehydration. Resolution of disease is measured by abatement of diarrhea (e.g., the absence of a 24 hour period with more than three unformed stools) and resolution of other symptoms described above. Clearance of infection may be verified by the absence of a positive stool test for *C. difficile*.

In one embodiment, methods are provided to prevent, treat, ameliorate symptoms of, and/or prevent initial colonization or relapse of colonization by pathogens. In some embodiments, the relapse occurs during or after first-line or standard-of-care treatment regimen. In some cases, a pathogen load may initially lighten upon the standard-of-care treatment but then the load begins to increase again, potentially triggering a relapse of the disease. In some embodiments, glycan therapeutics may be administered (e.g. at the beginning, during or after the initial treatment regimen) to prevent the relapse or treat one or more relapse symptoms. In some embodiments, disease-associated bacteria, pathobionts or pathogens are selected from the group consisting of the species *Bilophila wadsworthia*, *Campylobacter jejuni*, *Citrobacter farmer*, *Clostridium difficile*, *Clostridium perfringens*, *Clostridium tetani*, *Collinsella aerofaciens*, *Enterobacter hormaechei*, *Enterococcus faecalis*, *Enterococcus faecium*, *Escherichia coli*, *Fusobacterium varium*, *Fusobacterium nucleatum*, *Haemophilus parainfluenzae*, *Klebsiella pneumonia*, *Peptostreptococcus stomatis*, *Porphyromonas asaccharolytica*, *Pseudomonas aeruginosa*, *Salmonella bongori*, *Salmonella enteric*, *Shigella boydii*, *Shigella dysenteriae*, *Shigella flexneri*, *Shigella sonnei*, *Staphylococcus aureus*, *Streptococcus infantarius*, *Vibrio cholera*, and *Yersinia enterocolitica*.

In some embodiments, disease-associated bacteria, pathobionts or pathogens include the genera *Bilophila, Campylobacter, Candidatus, Citrobacter, Clostridium, Collinsella, Desulfovibrio, Enterobacter, Enterococcus, Escherichia, Fusobacterium, Haemophilus, Klebsiella, Lachnospiraceae, Peptostreptococcus, Porphyromonas, Portiera, Providencia, Pseudomonas, Salmonella, Shigella, Staphylococcus, Streptococcus, Vibrio*, and *Yersinia*.

In one embodiment, provided herein is a method of preventing relapse of *C. difficile* symptoms in a subject having been treated with a first-line drug (e.g. vancomycin, metronidazole, fidaxomicin). The method includes the steps of identifying a subject infected with *C. difficile* and having been administered an antibiotic and administering to the subject a pharmaceutical composition comprising a glycan therapeutic in an amount effective to prevent the recurrence of one or more symptoms associated with *C. difficile* infection. In some embodiments, viable *C. difficile* pathogen is retained in the gastrointestinal tract of the subject (e.g. CFU counts are detectable in a sample taken from the subject, e.g. a fecal sample) even post-treatment with the antibiotic but *C. difficile* associated symptoms are significantly reduced.

In some embodiments, subjects exhibiting vancomycin-resistant enterococci (VRE) colonization and infection may be treated according to the methods provided herein. Bacteria of the genus *Enterococcus* are common members of the gut microbiota. Vancomycin-resistant members of this genus, commonly *E. faecalis* and *E. faecium*, can cause vancomycin-resistant enterococci (VRE) colonization and infection. Subjects colonized with VRE may present with a VRE-positive stool sample, rectal swab, perirectal swab, or sample from another body site. Vancomycin resistance can be assessed by bacterial culture or by PCR-based assays that detect vancomycin resistance (Van) gene operons. Although colonized subjects may be asymptomatic, this population is at increased risk for infection with VRE. Subjects with VRE infection may present with diarrhea, fever, chills, urinary tract infection (UTI), bacteremia, endocarditis, intra-abdominal and pelvic infection, respiratory infection, or infection at another body site. Patient populations include subjects who are colonized with VRE, subjects suffering from a VRE infection, and subjects who are at risk for colonization or infection with VRE due to the presence of risk factors such as hospitalization, residence in a long-term care facility, long-term antibiotic use, immunosuppression, surgery, open wounds, indwelling devices (e.g., intravenous lines or urinary catheters), or employment as a health care worker. Standard prevention measures for VRE colonization or infection include strict adherence to good hygiene practices (e.g., hand washing) and avoidance of risk factors where possible (e.g., removal of indwelling devices). Subjects colonized with VRE but not suffering from a VRE infection are typically not treated. Standard-of-care treatment options for VRE infections are limited due to resistance to standard antibiotics, but can include combinations of antibiotics and/or antibiotics such as quinupristin-dalfopristin, linezolid, daptomycin, and tigecycline that have been demonstrated to retain activity against many strains of VRE. Treatments may also include probiotics or supportive care. Resolution of disease is measured by clearance of infection and resolution of other symptoms described above. Clearance of infection or colonization may be verified by the absence of a VRE-positive test in a relevant biological sample. Prevention of infection or colonization may be quantified in a similar manner.

Inflammatory Diseases

In some embodiments, administration of the glycan therapeutic reduces inflammation. In some embodiments, a subject is identified to be suitable for treatment if the subject has or is suspected of having a disease, disorder or condition including: gastrointestinal inflammatory diseases including inflammatory bowel disease (IBD), ulcerative colitis (UC), Crohn's disease (CD), idiopathic inflammation of the small bowel, indeterminatal colitis, pouchitis; irritable bowel syndrome (IBS), colon and liver cancers, necrotizing enterocolitis (NEC), intestinal inflammation, constipation, microscopic colitis, diarrhea; graft versus host disease (GVHD); (food) allergies; pseudomembranous colitis; indigestion or non-ulcer dyspepsia; diverticulosis or diverticulitis, ischemic colitis; radiation colitis or enteritis; collagenous colitis; gastroenteritis; and polyps.

In one embodiment, the subject being identified to be suitable for treatment with a glycan therapeutic has or is suspected of having inflammatory bowel disease (IBD), ulcerative colitis (UC), Crohn's disease (CD), intestinal inflammation, microscopic colitis or similar disease, disorder or condition that is associated with inflammation of the intestine.

In one embodiment, the subject being identified to be suitable for treatment with a glycan therapeutic has or is suspected of having idiopathic inflammation of the small bowel, indeterminatal colitis, pouchitis, pseudomembranous colitis, ischemic colitis, radiation colitis (enteritis), collagenous colitis or similar disease, disorder or condition that is associated with inflammation of the intestine.

In one embodiment, the subject being identified to be suitable for treatment with a glycan therapeutic has or is suspected of having gastroenteritis; graft versus host disease (GVHD), or a (food) allergy.

In one embodiment, the subject being identified to be suitable for treatment with a glycan therapeutic has or is suspected of having irritable bowel syndrome (IBS), constipation, diarrhea, indigestion, non-ulcer dyspepsia or similar disease, disorder or condition that is associated with an altered intestinal transit.

In one embodiment, the subject being identified to be suitable for treatment with a glycan therapeutic has or is suspected of having colon cancer, liver cancers, necrotizing enterocolitis (NEC); diverticulosis or diverticulitis; polyps or similar disease, disorder or condition that is associated with structural alteration of the intestine.

Subjects with inflammatory bowel disease (IBD) may present with abdominal cramps and pain, diarrhea that may be bloody, urgency of bowel movements, constipation, nausea, vomiting, fever, weight loss, loss of appetite, and/or iron deficiency anemia due to blood loss. Symptoms of IBD may occur in flares, with alternating periods of symptomatic and asymptomatic disease. IBD may be diagnosed by a combination of tests, including stool exams (to eliminate the possibility of infectious causes of diarrhea, check for trace amounts of blood in the stool, and quantify biomarkers associated with IBD such as fecal calprotectin), a complete blood count to assess levels of inflammation, blood tests to assess biomarkers including C-reactive protein (CRP) and perinuclear anti-neutrophil cytoplasmic antibody (pANCA), barium X-ray, sigmoidoscopy, colonoscopy, and endoscopy. Patient populations include subjects with ulcerative colitis (UC; limited to the colon or large intestine), subjects with Crohn's disease (CD; affecting any segment of the gastrointestinal tract), and subjects with different disease severities (mild, moderate, severe). Standard-of-care treatments for IBD include aminosalicylates (e.g., sulfasalazine, mesalamine, balsalazide, olsalazine), corticosteroids (e.g., hydrocortisone, prednisone, methylprednisolone, prednisolone, budesonide, dexamethasone), immunosuppressants (e.g., azathioprine, 6-mercaptopurine, methotrexate, cyclosporine), antibiotics (e.g., metronidazole, ciprofloxacin, rifaximin), tumor necrosis factor inhibitors (e.g, infliximab, adalimumab, certolizumab pegol), integrin inhibitors (e.g., natalizumab, vedolizumab), and surgery. Resolution or control of disease may be quantified by endoscopic or sigmoidoscopic assessment of disease severity according to standard scoring metrics, abatement of symptoms described above, reduction in disease severity as determined by composite indexes such as the Crohn's Disease Activity Index (CDAI), or improvement in health-related quality of life as measured by the IBD Questionnaire (IBD-Q).

Metabolic Diseases

In some embodiments, a subject is identified to be suitable for treatment if the subject has or is suspected of having a disease, disorder or condition including: obesity, pre-diabetes, type II diabetes, high blood cholesterol, high LDL, high blood pressure, high fasting blood sugar, high triglyceride levels, low HDL non-alcoholic fatty liver disease (NAFLD), nonalcoholic steatohepatitis (NASH); metabolic syndrome; hyperammonemia, essential nutrient deficiency, hemochromatosis, lactose intolerance, gluten intolerance; and acrodermatitis enteropathica.

In one embodiment, the subject being identified to be suitable for treatment with a glycan therapeutic has or is suspected of having obesity, (insulin resistance) pre-diabetes, type II diabetes, high fasting blood sugar (hyperglycemia), metabolic syndrome or similar disease, disorder or condition associated with metabolic disease symptoms.

In one embodiment, the subject being identified to be suitable for treatment with a glycan therapeutic has or is suspected of having high blood cholesterol, high LDL, high blood pressure (hypertension), high triglyceride levels, low HDL or similar cardiovascular risk factor.

In one embodiment, the subject being identified to be suitable for treatment with a glycan therapeutic has or is suspected of having non-alcoholic fatty liver disease (NAFLD), nonalcoholic steatohepatitis (NASH), hyperammonemia or similar disease, disorder or condition of the liver.

In one embodiment, the subject being identified to be suitable for treatment with a glycan therapeutic has or is suspected of having lactose intolerance, gluten intolerance or similar disease, disorder or condition that is associated with food intolerance.

In one embodiment, the subject being identified to be suitable for treatment with a glycan therapeutic has or is suspected of having essential nutrient deficiency, hemochromatosis, acrodermatitis enteropathica or similar disease, disorder or condition that is associated with a nutrient mismanagement.

In one embodiment, provided is a method of treating a metabolic disorder in a human in need thereof, by: administering to the human a pharmaceutical glycan therapeutic composition to treat the metabolic disorder. In one embodiment, the metabolic disorder is selected from obesity, adiposity, insulin resistance, diabetes, and fatty liver syndrome.

Metabolic disorders may include disorders, diseases, and conditions that are caused or characterized by abnormal weight gain; energy use or consumption; altered responses to nutrients, energy sources, hormones, or other signaling molecules; or altered metabolism of carbohydrates, lipids, proteins, or nucleic acids, or a combination thereof. Examples of metabolic disorders include insulin resistance, insulin sensitivity, fatty liver syndrome, obesity, adiposity, and diabetes (e.g., type 1 diabetes, type 2 diabetes). In one variation, the methods provided herein treat obesity. Provided herein are methods for treating obesity in a subject in need thereof using a pharmaceutical glycan therapeutic composition that can alter gut microbiota of the subject in a way that results in weight loss and/or decreased body fat in the subject.

In one embodiment, provided is a method of reducing adiposity in a subject in need thereof, by: administering to the human a pharmaceutical glycan therapeutic composition in an amount effective to reduce adiposity. Adiposity may be determined using any appropriate method known in the art, including, for example, waist circumference, waist to hip ratio, skinfold thickness, bioelectric impedance, underwater weighing, air-displacement plethysmography, or hydrometry.

In one embodiment, provided is a method of improving glucose metabolism in a subject in need thereof, by: administering to the subject a pharmaceutical glycan therapeutic composition in an amount effective to improve glucose metabolism. Glucose metabolism may be determined by any appropriate method known in the art, including, for example, fasting blood sugar level, fasting insulin level, postprandial blood sugar test, postprandial insulin test, oral glucose tolerance test, intravenous glucose tolerance test, glycated hemoglobin level, or random blood sugar test.

In one embodiment, provided is a method of increasing insulin sensitivity in a human, by: administering to the subject a pharmaceutical glycan therapeutic composition in an amount effective to increase insulin sensitivity, wherein the human has an insulin sensitivity prior to the administration of the glycan therapeutic and an insulin sensitivity after the administration of the glycan therapeutic, and the insulin sensitivity of the human after the administration of the glycan therapeutic is higher than the insulin sensitivity of the human prior to the administration of the glycan therapeutic. Insulin sensitivity may be determined by any appropriate method known in the art, including, for example, fasting blood sugar level, fasting insulin level, postprandial blood sugar test, postprandial insulin test, oral glucose tolerance test, intravenous glucose tolerance test, glycated hemoglobin level, or random blood sugar test.

In some embodiments, subjects with type 2 diabetes may be treated according to the methods provided herein. Subjects with type 2 diabetes may present with blurred vision, peripheral neuropathy, increased urination, increased thirst, fatigue, increased hunger, weight loss, or yeast, bladder, kidney, skin, or other infections. Type 2 diabetes is diagnosed by criteria described by the American Diabetes Association (ADA), including the following: fasting plasma glucose (FPG) of 126 mg/dL (7 mM) or higher, or a 2 hour plasma glucose level of 200 mg/dL (11.1 mM) or higher during a 75 g oral glucose tolerance test (OGTT), or a random plasma glucose of 200 mg/dL (11.1 mM) or higher in a patient with classic symptoms of hyperglycemia or hyperglycemic crisis, or a hemoglobin A1c (HbA1c) level of 6.5% or higher. Patient populations include adults and children with type 2 diabetes, subjects at risk for developing type 2 diabetes (e.g., subjects with prediabetes or subjects who are overweight), and subjects with type 2 diabetes in conjunction with conditions of metabolic syndrome including obesity, elevated blood pressure, elevated serum triglycerides, and low high-density lipoprotein (HDL) levels. Standard-of-care treatments for type 2 diabetes include lifestyle management (diet, exercise, and behavioral modifications), alpha-glucosidase inhibitors, biguanides (e.g., metformin), sulfonylureas, dipeptidyl peptidase IV (DPP-4) inhibitors, glucagon-like peptide-1 (GLP-1) analogs, meglitinides, selective sodium-glucose transporter-2 (SGLT2) inhibitors, thiazolidinediones, insulin, and amylinomimetics. Treatment efficacy may be assessed by resolution of the symptoms or diagnostic criteria listed above (e.g., decrease in FPG to healthy levels), or, in subjects at risk for developing type 2 diabetes, by decreased rates of conversion to a type 2 diabetic state.

In some embodiments, subjects exhibiting Non-alcoholic fatty liver disease (NAFLD) and/or non-alcoholic steatohepatitis (NASH) may be treated according to the methods provided herein. Non-alcoholic fatty liver disease (NAFLD) is characterized by an abnormal buildup of fat in the liver. NAFLD can progress to non-alcoholic steatohepatitis (NASH), which is characterized by liver inflammation, fibrosis, and cirrhosis. Subjects with NAFLD may be asymptomatic. Subjects with NAFLD or NASH may present with increased liver size (noted during physical exam), fatigue, weight loss, general weakness, and/or ache in the upper right of the belly. Diagnosis of NAFLD/NASH includes elevated blood levels of alanine aminotransferase (ALT) or aspartate aminotransferase (AST), enlarged liver and specific histopathologic markers (e.g. by liver biopsy, abdominal ultrasound, CT scan, or an MRI scan). Patient populations include subjects with NAFLD, subjects with NASH, subjects at risk of developing NAFLD/NASH (e.g., subjects who are overweight or have elevated cholesterol levels), and subjects with NAFLD/NASH in conjunction with conditions of metabolic syndrome including obesity, elevated fasting plasma glucose, elevated blood pressure, elevated serum triglycerides, and low high-density lipoprotein (HDL) levels. Standard-of-care treatments for NAFLD/NASH include lifestyle management (diet, exercise, behavioral modifications, and avoidance of alcohol).

Treatments in clinical trials or under development include farnesoid X receptor (FXR) agonists (e.g., obeticholic acid), Takeda G protein-coupled receptor 5 (TGR5) agonists, fatty acid-bile acid conjugates (e.g., aramchol), antioxidants (e.g., vitamin E), antifibrotic agents, peroxisome proliferator-activated receptor (PPAR)-gamma agonists, PPAR alpha/delta agonists, caspase inhibitors (e.g., Emricasan), and/or galectin-3 inhibitors. Treatment efficacy may be assessed by resolution of the symptoms or diagnostic criteria listed above (e.g., decrease in ALT to healthy levels), or, in subjects at risk for developing NAFLD/NASH, by decreased rates of conversion to NAFLD/NASH.

In some embodiments, obese subjects may be treated according to the methods provided herein. Obesity is a significant health concern, and may have a negative effect on health. For example, obesity may lead to reduced life expectancy and/or increased health problems, such as diabetes, high blood pressure, heart disease, stroke, high cholesterol, sleep apnea, and arthritis. Obese subjects present with a body mass index (BMI) of greater than 30 kg/m$^2$. Alternatively, obese subjects may be classified based on body fat percentage (greater than 25% for males or greater than 33% for females). Diagnosis may also include an evaluation of fasting lipid levels (cholesterol, triglycerides), liver function, glucose levels, insulin levels, glycosylated hemoglobin (HbA1c), and/or glucose tolerance. Patient populations include subjects with childhood obesity, moderate obesity, morbid/severe obesity, genetic causes of obesity (including Prader-Willi syndrome, Bardet-Biedl syndrome, Cohen syndrome, and MOMO syndrome), and obesity in conjunction with other conditions of metabolic syndrome (elevated blood pressure, elevated fasting plasma glucose, elevated serum triglycerides, and low high-density lipoprotein (HDL) levels). Standard-of-care treatments for obesity include lifestyle management (diet, exercise, and behavioral modifications), bariatric surgery, medications that impair dietary absorption (e.g., tetrahydrolipstatin), medications that impair dietary intake, medications that increase energy expenditure, and medications to treat common comorbidities (e.g., medications for type 2 diabetes or hypertension). Treatment endpoints include change in body weight, fasting lipid levels, liver function, glucose levels, insulin levels, HbA1C, and/or glucose tolerance.

Other Diseases

In some embodiments, a subject is identified to be suitable for treatment if the subject has or is suspected of having a disease, disorder or condition including: autoimmune arthritis, type I diabetes, atopic dermatitis, autism, asthma, cardiovascular disease, chronic kidney disease, multiple sclerosis, heart disease, psoriasis, hyperammonemia, hepatic encephalopathy, cachexia, Gout, drug intolerance (e.g., to metformin), low oral bioavailability of drugs, fecal incontinence, Hirschsprung's disease, anismus, colic, ileus, hemorrhoids, and intussusceptions.

In one embodiment, the subject being identified to be suitable for treatment with a glycan therapeutic has or is suspected of having autoimmune arthritis, type I diabetes, multiple sclerosis, psoriasis or similar autoimmune disease, disorder or condition.

In one embodiment, the subject being identified to be suitable for treatment with a glycan therapeutic has or is suspected of having asthma, atopic dermatitis or similar environmental-driven allergy.

In one embodiment, the subject being identified to be suitable for treatment with a glycan therapeutic has or is suspected of having chronic kidney disease, heart disease, cardiovascular disease or similar disease, disorder or condition that is associated with organ failure.

In one embodiment, the subject being identified to be suitable for treatment with a glycan therapeutic has or is suspected of having autism, hyperammonemia, hepatic encephalopathy or similar disease, disorder or condition that is associated with neurological symptoms.

In one embodiment, the subject being identified to be suitable for treatment with a glycan therapeutic has or is suspected of having cachexia, Gout or similar nutritional disorder.

In one embodiment, the subject being identified to be suitable for treatment with a glycan therapeutic has or is suspected of having Hirschsprung's disease, ileus, anismus, intussusceptions, fecal incontinence, hemorrhoids or similar gastrointestinal disorder.

In some embodiments, subjects with atopic dermatitis (AD) may be treated according to the methods provided herein. Subjects with atopic dermatitis (AD) may present with skin that is dry, itchy, and/or inflamed. Diagnosis and severity of AD may be determined by using the SCORAD index (Oranje, A. P., et al. "Practical issues on interpretation of scoring atopic dermatitis: the SCORAD index, objective SCORAD and the three-item severity score." British Journal of Dermatology 157.4 (2007): 645-648) or the Eczema Area and Severity Index (EASI) score (Hanifin et al., The eczema area and severity index (EASI): assessment of reliability in atopic dermatitis, Experimental Dermatology, 2001, 10:11). AD may occur in flares, with alternating periods of symptomatic and asymptomatic disease. *Staphylococcus aureus* is commonly present on skin sites with AD, and biomarkers including IgE and inflammatory or Th2 cytokines and chemokines may also be elevated in the diseased skin or systemically. Patient populations include infants with early-onset AD, children with pediatric AD, adults with late-onset AD, pregnant women at risk for flares of AD ("atopic eruption of pregnancy"), subjects with mild, moderate, or severe AD flares, or subjects who are at risk of developing AD. Standard-of-care treatments for AD include topically applied moisturizers, topically applied steroid ointments such as hydrocortisone, bleach baths, antibiotics, immunomodulatory agents such as tacrolimus, antihistamines, antibody-based therapies (including antibodies to block IgE, the IL-4 receptor, IL-4, and IL-13), and other anti-inflammatory agents. Treatment may also include probiotics. Resolution or control of disease may be quantified by the standard SCORAD or EASI criteria described above.

In some embodiments, subjects with asthma may be treated according to the methods provided herein. Subjects with asthma may present with wheezing, coughing, shortness of breath, and/or chest tightness or pain. These symptoms are commonly episodic and may be triggered by factors such as exercise or exposure to allergens. Additionally, children with asthma may present with a history of recurrent bronchitis, bronchiolitis, or pneumonia or a persistent cough with colds. Diagnosis of asthma is established by lung function testing with spirometry in the presence and absence of treatment with a bronchodilator. Patient populations include infants with asthma; subjects with childhood asthma; adult-onset asthma; intermittent, mild persistent, moderate persistent, or severe persistent asthma; exercise-induced asthma; allergic asthma; cough-variant asthma; occupational asthma; nocturnal asthma; and subjects who are at risk of developing asthma, for example, due to a family history of atopy. Standard-of-care treatments for asthma include inhaled corticosteroids (e.g., budesonide, fluticasone, beclomethasone, mometasone, and ciclesonide), short-acting bronchodilators (e.g., albuterol), long-acting bronchodilators (e.g., salmeterol), leukotriene modifiers (e.g., montelukast) or other anti-inflammatory agents, anticholinergic agents (e.g., ipratropium, tiotropium), anti-IgE (e.g., omalizumab) for allergic asthma, and/or systemic steroids (e.g., prednisone, prednisolone, methylprednisolone, dexamethasone). Treatments may also include probiotics. Treatment efficacy may be assessed by a decrease in the frequency or severity of the symptoms described above, improvement in lung function (assessed by measurements such as peak expiratory flow rate (PEFR) or forced expiratory volume in 1 second (FEV1)), decrease in the need to continue or initiate treatments for asthma, or changes in the levels of biomarkers of airway inflammation (e.g., serum IgE, exhaled nitric oxide, sputum or blood eosinophil counts, inflammatory cytokines, Th2 cytokines, etc.).

In some embodiments, subjects with chronic kidney disease (CKD) may be treated according to the methods provided herein. Subjects with CKD may present with fatigue, trouble concentrating, poor appetite, trouble sleeping, nocturnal muscle cramping, swollen feet and ankles, skin rash/itching, nausea, vomiting, a metallic taste in the mouth, shortness of breath, and/or increased urination. Diagnosis of kidney disease, including CKD, is performed by tests of the glomerular filtration rate (GFR), blood levels of urea and creatinine, urine levels of albumin, kidney biopsy, ultrasound, and/or CT scan. Patient populations include subjects with CKD caused by diabetic nephropathy; subjects with CKD caused by high blood pressure; subjects with polycystic kidney disease, pyelonephritis, or glomerulonephritis; subjects with kidney damage due to long-term use of kidney-damaging medicines; and subjects at risk of developing CKD due to the presence of risk factors such as diabetes, high blood pressure, or family history of kidney disease. Standard-of-care treatments for CKD include medicines to lower blood pressure, control blood glucose, and lower blood cholesterol. Treatments may also include dietary modifications and probiotics. Treatment efficacy may be assessed by resolution of the symptoms or diagnostic criteria listed above (e.g., decrease in urine albumin and serum creatinine), reduction in the need to start dialysis or prolongation of the time before starting dialysis, reduction in blood levels of uremic solutes (e.g., p-cresol sulfate and indoxyl sulfate) or other potentially harmful circulating factors (e.g., trimethylamine N-oxide (TMAO), or, in subjects at risk for developing CKD, by decreased rates of conversion to CKD.

In some embodiments, subjects with Hepatic encephalopathy (HE) may be treated according to the methods provided herein. Hepatic encephalopathy includes multiple adverse neurological symptoms that occur when the liver is unable to remove toxic substances such as ammonia from the blood. Subjects with HE may present with confusion, forgetfulness, anxiety or excitation, sudden changes in personality or behavior, changes in sleep patterns, disorientation, sweet or musty smelling breath, slurred speech, and/or difficulty controlling motor functions. Diagnosis of HE is performed by tests of liver function, serum ammonia levels, EEG, and other blood and neurological tests. Patient populations include subjects with mild HE, severe HE, overt HE, subjects who have previously experience one or more episodes of HE, and patients who are at risk for HE due to the presence of risk factors such as liver damage. Standard-of-care treatments for HE include lactulose, lactitol, and antibiotics (e.g., rifaximin or neomycin). Treatments may also include dietary modifications and probiotics. Treatment efficacy may be assessed by resolution of the symptoms or diagnostic criteria listed above (e.g., reduction in serum ammonia levels), decreased incidence of future episodes of HE, or, in subjects at risk of HE, by decreased occurrence of an initial episode of HE.

Drug- or Treatment-Induced Digestive Abnormalities

Provided herein are methods of reducing drug- or treatment-induced symptoms in a human subject. Such drug- or treatment-induced symptoms include any digestive abnormalities. Exemplary digestive abnormalies include, but are not limited to weight-gain, constipation, heartburn, upset stomach, gas, bloating, flatulence, diarrhea, abdominal pain, cramping, nausea, and vomiting. In some embodiments, the digestive abnormality is diarrhea. The method include administering to the human subject a pharmaceutical composition comprising a glycan therapeutic preparation in an amount effective to reduce one or more symptoms induced by a drug or treatment. In one embodiment, the treatment is radiation treatment.

In one embodiment, the subject being identified to be suitable for treatment with a glycan therapeutic has or is suspected of having drug-induced diarrhea, drug-induced constipation, drug-induced toxicity, drug-induced intolerance (e.g. to metformin, to chemotherapies), drug-induced microbiome damage, drug-induced microbiome disease, drug-induced gastrointestinal disease, drug-induced enteritis or colitis or similar drug-induced disorder or condition.

In some embodiments, the pharmaceutical composition comprising a glycan therapeutic preparation is administered prior to, concomitant with or after administration of the drug (or radiation treatment), administration of which induces the symptoms. Exemplary drugs which often are associated with drug- or treatment-induced symptoms include, but are not limited to a cancer drug, an anti-diabetic, an immune-suppressive drug, an antimicrobial drug, a chemotherapeutic, an anti-psychotic, a proton pump inhibitor, and a non-steroid anti-inflammatory drug (NSAID). Administration of these drugs generally is associated with dysbioses that can, e.g., occur during the treatment regimen. In some embodiments, the dysbiosis causes or amplifies the drug- or treatment-induced symptoms, such as digestive abnormalities. In some embodiments, administration of the glycan therapeutic modulates the microbiome such that the drug- or treatment-induced symptoms are reduced. In some embodiments, the glycan therapeutic promotes the growth of commensal bacteria and/or supports the growth of beneficial microbial communities which would negatively be affected or lost in response to the drug treatment or which can complement commensal bacteria that have been negatively affected or lost in response to the drug treatment.

Specific examples of drugs associated with digestive abnormalities symptoms of which can be reduced by administration of the glycan therapeutic include, but are not limited to ciprofloxacin, clindamycin, amoxicillin-clavulanate, cefixime, ephalosporins, fluoroquinolones, azithromycin, clarithromycin, erythromycin, tetracycline, azithromycin, irinotecan (camptosar), 5-fluorouracil, leucovorin, oxaliplatin, bortezomib, imatinib, lenalidomide, imbruvica, ipilimumab, pertuzumab, capecitabine, docetaxel, lapatinib, erlotinib, carmustine, etoposide, aracytine, melphalan, cytarabine, daunorubicine, amsacrine, mitoxantrone, olanzapine, ranitidine, famotidine, cimetidine, omeprazole, sucralfate, esomeprazole, naproxen, diclofenac, indomethacin, ibuprofen, ketoprofen, piroxicam, celecoxib, nimesulid, aspirin, metformin, paroxetine, valproic acid, or clozapine.

In some embodiments, the digestive abnormalities are associated with treatment of the subject with a chemotherapeutic agent. In one embodiment, the digestive abnormality is diarrhea. In specific embodiments, the chemotherapeutic agent is Irinotecan, 5-fluorouracil, leucovorin, or combinations thereof. In specific embodiments, the chemotherapeutic agent is oxaliplatin, leucovorin, 5-fluorouracil, or combinations thereof. In specific embodiments the chemotherapeutic agent is bortezomib, imatinib, lenalidomide, imbruvica, ipilimumab, pertuzumab, capecitabine, docetaxel, lapatinib, erlotinib, or combinations thereof. In some embodiments, the chemotherapeutic agent is Carmustine, Etoposide, Aracytine, Melphalan, or combinations thereof. In specific embodiments the chemotherapeutic agent is cytarabine, daunorubicine, etoposide, or combinations thereof. In specific embodiments the chemotherapeutic agent is amsacrine, cytarabine, etoposide, or combinations thereof. In specific embodiments, the chemotherapeutic agent is mitoxantrone, cytarabine, or combinations thereof.

In some embodiments, the digestive abnormalities are associated with treatment of the subject with an antibiotic. In one embodiment, the digestive abnormality is diarrhea. In specific embodiments, the antibiotic is ciprofloxacin, clindamycin, amoxicillin-clavulanate, cefixime, ephalosporins, fluoroquinolones, azithromycin, clarithromycin, erythromycin, tetracycline, or azithromycin.

In some embodiments, the digestive abnormalities are associated with treatment of the subject with an anti-psychotic drug. In one embodiment, the digestive abnormality is weight gain. In one embodiment, the drug is olanzapine.

In some embodiments, the digestive abnormalities are associated with treatment of the subject with a proton-pump inhibitor drug. In one embodiment, the digestive abnormality is diarrhea. In specific embodiments, the drug is ranitidine, famotidine, cimetidine, omeprazole, sucralfate, or esomeprazole.

In some embodiments, the digestive abnormalities are associated with treatment of the subject with a non-steroidal anti-inflammatory drug (NSAID). In one embodiment, the digestive abnormality is diarrhea. In specific embodiments, the drug is naproxen, diclofenac, indomethacin, ibuprofen, ketoprofen, piroxicam, celecoxib, nimesulid, or aspirin.

In some embodiments, the digestive abnormalities are associated with treatment of the subject with metformin, paroxetine, valproic acid, or clozapine.

In one embodiment, reducing the one or more symptoms increases compliance by the subject to the treatment regimen. In one embodiment, reducing one or more symptom enables the physician to prescribe a higher-dose of the drug to be administered. In such embodiments, treatment of the underlying disease is more effective (e.g. increased reduction of symptoms, shorter period to achieve a disease or symptom-free state, or longer maintenance of a disease or symptom-free state, etc.).

Other Embodiments

In some embodiments, the subject experiences a reduction in at least one symptom of the gastrointestinal disease, disorder or condition following treatment. In some embodiments, a reduction in the severity of a symptom following treatment can be determined (e.g. by measuring a known biomarker) and is in the order of about 3%, 5%, 7%, 10%, 20%, 30%, 40%, 50%, 60%, 70%, 80%, 90%, 95%, or about 100%. In some embodiments, the symptoms, measured as described herein, are decreased by an average of about 10%, 20%, 30%, 40%, 50%, 60%, 70%, 80%, 90%, 95%, or about 100% when compared to symptoms prior to the administration of a pharmaceutical glycan therapeutic composition. In some embodiments, the reduction in the severity of the symptom persists for at least about a day, two days, three days, four days, five days, a week, two weeks, three weeks, a month, 3 months, 6 months, 9 months, a year, two years, five years, ten years after treatment or the reduction is permanent.

In one embodiment, a symptom of a gastrointestinal disease, disorder or condition remains partially, substantially, or completely eliminated or decreased in severity in a subject for at least about 1 day, 1 week, 1 month, 2 months, 3 months, 4 months, 5 months, 6 months, 9 months, one year, 18 months, two years, three years, four years, five years, ten years, or more than ten years after the termination of treatment. In another embodiment a symptom of a gastrointestinal disease, disorder or condition is permanently eliminated or decreased in severity in a subject after the termination of treatment.

In some embodiments, administration of the pharmaceutical glycan therapeutic compositions improves the overall health of the host and/or the health of a specific niche, such as the GI tract, e.g. by modulating (e.g. increasing or decreasing) the growth or abundance of one or more members of the microbial community in the niche (such as resident commensal bacteria and/or acquired pathogens or pathobionts).

Research from the gut has led to the identification of biomarkers with the potential to demonstrate the health effects of prebiotics, which may also be used to characterize the health effects and treatment efficacies of the pharmaceutical glycan therapeutic compositions described herein on the gastrointestinal microbiota and environment. These markers include: i) changes in gastrointestinal microbiota and the overall metabolism of the gastric environment, such as the production of organic acids, ii) modulation of the immune system, assessing inflammatory and immune globulins iii) increase the absorption of minerals in the colon, such as calcium, zinc or magnesium iv) regulation of lipid metabolism, lowering cholesterol, v) induction of other important processes for host homeostasis (see, reviews by Pool-Zobel B L. Inulin-type fructans and reduction in colon cancer risk: review of experimental and human data. 2005. British Journal of Nutrition 93 Suppl 1:S73-90; and Liong M T. Roles of Probiotics and Prebiotics in Colon Cancer Prevention: Postulated Mechanisms and In-vivo Evidence.2008. International Journal of Molecular Sciences 9(5):854-63).

The pharmaceutical glycan therapeutic compositions when administered to a subject in an effective amount may modulate one or more host pathways. The glycan therapeutic treatment may result in increases or decreases of one or more biomarkers that can be determined by methods known in the art. An investigator can easily determine at which point or points during treatment the biomarker(s) should be measured, e.g. prior to treatment, at various intervals during treatment and/or after treatment. Any suitable sample, e.g. a gastrointestinal-specific sample such as, e.g. a tissue sample or biopsy, a swab, a gastrointestinal secretion (such as feces/a stool sample), etc. may be drawn from the subject and the sample may be analyzed. In some embodiments, a substantial increase or decrease in a biomarker may be detected.

In some embodiments, the glycan therapeutic is digested by the gut microbiota (e.g. Clostridia), resulting, e.g., in the release of short-chain fatty acids such as butyrate, acetate, and propionate, which may act in an immunomodulatory capacity (e.g. anti-inflammatory) and other metabolites (e.g. bile acids, and lactate) that may confer beneficial health effects on the host.

To evaluate the effect of administered pharmaceutical glycan therapeutic compositions on SCFA production in the gut, fecal samples can be collected. SCFA levels, particularly acetate, propionate, and butyrate may be quantified. SCFAs, creatines, and hydroxy-SCFAs can be quantified by alkalinizing stool samples, obtaining fingerprints of the metabolic composition of the sample using, e.g., 1D 1H NMR spectrometer, and analyzing with supervised multivariate statistical methods. Inulin may serve as a positive control.

In some embodiments, microbial metabolite profiles of patient samples or microbes cultures from subject samples are used to identify risk factors for developing a gastrointestinal infectious and/or inflammatory disease, disorder or condition. Exemplary metabolites for the purposes of diagnosis, prognostic risk assessment, or treatment assessment purposes include those listed in Table 2. In some embodiments, microbial metabolite profiles are taken at different time points during a subject's disease and treatment in order to better evaluate the subject's disease state including recovery or relapse events. Such monitoring is also important to lower the risk of a subject developing a new gastrointestinal disease, disorder or condition. In some embodiments, metabolite profiles inform subsequent treatment.

Further, if determined useful by a treating physician or other healthcare provider, the pharmaceutical glycan therapeutic compositions described herein can be administered in combination with various other standard of care therapies. In some embodiments, the combination of administration of the glycan therapeutic and the standard-of-care therapy agent has additive or synergistic treatment effects. The pharmaceutical glycan therapeutic compositions may be administered prior to, concurrent with, or post treatment with standard of care therapies. In some instances, the therapies disrupt the composition and health of the GI tract's normal microbiota (e.g. use of anti-bacterial, anti-viral or anti-fungal agents), which may lead to the undesirable proliferation of harmful bacteria or pathogens, which may cause one or more of the symptoms described herein. In some embodiments, administration of the pharmaceutical glycan therapeutic compositions described herein is useful for alleviating those symptoms and improving the composition of the gastrointestinal microbial community.

Administration of Glycan Therapeutics

For any pharmaceutical glycan therapeutic composition used in a method described herein, a therapeutically effective dose can be estimated initially from laboratory animal models known to those of skill in the art. Such information can be used to more accurately determine useful doses in humans. Initial dosages can also be estimated from in vitro or in vivo data. Initial dosages can also be formulated by comparing the effectiveness of the compounds used in the methods described herein in model assays with the effectiveness of known compounds. For instance, initial dosages can be formulated by comparing the effectiveness of the glycan therapeutic preparations in model assays with the effectiveness of other compounds that have shown efficacy in treating the present conditions. In this method, an initial dosage can be obtained by multiplying the ratio of effective concentrations obtained in the model assay for the glycan therapeutic preparations used in methods described herein and the control compound by the effective dosage of the control compound. For example, if a preparation useful in a present method is twice as effective in a model assay as a known compound (e.g., the efficacious concentration ($EC_{50}$) of the glycan therapeutic preparation is equal to one-half the $EC_{50}$ of the known compound in the same assay), an initial effective dosage of the glycan therapeutic preparation would be one-half the known dosage for the known compound. Using these initial guidelines an effective dosage in subjects, such as humans, can be determined by one of ordinary skill. Dosage amount and interval may be adjusted individually to provide levels of the glycan therapeutic preparation which are sufficient to maintain therapeutic effect. One of skill in the art will be able to optimize therapeutically effective local dosages without undue experimentation.

Depending upon the disorder and subject to be treated and the route of administration, the compositions may be administered at varying doses. In one embodiment, the smallest effective amount or dose of glycan therapeutic is used. In some embodiments, the glycan therapeutic is administered in a dose from about 0.01 mg/kg to about 10,000 mg/kg, from about 0.1 mg/kg to about 1,000 mg/kg, from about 1 mg/kg to about 100 mg/kg, 0.05 mg/kg to about 5,000 mg/kg, from about 0.5 mg/kg to about 5,000 mg/kg, from about 5 mg/kg to about 500 mg/kg. This dose may be given as mg/kg/day and may be administered as an initial dose or may be increased or decreased over time (e.g., days or week) to reach a final dose.

In some embodiments, the glycan therapeutic is administered in a total daily dose per subject from about 1 mg per day to about 100 grams per day; from about 10 mgs per day to about 10 grams per day; from about 100 mgs per day to about 10 grams per day; from about 1 gram per day to about 10 grams per day, from about 2 grams per day to about 20 grams per day; from about 5 grams per day to about 50 grams per day.

In some embodiments, a symptom of a gastrointestinal disease, disorder or condition in a subject exhibiting the symptoms is decreased or eliminated by administering to the subject increasing, decreasing or constant amounts (or doses) of a pharmaceutical glycan therapeutic composition for a period of time (e.g. a treatment period).

In one embodiment, the composition contains beneficial, commensal and/or probiotic bacterial strains in an amount comprised from $1\times10^7$ to $1\times10^{13}$ CFU/dose and bacterial strain, or from $1\times10^9$ to $1\times10^{11}$ CFU/dose and bacterial strain.

In some embodiments, the pharmaceutical composition is administered one, two, or three times a day. In some embodiments, the pharmaceutical composition is administered twice a day. In some embodiments, the pharmaceutical composition is administered each day for a predetermined number of days (the treatment period). In some embodiments, the treatment period is 1, 2, 3, 4, 5, 6, 7, 8, 9, 10, 11, 12, 13, 14, 21, 28, 35, 42, 49, 56, 63, 70, 100, 200, 300 or 365 days. In some embodiments, the treatment period is 1, 2, 3, 4, 5, 6, 7, 8, 9, 10, 11, or 12 months. In some embodiments, the treatment period is 1, 2, 3, 4, 5, 6, 7, 8, 9, 10, 11, 12 years, or life-long.

In one embodiment the total duration of treatment periods for a gastrointestinal disease, disorder or condition can be from about one day to 10 years, one day to 1 year, 1 day to 6 months, 1 day to 3 months, 1 day to 1 months, one day to one week, one day to five days, one day to 10 days, one week to about 12 weeks, or about four weeks to about ten weeks, or about four weeks to about eight weeks, or about six weeks. The subject may undergo a suitable number of treatment periods, such as, e.g. 1, 2, 3, 4, 5, 6, 7, 8, 9, 10 or more than 10 treatment periods. During a treatment period, the subject takes a pharmaceutical glycan therapeutic composition described herein, optionally along with ingestion of prebiotic and/or probiotic containing food products. In one embodiment, a pharmaceutical glycan therapeutic composition can also be administered in combination with another substance (such as a probiotic or commensal beneficial bacteria, a prebiotic substance or a therapeutic agent), as described herein.

In some embodiments, the pharmaceutical glycan therapeutic composition may also be combined with an antibiotic that disrupts normal gastrointestinal microbiota growth. Typically durations for antibiotic treatments are 1-14 days, or 2-10 days, or 5-7 days. In some embodiments, a glycan therapeutic is administered to a subject in need thereof immediately after one or more antibiotic treatment(s) has ended (e.g. 1 hour, 6 hours, 12 hours, 24 hours, 36 hours, 48 hours, 3 days, 4 days, 5 days, 6 days, 7 days, 2 weeks, 3 weeks or 4 weeks after the antibiotic treatment has ended). During a course of antibiotic treatment, the pharmaceutical glycan therapeutic composition may be provided at the initiation of antibiotic treatment; shortly following antibiotic treatment, e.g. 1, 2, 3, 4, 5, 6, 7, or more days following treatment; or may be administered upon diagnosis of undesirable pathogen growth.

In some embodiments, the pharmaceutical glycan therapeutic composition may also be combined with a dysbiosis-causing drug, e.g. a drug that disrupts normal gastrointestinal microbiota growth, e.g. a chemotherapeutic drug, an anti-diabetic drug, an immune-suppressive drug, an antimicrobial drug, an anti-psychotic drug, a proton pump inhibitor drug, or a non-steroid anti-inflammatory drug (NSAID). The pharmaceutical glycan therapeutic composition, in some embodiments, reduces the drug- or treatment-induced symptoms in a human subject. The symptoms include digestive abnormalities, such as, e.g., weight-gain, constipation, heartburn, upset stomach, gas, bloating, flatulence, diarrhea, abdominal pain, cramping, nausea, and vomiting. In some embodiments, a glycan therapeutic is administered to a subject in need thereof immediately after one or more drug treatment(s) has ended (e.g. 1 hour, 6 hours, 12 hours, 24 hours, 36 hours, 48 hours, 3 days, 4 days, 5 days, 6 days, 7 days, 2 weeks, 3 weeks or 4 weeks after the antibiotic treatment has ended). During a course of drug treatment, the pharmaceutical glycan therapeutic composition may be provided prior to the initiation of drug treatment (e.g. 1, 2, 3, 4, 5, 6, 7 days prior); at the day of initiation of drug treatment; or shortly following antibiotic treatment, e.g. 1, 2, 3, 4, 5, 6, 7, or more days following treatment, and may optionally be provided only initially (e.g. for a short period) or throughout the duration of the drug-treatment, and may even be continued for a desired period after the drug treatment period has ended (e.g. for 1-7 days, 1-14 days, or 1-21 days thereafter). In some embodiments, administration of the pharmaceutical glycan therapeutic composition is initiated or continued when one or more adverse effects occur and/or are diagnosed (e.g. digestive abnormalities or pathogen growth) in conjunction with the drug treatment. In some embodiments, the treatment agent causing a dysbiosis is not a drug but radiation treatment or surgery and the pharmaceutical glycan therapeutic composition may also be administered as described herein.

In some embodiments, the total number and duration of treatment periods is based on a subject's response to the treatment. For example, an individual can experience a reduction in symptoms after 1, 2, 3, 4, 5, 6, 7, 8, 9, 10, 11, 12, 13, or 14 days of treatment with a pharmaceutical glycan therapeutic composition. In another example, an individual can experience a reduction in symptoms after 1, 2, 3, 4, 5, 6, 7, 8, 9, 10, 11, 12 months of treatment with a pharmaceutical glycan therapeutic composition. Thus, the duration of treatment is determined by an individual subject's response to a pharmaceutical glycan therapeutic composition and the onset of relief from one or more symptoms. Thus, a subject can experience symptoms at a given dose of a pharmaceutical glycan therapeutic composition and can require that the subject stay at that dose, or a lower dose, until symptoms subside. Thus, in one embodiment, the duration of the treatment is not determined at the outset, but continues until the maximum dose of a pharmaceutical glycan therapeutic composition is achieved per day, or until the desired level of reduction in symptoms is achieved. In one embodiment, the treatment is continuous.

In one embodiment, a subject can be given one dose for the first treatment period during a treatment regimen and a second dose during a second treatment period. For example, a subject can be administered one dose of pharmaceutical glycan therapeutic composition for a one week period and a second dose for a subsequent one week period.

A subject may self-administer a pharmaceutical glycan therapeutic composition and the glycan therapeutic composition is supplied or recommended (or prescribed) by a health professional, e.g., a physician or other qualified health professional and optionally test results (e.g. obtained for biomarkers from samples taken from the subject) and/or health changes and treatment endpoints are monitored by a health professional. In some embodiments, the pharmaceutical glycan therapeutic composition is administered by a health professional.

In one embodiment, a subject in need thereof can undergo repeated courses of treatment with a pharmaceutical glycan therapeutic composition. The course of treatment can be repeated when symptoms reappear or increase to an undesirable level. Alternatively, the course of treatment can be repeated at regular or predetermined intervals. Thus, treatment can be repeated after about one month, two months, three months, four months, six months, eight months, ten months, one year, 18 months, two years, three years, four years, five years, or more than five years, or any combination thereof (e.g., treatment can be repeated after one year, then every two to five years thereafter). The treatment can be repeated in the same form (e.g., duration, dosage, timing of dosage, additional substances, etc.) as used in the first treatment or it can be modified. For example, treatment duration can be shortened or lengthened, dosage can be increased or decreased. Optionally, treatment with the glycan therapeutic can occur in combination with a different number or compositions of agents, e.g., containing more or less of other substances, or fewer or more substances (such as, e.g., a prebiotic substance, a probiotic bacterium or a therapeutic agent) in addition to the glycan therapeutic.

Additional substances can be given in conjunction with a pharmaceutical glycan therapeutic composition. These substances can enhance the action of the doses of glycan therapeutic by, e.g., encouraging the growth of bacteria in the GI tract that alleviate symptoms of the gastrointestinal disease, disorder or condition, increasing adhesion of probiotic or beneficial commensal bacteria in the niche or in the gut. These substances can be given prior to treatment with glycan therapeutic, during treatment with glycan therapeutic, after treatment with glycan therapeutic, or any combination thereof. If administered during glycan therapeutic treatment, they can be administered with the dose of glycan therapeutic being given, or before or after the dose of glycan therapeutic, or any combination thereof. In one embodiment substances of use in conjunction with a pharmaceutical glycan therapeutic composition include a probiotic microbe(s), prebiotics, therapeutic agents, or buffers/carriers/excipients. One or more of these substances can be used in combination with pharmaceutical glycan therapeutic composition at any suitable time before, during, after treatment, or some combination thereof.

Definitions

"Abundance" of a microbial taxa as used herein is a relative term and refers to the relative presence of a microbial taxa to other taxa in a community in a defined microbial niche, such as the GI tract, or in the entire host organism (e.g. a human or a laboratory animal model of disease).

"Acquire" or "acquiring" as the terms are used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing a synthetic or analytical method or protocol) to obtain the value or physical entity. "Indirectly acquiring" refers to receiving the value or physical entity from another party or source (e.g., a third party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., an NMR spectrometer to obtain an NMR spectrum.

The "colonization" of a host organism includes the non-transitory residence of a bacterium or other microbial organism. As used herein, "reducing colonization" of a host subject's microbiota, such as in the GI tract by a pathogenic bacterial taxa includes a reduction in the residence time of the pathogenic bacterial taxa in the niche as well as a reduction in the number, concentration or abundance of the pathogenic bacterial taxa in the niche or adhered to the surface of the niche. Measuring reductions of adherent pathogenic bacterial taxa may be demonstrated, e.g., by a biopsy sample, or reductions may be measured indirectly, e.g., by measuring the pathogenic burden, e.g., in the GI tract of a host.

"Distinct" as used herein, e.g. with reference to a species in a glycan therapeutic, is meant to denote that it is chemically and/or structurally different from another. For example, two sugars are "distinct" if they are chemically different, e.g. a fucose and a xylose, or structurally different, e.g. cyclic vs. acyclic, L- vs. D-form. Two dimers are distinct if they consist of the same two monomers but one pair contains alpha-1,4 bond and the other contains a beta-1,6 bond. Distinct entities may have any other suitable distinguishing characteristic or property that can be detected by methods known in the art and/or described herein.

"Diversity of a microbial community" or "microbial diversity" as used herein refers to the diversity found in the microbiota of a given niche or within a host subject. It can relate to the number of distinct microbial taxa and/or richness within the host or niche. Diversity can be expressed, e.g. using the Shannon Diversity index (Shannon entropy), alpha-beta diversity, total number of observed OTUs, or Chao1 index, as described herein. In some embodiments, the glycan therapeutics described herein modulate (e.g. increase or decrease) diversity within a microbial community, which may be expressed using Shannon entropy as a measure. For example, the more unequal the abundances of the bacterial taxa, the larger the weighted geometric mean of the $p_i$ values in Shannon's formula, and the smaller the corresponding Shannon entropy. If practically all abundance is concentrated to one taxa, and the other taxa are very rare (even if there are many of them), Shannon entropy approaches zero. When there is only one taxa Shannon entropy exactly equals zero.

As used herein, a "dosage regimen", "dosing regimen", or "treatment regimen" is a modality of drug administration that achieves a therapeutic objective. A dosage regimen includes definition of one, two, three, or four of: a route of administration, a unit dose, a frequency of dosage, and a length of treatment.

"Dysbiosis of the gastrointestinal microbiota" refers to an imbalanced state of the microbiota, e.g., within the GI tract, in which the normal diversity, proportion of a first bacterial taxa to a second bacterial taxa and/or function of the ecological network is disrupted or disturbed. This undesired, e.g., unhealthy, state can be due to a number of factors including, but not limited to, a decrease or increase in the diversity of the microbiota (e.g. bacterial taxa), the overgrowth of one or more pathogens or pathobionts, or the shift to an ecological microbial community that no longer provides an essential function to the host subject, and, in an embodiment, therefore no longer promotes health or, which is associated with unwanted symptoms in the subject.

"Ecological Niche" or simply "Niche" refers to the ecological space in which an organism or group of organisms occupies (such as the GI tract or one or more subsection of the GI tract, such as, e.g., the stomach, the large or small intestine, the rectum, etc.). In some embodiments, niche specifically refers to a space that microorganisms occupy. Niche may describe how an organism or population of organisms responds to the distribution of resources, physical parameters (e.g., host tissue space) and competitors (e.g., by growing when resources are abundant, and when predators, parasites and pathogens are scarce) and how it in turn alters those same factors (e.g., limiting access to resources by other organisms, acting as a food source for predators and a consumer of prey).

By the terms "effective amount" and "therapeutically effective amount" of a pharmaceutical composition or a drug agent is meant a sufficient amount of the composition or agent to provide the desired effect. In some embodiments, a physician or other health professional decides the appropriate amount and dosage regimen. An effective amount also refers to an amount of a pharmaceutical composition or a drug agent that prevents the development or relapse of a medical condition.

As used herein, a "glycan therapeutic preparation" (also referred to as a "preparation of glycan therapeutics", "glycan preparation" or "glycan therapeutic") is a preparation comprising glycans (sometimes referred to as glycan species) that exhibits a therapeutic effect. A glycan therapeutic comprises a synthetic mixture of a plurality of mono-, di-, oligomeric and/or polymeric glycan species (e.g. oligo- and/or polysaccharides, sometimes referred to as "oligosaccharides"), wherein the oligomeric and/or polymeric glycan species comprise glycan units that are linked by glycosidic bonds. A glycan therapeutic may be formulated into a pharmaceutical composition or medical food for human use. A glycan therapeutic may be formulated in any suitable dosage form including a kit. In some embodiments, preparations of glycan therapeutics do not contain one or more naturally occurring oligo- or polysaccharide, including: glucooligosaccharide, mannanoligosaccharide, inulin, lychnose, maltotretraose, nigerotetraose, nystose, sesemose, stachyose, isomaltotriose, nigerotriose, maltotriose, melezitose, maltotriulose, raffinose, kestose, fructooligosaccharide, 2'-fucosyllactose, galactooligosaccharide, glycosyl, idraparinux, isomaltooligosaccharide, maltodextrin, xylooligosaccharide, agar, agarose, alginic acid, alguronic acid, alpha glucan, amylopectin, amylose, arabioxylan, beta-glucan, callose, capsulan, carrageenan, cellodextrin, cellulin, cellulose, chitin, chitin nanofibril, chitin-glucan complex, chitosan, chrysolaminarin, curdlan, cyclodextrin, alpha-cylcodextrin, dextran, dextrin, dialdehyde starch, ficoll, fructan, fucoidan, galactoglucomannan, galactomannan, galactosamineogalactan, gellan gum, glucan, glucomannan, glucoronoxyland, glycocalyx, glycogen, hemicellulose, hypromellose, icodextrin, kefiran, laminarin, lentinan, levan polysaccharide, lichenin, mannan, mucilage, natural gum, paramylon, pectic acid, pectin, pentastarch, phytoglycogen, pleuran, poligeenan, polydextrose, porphyran, pullulan, schizophyllan, sepharose, sinistrin, sizofiran, sugammadex, welan gum, xantham gum, xylan, xyloglucan, zymosan, and the like. In some embodiments, a glycan exists as a salt, e.g., a pharmaceutically acceptable salt.

A "glycan unit" (sometimes referred to as "feed sugar") as used herein refers to the individual unit of a glycan species disclosed herein, e.g., the building blocks from which the glycan species is made. In an embodiment, a glycan unit is a monomer. In an embodiment, a glycan unit is a dimer. In an embodiment a glycan unit is a monosaccharide. In an embodiment, a glycan unit is a disaccharide. In some embodiments, the glycan unit is a carbohydrate and may be selected from a sugar alcohol, a short-chain fatty acid, a sugar acid, an imino sugar, a deoxy sugar, and an amino sugar. In some embodiments, the glycan unit is erythrose, threose, erythulose, arabinose, lyxose, ribose, xylose, ribulose, xylulose, allose, altrose, galactose, glucose, gulose, idose, mannose, talose, fructose, psicose, sorbose, tagatose, fucose, fuculose, rhamnose, mannoheptulose, sedoheptulose, and the like. In some embodiments, the glycan unit is glucose, galactose, arabinose, mannose, fructose, xylose, fucose, or rhamnose. In embodiments, a glycan comprises distinct glycan units, e.g., a first and a second monosaccharide, or a first and a second disaccharide, or a monosaccharide and a disaccharide. In embodiments, a glycan comprises distinct glycan units, e.g., a first, a second, a third, a fourth, and/or a fifth distinct glycan unit.

As used herein, an "isolated" or "purified" glycan therapeutic preparation (also sometimes referred to as "polished") is substantially pure and free of contaminants, e.g. pathogens or otherwise unwanted biological material, or toxic or otherwise unwanted organic or inorganic compounds. In some embodiments, pure or isolated compounds, compositions or preparations may contain traces of solvents and/or salts (such as less than 10%, 9%, 8%, 7%, 6%, 5%, 4%, 3%, 2%, 1%, less than 0.5% or 0.1% by w/w, w/v, v/v or molar %). Purified compounds are or preparations contain at least about 60% (by w/w, w/v, v/v or molar %), at least about 75%, at least about 90%, at least about 95%, at least about 97%, at least about 98%, or at least about 99% by w/w, w/v, v/v or molar % the compound(s) of interest. For example, a purified (substantially pure) or isolated preparation of glycan therapeutics is one that is at least 80%, 85%, 90%, 91%, 92%, 93%, 94%, 95%, 98%, 99%, 99.5%, 99.8%, 99.9% or 100% of the glycan therapeutic by w/w, w/v, v/v or molar % (i.e. not including any solvent, such as e.g. water, in which the glycan therapeutic preparation may be dissolved) and separated from the components that accompany it, e.g. during manufacture, extraction/purification and/or processing (e.g. such that the glycan therapeutic is substantially free from undesired compounds). Purity may be measured by any appropriate standard method, for example, by column chromatography (e.g., size-exclusion chromatography (SEC)), thin layer chromatography (TLC), gas chromatography (GC), high-performance liquid chromatography (HPLC) or nuclear magnetic resonance (NMR) spectroscopy. Purified or purity may also define a degree of sterility that is safe for administration to a human subject, e.g., lacking viable infectious or toxic agents.

"Microbiome" as used herein refers to the genetic content of the communities of microbes that live in and on a subject (e.g. a human subject), both sustainably and transiently, including eukaryotes, archaea, bacteria, and viruses (including bacterial viruses (e.g., phage)), wherein "genetic content" includes genomic DNA, RNA such as ribosomal RNA and messenger RNA, the epigenome, plasmids, and all other types of genetic information. In some embodiments, microbiome specifically refers to genetic content of the communities of microorganisms in a niche.

"Microbiota" as used herein refers to the community of microorganisms that occur (sustainably or transiently) in and on a subject (e.g. a human subject), including eukaryotes, archaea, bacteria, and viruses (including bacterial viruses, e.g. phage). In some embodiments, microbiota specifically refers to the microbial community in a niche.

"Pathobionts" or "(Opportunistic) Pathogens" as used herein refer to symbiotic organisms able to cause disease only when certain genetic and/or environmental conditions are present in a subject.

As used herein, the term "pathogenic" (e.g. "pathogenic bacteria") refers to a substance, microorganism or condition that has the capability to cause a disease. In certain contexts, pathogens also include microbes (e.g. bacteria) that are associated with a disease or condition but for which a (direct) causative relationship has not been established or has yet to be established. As used herein, the term "pathogens" refers to viruses, parasites and bacteria or other pathogens that may cause infections in a subject, e.g. a human.

As used herein, a "pharmaceutical composition" or "pharmaceutical preparation" is a composition or preparation, having pharmacological activity or other direct effect in the mitigation, treatment, or prevention of disease, and/or a finished dosage form or formulation thereof and is for human use. A pharmaceutical composition or pharmaceutical preparation is typically produced under good manufacturing practices (GMP) conditions. Pharmaceutical compositions or preparations may be sterile or non-sterile. If non-sterile, such pharmaceutical compositions or preparations typically meet the microbiological specifications and criteria for non-sterile pharmaceutical products as described in the U.S. Pharmacopeia (USP) or European Pharmacopoeia (EP). Pharmaceutical compositions may further comprise or may be co-administered with additional active agents, such as, e.g. additional therapeutic agents. Pharmaceutical compositions may also comprise e.g. additional therapeutic agents, polyphenols, prebiotic substances, probiotic bacteria, pharmaceutically acceptable excipients, solvents, carriers or any combination thereof. "Pharmaceutical glycan therapeutic compositions" (or simply "glycan therapeutic compositions") are pharmaceutical compositions as described herein comprising glycan therapeutic preparations and optionally additional agents, ingredients, excipients, or carriers. Any glycan therapeutic described herein may be formulated as a pharmaceutical composition.

The term "phenotype" as used herein refers to a set of observable characteristics of an individual entity. As example a subject may have a phenotype of "healthy" or "diseased". Phenotypes describe the state of an entity and all entities within a phenotype share the same set of characteristics that describe the phenotype. The phenotype of an individual results in part, or in whole, from the interaction of the entities genome and/or microbiome with the environment.

The term "subject" (in some cases "patient") as used herein refers to any human subject. The term does not denote a particular age or gender. Subjects may include pregnant women. Subjects may include a newborn (a preterm newborn, a full term newborn), an infant up to one year of age, young children (e.g., 1 yr to 12 yrs), teenagers, (e.g., 13-19 yrs), adults (e.g., 20-64 yrs), and elderly adults (65 yrs and older). A subject does not include an agricultural animal, e.g., farm animals or livestock, e.g., cattle, horses, sheep, swine, chickens, etc.

A "substantial decrease" as used herein (e.g. with respect to a biomarker or metabolite) is a decrease of 5%, 10%, 20%, 30%, 40%, 50%, 60%, 70%, 80%, 90%, 95%, 97%, 98%, 99%, 99.9% or 100%.

A "substantial increase" as used herein (e.g. with respect to a biomarker or metabolite) is an increase of 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, or more than 1000%.

"Synthetic" as used herein refers to a man-made compound or preparation, such as a glycan therapeutic preparation, that is not naturally occurring. In one embodiment, the polymeric catalyst described herein is used to synthesize the glycans of the preparation under suitable reaction conditions, e.g. by a polymerization reaction that creates oligomers and polymers from individual glycan units that are added to the reaction. In some embodiments, the polymeric catalyst acts as a hydrolysis agent and can break glycosidic bonds. In other embodiments, the polymer catalyst can form glycosidic bonds. Synthetic glycan therapeutic preparations may also include glycan therapeutics that are not isolated from a natural oligo- or polysaccharide source. It is to be understood that while the glycan therapeutic preparation is not isolated from a natural oligo- or polysaccharide source, the glycan units making up the glycan therapeutic can be and often are isolated from natural oligo- or polysaccharide sources, including those listed herein, or are synthesized de novo.

The terms "treating" and "treatment" as used herein refer to the administration of an agent or composition to a subject (e.g., a symptomatic subject afflicted with an adverse condition, disorder, or disease) so as to affect a reduction in severity and/or frequency of a symptom, eliminate a symptom and/or its underlying cause, and/or facilitate improvement or remediation of damage, and/or preventing an adverse condition, disorder, or disease in an asymptomatic subject who is susceptible to a particular adverse condition, disorder, or disease, or who is suspected of developing or at risk of developing the condition, disorder, or disease.

EXAMPLES

The invention is further illustrated by the following examples. The examples are provided for illustrative purposes only, and are not to be construed as limiting the scope or content of the invention in any way. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); Green & Sambrook et al., Molecular Cloning: A Laboratory Manual, 4th Edition (Cold Spring Harbor Laboratory Press, 2012); Colowick & Kaplan, Methods in Enzymology (Academic Press); Remington: The Science and Practice of Pharmacy, 22nd Edition (Pharmaceutical Press, 2012); Sundberg & Carey, Advanced Organic Chemistry: Parts A and B, 5th Edition (Springer, 2007).

Example 1

Preparation of Glycan Therapeutics

To a round bottom flask equipped with an overhead stirrer and a jacketed short-path condenser was added one or more mono- or disaccharides along with 3-20% by dry weight of one or more of the catalysts described in U.S. Pat. No. 8,466,242 and WO 2014/031956, which are incorporated herein by reference in their entirety. Water or another compatible solvent (1.54 equiv) was added to the dry mixture and the slurry was combined at approximately 100 rpm using a paddle sized to match the contours of the selected round bottom flask as closely as possible. The mixture was then heated to 80-155° C. Once the solids achieved a molten state, the vessel was placed under 10-1000 mbar vacuum pressure. The reaction was stirred for 30 minutes to 8 hours, constantly removing water from the reaction. Reaction progress was monitored by HPLC. When sufficient oligomerization had occurred, the stirrer was shut off, the reaction was cooled to room temperature and vented to atmospheric pressure, and the solid mass was dissolved in a volume of water sufficient to create a solution of approximately 50 Brix (grams sugar per 100 g solution). Once dissolution was complete, solid catalyst was removed by filtration and the oligomer solution was concentrated to approximately 50-75 Brix by rotary evaporation. In cases in which an organic solvent has been used, water immiscible solvents can be removed by biphasic extraction and water miscible solvents can be removed by rotary evaporation concomitant to the concentration step.

Among others, the following 25 glycans were made in multiple batches and tested in various assays described herein:

Single glycan unit (homo-glycans): xyl100, rha100, ara100, gal100, glu100, and man100.

Two glycan units (hetero-glycans): ara50gal50, xyl75gal25, ara80xyl20, ara60xyl40, ara50xyl50, glu80man20, glu60man40, man60glu40, man80glu20, gal75xyl25, glu50gal50, man62glu38, and the hybrid glycans glu90sor10 and glu90gly10.

Three glycan units (hetero-glycans): xyl75glu12gal12, xyl33glu33gal33, glu33gal33fuc33, man52glu29gal19, and glu33gal33neu33.

Example 2

Purification of Glycan Therapeutics

Oligo- and polysaccharides synthesized as in Example 1 were dissolved in deionized water to a final concentration of 25-50 Brix. The material was then exposed to at least 2 mass equivalents of Dowex Monosphere 88 ion exchange resin. Exposure may occur by swirling in a flask at 120-170 rpm or by filtration through a wet slurry packed column as long as the residence time is sufficient for the solution to achieve a final pH between 3 and 5. The oligomer solution was isolated by filtration (as in the case of swirled reactions) or elution (as in the case of column filtration) and the process was repeated with Dowex Monosphere 77 ion exchange resin in an analogous fashion until the solution pH was above 5.5. Finally the solution was exposed to Dowex Optipore SD-2 Adsorbent decolorizing resin until the solution was sufficiently clarified and filtered through a 0.2 micron filter to remove residual resin and resin fines. The final solution was then concentrated to 50-85 Brix by rotary evaporation or to a solid by lyophilization.

Example 3

High-Throughput Preparation of Glycan Therapeutics at Small Scale

The oligomers and polymers typified in Example 1 were synthesized in a parallel fashion in 24-, 48-, or 96-well plates or similarly sized arrays of 1 dram vials housed in aluminum heating blocks. In this example, all liquid transfers were handled by a programmable robot or manually using calibrated pipettes. To each vial or well was added 20-100% by dry weight of one or more of the catalysts described in U.S. Pat. No. 8,466,242 and WO 2014/031956. The plate or heating block was placed uncovered in a vacuum oven heated to 50 to 150° C. under a vacuum of 10-800 mbar. The oven vacuum pump was protected by a two-stage condenser consisting of a recirculating chiller trap followed by a dry ice/acetone trap. The plates or blocks are heated for 30 minutes to 6 hours under elevated temperature and reduced pressure without stirring. After a pre-established period of time, the oven was vented to atmospheric pressure, the plates or blocks were cooled to room temperature, and each well or vial was diluted to approximately 50 Brix with deionized water. The solid-phase extraction steps described in Example 2 were performed by elution through sequential wet-packed columns in which the eluent from each column flows immediately into the top of the next column at a rate between 2 and 6 bed volumes/hour using a peristaltic pump or other suitable small pump. The column stack was then rinsed with deionized water and the combined effluents are concentrated by lyophilization to isolate solid powders with residual water content of 1-10% by mass.

Example 4

Modification of Glycan Therapeutics by Removal of Low Molecular Weight Species

Oligomers or polymers prepared and purified as in Examples 1 and 2 were modified so as to remove low molecular weight species. The separation was achieved by osmotic separation. Approximately 45 cm of 1.0 kD MWCO Biotech CE dialysis tubing (31 mm flat width) from Spectrum Labs was placed into deionized water and soaked for 10 minutes, then one end was sealed with a dialysis tubing clip. A 25 Brix solution of 8 grams dry oligosaccharide was sterile filtered and sealed into the tube with a second clip along with a few mL of air to permit the tube to float. The filled tube was then placed in a 3 gallon tank of deionized water which was stirred with sufficient force to induce slow swirling of the sealed tubes. After 8 hours, the water in the tank was replaced and the tube was allowed to stir for an additional 16 hours. Once the dialysis was complete and the material had a DP2+ yield greater than 95% and a DP3+ yield greater than 90%, the dilute solution was sterile filtered and concentrated in vacuo to a final concentration of approximately 65 Brix or lyophilized to a solid with a residual moisture between 1 and 10%. Alternatively, the separation was achieved by tangential flow filtration (TFF). In this case, 100 mL of 25 Brix glycan sample dissolved in deionized water and sterile filtered was placed into the feed bottle of a Spectrum Labs KrosFlo Research IIi TFF system that was prepared according to the manufacturer's recommendation. The sample was then diafiltered through a 1 kD mPES MidiKros hollow-fiber filter at a transmembrane pressure of 25 psig. HPLC samples of the feed stock taken every 0.5 diafiltration volumes were used to determine when the material had a DP2+ yield greater than 95% and a DP3+ yield greater than 90% at which point the solution was sterile filtered and concentrated in vacuo to a 65 Brix syrup or lyophilized to a solid with residual water content of 1-10% by mass.

Example 5

Methods for Analyzing Preparations of Glycan Therapeutics

Measurement of Glycan Content by Liquid Refractometry

This experiment was designed to quantitate the amount of glycan in any given aqueous solution. A Mettler-Toledo Refracto 30GS portable sugar refractometer was calibrated using high-purity reverse-osmosis deionized water. Several drops of the glycan solution were filtered through a 0.2 micron syringe filter directly onto the lens of the refractometer. The measurement was taken at room temperature and reported as Brix. The glycans were routinely concentrated to 75 Brix without obvious solidification or crystallization at 23° C. Brix can then be converted to solubility assuming a specific density of water equal to 1.0 g/mL. Thus, 75 Brix (100 grams of solution consisting of 75 grams of glycan and 25 grams of water) equals an aqueous solubility of 3.0 g/mL. As a comparison, the aqueous solubility of D-glucose is reported to be 0.909 g/mL (48 Brix) at 25° C. by Sigma-Aldrich.

Monomeric Composition by Hydrolysis and GC-MS

This experiment was designed to quantitate the ratio of monomer content within a given oligosaccharide. Glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis as described previously by Santander et al. (2013) Microbiology 159:1471. Between 100 and 200 µg of sample were lyophilized into a suitable test tube. Inositol (20 µg) was added to the sample as an internal standard, then the sample was heated to 80° C. in 1M HCl/methanol for 18 hours. The resulting monosaccharides were then re-acetylated using pyridine and acetic anhydride in MeOH, and per-O-trimethylsilylated with Tri-Sil (Pierce) at 80° C. for 30 minutes. GC/MS analysis of the TMS methyl glycosides was performed on an Agilent 7890A GC interfaced to a 5975C MSD, using a Supelco Equity-1 fused silica capillary column (30 m×0.25 mm ID). Each peak was assigned to a component sugar based upon comparison to known standards and integration of the respective peaks allowed clean calculation of the relative percentage of monomers within an exemplified glycan. In all tested cases, the monomer composition of a given oligosaccharide matched the input ratio within experimental error and the output composition matched the input composition within the precision of the measurement.

Molecular Weight Distribution by Size-Exclusion Chromatography (SEC)

This experiment was designed to quantitate the distribution of molecular weights within a given oligosaccharide. The measurement was made by HPLC using the method described in Monograph of United States Pharmacopeia, 38(6) In-Process Revision: Heparin Sodium (USP37-NF32). Separations were achieved on an Agilent 1200 HPLC system via a GE superpose 12 column using 50 mM ammonium acetate as an eluent at 1.0 mL/min flow rate and an ELSD detector. The column temperature was set at 30° C. and dextran (1 kD, 5 kD, 10 kD weight) were used to draw a standard curve. A 2 mg/ml solution of the samples was prepared and passed through a 0.45 µm spin filter, followed by 40 µl injections into the HPLC. A third-order polynomial curve was constructed based on the logarithmic molecular weights and elution volumes of the listed standards. The weight-average molecular weight (Mw), the number average molecular weight (Mn), and the polydispersity index (PDI) for the sample were calculated by comparison to the standard curve. FIG. 1 shows the curve generated during the SEC evaluation of a glu100 sample in which the average molecular weight was determined to be 1212 g/mol or approximately DP7. The upper end of molecular weight of the material as defined by the point of the curve at 10% of maximum absorption leading the curve was determined to be 4559 g/mol or approximately DP28. The lower end of molecular weight of the material as defined by 10% of the maximum absorption trailing the curve was determined to be 200 g/mol or approximately DP1. Similar analysis of a glu50gal50 sample showed a MW, high mass, and low mass of 1195 g/mol (~DP7), 4331 g/mol (~DP27), and 221 g/mol (~DP1) respectively.

Molecular Weight Distribution by Ion-Affinity Chromatography (IAC)

The proportion of glycan with DP greater than or equal to 2 (DP2+) and 3 (DP3+) may be measured by ion-affinity chromatography. A sample of glycan was diluted out to 50-100 mg/mL and 10 µL of this solution was injected onto an Agilent 1260 BioPure HPLC equipped with a 7.8×300 mm BioRad Aminex HPX-42A column and RI detector. Using pure HPLC-grade water as an eluent, the sample was eluted at 0.6 mL/min through an 80° C. column and an RI detector maintained at 50° C. The peaks representing DP1-6 are assigned by comparison to reference standards and integrated using the Agilent ChemStation software. Peaks are typically integrated as DP1, DP2, DP3, DP4-7, and DP8+. The DP that is achievable by the reaction described in Example 1 varies from monomer to monomer although it is consistent across batches if the procedure is followed correctly, e.g. glucose reliably achieves higher DP values than arabinose. For example, across 17 batches of glu100, DP2+ values ranged from 85-93% and DP3+ values ranged from 80-90%. Conversely, across 6 batches of ara100, DP2+ values ranged from 63-78% and DP3+ values ranged from 48-71%. Mixtures of monomers behaved as averages of the individual components.

Alpha-/Beta-Distribution by 2D NMR

Figure 2:
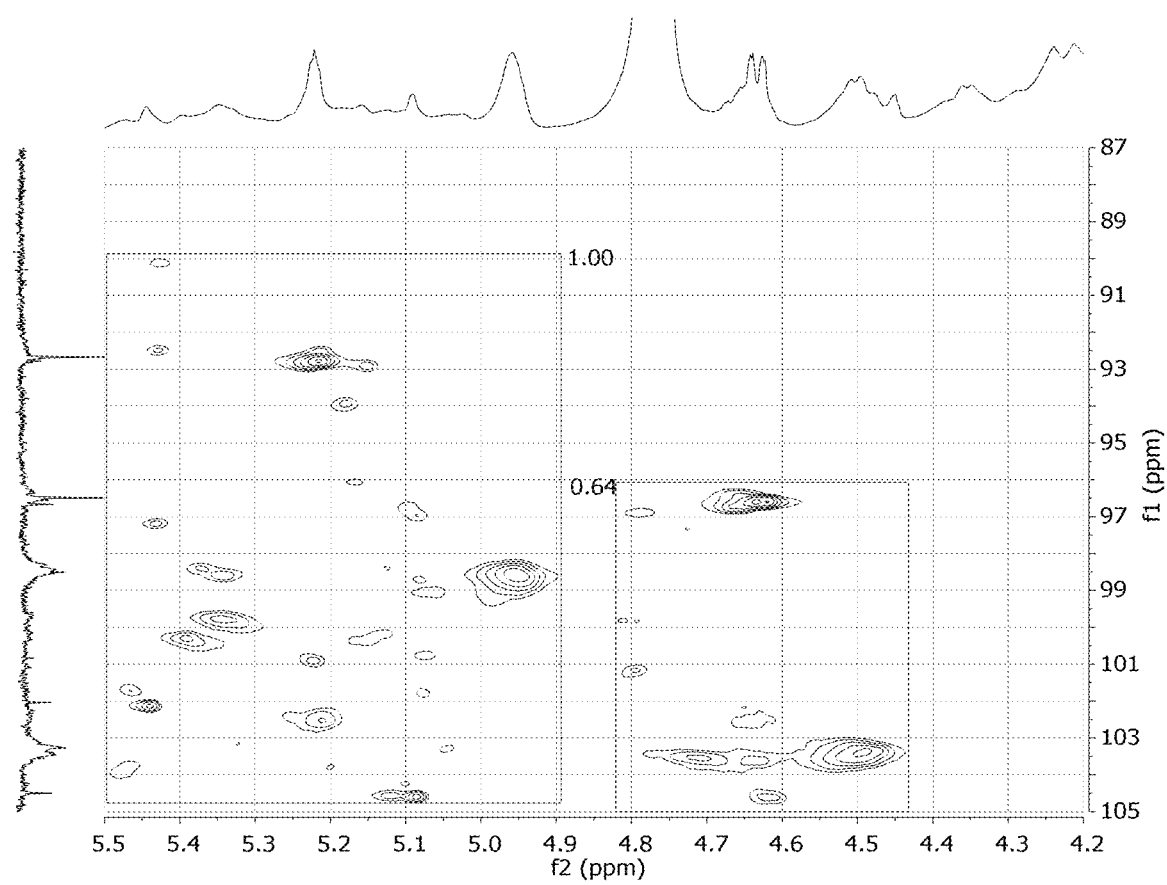
FIG. 2. A representative anomeric region of an $^1$H-$^{13}$C HSQC spectrum of a glu100 sample showing the signal distribution of alpha- and beta-glycosidic bonds FIGS. 3A-3C. A representative anomeric region of an $^1$H-$^{13}$C HSQC spectrum of glu100 (FIG. 3A), glu50gal50 (FIG. 3B), and gal100 (FIG. 3C) samples, demonstrating the additive effect of the fingerprint peaks.

This experiment was designed to quantitate the ratio of alpha- and beta-glycosidic bonds within a given sample by two-dimensional NMR. Approximately 150 mg of 65 Brix oligosaccharide solution was dried to stable mass in a vacuum oven at 45-95° C. under 400 mbar pressure. The sample was subjected to two cycles of dissolution in $D_2O$ and drying to remove residual $H_2O$. Once dried, the sample was dissolved in 750 µL $D_2O$ with 0.1% acetone, placed into a 3 mm NMR tube, and analyzed in a Bruker Avance-III operating at 500.13 MHz 1H (125.77 MHz 13C) equipped with a Bruker BBFO probe operating at 21.1° C. The sample was analyzed using a heteroatomic single quantum coherence pulse sequence (HSQC) using the standard Bruker pulse sequence. Anomeric protons between 4-6 ppm (1H) and 80-120 ppm (13C) were assigned by analogy to glucose as reported in Roslund, et al. (2008) Carbohydrate Res. 343:101-112. Spectra were referenced to the internal acetone signal: 1H—2.22 ppm; 13C—30.8 ppm. Isomers were quantitated by integration of their respective peaks using the MNova software package from Mestrelab Research (Santiago de Compostela, Spain). FIG. 2 shows the anomeric region of a representative spectrum. Table 6 lists the distribution across 13 distinct combinations of monomers showing the alpha-/beta-ratio to be as high as 4:1 as in the case of rha100 and as low as 1:1 as in the case of glu50gal50.

TABLE 6

Distribution of alpha- and beta-bonds across batches and types of glycans

| glycans | alpha-bonds (%) | beta-bonds (%) |
|---|---|---|
| Glu100 | 58 | 42 |
|  | 61 | 39 |
|  | 60 | 40 |
| Gal100 | 60 | 40 |
| Glu50gal50 | 50 | 50 |
|  | 56 | 44 |
| Glu33gal33fuc33 | 55 | 45 |
| Man100 | 57 | 43 |
| Man52glu29gal19 | 76 | 24 |
| Ara100 | 67 | 33 |
| Rha100 | 80 | 20 |
| Xyl100 | 57 | 43 |
|  | 59 | 41 |
| Xyl75gal25 | 56 | 44 |

Identification of Composition by NMR

Figure 3A:
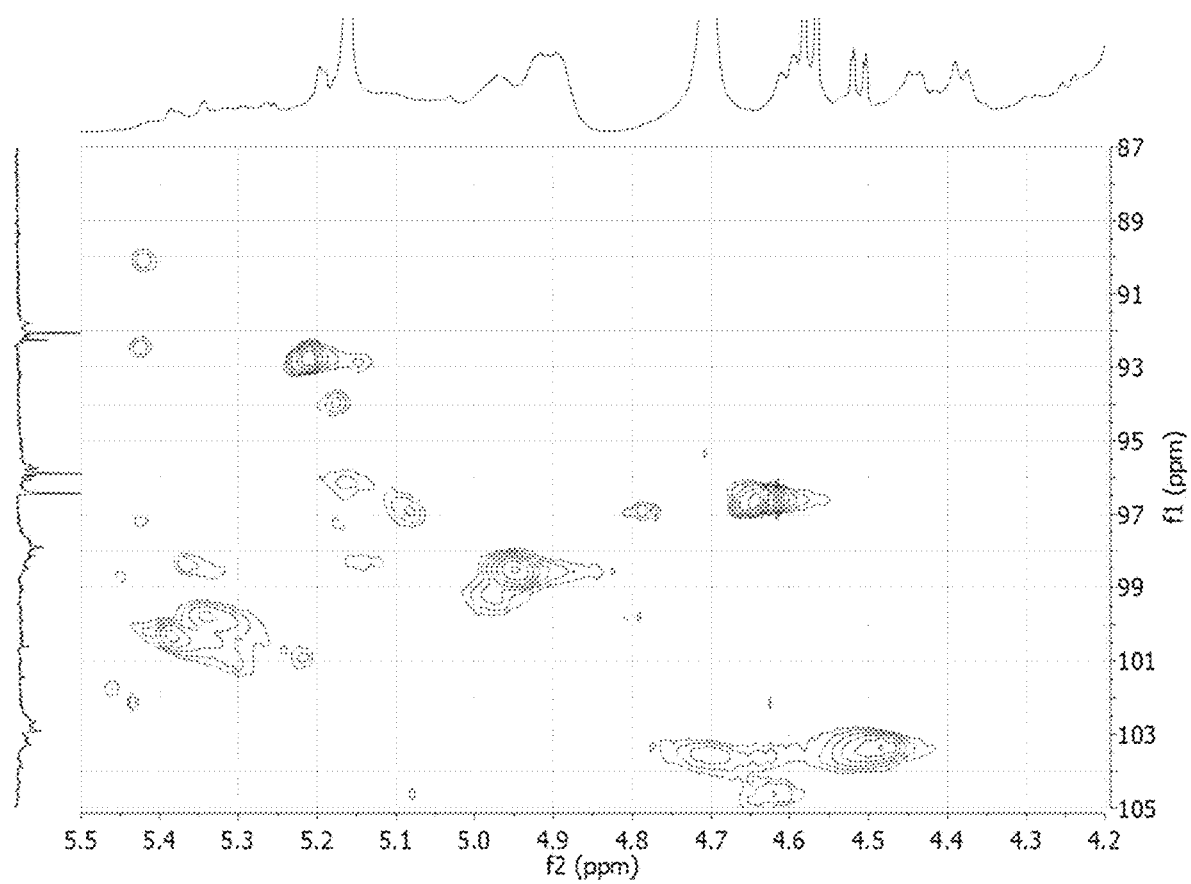
Figure 3B:
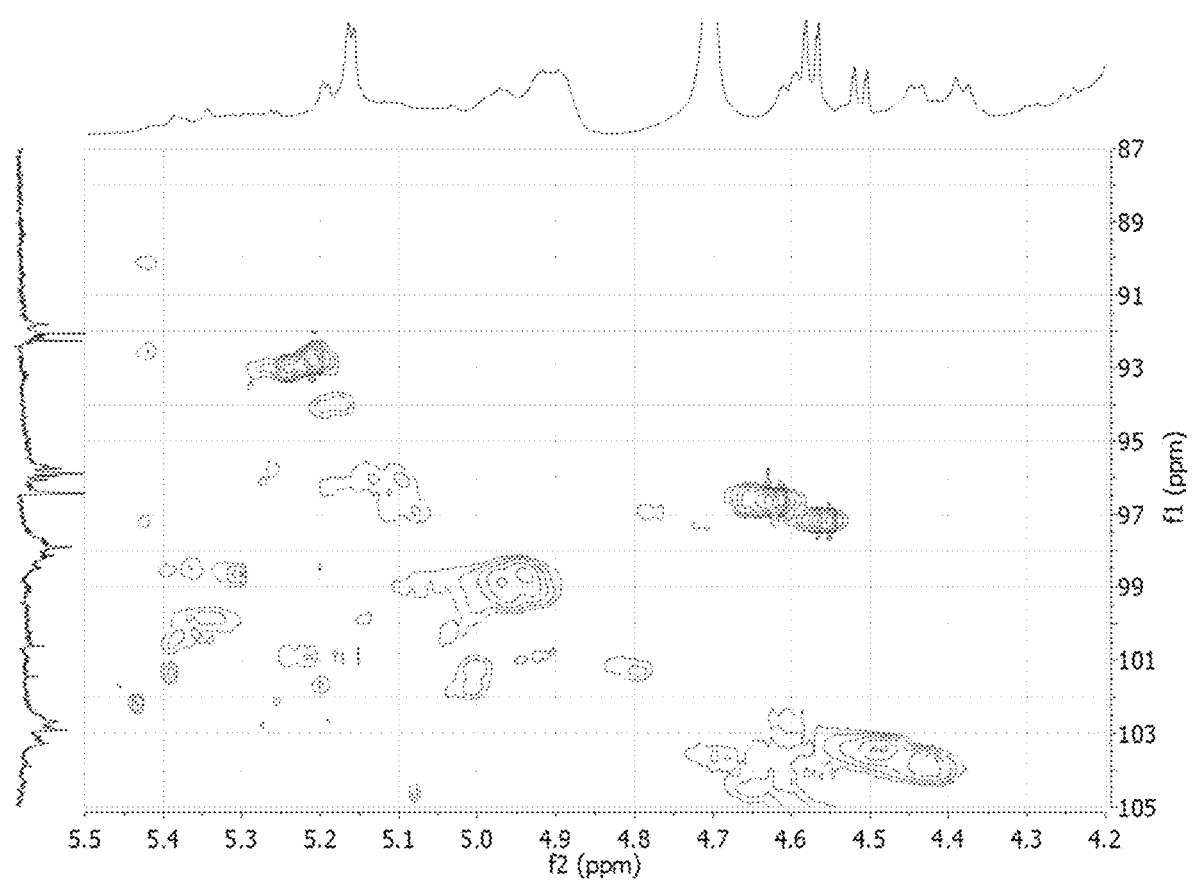
Figure 3C:
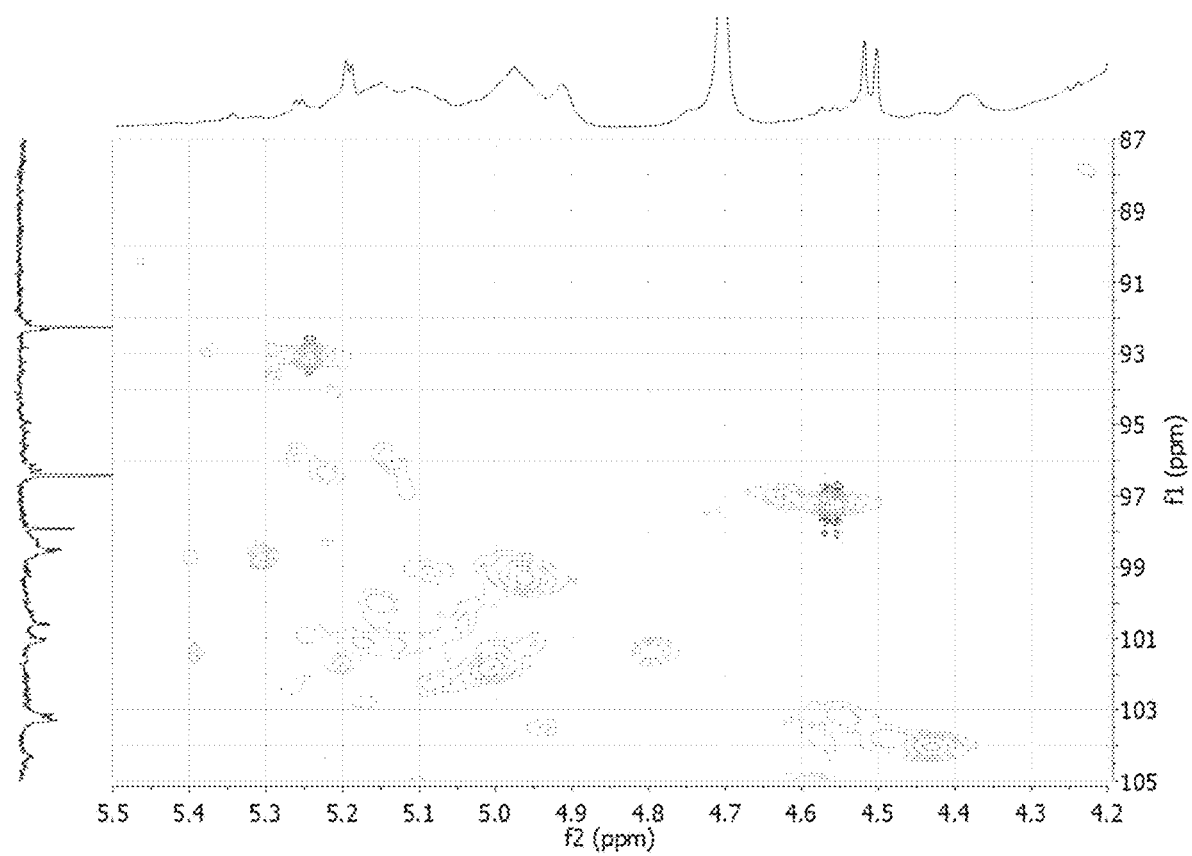

This experiment was designed to identify the composition of a glycan by 2D-NMR identification of the constituent monomers. Approximately 150 mg of 65 Brix oligosaccharide solution was dried to stable mass in a vacuum oven at 45-95° C. under 400 mbar pressure. The sample was subjected to two cycles of dissolution in $D_2O$ and drying to remove residual $H_2O$. Once dried, the sample was dissolved in 750 µL $D_2O$ with 0.1% acetone, placed into a 3 mm NMR tube, and analyzed in a Bruker Avance-III operating at 500.13 MHz 1H (125.77 MHz 13C) equipped with a Bruker BBFO probe operating at 70° C. The sample was analyzed using a heteroatomic single quantum coherence pulse sequence (HSQC) using the standard Bruker pulse sequence. The anomeric region of each glycan spectra derived from a single sugar monomer was then examined for peaks representing specific glycosidic bonds characteristic to that monomer. Due to the spin-isolated nature of single carbohydrate rings within polysaccharides, the HSQC spectra of a glycan with more than one monomer is predicted to be represented by the sum of the HSQC peaks of each of its constituent sugars. Therefore, each constituent monomer has unique HSQC peaks that will appear in any glycan that contains that monomer irrespective of other constituent monomers and furthermore, the monomers used to synthesize a glycan can be determined by identifying the fingerprint peaks unique to each constituent monomer. For example, FIGS. 3A-3C show that the HSQC spectra of glu50gal50 is a hybrid of the spectra of glu100 and gal100. Table 7 lists the fingerprint peaks for selected glycan units.

TABLE 7

Diagnostic HSQC peaks for each component sugar.

| Monomer | 1H shift | 13C shift |
|---|---|---|
| Glucose | 5.42 | 92.5 |
|  | 5.21 | 92.8 |
|  | 5.18 | 93.9 |
|  | 5.08 | 97.0 |
|  | 5.36 | 98.4 |
|  | 5.34 | 99.8 |
|  | 5.38 | 100.3 |
|  | 4.95 | 98.6 |
|  | 4.62 | 96.6 |
|  | 4.70 | 103.6 |
|  | 4.49 | 103.4 |
| Galactose | 5.37 | 92.9 |
|  | 5.24 | 93.1 |
|  | 5.14 | 96.0 |
|  | 4.96 | 99.3 |
|  | 5.31 | 98.7 |
|  | 5.39 | 101.4 |
|  | 5.00 | 101.8 |
|  | 4.80 | 101.3 |
|  | 4.63 | 97.0 |
|  | 4.56 | 97.2 |
|  | 4.53 | 103.1 |
|  | 4.43 | 104.1 |
| Fucose | 5.18 | 92.9 |
|  | 5.33 | 92.4 |
|  | 5.04 | 96.3 |
|  | 4.90 | 99.7 |
|  | 4.52 | 97.0 |
|  | 4.39 | 103.6 |
| Mannose | 5.37 | 93.0 |
|  | 5.16 | 94.6 |
|  | 4.88 | 94.2 |
|  | 5.39 | 101.7 |
|  | 5.24 | 101.9 |
|  | 5.13 | 102.8 |
|  | 5.03 | 102.7 |
|  | 5.24 | 105.6 |

TABLE 7-continued

Diagnostic HSQC peaks for each component sugar.

| Monomer | 1H shift | 13C shift |
|---|---|---|
|  | 5.09 | 108.0 |
|  | 4.88 | 94.2 |
|  | 4.89 | 100.0 |
|  | 4.70 | 101.1 |
| Xylose | 5.18 | 93.0 |
|  | 5.10 | 94.3 |
|  | 5.34 | 98.2 |
|  | 5.31 | 99.6 |
|  | 5.11 | 100.8 |
|  | 4.91 | 99.4 |
|  | 4.56 | 97.3 |
|  | 4.64 | 104.2 |
|  | 4.54 | 103.4 |
|  | 4.44 | 102.6 |
|  | 4.44 | 104.1 |
| Arabinose | 5.22 | 93.2 |
|  | 5.13 | 93.2 |
|  | 5.29 | 96.0 |
|  | 5.26 | 97.2 |
|  | 5.12 | 96.6 |
|  | 5.18 | 99.6 |
|  | 5.06 | 99.2 |
|  | 4.99 | 100.0 |
|  | 5.26 | 101.9 |
|  | 5.06 | 102.1 |
|  | 4.55 | 97.4 |
|  | 4.54 | 105.2 |
|  | 4.50 | 105.5 |
|  | 4.38 | 103.9 |
| Rhamnose | 5.21 | 93.2 |
|  | 5.10 | 94.5 |
|  | 4.85 | 94.1 |
|  | 5.01 | 95.8 |
|  | 5.35 | 100.5 |
|  | 5.15 | 102.2 |
|  | 5.04 | 102.9 |
|  | 4.78 | 97.9 |
|  | 4.71 | 99.0 |
|  | 4.72 | 101.0 |

At least 5 peaks appeared for each glycan unit used as a starting material in the synthesis of a glycan therapeutic containing 3 or fewer distinct glycan units. The HSQC spectra of glycan therapeutics containing 4 or more distinct glycan units have at least 4 peaks for each constituent glycan unit.

Branching Analysis

Figure 4A:
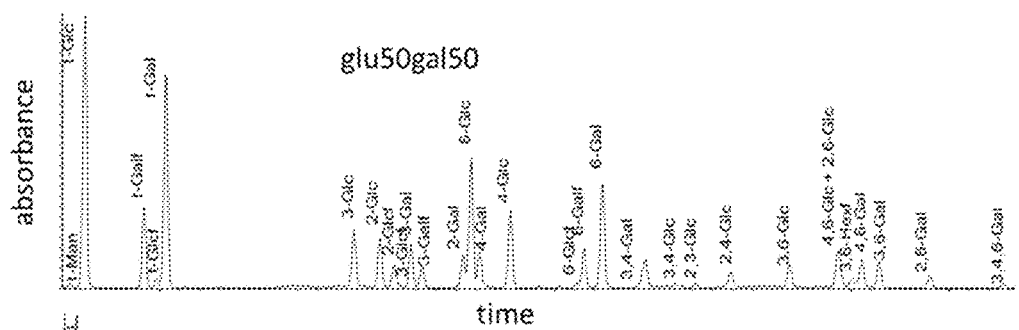
FIGS. 4A-4C, Representative GC chromatograms of three representative permethylated and hydrolyzed glycans, glu50gal50 (FIG. 4A), man52glu29gal19 (FIG. 4B), and glu100 (FIG. 4C), showing distribution of regiochemistry as assigned by comparison to known standards.
Figure 4B:
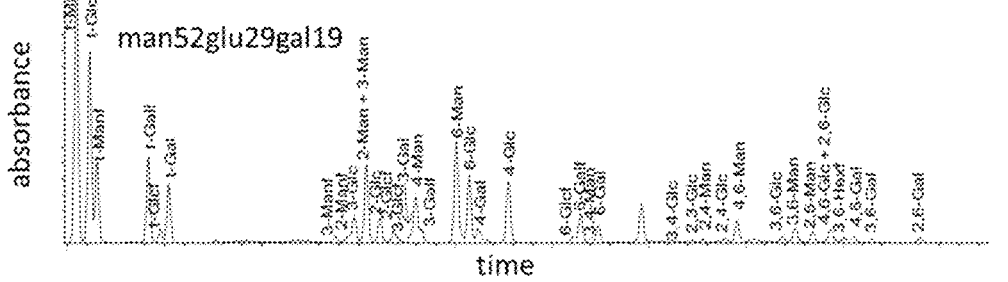
Figure 4C:
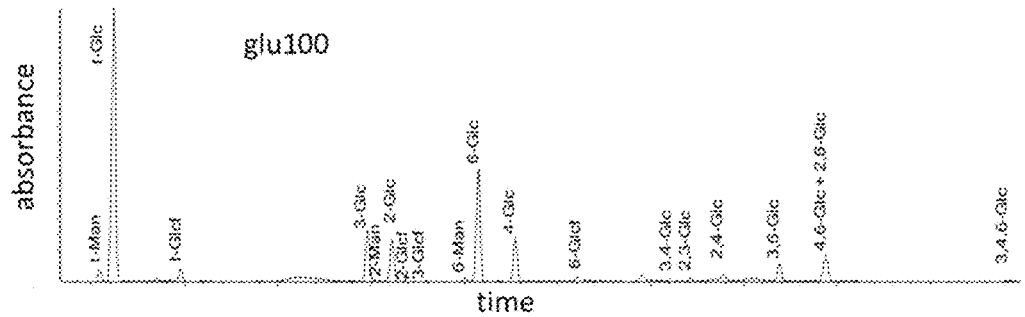

This experiment was designed to quantitate the distribution of glycosidic regioisomers (branching) within a given oligosaccharide. For glycosyl linkage analysis, the samples were permethylated, depolymerized, reduced, and acetylated; and the resultant partially methylated alditol acetates (PMAAs) analyzed by gas chromatography-mass spectrometry (GC-MS) as described by Heiss et al (2009) Carbohydr. Res. 344:915. The samples were suspended in 200 µl of dimethyl sulfoxide and left to stir for 1 day. Permethylation was effected by two rounds of treatment with sodium hydroxide (15 min) and methyl iodide (45 min). The aqueous solution was hydrolyzed by addition of 2M trifluoroacetic acid and heating to 121° C. for 2 hours. Solids were isolated in vacuo and acetylated in acetic acid/trifluoroacetic acid. The resulting PMAAs were analyzed on an Agilent 7890A GC interfaced to a 5975C MSD (mass selective detector, electron impact ionization mode); separation was performed on a 30 m Supelco SP-2331 bonded phase fused silica capillary column. FIG. 4A, FIG. 4B, and FIG. 4C show three representative GC spectra from this analysis. These analyses show that the glycans had at least 0.1-10% of each of the 1,2-; 1,3-; 1,4-, and 1,6-glycoside bond types.

The materials also contained at least 5% of the branched bond types (including but not limited to 1,3,6-; 1,4,6-; or 1,2,4-glycosides) and at least 3% of the monomeric units existed in the furanose form. A glycan originating from a single monomer consisted of at least 12 distinct non-terminal substitution patterns. A glycan originating from two monomers consisted of at least 18 distinct non-terminal substitution patterns. A glycan originating from three or more monomers consisted of at least 24 distinct non-terminal substitution patterns.

Example 6

Collection of Fecal Samples

Fecal samples were collected by providing subjects with the Fisherbrand Commode Specimen Collection System (Fisher Scientific) and associated instructions for use. Collected samples were stored with ice packs or at −80° C. until processing (McInnes & Cutting, Manual of Procedures for Human Microbiome Project: Core Microbiome Sampling Protocol A, v12.0, 2010, hmpdacc.org/doc/HMP_ MOP_ Version12_0_072910.pdf). Alternative collection devices may also be used. For example, samples may be collected into the Globe Scientific Screw Cap Container with Spoon (Fisher Scientific) or the OMNIgene-GUT collection system (DNA Genotek, Inc.), which stabilizes microbial DNA for downstream nucleic acid extraction and analysis. The subjects donating the fecal samples were given the manufacturer-supplied instructions for use of each collection device. Aliquots of fecal samples were stored at −80° C. following standard protocols known to one skilled in the art.

Example 7

Determining the Titer of Microbial Samples Collected from Feces and Culturing Samples To determine the titer of common bacteria of the gastrointestinal tract, fecal samples were collected as described in Example 6 and prepared as a 10% weight/volume suspensions in sterile phosphate buffered saline (PBS). Ten-fold serial dilutions were prepared in sterile PBS and plated (100 μL per dilution) to Brucella Blood Agar (Anaerobe Systems; incubated anaerobically to non-selectively titer common member of the gut microbiota, including *Bacteroides*, or incubated aerobically to non-selectively titer facultative anaerobes such as Proteobacteria). *Bacteroides* Bile Esculin Agar (Anaerobe Systems; cultured anaerobically to titer *Bacteroides fragilis* group), Cycloserine-Cefoxitin Fructose Agar (Anaerobe Systems; cultured anaerobically to titer *Clostridium difficile*), *Lactobacillus*-MRS Agar (Anaerobe Systems; cultured anaerobically to titer *Lactobacillus*), Eosin Methylene Blue Agar (Teknova; cultured aerobically to titer *Escherichia coli* and other Gram-negative enteric bacteria), Bile Esculin Agar (BD; cultured aerobically to titer *Enterococcus* species), *Bifidobacterium* Selective Agar (Anaerobe Systems; to titer *Bifidobacterium* species), or MacConkey Agar (Fisher Scientific; to titer *E. coli* and other Gram-negative enteric bacteria) may also be used. Plates were incubated at 37° C. under aerobic or anaerobic conditions as appropriate for the target species. After 24-48 hours, colonies were counted and used to back-calculate the concentration of viable cells in the original sample.

To non-selectively culture samples containing bacteria collected from a human or laboratory animal model, rich media or agar such as Brucella Blood Agar (Anaerobe Systems), Brain Heart Infusion Broth (Teknova), or Chopped Meat Glucose Broth (Anaerobe Systems) were used. A minimal media formulation such as M9 (Life Technologies) supplemented with amino acids, carbon sources, or other nutrients as needed were used to non-selectively culture bacteria during in vitro assays testing the effects of glycans or other compounds on bacterial populations. Alternatively, other minimal media formulations known to one skilled in the art were used, for example, as reported in Martens et al. (Mucosal Glycan Foraging Enhances Fitness and Transmission of a Saccharolytic Human Gut Bacterial Symbiont, 2008, Cell Host & Microbe, 4:447-457). Alternatively, fecal slurries at a concentration of 0.1%-10% weight/volume in PBS were used in the presence or absence of additional media elements for in vitro assays testing the effects of glycans or other compounds on bacterial populations.

Example 8

Single Strain Growth Assays

An in vitro assay was performed to assess the ability of various bacterial strains, including commensals and pathogens of the gastrointestinal tract, to utilize different glycans as growth substrates. This assay was designed to assess the ability of selected glycans to promote the growth of healthy-state microbiota. Additionally, the ability of selected glycans to promote the growth of commensals was compared to the ability of the glycans to promote the growth of microbes associated with a disease state. By testing preparations of glycans against a panel of bacteria (individually) which are characteristic of a healthy or disease state preparations of glycans that selectively enhance the growth of healthy-state bacteria over disease-state bacteria can be selected. Bacterial strains were handled at all steps in an anaerobic chamber (AS-580, Anaerobe Systems) featuring a palladium catalyst. The chamber was initially made anaerobic by purging with an anaerobic gas mixture of 5% hydrogen, 5% carbon dioxide and 90% nitrogen and subsequently maintained in an anaerobic state using this same anaerobic gas mixture. Anaerobicity of the chamber was confirmed daily using Oxoid anaerobic indicator strips that change color in the presence of oxygen. All culture media, assay plates, other reagents and plastic consumables were pre-reduced in the anaerobic chamber for 24-48 hours prior to contact with bacteria. Glycans ara50gal50, glu33gal33fuc33, glu50gal50, gal100, glu100, ara50xyl50, xyl100, ara100, ara60xyl40, rha100, gal75xyl25, glu90gly10, man62glu38, man52glu29gal19, and two commercially available controls: acacia fiber (Acacia Fiber Organic Powder; NOW Foods, Bloomingdale Ill.) and FOS (Nutraflora FOS; NOW Foods, Bloomingdale Ill.) were prepared at 5% w/v in water, filter-sterilized and added to Costar 3370 assay plates for a final concentration of 0.5% w/v in the assay, with each glycan assayed in two non-adjacent wells and dextrose and water supplied as positive and negative controls.

Bacterial isolates were obtained from the American Type Culture Collection (ATCC) and Leibniz Institute DSMZ-German Institute of Microorganisms and Cell Cultures (DSMZ). 8 commensal species (*Bacteroides caccae* ATCC 43185 "BCA.26", *Prevotella copri* DSM 18205 "PCO.72", *Bacteroides thetaiotaomicron* ATCC 29741 "BTH.8", *Bacteroides cellulosilyticus* DSM 14838 "BCE.71", *Clostridium scindens* ATCC 35704 "CSC.32", *Ruminococcus obeum* ATCC 29714 "ROB.74", *Clostridium nexile* ATCC 27757 "CNE.31" and *Parabacteroides distasonis*

ATCC 8503 "PDI.6") and three pathogenic species (*Clostridium difficile* ATCC BAA-1382 "CDI.23" and ATCC 43255 "CDI.24", *Enterococcus faecium* ATCC 700221 "EFM.66" and *Salmonella enterica* ATCC 27869 "SEN.52") were grown anaerobically on Brucella Blood Agar (Anaerobe Systems), a pre-reduced enriched medium including enzymatic digests of casein and animal tissues, yeast extract, sodium chloride, dextrose, sodium bisulfite, sheep's blood, hemin and Vitamin K1, for 18-48 hours at 37° C. The commensal species *Akkermansia muciniphila* ATCC BAA-835 "AMU.73" was grown anaerobically on MTGE agar plates (Anaerobe Systems), a rich medium including a protein formulation, yeast extract, vitamin K1 and volatile fatty acids. Inocula were prepared by scraping colonies from agar plates, suspending them in phosphate buffer, determining the cell suspensions' optical density at 600 nM ($OD_{600}$) in a Costar 3370 polystyrene 96-well flat-bottom assay plate using a Biotek Synergy 2 plate reader with Gen5 2.0 All-In-One Microplate Reader Software according to manufacturer's protocol, and diluting the cells to $OD_{600}$ 0.01-0.02 final in defined and semi-defined media that were prepared without sugars. *D. formicigenerans, P. distasonis, C. difficile* and *E. faecium* isolates were tested in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114), supplemented with 3.5% (v/v) Chopped Meat Glucose Broth (CMG, Anaerobe Systems), a rich medium including yeast extract, peptone, chopped beef and phosphate buffer. *B. thetaiotaomicron, B. caccae, B. cellulosyliticus* and *S. enterica* were tested in 100 mM potassium phosphate buffer (pH 7.2), 15 mM sodium chloride, 8.5 mM ammonium sulfate, 4 mM L-cysteine, 1.9 μM hematin, 200 μM L-histidine, 100 μM magnesium chloride, 1.4 μM iron sulfate heptahydrate, 50 μM calcium chloride, 1 μg/mL vitamin K3 and 5 ng/mL vitamin B12 (Martens E C et al. Cell Host & Microbe 2008; 4, 447-457). *C. scindens, P. copri* and *R. obeum* were tested in 10 g/L tryptone peptone, 5 g/L yeast extract, 0.5 g/L L-cysteine hydrochloride, 0.1 M potassium phosphate buffer pH 7.2, 1 μg/mL vitamin K3, 0.08% w/v calcium chloride, 0.4 μg/mL iron sulfate heptahydrate, 1 μg/mL resazurin, 1.2 μg/mL hematin, 0.2 mM histidine, 0.05% Tween 80, 0.5% meat extract (Sigma), 1% trace mineral supplement (ATCC), 1% vitamin supplement (ATCC), 0.017% v/v acetic acid, 0.001% v/v isovaleric acid, 0.2% v/v propionic acid and 0.2% v/v N-butyric acid (Romano K A et al. mBio 2015; 6(2):e02481-14); for *C. nexile* and *A. muciniphila*, this medium was supplemented with 3.5% v/v final of CMG broth. Bacteria were exposed to glycans ara50gal50, glu33gal33fuc33, glu50gal50, gal100, glu100, ara50xyl50, xyl100, ara100, ara60xyl40, rha100, gal75xyl25, man62glu38, man52glu29gal19, commercial acacia fiber, commercial FOS and dextrose at a final concentration of 0.5% w/v in 96-well microplates, 200 μL final volume per well, at 37° C. for 18-48 hours, anaerobically, until turbidity was observed in the positive growth control wells containing 0.5% w/v dextrose. $OD_{600}$ measurements for each isolate at the end of the incubation period were obtained using a Biotek Synergy2 reader with Gen5 2.0 software according to manufacturer's specifications. Measurements were normalized by dividing the $OD_{600}$ readings of the isolate on test glycans by the $OD_{600}$ of the isolate in medium supplemented with 0.5% w/v dextrose to facilitate comparison of glycan utilization by strains that grow within significantly different $OD_{600}$ ranges. Tables 8 and 9 summarize the results obtained.

| Key to glycans | | |
|---|---|---|
| glycan # | glycan identity | % DP3+ |
| 1 | gal75xyl25 | 50 |
| 2 | glu50gal50 | 68-80 |
| 3 | gal100 | 78-83 |
| 4 | glu33gal33fuc33 | 54-82 |
| 5 | man62glu38 | 63 |
| 6 | ara50gal50 | 73 |
| 7 | glu100 | 79-80 |
| 8 | man52glu29gal19 | 47-77 |
| 9 | xyl100 | 37-73 |
| 10 | ara50xyl50 | 63 |
| 11 | ara100 | 48-85 |
| 12 | ara60xyl40 | 70 |
| 13 | rha100 | 45-49 |
| 14 | FOS | |
| 15 | acacia fiber | |

Most glycans supported growth of the commensal strains tested in this assay. Gal75xyl25, glu33gal33fuc33, glu50gal50, gal100, man62glu38, ara50gal50, glu100, man52glu29gal19, ara50xyl50 xyl100 and ara100 supported growth of at least 5 of 9 commensals (see Table 8).

TABLE 8

Glycan-supported growth of commensal bacteria.

| | Isolates | Commensals, Average Normalized Growth (NG) | | | | | | | |
|---|---|---|---|---|---|---|---|---|---|
| glycan # | w/NG >0.2 | PDI.6 | BTH.8 | BCA.26 | CNE.31 | CSC.32 | BCE.71 | PCO.72 | AMU.73 | ROB.74 |
| 1 | 9/9 | +++ | ++ | ++ | + | + | ++ | +++ | ++ | + |
| 2 | 9/9 | +++ | + | ++ | + | + | ++ | +++ | + | + |
| 3 | 9/9 | +++ | + | + | ++ | + | + | ++ | + | + |
| 4 | 9/9 | +++ | + | + | + | + | + | ++ | + | + |
| 5 | 8/9 | +++ | ++ | ++ | + | + | ++ | − | + | + |
| 6 | 8/9 | +++ | + | + | − | + | + | ++ | + | + |
| 7 | 8/9 | +++ | + | + | + | − | + | ++ | + | + |
| 8 | 7/9 | +++ | + | + | − | + | + | − | + | + |
| 9 | 6/9 | +++ | + | + | − | − | + | ++ | − | + |
| 10 | 6/9 | ++ | + | + | − | − | + | ++ | − | + |
| 11 | 5/9 | − | + | + | − | − | + | ++ | − | + |
| 12 | 4/9 | ++ | − | + | − | − | + | + | − | − |

TABLE 8-continued

Glycan-supported growth of commensal bacteria.

| 13 | 2/9 | –   | –  | –  | – | – | – | +  | – | +  |
| 14 | 5/9 | +++ | ++ | ++ | – | – | – | ++ | – | ++ |
| 15 | 1/9 | +   | –  | –  | – | – | – | –  | – | –  |

Key to Symbols
| Symbol | NG |
|--------|------|
| –      | <0.2 |
| +      | 0.2-6 |
| ++     | 0.6-1.2 |
| +++    | >1.2 |

Some glycans supported growth of tested commensals better than tested pathogens: ara50gal50, glu33gal33fuc33, gal100, glu100 ara50xyl50, xyl100 and commercial FOS control supported growth of 5 or more of 9 commensal isolates and 2 or fewer of 4 pathogenic isolates, with normalized growth values of at least 0.2. In the assay, commensals with normalized growth values >0.6. In the assay, one glycan did not support a majority of commensals or pathogens: rha100 and commercial acacia fiber control supported 2 or fewer of 9 commensals and 2 or fewer of 4 pathogens with normalized growth values of >0.2 (see Table 9).

TABLE 9

Differential growth of commensals and pathogenic bacteria on selected glycans

| glycan | Commensals | Pathogens | Commensals | | | | |
|---|---|---|---|---|---|---|---|
| # | w/NG >0.2 | w/NG >0.2 | PDI.6 | BTH.8 | BCA.26 | CNE.31 | CSC.32 |
| 3  | 9/9 | 0/4 | +++ | +  | +  | ++ | +  |
| 7  | 8/9 | 2/4 | +++ | +  | +  | +  | –  |
| 6  | 8/9 | 0/4 | +++ | +  | +  | –  | +  |
| 10 | 6/9 | 0/4 | ++  | +  | +  | –  | –  |
| 9  | 6/9 | 0/4 | +++ | +  | +  | –  | –  |
| 14 | 5/9 | 1/4 | +++ | ++ | ++ | –  | –  |
| 1  | 9/9 | 3/4 | +++ | ++ | ++ | +  | +  |
| 2  | 9/9 | 4/4 | +++ | +  | ++ | +  | +  |
| 5  | 8/9 | 4/4 | +++ | ++ | ++ | +  | +  |
| 13 | 2/9 | 0/4 | –   | –  | –  | –  | –  |
| 15 | 1/9 | 2/4 | +   | –  | –  | –  | –  |

| glycan | Commensals | | | | Pathogens | | | |
|---|---|---|---|---|---|---|---|---|
| # | BCE.71 | PCO.72 | AMU.73 | ROB.74 | CDI.23 | CDI.24 | SEN.52 | EFM.66 |
| 3  | +  | ++  | +  | +  | –  | –  | –  | –  |
| 7  | +  | ++  | +  | +  | +  | –  | –  | +  |
| 6  | +  | ++  | +  | +  | –  | –  | –  | –  |
| 10 | +  | ++  | –  | +  | –  | –  | –  | –  |
| 9  | +  | ++  | –  | +  | –  | –  | –  | –  |
| 14 | –  | ++  | –  | ++ | –  | –  | –  | +  |
| 1  | ++ | +++ | ++ | +  | +  | –  | +  | +  |
| 2  | ++ | +++ | +  | +  | +  | +  | +  | ++ |
| 5  | ++ | –   | +  | +  | ++ | ++ | +  | ++ |
| 13 | –  | +   | –  | +  | –  | –  | –  | –  |
| 15 | –  | –   | –  | –  | +  | –  | –  | +  |

Key to Symbols
| Symbol | NG |
|--------|------|
| –      | <0.2 |
| +      | 0.2-6 |
| ++     | 0.6-1.2 |
| +++    | >1.2 | glu50gal50 and gal75xyl25 each supported the majority of commensals and pathogens with normalized growth values of at least 0.2; however, they supported a higher level of growth with a larger fraction of commensals than pathogens: gal75xyl25 produced normalized growth values >0.6 for 6 of 9 commensals and 1 of 4 pathogens, and glu50gal50 produced normalized growth values >0.6 for 4 of 9 commensals and 0 of 4 pathogens. In the assay, one glycan supported growth of pathogens as well as commensals: man62glu38 supported growth of 4 of 4 pathogens and at least 8 of 9 commensals with normalized growth values of at least 0.2 and 3 of 4 pathogens and 6 or fewer of 9 commensals with normalized growth values >0.6. In the assay, one glycan did not support a majority of commensals or pathogens: rha100 and commercial acacia fiber control supported 2 or fewer of 9 commensals and 2 or fewer of 4 pathogens with normalized growth values of >0.2 (see Table 9).

These data suggest that glycan therapeutics support growth of commensal bacteria and certain sub-groups of glycans differentially support growth of commensals over pathogens.

Example 9

Effect of Glycans on Microbial Populations In Vitro

To determine the desired composition of glycans, bacterial cultures are grown in the presence of candidate glycans and assayed for their growth, community composition (e.g., by 16S rRNA gene sequencing), production of metabolites, and phenotypic or transcriptomic properties. Desired glycans are selected based on their ability to elicit desired properties within the bacterial culture. Bacterial cultures include monocultures, mixed cultures, cultures isolated from humans or laboratory animal models, cultures isolated from a human or laboratory animal model and spiked with an isolate or collection of isolates, or cultures isolated from a human or laboratory animal model and depleted of a collection of species (for example, by application of an antibiotic). The titer of the bacterial cultures is determined as in Example 7 and the composition and properties of the bacterial cultures are quantified as described herein or using standard protocols. This assay can be performed in the presence of antibiotics or other test compounds. The results obtained from the in vitro assays are compared with those obtained after treating humans with glycans or administering the glycans to a laboratory animal in an animal model as described, e.g., in Example 10 and Example 12, thus establishing the in vitro—in vivo correlation of results.

Example 10

Effect of Glycans on the Intestinal Microbiota of Naïve Mice

This experiment was carried out to assess the effect of glycan therapeutics on the gut microbiota and short term weight of naïve mice. In this model, normal mice are administered glycans in their drinking water over a period of 6 days with fecal samples taken from each mouse for 16S rRNA analysis.

Mice, C57Bl/6 (B6N Tac), mouse pathogen free (MPF; Taconic Biosciences, Germantown, N.Y.) aged 8-10 weeks were housed singly in cages, with 6 animals per dose group. Animals were fed PicoLab Rodent Diet 20 ("5053"; Lab-Diet, St. Louis, Mo.) or zero fiber diet ("ZFD"; Modified rodent diet AIN-93G: D15091701, Research Diets, New Brunswick, N.J.) ad libitum throughout the course of the study and had free access to water. Mice were maintained on a 12 h light/dark cycle. Mice were acclimated for 7 days (days −7 to −1) prior to glycan administration.

Glycans were administered to the mice by inclusion in their drinking water at 1% weight/volume (w/v) from day 0 through day 5. Control mice received water containing no glycan. Fresh fecal collections were performed for each mouse from days −2 to 5. Mouse weights were monitored on days −1, 1, 3 and 4. Body weights of the mice did not change significantly throughout the course of the study.

Genomic DNA was extracted from the fecal samples and variable region 4 of the 16S rRNA gene was amplified and sequenced (Earth Microbiome Project protocol www.earthmicrobiome.org/emp-standard-protocols/16s/ and Caporaso J G et al. 2012. Ultra-high-throughput microbial community analysis on the Illumina HiSeq and MiSeq platforms. ISME J.). Operational Taxonomic Units (OTUs) were generated by aligning 16S rRNA sequences at 97% identity. Microbial communities were compared to each other using UniFrac distance metric (Lozupone C. et al., Appl. Environ. Microbiol. December 2005 vol. 71 no. 12 8228-8235).

Figure 7:
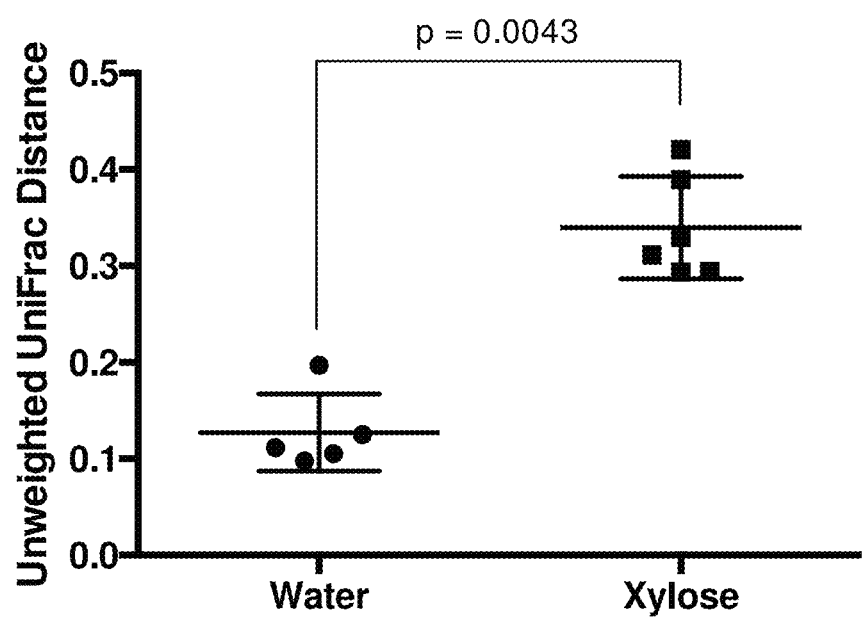
FIG. 7. Distances were calculated for each mouse between microbiota sampled at 1 day before and 5 days after glycan or water administrated as described in Example 10. The larger the distance, the bigger change in microbial composition is observed.
Figure 8:
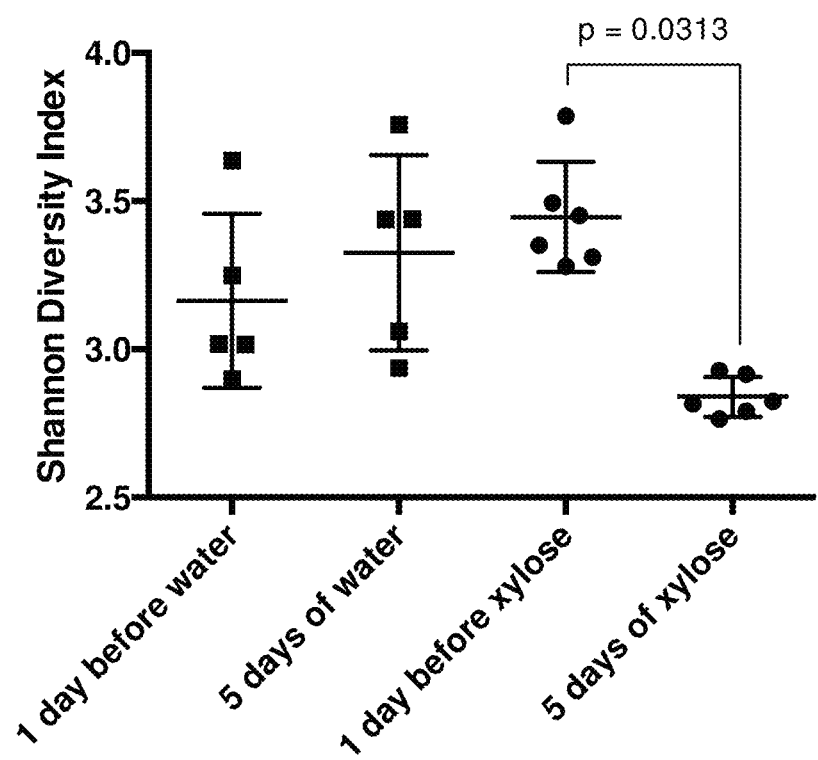
FIG. 8. Shannon diversity index. Paired Wilcoxon test was used to calculate the significance of observed differences as described in Example 10.

Significant changes were observed when mice were administered a xyl 100 preparation. UniFrac distances between microbiota sampled at one day before and 5 days after glycan administration were significantly larger in mice treated with xylose compared to mice who did not receive any glycan (p=0.0043, Mann-Whitney test, FIG. 7). Alpha diversity was measured by calculated Shannon Index in microbiota before and after glycan or water administration. Shannon index significantly decreased after 5 days of xylose administration (p=0.0313, Wilcoxon paired test, FIG. 8).

Figure 9A:
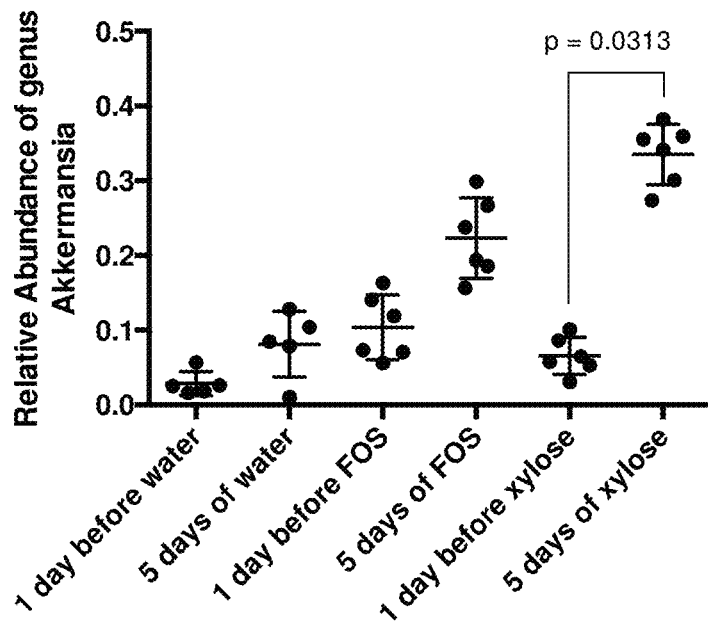
FIGS. 9A-9B. Relative abundance of sequences assigned to genus *Akkermansia*, phylum Verrucomicrobia is shown in FIG. 9A. Relative abundance of sequences assigned to genus *Blautia*, phylum Firmicutes is shown in FIG. 9B.
Figure 9B:
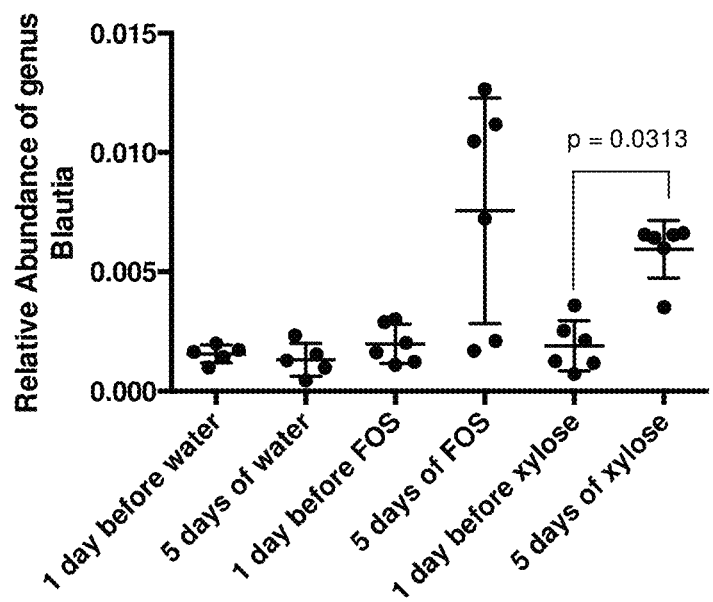

The changes in observed shifts with administration of xylose were attributed to an increase in relative abundance of sequences assigned to genus *Akkermansia* (phylum Verrucomicrobia, p=0.0313, Wilcoxon paired test, FIG. 9A), and genus *Blautia* (phylum Firmicutes, family Lachnospiraceae, p=0.0313, Wilcoxon paired test, FIG. 9B).

The most prominent *Akkermansia* species in the mammalian gut is *Akkermansia muciniphila*. Its preferred energy source is host intestinal mucin. Consumption of a low fiber diet and high intake of simple sugars and fat results in decreased mucus production (British Journal of Nutrition/Volume 102/Issue 01/July 2009, pp 117-125, Quantitative Imaging of Gut Microbiota Spatial Organization, Earle K A et al, Cell Host Microbe. 2015 Oct. 14; 18(4):478-88). Thinning of intestinal mucus may result in increased gut permeability and translocation of microorganisms or their components, such as lipopolysaccharide (LPS), which induce inflammation. LPS levels are increased upon consumption of high fat diet in rodents which then develop metabolic syndrome (Metabolic endotoxemia initiates obesity and insulin resistance, Cani P D et al, Diabetes. 2007 July; 56(7):1761-72).

Although *Akkermansia muciniphila* was not shown to degrade xylose in vitro (Example 8, Table 8, AMU.73), other species may be responsible for primary fermentation of xyl100, such as, e.g., Bacteroidetes, which in turn may induce the growth of *Akkermansia*. For example, colonization of germ free mice with *Bacteroides thetaiotaomicron* induces mucus production by intestinal goblet cells (Wrzosek et al. *BMC Biology* 2013 11:). This may create a favorable environment for *Akkermansia* growth. Consumption of mucus by *Akkermansia* may stimulate increased mucus production and play a role in the restoration of the gut barrier that prevents leaking of microbial endotoxin LPS. Decreased endotoxemia reduces inflammation and may alleviate symptoms that are associated with metabolic syndrome. For example, administration of FOS or *Akkermansia muciniphila* to rodents in a diet-induced obesity model result in decreased levels of serum LPS and reduced fat mass and body weight. (Cross-talk between *Akkermansia muciniphila* and intestinal epithelium controls diet-induced obesity, Everard A, PNAS. 2013 May 28; 110(22):9066-71).

*Akkermansia muciniphila* metabolites, including the SCFA propionate, have been shown to reduce expression of adiposity regulators Gpr43 and peroxisome proliferator-activated receptor gamma and increase expression of the gene regulators histone deacetylases Hdac3 and Hdac5 (Lukovac et al. 2014. Differential Modulation by *Akkermansia muciniphila* and *Faecalibacterium prausnitzii* of Host Peripheral Lipid Metabolism and Histone Acetylation in Mouse Gut Organoids mBio 5(4):e01438-14). Glycan therapeutics when administered in an effective amount may modulate bacterial species that produce SCFAs and thereby modulate host adiposity and obesity. In the in vitro assay (Example 8), growth of AMU.73, an *A. muciniphila* isolate, was supported by 8 out of 15 glycans, as shown in Table 8.

Example 11

In Vitro Co-Culture Models to Test the Effect of Glycans on Host Responses to Bacterial Communities at Intestinal Sites Bacteria can elicit both pro- and anti-inflammatory responses from host (mammalian) cells, and different bacterial species can elicit different host responses. Preparations of glycans are used to alter the bacterial population to elicit a desired host response. An in vitro co-culture model is used to measure the host responses elicited by bacterial populations grown in the presence of glycans. Glycans that promote bacterial populations that elicit beneficial host responses or minimize detrimental host responses are selected using this assay.

Epithelial cell lines or tissues from the intestine are used in a co-culture model (Haller D, Bode C, Hammes W P, Pfeifer A M A, Schiffrin E J, Blum S, 2000. Non-pathogenic bacteria elicit a differential cytokine response by intestinal epithelial cell/leucocyte co-cultures. Gut. 47:79-97) (Borruel et al., 2003. Effects of nonpathogenic bacteria on cytokine secretion by human intestinal mucosa. Am J Gastroenterology. 98:865-870). Human enterocyte-like CaCO-2 cells are seeded at a density of $2.5 \times 10^5$ cells/ml on 25 mm cell culture inserts (0.4 μm nucleopore size; Becton Dickinson). The inserts are placed into 6-well tissue culture plates (Nunc) and cultured 18-22 days at 37° C./10% $CO_2$ in DMEM (glutamine, high glucose; Amimed) supplemented with 20% heat-inactivated fetal calf serum (56° C., 30 minutes; Amimed), 1% MEM non-essential amino acids (Gibco BRL), 10 μg/ml gentamycin (Gibco BRL), and 0.1% penicillin/streptomycin (10 000 IU/ml/10 000 UG/ml; Gibco BRL). The cell culture medium is changed every second day until the cells are fully differentiated. Alternatively, a 3D reconstructed tissue model produced from normal, human cell-derived small intestine epithelial and endothelial cells and fibrobasts (EpiIntestinal model; MatTek Corporation, Ashland, Mass.) is used. Transepithelial electrical resistance (TEER) is determined using a MultiCell-ERS voltmeter/ohmmeter. Tissue culture inserts are washed twice with prewarmed antibiotic-free medium prior to challenge with bacterial cultures. Separately, bacterial cultures are grown in the presence of preparations of glycan as described in Example 9. After 16-24 hours of growth in the presence of glycans, the bacterial suspensions are prepared in antibiotic-free medium and $10^6$-$10^8$ CFU are added to confluent cell or tissue cultures. The co-cultures are incubated at 37° C. for 4-24 hours.

At the conclusion of the co-incubation period, the supernatant is collected and analyzed for inflammatory and immunomodulatory cytokines including IL-1α, IL-1β, TNF, IL-8, RANTES, IL-10, TGF-β, IFN-γ, IL-4, IL-6, IL-12, IL-17, and IL-23. This analysis is performed by enzyme linked immunosorbent assay (ELISA) or other comparable quantification technique (e.g., Luminex Assay; Life Technologies, Carlsbad, Calif.) following standard protocols. To analyze a broader range of responses, gene expression (e.g., by microarray) or transcriptomic (e.g., by RNA-Seq) analysis is performed by lysing the cells, purifying RNA, and following standard protocols. This procedure is used to analyze the expression of genes encoding inflammatory cytokines, immunomodulatory cytokines, antimicrobial peptides, and other relevant host responses.

Example 12

Effect of Glycans in a Mouse Model of *Clostridium difficile* Infection

This experiment was conducted to analyze the effects of glycan therapeutics in a mouse model of *Clostridium difficile* infection (Chen et al, 2008, A Mouse Model of *Clostridium difficile*-Associated Disease. Gastroenterology 135(6), 1984-1992). In this model, normal mice were exposed to an antibiotic regimen that renders them susceptible to *C. difficile* infection and disease symptoms, similar with respect to their development and manifestation of human clinical disease. In humans, the disease is most often the result of exposure to broad spectrum antibiotics which is thought to result in intestinal dysbiosis and subsequent increased colonic colonization with *C. difficile*. The increased bioburden of *C. difficile* leads to toxin production by the bacterium and colonic inflammation. Clinical manifestations in humans include diarrhea, weight loss, intestinal inflammation, fever and dehydration. The clinical incidence of *C. difficile* infection and disease is about 750,000 cases per year in the US.

Mice (female C57BL/6, 8-10 weeks old, 16-18 grams each; Harlan Laboratories, Indianapolis, Ind.) were housed in groups of 3 per cage, with 4 cages per treatment group. Mice were exposed to a cocktail of antibiotics in their drinking water for a period of 9 days, starting on day −14, fourteen days before *Clostridium difficile* challenge on day 0. The antibiotic cocktail consisted of 1% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and vancomycin (0.056 mg/ml). Three days prior to *Clostridium difficile* challenge (on Day −3), mice received a single dose of clindamycin (10 mg/kg) in a volume of 0.5 mL distilled water by oral gavage (PO) (see Table 10). All chemicals were purchased from Sigma-Aldrich Corp. (St. Louis, Mo.). On day 0, mice were challenged with *Clostridium difficile* (strain VPI 10463 (ATCC-43255)) spores at approximately 4.5 $\log_{10}$ spores per mouse, PO, in a dose volume of 0.5 mL distilled water.

TABLE 10

Treatments

| Treatment | Route of administration | Treatment duration |
| --- | --- | --- |
| Plain water (control) | Drinking water | QD days −15 to 6 (L) |
| Vancomycin (control) | PO gavage | QD days 0 to 4 |
| glu100 (L) | Drinking water | QD days −15 to 6 |
| glu100 (S) | Drinking water | QD days −1 to 6 (S) |
| glu33gal33fuc33 (L) | Drinking water | QD days −15 to 6 |
| glu33gal33fuc33 (S) | Drinking water | QD days −1 to 6 |
| ara100 (L) | Drinking water | QD days −15 to 6 |
| ara100 (S) | Drinking water | QD days −1 to 6 |
| glu50gal50 (L) | Drinking water | QD days −15 to 6 |
| glu50gal50 (S) | Drinking water | QD days −1 to 6 |
| FOS**FOS (Nutraflora FOS; NOW Foods, Bloomingdale IL) (L) | Drinking water | QD days −15 to 6 |
| FOS (S) | Drinking water | QD days −1 to 6 |

A. Disease-Associated Phenotypes

Disease-associated phenotypes were recorded for a duration of ten days starting on the day of *Clostridium difficile* challenge (on day 0) through day 10. The phenotypes, including lethargy, hunched posture and ruffled coat, wet tail/abdomen and hypothermia were scored from 0 to 4: Normal=0; Lethargic=1; Lethargic+Hunched=2; Lethargic+Hunched+Wet tail/abdomen (diarrhea)=3; and Lethargic+Hunched+Wet tail/abdomen+Hypothermic=4. Death (day 0 to day 10 or 11) and weight (day 1 to day 7 and day 10) of the animals was also monitored and recorded. Mice that showed a body weight loss of more than 25% relative to Day 0 were humanely euthanized.

In these studies, all animals with wet tail/abdomen (diarrhea; clinical score of "3") progressed to death. Diarrhea is an indication of colonic inflammation and hemorrhage and is a contributing factor to the weight loss seen in rodent models of C. difficile colonization/infection.

A treatment's ability to protect animals from death through day 6 in these experiments indicates disease prevention, e.g., in a human. A treatment's ability to protect animals from death between days 7 and 11 indicates that animals were protected from disease relapse in these models.

In addition, carriage of Clostridium difficile spores, which is indicative of Clostridium difficile gut colonization in both mice and humans, was assessed daily from day 0 to day 6. For spore CFU enumeration, fecal pellets from the mice were suspended in 50% ethanol in phosphate-buffered saline (PBS) and vortexed. Samples were incubated at room temperature for 1 hour, vortexed well and serially-diluted in PBS. The resulting suspensions were applied to Clostridium difficile-selective TCCFA agar (Teknova, Hollister Calif.) and grown in an anaerobic atmosphere at 37° C. overnight to enumerate CFU.

Effects of treatments was assessed by comparing the disease-associated phenotypes in glycan-treated, untreated (plain water) and vancomycin-treated groups. FOS is a commercially-available, non-digestible fructooligosaccharide. Clinical trials using commercial FOS as an intervention for antibiotic and Clostridium difficile-associated diarrhea (Lewis et al., Failure of dietary oligofructose to prevent antibiotic-associated diarrhea. Aliment Pharmacol Ther 2005; 21: 469-477) and Clostridium difficile relapse (Lewis et al, Effect of the Prebiotic Oligofructose on Relapse of Clostridium difficile-Associated Diarrhea: A Randomized, Controlled Study. Clin Gastroent Hepatol 2005 (3):442-448.) have yielded different results, with the former trial showing no effect of FOS treatment and the latter demonstrating a reduction in disease recurrence.

Survival

Figure 10:
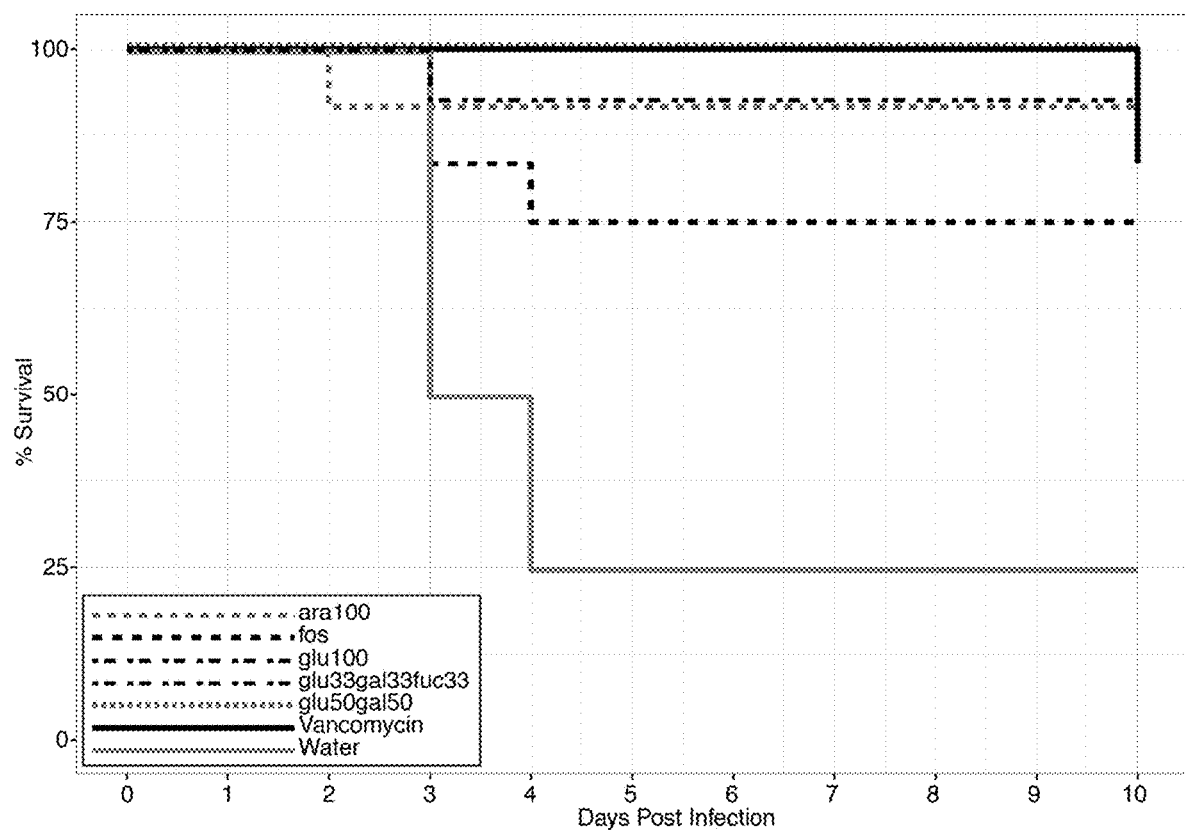
FIG. 10. Kaplan-Meier survival curve post *C. difficile* infection by treatment group for all short treatment groups as described in Example 12.

With regard to animal survival, there was a significant difference between animals treated with water (vehicle) versus animals treated with either glycans or vancomycin (FIG. 10). Animal treatments were discontinued on day 4 (for vancomycin) and day 6 (for glycans) and animal deaths/ clinical scores assessed through day 10 or 11. For water treated animals, 75% of the animals died by day 4 (FIG. 10). All (100%) of vancomycin-treated animals survived to day 7. However, 17% of the animals in the vancomycin-treated group died by day 10. The remaining survivors in the vancomycin-treated group had clinical scores above 0. For glycan-treated groups (L=treatment days −15 to 6; S=days −1 to 6), deaths through day 6 were as follows: For glu100 (L), glu33gal33fuc33 (L), and glu50gal50 (L and S) death was 0%. For ara100 (S), glu33gal33fuc33 (S), glu100 (L), and FOS (L) 8% of animals died. For ara100 (L), and FOS (S) 25% of the animals died. All glycan-treated survivors remained at a clinical score of 0 and there were no deaths from day 7-11. No animals in the glu100 (L and S), glu33gal33fuc33 ((L and S), ara100 (S) and glu50gal50 (L and S) groups exhibited a clinical score of "3", indicating that these treatments prevented diarrhea. Two of the animals in the untreated control group exhibited diarrhea.

Weight Loss

Figure 11:
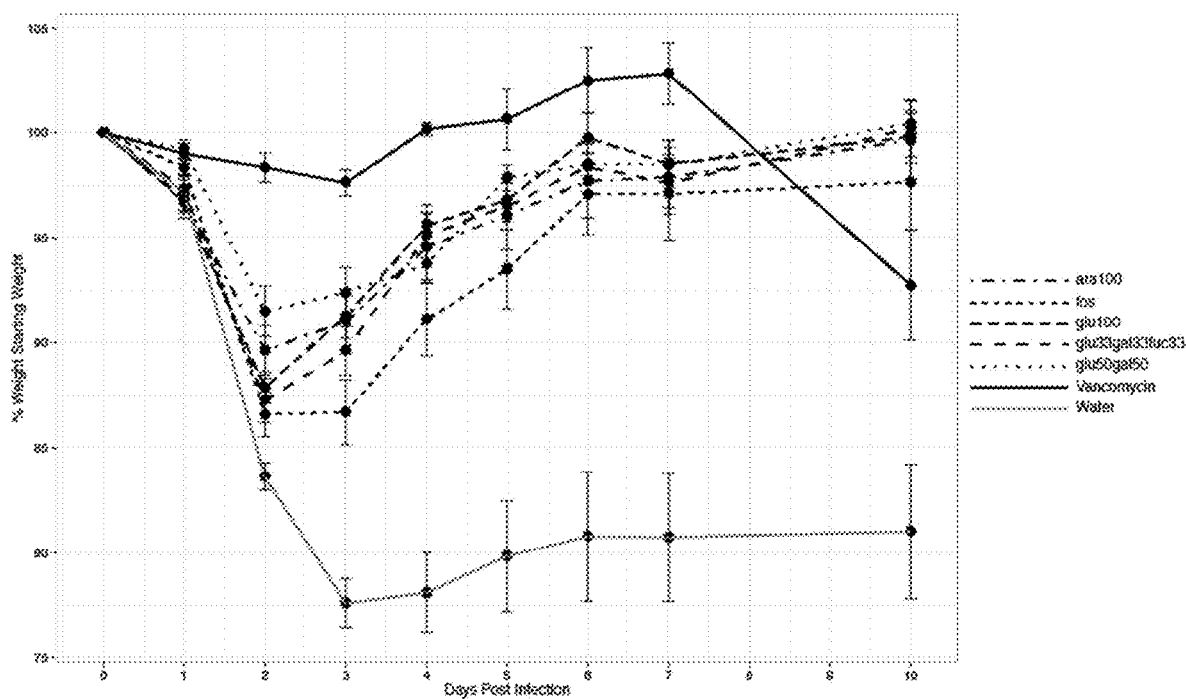
FIG. 11. Weight change 10 days post *C. difficile* infection for all short treatment groups (mean+/−s.e.) as described in Example 12.

Weight loss in animals treated with any of the glycans tested was significantly less than water-treated animals (FIG. 11, ***P<0.001; repeated measures ANOVA, Bonferonni-corrected multiple comparisons). The weight loss profile in glycan-treated animals was not significantly different than that of the vancomycin-treated group.

B. Effect of Treatments on Carriage of C. difficile Spores.

On days 0-6 the presence of C. difficile spores in the feces of mice was assessed. Vancomycin-treated animals had no detectable spores in their feces on any day. Mice that were treated with glycans or water had between 2 and 6 $\log_{10}$ CFU/gram feces. Despite carriage of C. difficile spores on day 6, the glycan-treated animals remained healthy through day 10 with clinical scores on days 7 and 10 of 0. All vancomycin-treated animals exhibited clinical signs on day 10, with 17% deaths.

C. Glycan-Associated Shifts in Microbial Gut Constituents

To determine how the gut microbiota composition responds to treatment with glycan therapeutics, 16S rRNA sequencing of fecal pellets on the V4 variable region using standard protocols from the Earth Microbiome Project was performed (www.earthmicrobiome.org/emp-standard-protocols/).

On day 6 after the termination of glycan treatment, there was a significant difference between the gut microbiota phylogenetic composition of mice treated with glycans (L or S) and either FOS or vehicle and vancomycin controls (Table 11).

TABLE 11

Comparison of ending composition between glycan treatments with vehicle, vancomycin, or FOS controls.

| | Vehicle | Vancomycin | FOS |
|---|---|---|---|
| Glu100 | — | — | * |
| Glu33gal33fuc33 | ** | ** | * |
| Glu50gal50 | *** | *** | *** |
| Ara100 | ** | ** | * |

Figure 12:
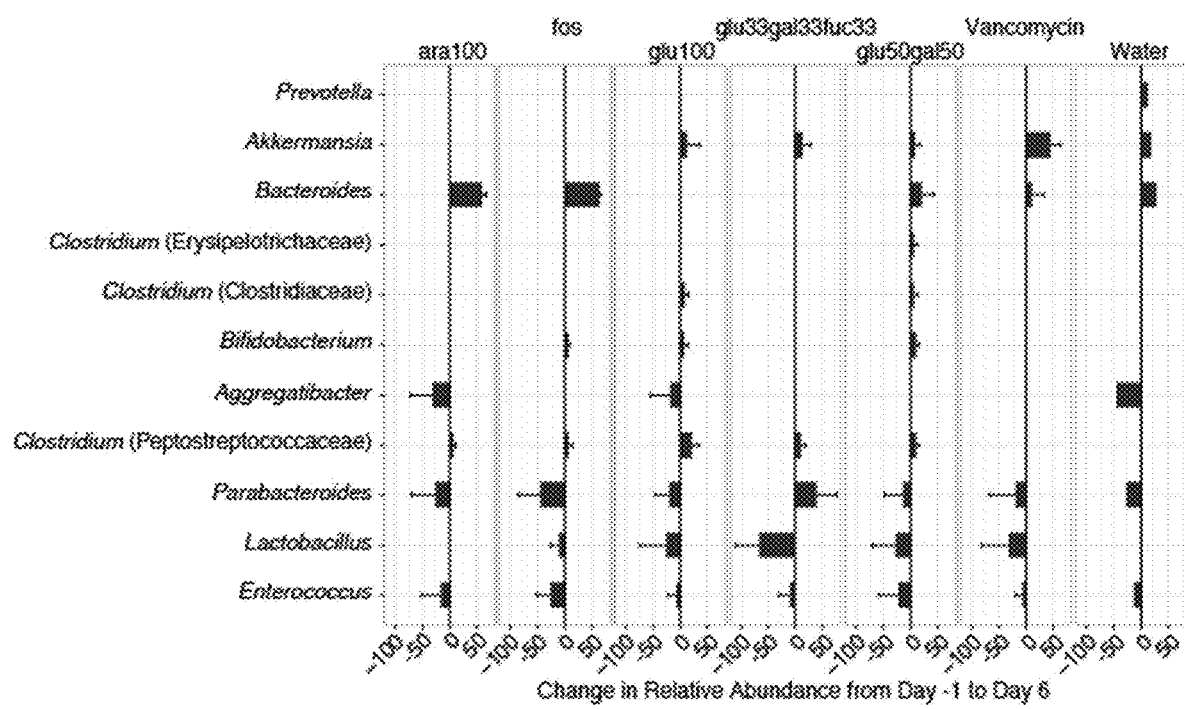
FIG. 12. Change in relative abundance of bacteria by genus from directly before glycan treatment and *C. difficile* infection (Day −1) to directly after 6 days of glycan treatments and 4 days of Vancomycin treatment (Day 6) as described in Example 12. Only genera that change on average 5% relative abundance are shown. Only 1 cage in the Water treatment group had surviving animals on day 6.

*adj. P < 0.05,
**adj. P < 0.01,
***adj. P < 0.001; pairwise adonis, Bonferonni-corrected multiple comparisons Different bacterial genera were increased in relative abundance with various glycan treatments, vancomycin treatment, or water control. FIG. 12 shows changes in relative abundance of specific bacterial genera from directly before (Day −1) to directly after (Day 6) treatment with glycans or vancomycin. The genus Bacteroides was increased in ara100, FOS, and glu50gal50 treatments. The genus Parabacteroides was increased in glu33gal33fuc33 treatments. The genus Bifidobacterium was increased in FOS, glu100, and glu50gal50 treatments. Bacteroides, Parabacteroides, and Bifidobacterium have been shown to positively correlate with a C. difficile resistant microbiome composition (Seekatz and Young, 2014, The Journal of Clinical Investigation). Notably, the genera Enterococcus was decreased in all treatments and Lactobacillus was decreased in FOS, glu100, and glu50gal50 treatments. Enterococcus and Lactobacillus have both been previously observed to be positively correlated with a C. difficile susceptible microbiome composition (Seekatz and Young, 2014, The Journal of Clinical Investigation).

Figure 13:
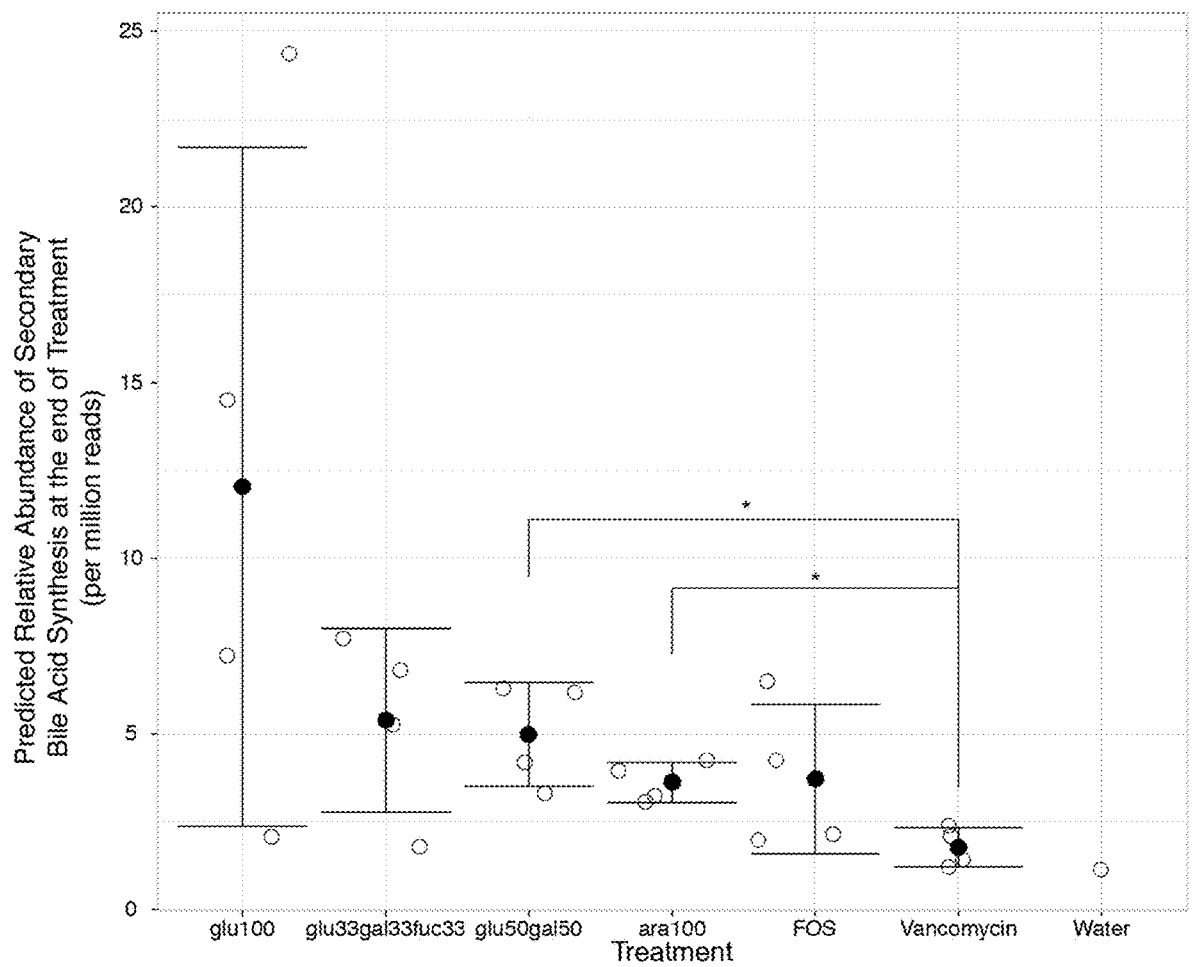
FIG. 13. Predicted relative abundance of secondary bile acid biosynthesis pathway on Day 6, directly following treatment with glycans or vancomycin as described in Example 12. Open circles represent cages and black circles represent mean with +/−s.d. *C. difficile* infection occurred on Day 0 and only cages with animals that survived infection are shown (n=4 cages on Day 0). (*P<0.05, Wilcoxon Rank Sum Test).

Some secondary bile acids have been shown to impair C. difficile growth in vitro. The capacity for the gut microbiome to convert primary bile acids to secondary bile acids has been hypothesized to directly antagonize C. difficile infection. Three glycans (glu33gal33fuc33, ara100, and glu50gal50) all increased the predicted functional potential of the gut microbiome to convert primary bile acids to secondary bile acids (FIG. 13). This was not observed in vancomycin controls. In addition, one glycan (glu100) and commercially available FOS both decreased the predicted functional potential of the gut microbiome on average. Functional predictions were made from 16S rRNA sequencing using PICRUST (picrust.github.io/picrust/).

Secondary bile acid production is linked to reduced germination and growth of *C. difficile*, and members of the Lachnospiraceae and Ruminococcaceae families have been associated with secondary bile acid production and resistance to *C. difficile* germination and growth (Theriot C M, Bowman A A and Young V B. 2016. Antibiotic-induced alterations of the gut microbiota alter secondary bile acid production and allow for *Clostridium difficile* spore germination and outgrowth in the large intestine. mSphere 1(1): e00045-15.) Glycan therapeutics when administered in an effective amount may modulate bacterial species that produce secondary bile acids and thereby promote resistance to *C. difficile* germination, outgrowth and colonization.

In the in vitro assay of Example 8, growth of ROB.74, a member of the Ruminocacceae family, was supported by 13 out of 15 glycans, and growth of CSC.32 and CNE.31, members of the Lachnospiraceae family, were supported by 6 and 7 out of 15 glycans, respectively, as shown in Table 8. Two glycan treatments, glu50gal50 and ara100, significantly increased the relative abundance of the secondary bile acid biosynthesis pathway in the mouse model of *C. difficile* infection (FIG. 13).

Figure 14:
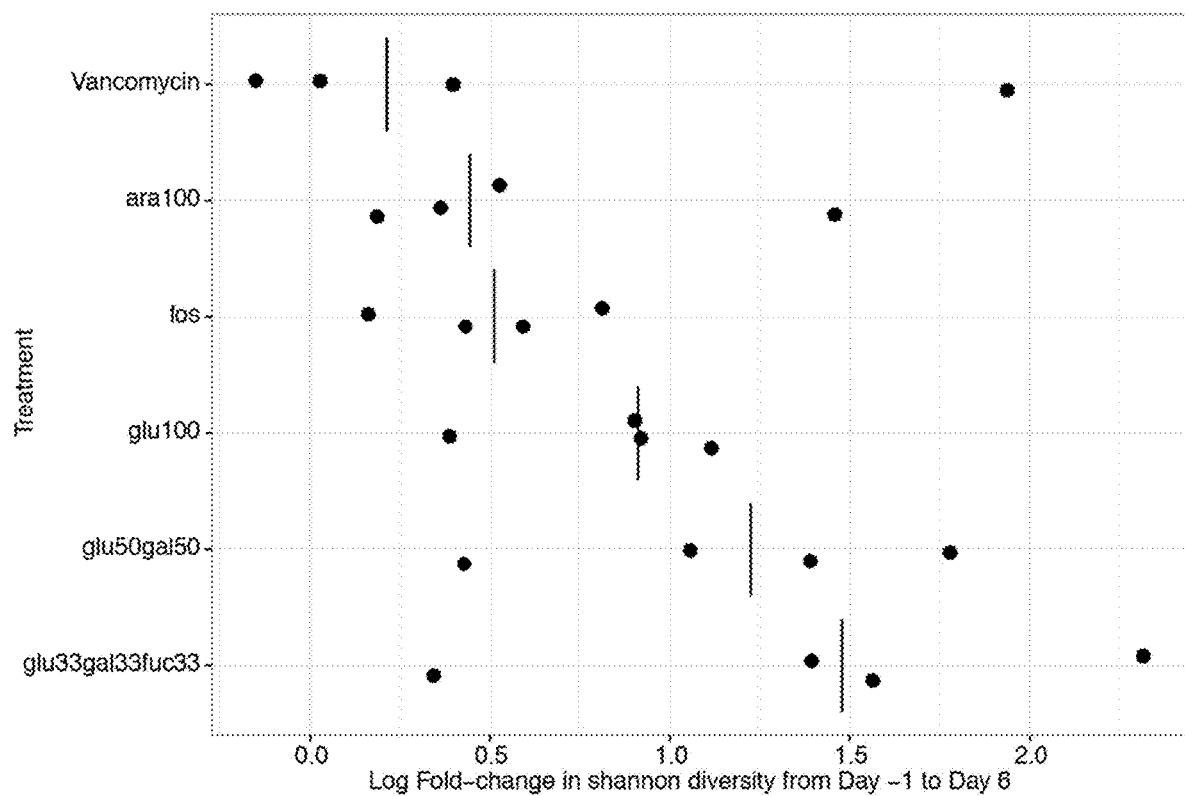
FIG. 14. Log fold-change in alpha diversity (as measured by Shannon index) from Day −1, directly before glycan treatment in infection with *C. difficile*, to Day 6, following treatment with glycans or vancomycin as described in Example 12. Points represent alpha diversity of a single cage and lines represent median alpha diversity.

The alpha diversity (as measured by Shannon index) of the gut microbiota all increased directly before (Day −1) to directly after (Day 6) treatment with glycan (FIG. 14).

These results, obtained in a widely used animal model for *Clostridium difficile* infection suggest that glycan therapeutics reduced *C. difficile*-induced weight loss and improved survival. Selected glycans appear to promote the growth of bacterial genera that contribute to *C. difficile* resistance (*Bacteroides, Parabacteroides*, and *Bifidobacterium*) and conditions that are less favorable for *C. difficile* growth (e.g. increased presence of secondary bile acids).

Example 13

Effect of Glycans in a Mouse Model of Colitis

This experiment was conducted to analyze the effects of glycan therapeutics in a mouse model of colitis (Okayasu et al, 1990, A Novel Method in the Induction of Reliable Experimental Acute and Chronic Ulcerative Colitis in Mice. Gastroenterology 98:694-702). In this model, normal mice were exposed to dextran sulfate sodium (DSS) in their drinking water which induced an onset of disease symptoms similar with respect to their development and manifestation in human clinical disease. Human ulcerative colitis is a progressive, inflammatory disorder of the intestinal tract with a prevalence of about 150-300 per 100,000 people. Ulcerative colitis is a result of an aberrant host immune response to commensal flora, is limited to the colon and involves diffuse mucosal inflammation. Symptoms in humans include colonic inflammation/ulceration, weight loss and diarrhea which may contain blood.

Mice (male C57BL/6, 6-8 weeks old, 22-24 grams each; Charles River Laboratories, Wilmington Mass.) were housed in groups of 8 per cage, with 1 cage per treatment group. The vehicle control group not administered 2.5% DSS was comprised of 6 mice. Mice were administered glycan therapeutics at 1% concentration in their drinking water from day −7 (7 days prior to DSS administration) to day 14. On days 0 to 5 mice were administered DSS (MP Bio, Santa Ana Calif.; 36,000-50,000 Da) at 2.5% in their drinking water to induce colitis phenotypes.

Disease-associated phenotypes were recorded for a duration of twelve days starting on day 0 through day 11. The phenotypes that were scored were: weight, incidence of diarrhea and blood in stool. In addition, endoscopic analysis of colon inflammation was performed on day 14. The following scoring system was used: Naïve, no edema or mucosal sloughing, clear vascularity=0; edema, mucosal sloughing, decreased vascularity=1; edema, mucosal sloughing, decreased vascularity, friability=2; active bleeding, erosion=3; active ulceration, erosion=4. Histopathologic analysis was undertaken on terminal colon samples of all of the mice. Colon sections were fixed in formalin and stained with hematoxylin and eosin (H&E). A semi-quantitative analysis of colonic lesions including mucosal erosion, loss of colonic glands, and mucosal to transmural inflammation with regenerating (hyperplastic) mucosal and glandular epithelium was used. All of the phenotypes mimic those of human colitis. In this model peak weight loss generally occurs at day 10.

All animals were administered 2.5% DSS in the drinking water for days 0-5. The following glycan treatments were delivered in the animals' drinking water at a concentration of 1%: FOS (commercial, control); glu100; man52glu29gal19; acacia fiber (commercial, control) from day −7 to day 14. The control group received plain drinking water in place of glycan containing water.

Effects of test treatments was assessed by comparing the disease-associated phenotypes in glycan-treated and untreated (plain water) groups. FOS (Nutraflora FOS; NOW Foods, Bloomingdale Ill.) is a commercially-available non-digestible fructooligosaccharide. Acacia fiber (Organic Powder, NOW Foods, Bloomingdale, Ill.) is a commercially-available fiber supplement.

Figure 15:
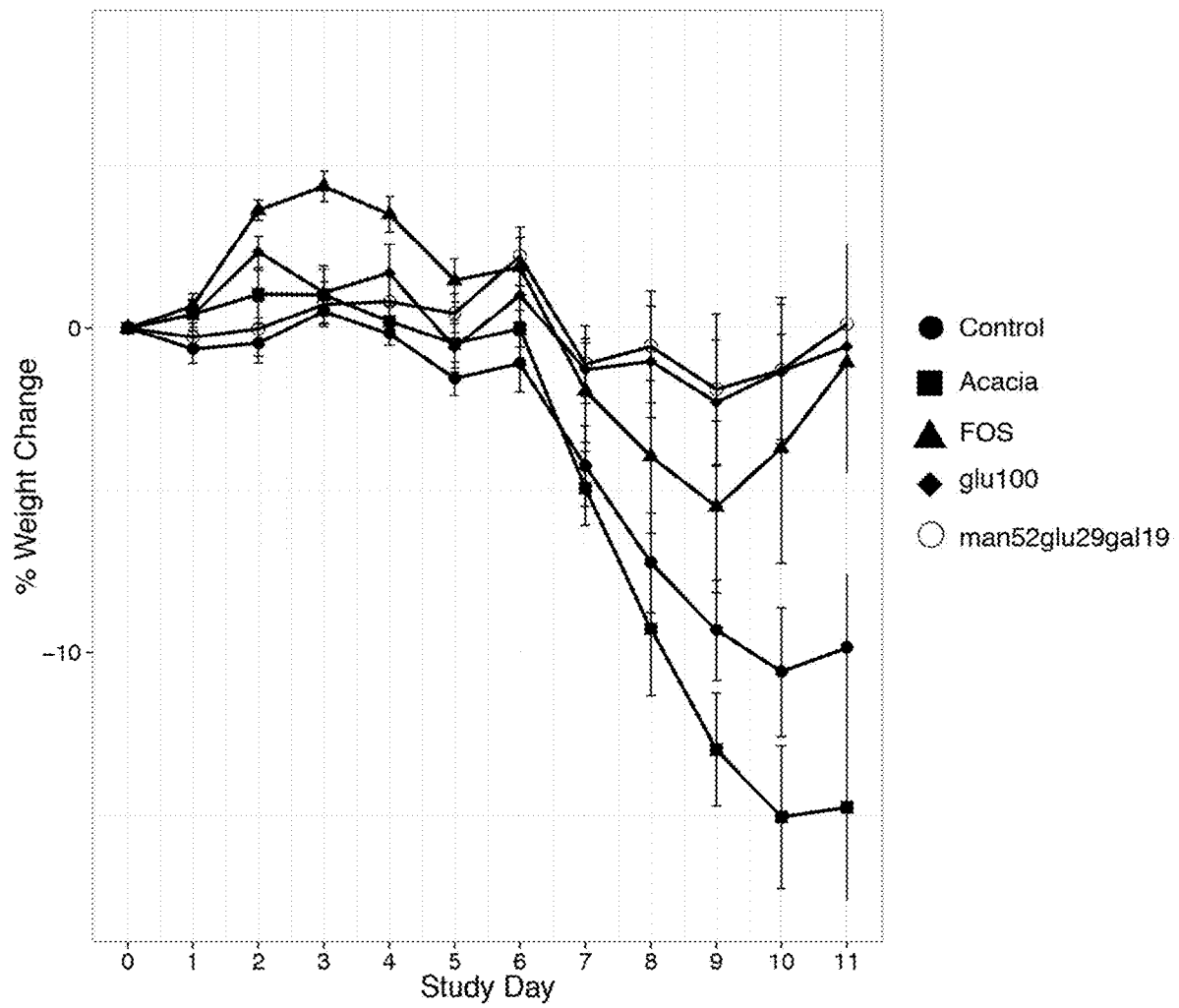
FIG. 15. Percent weight change of mice compared to day 0 of study (mean+/−s.e.). 2.5% DSS was administered from days 0 to 5 in all groups as described in Example 13. Acacia fiber, glu100, and man52glu29gal19 was administered from days −7 to day 14 in treatment groups.
Figure 16:
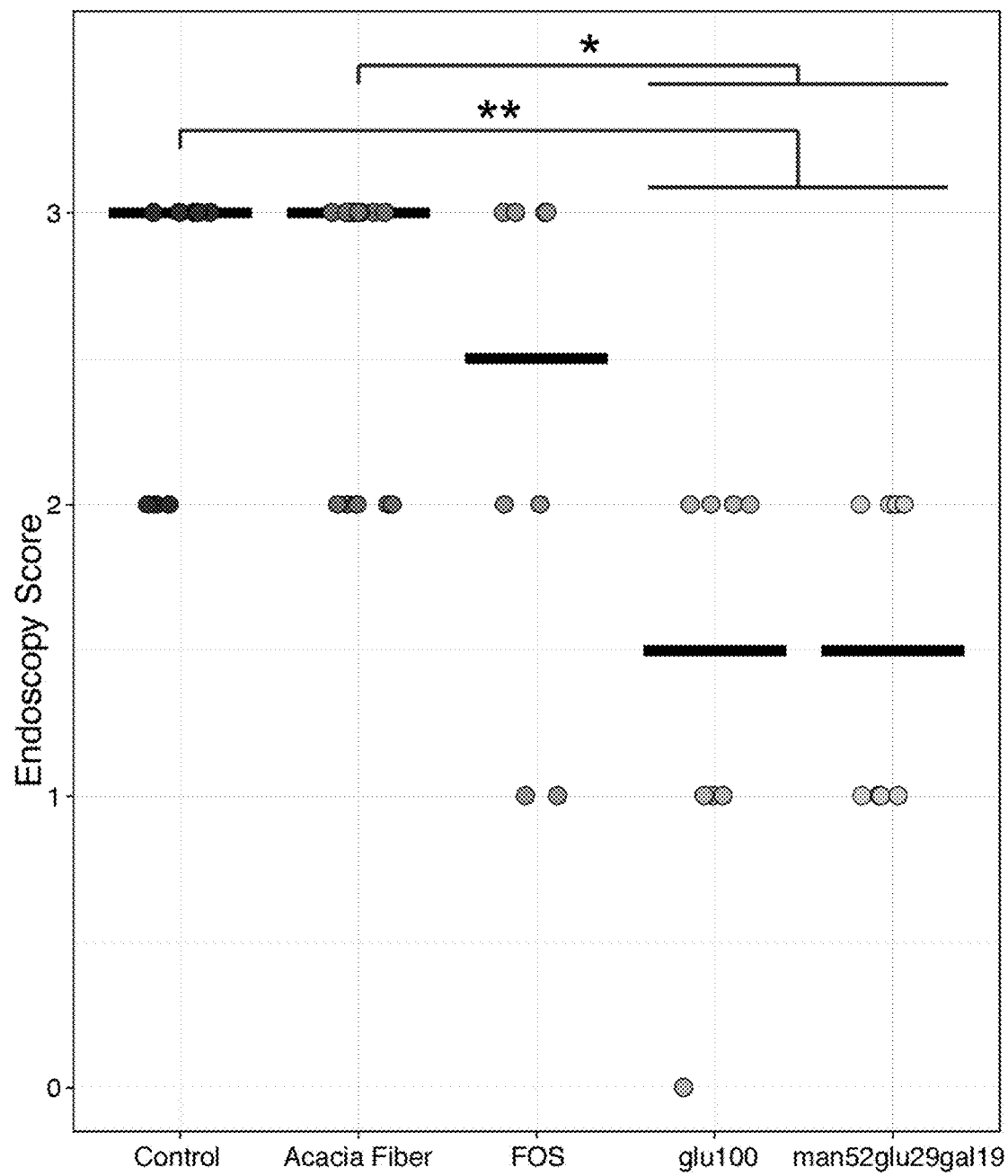
FIG. 16. Endoscopy score measuring colonic inflammation on day 14 of the study as described in Example 13. Horizontal bars represent median endoscopy score. **P<0.01,*P<0.05; Wilcoxon Rank Sum Test with bonferroni correction for multiple hypotheses.

Treatment with glu100 and man52glu29gal19 reduced the incidence of diarrhea, and weight loss from day 0 to 11 (FIG. 15), as well as significantly reduced colonic inflammation (day 14; FIG. 16) as assessed by endoscopy in mice as compared with either plain water (vehicle control) or acacia fiber-treated animals. Histopathological results of colon samples from the mice mirrored those from endoscopic analysis with regard to glycan efficacy. Cumulative days of diarrhea incidence in the control and treatment groups were as follows: water control group: 10 days; acacia fiber: 14 days; FOS: 4 days; glu100: 2 days; man52glu29gal19: 3 days. Taken together these data demonstrate that glycan treatments have significant protective effects in a mouse model of colitis.

These results, obtained in a widely used animal model of colitis, suggest that glycan therapeutics reduce DSS-induced weight loss, diarrhea and colonic inflammation and damage as assessed by endoscopy and histopathology.

Example 14

Effect of Glycans in a Mouse Model of Diet-Induced Obesity

This experiment was conducted to analyze the effects of glycan therapeutics in a mouse model of high fat diet-induced obesity (Wang and Liao, A Mouse Model of Diet-Induced Obesity and Insulin Resistance. Methods Mol Biol. 2012; 821: 421-433). In this model, normal mice were fed a diet containing 60% fat content over 6 weeks. These mice exhibited a significant increase in weight compared with mice fed a low (10%) fat diet. In humans, obesity is the accumulation of excess body fat to the extent that it may have a negative effects on health, including the development of type 2 diabetes and cardiovascular disease. The major causes of obesity are excessive food energy intake, lack of physical activity, and genetic predisposition. In the US, about 38% of adults (78 million) and 17% of children and adolescents (13 million) are obese. The mouse model of diet-induced obesity recapitulates human disease endpoints including weight gain, decreased lean body mass, changes in organ physiology and changes in markers of diabetes.

Mice (male C57BL/6, 8-10 weeks old, 16-18 grams each; Taconic Labs, Germantown, N.Y.) were housed in groups of 1-2 per cage, with 8 animals per treatment group. Mice were fed a high (60%) fat diet (60% of total kcal contributed by fat) (D12492; Research Diets, New Brunswick, N.J.) or matched diet containing 10% fat (10% of total kcal contributed by fat) (D12450; Research Diets). After one week on this diet regimen, mice on high fat diet were administered glycans (self-administered in drinking water; day 0 to day 44): glu100 at 0.3% weight/volume (w/v) or man52glu29gal19 at 1% w/v in drinking water, commercial FOS (Nutraflora FOS; NOW Foods, Bloomingdale Ill.) at 6%, 1% or 0.3% w/v in drinking water, or plain water (control). The group of mice consuming the low fat diet was given plain water (control). Diets were kept the same for each group throughout the study.

Weight Gain

Figure 17A:
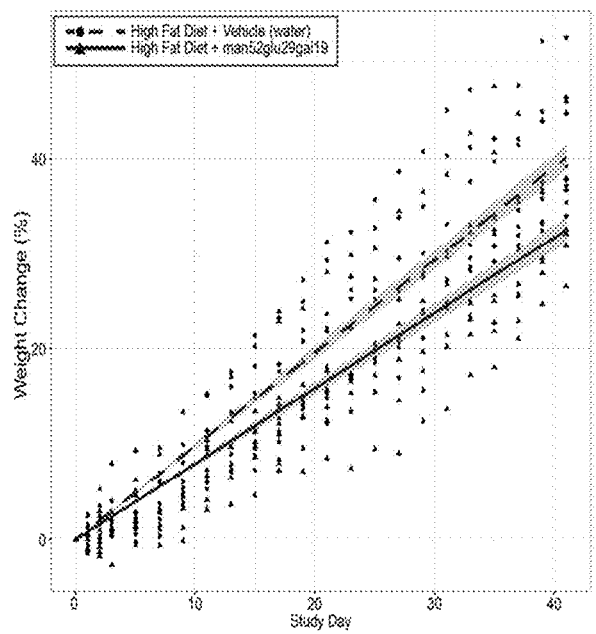
FIGS. 17A-17B. Slopes of % weight change from day 0 to day 41 in mice treated with glu100 (0.3%.
Figure 17B:
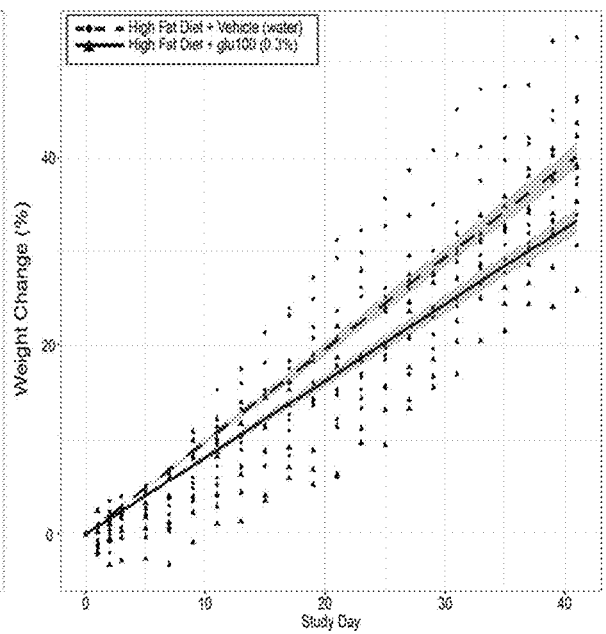

Weight was monitored every other day from day 0 through day 44. Mice on a high fat diet gained weight at a significantly faster pace than mice fed a low fat diet. Treatment with glu100 (0.3% in drinking water) and man52glu29gal19 (1% in drinking water) significantly decreased the slope of the weight gain curve from day 0 to 41 in high fat-fed mice as compared with water (vehicle)-treated mice (FIG. 17A and FIG. 17B). FOS at any dose had no significant effect on the percent (%) weight change slope as compared with water-control animals.

Glucose Tolerance

Figure 18:
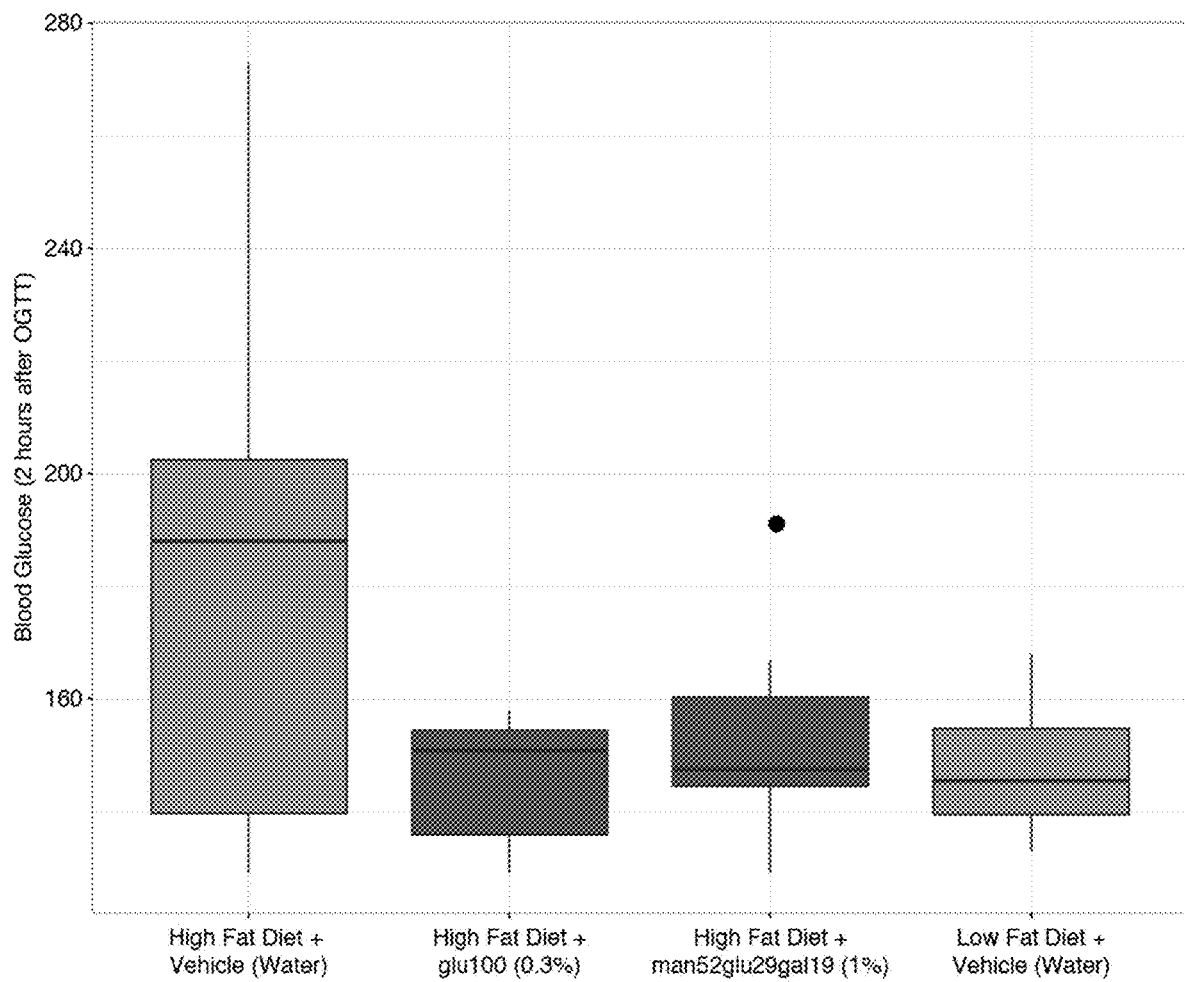
FIG. 18. Day 39 blood glucose levels in mice fed a high fat diet, low fat diet, or high fat diet with glu100 (0.3%) or man52glu29gal19 (1%) treatment as described in Example 14. Upper and lower hinges on boxplot correspond to the first and third quartiles and upper and lower whisker extend to the highest and lowest value that is within 1.5 times the inter-quartile range, or distance between the first and third quartiles. Mice were gavaged with 2 g/kg (at a dose rate of 5 mL/kg) glucose in water and blood glucose levels assessed at 2 hours post dose. Units on the y-axis are mg/dL glucose.

On day 42, mice were subjected to an oral glucose tolerance test by fasting them for 12 hours and then administering an orally-gavaged dose of glucose (2 grams/kg; Ayala et. al. Standard operating procedures for describing and performing metabolic tests of glucose homeostasis in mice Disease Models & Mechanisms 3, 525-534 (2010)). Blood glucose levels were monitored using a handheld glucometer (One Touch Ultra®; LifeScan Inc, Wayne Pa.) at 120 minutes post glucose dose. Mice on a high fat diet had a lower ability to clear glucose from their systemic circulation than mice fed a low fat diet (FIG. 18). High fat diet-fed mice treated with glu100 (0.3%) and man52glu29gal19 (1%) had lower blood glucose levels as compared to high fat diet-fed, water-control mice. These levels were more similar to the low fat diet-fed, water-control mice.

Fat Pad Development

Figure 19:
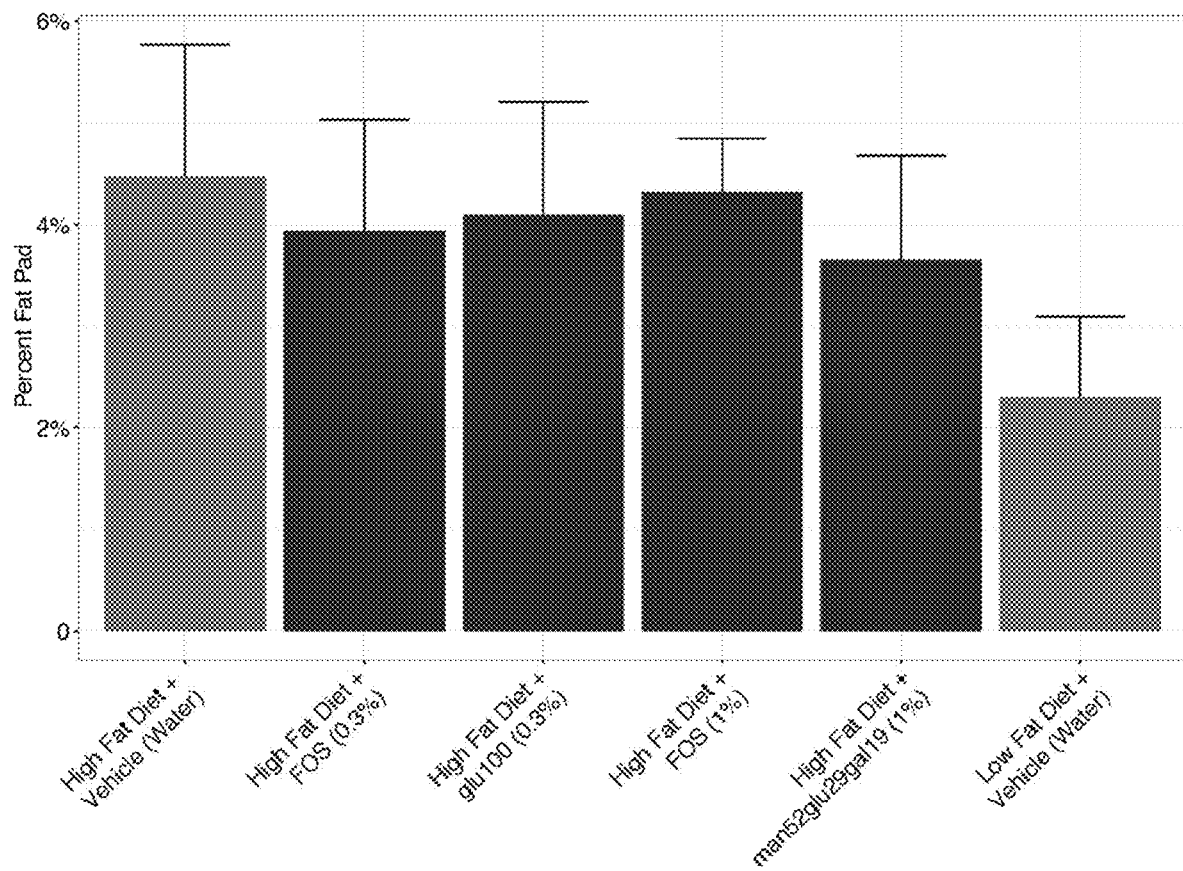
FIG. 19. Epididymal fat pad weight on day 41 as a percentage of total body weight in high fat-fed mice, low fat-fed mice and high fat-fed mice treated with man52glu29gal19 (1%), fos (0.3%, 1%), and glu100 (0.3%) as described in Example 14.

On day 44, the epididymal fat pads of the mice were removed and weighed. The weight of the fat pads as a percent of total body weight was used as a surrogate endpoint for lean body mass, with an increased fat pad weight corresponding to lower lean body mass. Mice treated with man52glu29gal19 (1%) and fed the high fat diet had a lower fat pad/body weight % than water-control mice (FIG. 19) or FOS-treated mice fed the high fat diet.

The results for these three endpoints in the obesity model suggest that a longer term model could lead to significant changes in other parameters that are assessed in the model (Wang and Liao, A Mouse Model of Diet-Induced Obesity and Insulin Resistance. Methods Mol Biol. 2012; 821: 421-433). For example, high fat diet-fed mice will exhibit multiple organ changes when compared with low-fat diet fed mice. In the $12^{th}$ week of the experiment and beyond, mice are sacrificed and certain tissues harvested/processed for analysis. The colon and cecum are collected, weighed and measured; obese mice will have a shorter colon and cecum and colon of decreased weight. The cecal contents are snap frozen for storage for subsequent analysis of 16S RNA and metabolites. Livers are collected, weighed and stored in formalin for histopathology. Mice fed a high fat diet tend to have higher liver weights than those fed a low fat diet. Blood samples are taken and processed to plasma for measurement of inflammatory markers (TNF-α, IFN-γ, IL-10, IL-13, IL-1β, IL-4, IL-5, IL-6 and KC/GRO), clinical chemistry (cholesterol, triglycerides), and lipopolysaccharide (LPS) levels. Mice fed a high fat diet have increased levels of markers of inflammation, and higher cholesterol, triglyceride and circulating LPS levels. All of these endpoints in the model test similar manifestations of obesity as are observed in humans. Selected glycans reduce the incidence or magnitude of shorter colon and cecum and decreased colon weight. Selected glycans reduce the incidence or magnitude of liver weight gain. Selected glycans reduce the incidence or magnitude of presence of inflammatory markers, reduce cholesterol and/or systemic LPS levels.

These results, obtained in a widely used animal model for diet-induced obesity suggest that glycan therapeutics may prevent high fat diet-induced weight gain, improve the ability to clear blood glucose and increase lean/fat body composition.

Example 15

Effect of Glycans on Gene Expression in a Mouse Model

The trial is conducted with two groups of mice. The control group of mice are fed with standard chow, and the different treatment groups of mice are fed with standard chow supplemented with glycans. After 1-30 days, blood samples are drawn from the mice, the mice are sacrificed, and tissues from the intestine, liver, skin, and other sites of interest are collected and stored at −80° C. RNA is isolated from the tissues and converted to cDNA. The GeneChip Mouse Genome 430 2.0 Array (Affymetrix) is used to analyze the differential expression between the untreated and glycan-treated animals of approximately 14,000 murine genes. The experimental protocol and raw data analysis are performed according to the manufacturer's instructions and standard protocols. The biological function of the differentially expressed genes and their involvement in various processes are obtained from the following databases: RefGene (Reference for genes, proteins and antibodies: refgene.com/), CTD (Comparative Toxicogenomics Database: ctd.mdibl.org/), MGI (Mouse Genomics Informatics: www.informatics.jax.org/), KEGG (Kyoto Encyclopedia of Genes and Genomes: www.genome.jp/kegg/genes.html). This procedure is used to identify the differential expression of genes encoding inflammatory cytokines, immunomodulatory cytokines, antimicrobial peptides, and other relevant effector molecules.

TABLE 1

Genus level Microbial Constituents of the GI tract.

| Phylum | Class | Genus |
|---|---|---|
| Actinobacteria | Actinobacteria | Actinomyces, Adlercreutzia, Atopobium, Bifidobacterium, Collinsella, Corynebacterium, Eggerthella, Mobiluncus, Propionibacterium, Rothia, Slackia |
| Bacteroidetes | Bacteroidia | Alistipes, Bacteroides, Dysgonomonas, Odoribacter, Parabacteroides, Porphyromonas, Prevotella, Tannerella |
| | Flavobacteria | Capnocytophaga |
| Firmicutes | Bacilli | Bacillus, Enterococcus, Gemella, Granulicatella, Lactobacillus, Lactococcus, Staphylococcus, Streptococcus, Turicibacter, Weissella |
| | Clostridia | Acidaminococcus, Anaerococcus, Anaerofilum, Anaerofustis, Anaerostipes, Anaerotruncus, Anaerovorax, Bacteroides, Bacteroides, Blautia, Clostridium, Coprococcus, Dehalobacterium, Dialister, Dorea, Eubacterium, Faecalibacterium, Finegoldia, Lachnobacterium, Lachnospira, Megamonas, Megasphaera, Mitsuokella, Moryella, Oribacterium, Oscillospira, Peptococcus, Peptoniphilus, Peptostreptococcus, Phascolarctobacterium, Pseudobutyrivibrio, Roseburia, Ruminococcus, Ruminococcus, Selenomonas, Subdoligranulum, Veillonella |
| Fusobacteria | Fusobacteria | Fusobacterium, Leptotrichia |
| | Betaproteobacteria | Comamonas, Herbaspirillum, Lautropia, Neisseria, Oxalobacter, Sutterella |
| | Deltaproteobacteria | Bilophila, Desulfovibrio, LE30 |
| | Epsilonproteobacteria | Campylobacter, Helicobacter |
| | Gammaproteobacteria | Actinobacillus, Aggregatibacter, Citrobacter, Escherichia, Haemophilus, Klebsiella, Moraxella, Pseudomonas, Raoultella |
| Spirochaetes | Spirochaetes | Treponema |
| Synergistetes | Synergistetia | Cloacibacillus, Synergistes |
| Tenericutes | Erysipelotrichi | Bulleidia, Catenibacterium, Clostridium, Coprobacillus, Holdemania, RFN20 |
| | Mollicutes | Asteroleplasma, Mycoplasma |
| Verrucomicrobia | Verrucomicrobiae | Akkermansia |
| Euryarchaeota | Methanobacteria | Methanobrevibacter |

40

TABLE 2

Microbial Metabolites 2-hydroxyisobutyrate, 3-hydroxyisovalerate, 3-methyl-crotonylglycine, 3-methylcrotonylglycine, allantoin, betaine, formate, mannitol, p-cresol glucuronide, phenylacetylglycine, sarcosine, taurine, acetic acid, acetylaldehyde, ascorbic acid, butanedione, butyric acid, deoxycholic acid, ethylphenyl sulfate, formic acid/formate, indole, isobutyric acid, isovaleric acid, propionic acid, serotonin, succinic acid/succinate, TMAO, tryptophan, valeric acid, ursodeoxycholic acid, lactate, lactic acid, hydrogen peroxide

TABLE 3

Genus level microbial constituents predominant in the large intestine (compared to small intestine) in healthy humans.

| Phylum | Class | Genus |
|---|---|---|
| Bacteroidetes | Bacteroidia | Bacteroides, Butyricimonas, Odoribacter, Parabacteroides, Prevotella |
| Firmicutes | Clostridia | Anaerotruncus, Phascolarctobacterium, Ruminococcus, |
| Proteobacteria | Deltaproteobacteria | Bilophila |
| Verrucomicrobia | Verrucomicrobiae | Akkermansia |

TABLE 4

Genus level microbial constituents predominant in the small intestine (compared to large intestine) in healthy humans.

| Phylum | Class | Genus |
| --- | --- | --- |
| Actinobacteria | Actinobacteria | *Cryocola, Mycobacterium* |
| Firmicutes | Bacilli | *Enterococcus, Lactococcus, Streptococcus, Turicibacter* |
|  | Clostridia | *Blautia, Coprococcus, Holdemania, Pseudoramibacter Eubacterium* |
| Proteobacteria | Alphaproteobacteria | *Agrobacterium, Sphingomonas* |
|  | Betaproteobacteria | *Achromobacter, Burkholderia, Ralstonia* |

TABLE 5

| Polyphenols | |
| --- | --- |
| Polyphenol Sub-Class | Compound Name |
| Anthocyanins | Malvidin 3-O-(6"-p-coumaroyl-glucoside), Cyanidin, total, Delphinidin 3-O-(6"-acetyl-galactoside), Cyanidin 3-O-(6"-acetyl-galactoside), Malvidin, Cyanidin 3-O-galactoside, Cyanidin 3-O-glucoside, Cyanidin 3-O-rutinoside, Cyanidin 3-O-sophoroside, Pelargonidin 3-O-glucoside, Cyanidin 3-O-(6"-malonyl-glucoside), Peonidin, Peonidin 3-O-glucoside, Peonidin 3-O-rutinoside, Pelargonidin 3-O-rutinoside, Pelargonidin, Cyanidin, Malvidin 3,5-O-diglucoside, Cyanidin 3-O-glucosyl-rutinoside, Pelargonidin 3-O-sophoroside, Pelargonidin 3-O-glucosyl-rutinoside, Cyanidin 3-O-(6"-succinyl-glucoside), Pelargonidin 3-O-(6"-succinyl-glucoside), Delphinidin, Delphinidin 3-O-galactoside, Delphinidin 3-O-glucoside, Delphinidin 3-O-arabinoside, Petunidin, Petunidin 3-O-galactoside, Cyanidin 3-O-arabinoside, Petunidin 3-O-glucoside, Peonidin 3-O-galactoside, Petunidin 3-O-arabinoside, Malvidin 3-O-glucoside, Malvidin 3-O-arabinoside, Cyanidin 3-O-(6"-acetyl-arabinoside), Delphinidin 3-O-(6"-acetyl-glucoside), Petunidin 3-O-(6"-acetyl-galactoside), Peonidin 3-O-(6"-acetyl-galactoside), Cyanidin 3-O-(6"-acetyl-glucoside), Malvidin 3-O-(6"-acetyl-galactoside), Petunidin 3-O-(6"-acetyl-glucoside), Polymeric anthocyanins, total, Malvidin 3-O-(6"-acetyl-glucoside), Peonidin 3-O-(6"-acetyl-glucoside), Pelargonidin 3-O-arabinoside, Delphinidin 3-O-rutinoside, Cyanidin 3-O-sambubioside, Pelargonidin 3-O-(6"-malonyl-glucoside), Peonidin 3-O-(6"-p-coumaroyl-glucoside), Cyanidin 3-O-xyloside, Malvidin 3-O-galactoside, Peonidin 3-O-arabinoside, Petunidin 3-O-rutinoside, Delphinidin 3-O-xyloside, Petunidin 3-O-(6"-p-coumaroyl-glucoside), Pelargonidin 3-O-galactoside, Pelargonidin 3-O-sambubioside, Delphinidin 3-O-sambubioside, Cyanidin 3-O-xylosyl-rutinoside, Vitisin A, Delphinidin 3-O-(6"-p-coumaroyl-glucoside), Pigment A, p-Coumaroyl vitisin A, Acetyl vitisin A, Cyanidin 3-O-(6"-p-coumaroyl-glucoside), Cyanidin 3-O-sambubioside 5-O-glucoside, Cyanidin 3-O-(6"-caffeoyl-glucoside), Cyanidin 3,5-O-diglucoside, Pinotin A, Delphinidin 3,5-O-diglucoside, Pelargonidin 3,5-O-diglucoside, Malvidin 3-O-(6"-caffeoyl-glucoside), Cyanidin 3-O-(6"-dioxalyl-glucoside), Cyanidin 3-O-laminaribioside, Cyanidin 3-O-(3"-malonyl-glucoside), Peonidin 3-O-(6"-malonyl-glucoside), Cyanidin 3-O-(6"-malonyl-laminaribioside), Cyanidin 3-O-dimalonyl-laminaribioside, Cyanidin 3-O-(6"-malonyl-arabinoside), Delphinidin 3-O-glucosyl-glucoside, Cyanidin 3-O-(6"-malonyl-3"-glucosyl-glucoside), Cyanidin 3-O-(2"-xylosyl-6"-glucosyl-galactoside), Cyanidin 3-O-(2"-xylosyl-6"-(6"'-caffeoyl-glucosyl)-galactoside), Cyanidin 3-O-(2"-xylosyl-galactoside), Cyanidin 3-O-(2"-xylosyl-6"-(6"'-p-hydroxybenzoyl-glucosyl)-galactoside), Cyanidin 3-O-(2"-xylosyl-6"-(6"'-sinapoyl-glucosyl)-galactoside), Cyanidin 3-O-(2"-xylosyl-6"-(6"'-feruloyl-glucosyl)-galactoside), Cyanidin 3-O-(2"-xylosyl-6"-(6"'-p-coumaroyl-glucosyl)-galactoside), Delphinidin 3-O-(6"-malonyl-glucoside), Malvidin 3-O-rutinoside, Luteolinidin 3-O-glucoside, Delphinidin 3-O-feruloyl-glucoside, Petunidin 3,5-O-diglucoside, Petunidin 3-O-rhamnoside, Luteolinidin, Vitisin A aglycone, Pigment A aglycone, Pinotin A aglycone, 4-O-Methylcyanidin 3-O-galactoside, Malvidin 3-O-(6"-O-acetyl)-glucoside, Cyanidin 3-O-diglucoside-5-O-glucoside, Peonidin 3-O-diglucoside-5-O-glucoside, Peonidin 3,5-O-diglucoside, Peonidin 3-O-(2-O-(6-O-(E)-caffeoyl-D-glucosyl)-D-glucoside)-5-O-D-glucoside, Peonidin 3-O-sophoroside, Peonidin 3-O-sambubioside, Peonidin 3-O-sambubioside-5-O-glucoside, Peonidin 3-O-xyloside, 4'-O-Methylcyanidin 3-O-D-glucoside, Cyanidin 3-O-glucuronide, Cyanidin 3-O-(3",6"-O-dimalonyl-glucoside), Cyanidin 3-sulfate, 4-O-Methyldelphinidin 3-O-L-arabinoside, 4-O-Methyldelphinidin 3-O-D-glucoside, Isopeonidin 3-O-arabinoside, Isopeonidin 3-O-galactoside, Isopeonidin 3-O-glucoside, Isopeonidin 3-O-rutinoside, Isopeonidin 3-O-sambubioside, Isopeonidin 3-O-xyloside, 4-O-Methylpetunidin 3-O-D- |

TABLE 5-continued

Polyphenols

| Polyphenol Sub-Class | Compound Name |
|---|---|
| | galactoside, 4-O-Methylpetunidin 3-O-D-glucoside, Cyanidin 3-O-(2-O-(6-O-(E)-caffeoyl-D glucoside)-D-glucoside)-5-O-D-glucoside, 4'-O-Methyldelphinidin 3-O-rutinoside, Pelargonidin 3-O-(6''-acetyl-glucoside) |
| Chalcones | Chalconaringenin, total, Butein, Xanthohumol, Chalconaringenin, Chalconaringenin 2'-O-glucuronide, Chalconaringenin 4'-O-glucuronide, Chalconaringenin 7-O-glucuronide |
| _Dihydro-chalcones | Phloretin, Phloridzin, Phloretin xylosyl-galactoside, Phloretin 2'-O-xylosyl-glucoside, 3-Hydroxyphloretin 2'-O-xylosyl-glucoside, 3-Hydroxyphloretin 2'-O-glucoside, Phloridzin, total, 3-Hydroxyphloretin, Phloretin 2'-O-glucuronide, 3-Methoxyphloretin 3*-O-glucoside, 3-Hydroxy-4-O-methylphloretin 3*-O-glucoside, 3-Hydroxyphloretin 3*-O-glucoside |
| Dihydro-flavonols | Dihydroquercetin 3-O-rhamnoside, Dihydroquercetin, Engeletin, Dihydromyricetin 3-O-rhamnoside, Dihydroquercetin 3-O-glucoside, Dihydromyricetin, Dihydrokaempferol |
| Flavanols | (+)-Catechin, (−)-Epicatechin, (+)-Gallocatechin, (−)-Epigallocatechin, (−)-Epicatechin 3-O-gallate, (−)-Epigallocatechin 3-O-gallate, Catechins, total, Theaflavins, total, Thearubigins, total, Theaflavin, Theaflavin 3-O-gallate, Theaflavin 3*-O-gallate, Theaflavin 3,3*-O-digallate, (+)-Gallocatechin 3-O-gallate, (−)-Catechin, (+)-Catechin 3-O-gallate, Theaflavic acid, Epitheaflavic acid, Epitheaflavic acid 3*-O-gallate, Isoneotheaflavin 3-O-gallate, (−)-Gallocatechin 3-O-gallate, (−)-Gallocatechin, (−)-Catechin 3-O-gallate, (+)-Epicatechin, (−)-Epicatechin 8-C-galactoside, Isoneotheaflavin, Procyanidin dimer B1, Procyanidin dimer B2, Procyanidin dimer B3, Procyanidin dimer B4, Procyanidin dimer B5, Procyanidin dimer B7, Prodelphinidin dimer B3, Procyanidin trimer C1, Procyanidin tetramer T4, 02 mers, Procyanidins, total, Procyanidin trimer EEC, 01 mers, Polymers (>10 mers), 03 mers, 04-06 mers, 07-10 mers, Procyanidin dimer B6, Procyanidin trimer T2, Procyanidin trimer C2, Procyanidin dimer B2 3'-O-gallate, Procyanidin dimer B1 3-O-gallate, Prodelphinidin trimer GC-GC-C, Procyanidin trimer T3, 04 mers, Procyanidin dimer A2, 05 mers, 06 mers, 07 mers, 08 mers, 09 mers, 10 mers, 02-03 mers, (+)-Epicatechin-(2a-7)(4a-8)-catechin 3-O-arabinoside, Cinnamtannin B1 3-O-galactoside, (+)-Epicatechin-(2a-7)(4a-8)-epicatechin 3-O-arabinoside, Cinnamtannin B1 3-O-arabinoside, Procyanidin dimer A1, Cinnamtannin B1, Proanthocyanidins, total, Prodelphinidin trimer GC-C-C, Prodelphinidin trimer C-GC-C, (+)-Epicatechin-(2a-7)(4a-8)-catechin, (+)-Epicatechin-(2a-7)(4a-8)-epicatechin, (−)-Epicatechin-(2a-7)(4a-8)-epicatechin 3-O-galactoside, Cinnamtannin A2, Bis-8,8'-Catechinylmethane, Cinnamtannin A3, (+)-Catechin 3-O-glucose, 3'-O-Methylepicatechin, 4'-O-Methyl-(−)-epicatechin 3*-O-glucuronide, Epicatechin 3*-O-glucuronide, Epigallocatechin 3-O-gallate-4''-O-glucuronide, 3'-O-Methylcatechin, 3'-O-Methyl-(−)-epicatechin 3-O-gallate, 4',4''-O-Dimethylepigallocatechin 3-O-gallate, 4'-O-Methylepigallocatechin, 4''-O-Methylepigallocatechin 3-O-gallate, 4'-O-Methylepicatechin, Epigallocatechin 3-O-gallate-7-O-glucoside-4''-O-glucuronide, Theasinensin A, 3-Methylepigallocatechin, 3',4''-Dimethyl-(−)-epicatechin 3-O-gallate, (−)-Epigallocatechin 3-O-glucuronide, 3'-O-Methyl-(−)-epigallocatechin 3-O-gallate, 3''-O-Methyl-(−)-epigallocatechin 3-O-gallate, 3',3''-O-Dimethyl-(−)-epigallocatechin 3-O-gallate, 3'-O-Methyl-(−)-epicatechin 7-O-glucuronide, Epicatechin 7-O-glucuronide, (−)-Epigallocatechin 3*-O-glucuronide, (−)-Epigallocatechin 7-O-glucuronide, 4'-O-Methyl-(−)-epigallocatechin 3*-O-glucuronide, 4'-O-Methyl-(−)-epigallocatechin 7-O-glucuronide, 4'-O-Methyl-(−)-epigallocatechin 3'-sulfate |
| Flavanones | Naringenin, Eriodictyol, Hesperetin, Hesperetin, total, Naringenin, total, Eriocitrin, Hesperidin, Naringin, Narirutin, Neoeriocitrin, Neohesperidin, Isosakuranetin 7-O-rutinoside, Poncirin, Didymin, Narirutin 4'-O-glucoside, Naringin 4'-O-glucoside, Naringin 6'-malonate, Isosakuranetin, Naringenin 7-O-glucoside, Pinocembrin, 8-Prenylnaringenin, 6-Prenylnaringenin, 6-Geranylnaringenin, Isoxanthohumol, Eriodictyol 7-O-glucoside, Sakuranetin, Hesperetin 3*-O-glucuronide, Hesperetin 7-O-glucuronide, Hesperetin 3'-sulfate, Hesperetin 7-sulfate, Homoeriodictyol, Naringenin 4'-O-glucuronide, Naringenin 5-O-glucuronide, Naringenin 7-O-glucuronide, Hesperetin 3',7-O-diglucuronide, Hesperetin 5,7-O-diglucuronide, Pinobanksin, 5-O-Methylpinobanksin |
| Flavones | Apigenin, Luteolin, Apigenin, total, Luteolin, total, Diosmin, Isorhoifolin, Neodiosmin, Rhoifolin, Sinensetin, Nobiletin, Tangeretin, Luteolin 7-O-diglucuronide, Chrysin, Diosmetin, Acacetin, Luteolin 7-O-rutinoside, Tetramethylscutellarein, Luteolin 7-O-glucoside, Apigenin 7-O-glucoside, Apigenin 6,8-di-C-glucoside, Sinensetin, total, Apigenin 6,8-C-arabinoside-C-glucoside, Apigenin 6,8-C-galactoside-C-arabinoside, Luteolin 7-O-glucuronide, Apigenin 7-O-glucuronide, Luteolin 7-O-malonyl-glucoside, Luteolin 6-C-glucoside, Luteolin 8-C-glucoside, Luteolin 6-C-glucoside 8-C-arabinoside, Luteolin 7-O-(2-apiosyl-glucoside), Luteolin 7-O-(2-apiosyl-4-glucosyl-6-malonyl)-glucoside, Apigenin 6-C-glucoside 8-C-arabinoside, Luteolin 7-O-(2-apiosyl-6-malonyl)-glucoside, Apigenin 7-O-apiosyl-glucoside, Apigenin 8-C-glucoside, 7,3',4'-Trihydroxyflavone, 7,4'- |

TABLE 5-continued

Polyphenols

| Polyphenol Sub-Class | Compound Name |
|---|---|
| | Dihydroxyflavone, Geraldone, Baicalein, Apigenin 6-C-glucoside, Hispidulin, Cirsimaritin, Luteolin 4'-O-glucoside, 5,6-Dihydroxy-7,8,3',4'-tetramethoxyflavone, Pebrellin, Gardenin B, Nepetin, Jaceosidin, Cirsilineol, Eupatorin, 6-Hydroxyluteolin, 6-Hydroxyluteolin 7-O-rhamnoside, Scutellarein, Apigenin 7-O-(6''-malonyl-apiosyl-glucoside), Chrysoeriol, Chrysoeriol 7-O-apiosyl-glucoside, Chrysoeriol 7-O-(6''-malonyl-apiosyl-glucoside), Chrysoeriol 7-O-glucoside, Chrysoeriol 7-O-(6''-malonyl-glucoside), Apigenin 7-O-diglucuronide, Rhoifolin 4'-O-glucoside, 3'-O-Demethylnobiletin, 4'-O-Demethylnobiletin, 6-O-Demethyleupatilin, 6-O-Methylscutellarin, Apigenin 4'-O-glucuronide, Apigenin 5-O-glucuronide, Eupatilin, Isoscutellarein, Scutellarein 4'-O-glucuronide, Scutellarein 5-O-glucuronide, Scutellarein 6,7-O-diglucuronide, Scutellarein 6-O-glucuronide, Scutellarein 7-sulfate, Scutellarein 7-O-glucuronide, Tricin, 6-O-Methylscutellarein |
| Flavonols | Kaempferol, Quercetin, Quercetin 3-O-galactoside, Quercetin 3-O-glucoside, Quercetin 3-O-xyloside, Quercetin 3-O-rhamnoside, Quercetin 3-O-rutinoside, Quercetin 3-O-sophoroside, Quercetin 3-O-arabinoside, Quercetin 3-O-xylosyl-glucuronide, Quercetin, total, Kaempferol, total, Myricetin, total, Isorhamnetin 3-O-glucoside 7-O-rhamnoside, Isorhamnetin 3-O-rutinoside, Kaempferol 3-O-glucuronide, Isorhamnetin 7-O-rhamnoside, Quercetin 3,4'-O-diglucoside, Myricetin 3-O-rutinoside, Myricetin, Morin, Kaempferide, Myricetin 3-O-galactoside, Myricetin 3-O-glucoside, Quercetin 3-O-glucosyl-xyloside, Quercetin 3-O-acetyl-rhamnoside, Kaempferol 3-O-galactoside, Galangin, Isorhamnetin, Kaempferol 3-O-glucoside, Kaempferol 3-O-rutinoside, Kaempferol 3-O-glucosyl-rhamnosyl-galactoside, Kaempferol 3-O-glucosyl-rhamnosyl-glucoside, Quercetin 3-O-glucosyl-rhamnosyl-galactoside, Quercetin 3-O-glucosyl-rhamnosyl-glucoside, Rhamnetin, Isorhamnetin 3-O-glucoside, Myricetin 3-O-rhamnoside, Quercetin 3-O-rhamnosyl-galactoside, Kaempferol 3-O-arabinoside, Quercetin 3-O-glucuronide, Isorhamnetin 3-O-glucuronide, Myricetin 3-O-arabinoside, Quercetin 3,7,4'-O-triglucoside, Quercetin 7,4'-O-diglucoside, Quercetin 4'-O-glucoside, Isorhamnetin 4'-O-glucoside, 3,7-Dimethylquercetin, Kaempferol 3-O-sophoroside, Kaempferol 3,7-O-diglucoside, Quercetin 3-O-diglucoside, Kaempferol 3-O-sophoroside 7-O-glucoside, Kaempferol 3-O-sophorotrioside 7-O-sophoroside, Kaempferol 3-O-sinapoyl-caffeoyl-sophoroside 7-O-glucoside, Kaempferol 3-O-feruloyl-caffeoyl-sophoroside 7-O-glucoside, Kaempferol 3-O-feruloyl-sophorotrioside, Kaempferol 3-O-sinapoyl-sophoroside 7-O-glucoside, Kaempferol 3-O-caffeoyl-sophoroside 7-O-glucoside, Kaempferol 3-O-feruloyl-sophoroside 7-O-glucoside, Quercetin 3-O-(6''-malonyl-glucoside), Kaempferol 3-O-(6''-malonyl-glucoside), Kaempferol 3-O-rhamnoside, Quercetin 3-O-(6''-malonyl-glucoside) 7-O-glucoside, Patuletin, Quercetagetin, Spinacetin, Patuletin 3-O-glucosyl-(1->6)-[apiosyl(1->2)]-glucoside, Spinacetin 3-O-glucosyl-(1->6)-[apiosyl(1->2)\-glucoside, Patuletin 3-O-(2''-feruloylglucosyl)(1->6)-[apiosyl(1->2)\-glucoside, Spinacetin 3-O-(2''-p-coumaroylglucosyl)(1->6)-[apiosyl(1->2)\-glucoside, Spinacetin 3-O-(2''-feruloylglucosyl)(1->6)-[apiosyl(1->2)\-glucoside, Spinacetin 3-O-glucosyl-(1->6)-glucoside, Jaceidin 4'-O-glucuronide, 5,3',4'-Trihydroxy-3-methoxy-6:7-methylenedioxyflavone 4'-O-glucuronide, 5,4'-Dihydroxy-3,3'-dimethoxy-6:7-methylenedioxyflavone 4'-O-glucuronide, Spinatoside, Spinatoside 4'-O-glucuronide, Kaempferol 3-O-xylosyl-glucoside, Kaempferol 3-O-acetyl-glucoside, Quercetin 3-O-xylosyl-rutinoside, Kaempferol 3-O-xylosyl-rutinoside, Quercetin 3-O-glucosyl-glucoside, Quercetin 7-O-glucoside, Quercetin 3-O-(6''-acetyl-glucoside), Kaempferol 3-O-robinoside 7-O-rhamnoside, Kaempferol 7-O-glucoside, Kaempferol 3-O-galactoside 7-O-rhamnoside, Kaempferol 3-O-(6''-acetyl-galactoside) 7-O-rhamnoside, Quercetin 3-O-galactoside 7-O-rhamnoside, Quercetin 3-O-(6''-acetyl-galactoside) 7-O-rhamnoside, Kaempferol 3-O-(2''-rhamnosyl-galactoside) 7-O-rhamnoside, Kaempferol 3-O-(2''-rhamnosyl-6''-acetyl-galactoside) 7-O-rhamnoside, 6,8-Dihydroxykaempferol, Isorhamnetin 3-O-galactoside, Quercetin 3-O-rhamnosyl-rhamnosyl-glucoside, Kaempferol 3-O-rhamnosyl-rhamnosyl-glucoside, Methylgalangin, Kaempferol 3,7,4'-triglucoside, 5,3',4'-Trihydroxy-3-methoxy-6:7-methylenedioxyflavone, 5,4'-Dihydroxy-3,3'-dimethoxy-6:7-methylenedioxyflavone, Jaceidin, Natsudaidain, 3-Methoxynobiletin, 3-Methoxysinensetin, Quercetin 3*-O-glucuronide, Quercetin 3'-sulfate, Quercetin 4'-O-glucuronide, Isorhamnetin 4'-O-glucuronide, Tamarixetin, Quercetin 3-O-glucosyl-rutinoside |
| Isoflavonoids | Daidzein, Formononetin, Genistein, Biochanin A, Glycitein, Glycitin, 6''-O-Acetyldaidzin, 6''-O-Malonylgenistin, Daidzin, Genistin, 6''-O-Acetylgenistin, 6''-O-Acetylglycitin, 6''-O-Malonyldaidzin, 6''-O-Malonylglycitin, 2',7-Dihydroxy-4',5'-dimethoxyisoflavone, 2-Dehydro-O-desmethylangolensin, 2'-Hydroxyformononetin, 3',4',7-Trihydroxyisoflavan, 3',4',7-Trihydroxyisoflavanone, 3',7-Dihydroxyisoflavan, 3'-Hydroxydaidzein, 3'-Hydroxy-O-desmethylangolensin, 4',6,7-Trihydroxyisoflavanone, 4',7,8-Trihydroxyisoflavanone, 4',7-Dihydroxy-3'- |

TABLE 5-continued

Polyphenols

| Polyphenol Sub-Class | Compound Name |
|---|---|
| | methoxyisoflavan, 4',7-Dihydroxy-6-methoxyisoflavan, 4-Hydroxyequol, 4'-O-Methylequol, 5,6,7,3',4'-Pentahydroxyisoflavone, 5,6,7,4'-Tetrahydroxyisoflavone, 5,7,8,3',4'-Pentahydroxyisoflavone, 5,7,8,4'-Tetrahydroxyisoflavone, 5'-Hydroxy-O-desmethylangolensin, 5'-Methoxy-O-desmethylangolensin, 6,7,3',4'-Tetrahydroxyisoflavone, 6,7,4'-Trihydroxyisoflavone, 6'-Hydroxyangolensin, 6'-Hydroxy-O-desmethylangolensin, 7,3',4'-Trihydroxy-6-methoxyisoflavone, 7,3',4'-Trihydroxyisoflavone, 7,8,3',4'-Tetrahydroxyisoflavone, 7,8,4'-Trihydroxyisoflavone, Angolensin, Calycosin, Daidzein 4',7-O-diglucuronide, Daidzein 4',7-disulfate, Daidzein 4'-O-glucuronide, Daidzein 4'-sulfate, Daidzein 7-O-glucuronide, Dihydrobiochanin A, Dihydrodaidzein, Dihydrodaidzein 7-O-glucuronide, Dihydroformononetin, Dihydrogenistein, Dihydroglycitein, Equol, Formononetin 7-O-glucuronide, Formononetin 7-sulfate, Genistein 4',7-O-diglucuronide, Genistein 4',7-disulfate, Genistein 4'-O-glucuronide, Genistein 4'-sulfate, Genistein 5-O-glucuronide, Genistein 7-O-glucuronide, Genistein 7-sulfate, Glycitein 4'-O-glucuronide, Glycitein 7-O-glucuronide, Koparin, O-Desmethylangolensin, Orobol, Prunetin, Pseudobaptigenin, Puerarin, Daidzin 4'-O-glucuronide, Irisolidone 7-O-glucuronide, Tectorigenin 7-sulfate, Tectorigenin 4'-sulfate, Irisolidone, Tectorigenin, Tectoridin, 5,7-Dihydroxy-8,4'-dimethoxyisoflavone, Isotectorigenin, Equol 7-O-glucuronide, Equol 4'-O-glucuronide, 8-Hydroxydaidzein, Daidzein 7-sulfate, Daidzein 4'-O-sulfo-7-O-glucuronide, Daidzein 7-O-sulfo-4'-O-glucuronide, Equol 4'-sulfate, 3',4',5,7-Tetrahydroxyisoflavanone, 3'-O-Methylequol, 6-O-Methylequol, 3'-Hydroxygenistein, 3'-Hydroxydihydrodaidzein, 6-Hydroxydihydrodaidzein, 3'-Hydroxyequol, cis-4-Hydroxyequol, 4'-Methoxy-2',3,7-trihydroxyisoflavanone, Irilone, Vestitone, Sativanone, Butin, 3'-Hydroxymelanettin, Liquiritigenin, Melanettin, Stevenin, Violanone, Isoliquiritigenin, Dalbergin, 3'-O-Methylviolanone, 8-Hydroxydihydrodaidzein |
| Lignans | Secoisolariciresinol, Matairesinol, Lariciresinol, Pinoresinol, Syringaresinol, Isolariciresinol, Arctigenin, Trachelogenin, Medioresinol, 1-Acetoxypinoresinol, Secoisolariciresinol di-O-glucoside, Sesamin, Sesamolin, Sesamolinol, Sesaminol, Sesaminol 2'-O-b-D-glucosyl (1->2)-O-[b-D-glucosyl (1->6)]-b-D-glucoside, Sesaminol 2'-O-b-D-glucosyl (1->6)-O-b-D-glucoside, Sesaminol 2'-O-b-D-glucoside, Sesamol, Sesamolinol 4'-O-b-D-glucosyl (1->6)-O-b-D-glucoside, 7-Hydroxymatairesinol, Isohydroxymatairesinol, Secoisolariciresinol-sesquilignan, Cyclolariciresinol, 7-Oxomatairesinol, Todolactol A, Conidendrin, 7-Hydroxysecoisolariciresinol, Nortrachelogenin, Lariciresinol-sesquilignan, Anhydro-secoisolariciresinol, Dimethylmatairesinol, Episesamin, Episesaminol, Sesaminol 2'-O-b-D-glucosyl (1->2)-O-b-D-glucoside, Enterodiol, Enterolactone, Sesaminol 2-O-triglucoside, Schisandrin, Gomisin D, Schisandrol B, Tigloylgomicin H, Schisanhenol, Schisantherin A, Gomisin M2, Deoxyschisandrin, Schisandrin B, Schisandrin C, 2-Hydroxyenterodiol, 4-Hydroxyenterodiol, 6-Hydroxyenterodiol, 2-Hydroxyenterolactone, 4-Hydroxyenterolactone, 6-Hydroxyenterolactone, 2'-Hydroxyenterolactone, 4'-Hydroxyenterolactone, 6'-Hydroxyenterolactone, 5-Hydroxyenterolactone, 7-Hydroxyenterolactone |
| Non-phenolic metabolites | 4-Ethylbenzoic acid, Glycine, 1,3,5-Trimethoxybenzene, Vanilloylglycine |
| Alkylmethoxy-phenols | 4-Vinylguaiacol, 4-Ethylguaiacol, 4-Vinylsyringol |
| Alkylphenols | 5-Heneicosenylresorcinol, 5-Heneicosylresorcinol, 5-Heptadecylresorcinol, 5-Nonadecenylresorcinol, 5-Nonadecylresorcinol, 5-Pentacosenylresorcinol, 5-Pentacosylresorcinol, 5-Pentadecylresorcinol, 5-Tricosenylresorcinol, 5-Tricosylresorcinol, Alk(en)ylresorcinols, total, Alkenylresorcinols, total, Alkylresorcinols, total, 3-Methylcatechol, 4-Methylcatechol, 4-Ethylcatechol, 4-Vinylphenol, 4-Ethylphenol |
| Betacyanins | Betanin, Isobetanin, Betanidin, Isobetanidin |
| Capsaicinoids | Capsaicin |
| Curcuminoids | Curcumin, Demethoxycurcumin, Bisdemethoxycurcumin |
| Dihydro-capsaicins | Dihydrocapsaicin, Nordihydrocapsaicin |
| Furano-coumarins | Bergapten, Psoralen, Xanthotoxin, Isopimpinellin, Angelicin |
| Hydroxy-benzaldehydes | Syringaldehyde, Protocatechuic aldehyde, Vanillin, 4-Hydroxybenzaldehyde, Gallic aldehyde, p-Anisaldehyde, Ethyl vanillin, Vanillin 4-sulfate |
| Hydroxy-benzoketones | 3-Methoxyacetophenone, 2,3-Dihydroxy-1-guaiacylpropanone, Paeonol, 2,4-Dihydroxyacetophenone 5-sulfate, 2-Hydroxy-4-methoxyacetophenone 5-sulfate, Resacetophenone, Norathyriol |
| Hydroxycinnam-aldehydes | Feruladehyde, Sinapaldehyde |

TABLE 5-continued

Polyphenols

| Polyphenol Sub-Class | Compound Name |
|---|---|
| Hydroxy-coumarins | Coumarin, Isocoumarin, Mellein, Scopoletin, Esculetin, Esculin, Umbelliferone, 4-Hydroxycoumarin, Urolithin D, Urolithin B 3-sulfate, Urolithin A 3,8-O-diglucuronide, Urolithin A 3,8-disulfate, Urolithin A, Urolithin B, Urolithin B 3-O-glucuronide, Urolithin C |
| Hydroxyphenyl-alcohols | Homovanillyl alcohol |
| Hydroxy-phenylpropenes | 2-Methoxy-5-prop-1-enylphenol, Anethole, Eugenol, Acetyl eugenol, [6]-Gingerol, Estragole |
| Methoxyphenols | Guaiacol, p-Anisidine |
| Naphtoquinones | Juglone, 1,4-Naphtoquinone |
| Phenolic terpenes | Carnosic acid, Rosmanol, Carnosol, Epirosmanol, Rosmadial, Thymol, Carvacrol |
| Tyrosols | Hydroxytyrosol, 3,4-DHPEA-AC, p-HPEA-AC, Oleuropein, Demethyloleuropein, 3,4-DHPEA-EA, Ligstroside, 3,4-DHPEA-EDA, Hydroxytyrosol 4-O-glucoside, Oleoside dimethylester, Oleoside 11-methylester, Hydroxytyrosol 1'-O-glucoside, p-HPEA-EDA, p-HPEA-EA, Oleuropein-aglycone, Ligstroside-aglycone, Elenolic acid, Tyrosol 4-O-glucuronide, Tyrosol 4-sulfate, Hydroxytyrosol, total |
| Other polyphenols | Coumestrol, Catechol, Pyrogallol, Phlorin, Phenol, Phloroglucinol, Arbutin, Hydroquinone, 3,4-Dihydroxyphenylglycol, 5,5',6,6'-Tetrahydroxy-3,3'-biindolyl, Resorcinol, 1-Phenyl-6,7-dihydroxy-isochroman, 1-(3-methoxy-4-hydroxy)-phenyl-6,7-dihydroxy-isochroman, Lithospermic acid, Lithospermic acid B, Salvianolic acid B, Salvianolic acid C, Salvianolic acid D, Salvianolic acid G, Isopropyl 3-(3,4-dihydroxyphenyl)-2-hydroxypropanoate |
| Hydroxybenzoic acids | Ellagic acid glucoside, Protocatechuic acid, Gallic acid, Vanillic acid, Ellagic acid, total, Gentisic acid, Ellagic acid, 4-Hydroxybenzoic acid, 3,4-Dimethoxybenzoic acid, Syringic acid, 5-O-Galloylquinic acid, Ellagic acid arabinoside, Ellagic acid acetyl-xyloside, Ellagic acid acetyl-arabinoside, 4-Methoxybenzoic acid, Gallic acid, total, Benzoic acid, 2-Hydroxybenzoic acid, 3-Hydroxybenzoic acid, 2,3-Dihydroxybenzoic acid, 2,4-Dihydroxybenzoic acid, 1-O-Galloyl glucose, 4-Hydroxybenzoic acid 4-O-glucoside, Protocatechuic acid 4-O-glucoside, Gallic acid 4-O-glucoside, 3,5-Dihydroxybenzoic acid, 2,6-Dihydroxybenzoic acid, Gallic acid 3-O-gallate, Gallic acid ethyl ester, Valoneic acid dilactone, 2,6-Dimethoxybenzoic acid, 2-Hydroxy-4-methoxybenzoic acid, Sanguisorbic acid dilactone, Galloyl glucose, Lambertianin C, Sanguiin H-6, Sanguiin H-10, Ellagitannins, total, Punicalagin, Gallagic acid, Tannic acid, Hydrolysable tannins, total, 3-O-Methylgallic acid, 4-O-Methylgallic acid, 3,4-O-Dimethylgallic acid, Punicalin, 4-Hydroxyhippuric acid, 3-Hydroxyhippuric acid, 2-Hydroxyhippuric acid, Hippuric acid, Paeoniflorin, Vanillic acid 4-sulfate, 2,3,4-Trihydroxybenzoic acid |
| Hydroxy-cinnamic acids | p-Coumaric acid, 5-p-Coumaroylquinic acid, 4-p-Coumaroylquinic acid, Caffeic acid, Feruloyl glucose, Ferulic acid, Caffeoyl tartaric acid, Rosmarinic acid, o-Coumaric acid, m-Coumaric acid, Sinapic acid, p-Coumaroyl glucose, p-Coumaroylquinic acid, 3-Caffeoylquinic acid, Verbascoside, 4-Caffeoylquinic acid, p-Coumaroyl tartaric acid, 2,5-di-S-Glutathionyl caftaric acid, Feruloyl tartaric acid, Caffeic acid ethyl ester, Cinnamoyl glucose, 5-Caffeoylquinic acid, 3-p-Coumaroylquinic acid, 2-S-Glutathionyl caftaric acid, 5-Feruloylquinic acid, 4-Feruloylquinic acid, 3-Feruloylquinic acid, 5-Sinapoylquinic acid, 4-Sinapoylquinic acid, 3-Sinapoylquinic acid, 3,5-Dicaffeoylquinic acid, Isoferulic acid, Caffeoyl glucose, p-Coumaric acid 4-O-glucoside, Caffeic acid 4-O-glucoside, Ferulic acid 4-O-glucoside, p-Coumaroyl tartaric acid glucosidic ester, p-Coumaric acid ethyl ester, Trans-Caffeoyl tartaric acid, Cis-Caffeoyl tartaric acid, Trans-p-Coumaroyl tartaric acid, Cis-p-Coumaroyl tartaric acid, Trans-Caffeic acid, Cis-Caffeic acid, Trans-p-Coumaric acid, Trans-Ferulic acid, Cis-p-Coumaric acid, Cis-Ferulic acid, 3,4-Dimethoxycinnamic acid, Hydroxycaffeic acid, Caffeic acid, total, Sinapic acid, total, Chicoric acid, 5-5'-Dehydrodiferulic acid, 5-8'-Dehydrodiferulic acid, 1,2-Disinapoylgentiobiose, 1-Sinapoyl-2-feruloylgentiobiose, 1,2-Diferuloylgentiobiose, 1,2,2'-Trisinapoylgentiobiose, 1,2'-Disinapoyl-2-feruloylgentiobiose, 1-Sinapoyl-2,2'-diferuloylgentiobiose, 1,2,2'-Triferuloylgentiobiose, 8-O-4'-Dehydrodiferulic acid, 8-8'-Dehydrodiferulic acid, 5-8'-Benzofuran dehydrodiferulic acid, Cis-3-Caffeoylquinic acid, 3,4-Dicaffeoylquinic acid, Cis-5-Caffeoylquinic acid, 3,4-Diferuloylquinic acid, 3,5-Diferuloylquinic acid, 1-Caffeoylquinic acid, 1,3-Dicaffeoylquinic acid, 1,5-Dicaffeoylquinic acid, 4,5-Dicaffeoylquinic acid, Dicaffeoylquinic acid, b-D-fructosyl-a-D-(6-O-(E))-feruloylglucoside, Avenanthramide 1p, Avenanthramide 1f, Avenanthramide 2p, Avenanthramide 2c, Avenanthramide 2f, Avenanthramide 1c, Avenanthramide 1s, Avenanthramide 2s, Sinapoyl glucose, p-Coumaroyl malic acid, p-Coumaroyl glycolic acid, 3-Caffeoyl-1,5-quinolactone, 4-Caffeoyl-1,5-quinolactone, Quinic acid esters, total, 3-Feruloyl-1,5-quinolactone, 4-Feruloyl-1,5-quinolactone, 3,4-Dicaffeoyl-1,5-quinolactone, 3-p-Coumaroyl-1,5- |

TABLE 5-continued

Polyphenols

| Polyphenol Sub-Class | Compound Name |
|---|---|
| | quinolactone, 4-p-Coumaroyl-1,5-quinolactone, Cinnamic acid, Caffeoyl 3-hydroxytyrosine, Caffeoyl aspartic acid, p-Coumaroyl aspartic acid, p-Coumaroyl tyrosine, Caffeoyl tyrosine, p-Coumaroyl 3-hydroxytyrosine, Isoverbascoside, Sinapine, Avenanthramide A2, Avenanthramide K, Campesteryl ferulate, Sitostanyl ferulate, 4-O-8',5'-5''-Dehydrotriferulic acid, 24-Methylcholestanol ferulate, 24-Methylcholesterol ferulate, 24-Methyllathosterol ferulate, Stigmastanol ferulate, Sitosterol ferulate, Schottenol ferulate, 24-Methylenecholestanol ferulate, Trans-5-Caffeoylquinic acid, Trans-3-Caffeoylquinic acid, 3-O-Methylrosmarinic acid, Sinapic acid 4-O-glucuronide, Sinapic acid 4-sulfate, Feruloylglycine 4-sulfate, Feruloylglycine, Isoferulic acid 3-O-glucuronide, Isoferulic acid 3-sulfate, Ferulic acid 4-sulfate, Ferulic acid 4-O-glucuronide, Caffeic acid 4-sulfate, Caffeic acid 3-sulfate, p-Coumaric acid 4-sulfate, Feruloyl C1-glucuronide, Isoferuloyl Ci-glucuronide, Caffeic acid 3-O-glucuronide, Caffeic acid 4-O-glucuronide, Caffeoyl C1-glucuronide, Chlorogenic acid, total, 1,5-Diferuloylquinic acid, 1-Caffeoyl-5-feruloylquinic acid, 1-Feruloyl-5-caffeoylquinic acid |
| Hydroxy-phenylacetic acids | 3,4-Dihydroxyphenylacetic acid, 4-Hydroxyphenylacetic acid, Homovanillic acid, Homoveratric acid, Methoxyphenylacetic acid, 3-Hydroxyphenylacetic acid, 2-Hydroxyphenylacetic acid, 4-Methoxyphenylacetic acid, Phenacetylglycine, Phenylacetic acid, 4-Hydroxymandelic acid, 2-Hydroxy-2-phenylacetic acid, Homovanillic acid 4-sulfate, 4-Hydroxyphenyllactic acid |
| Hydroxy-phenylpropanoic acids | Dihydro-p-coumaric acid, Dihydrocaffeic acid, 3,4-Dihydroxyphenyl-2-oxypropanoic acid, 3-Hydroxy-3-(3-hydroxyphenyl)propionic acid, 3-(3,4-Dihydroxyphenyl)-2-methoxypropionic acid, 3-Hydroxyphenylpropionic acid, Dihydroferulic acid 4-sulfate, Dihydroisoferulic acid 3-O-glucuronide, Dihydrocaffeic acid 3-O-glucuronide, Dihydrocaffeic acid 3-sulfate, Dihydroferulic acid, Dihydroferulic acid 4-O-glucuronide, Dihydrosinapic acid, Dihydroferuloylglycine 4-sulfate, Dihydroferuloylglycine, Danshensu, 3-Methoxy-4-hydroxyphenyllactic acid, 3,4-Dihydroxyphenyllactic acid methyl ester, Hydroxydanshensu, 3-Phenylpropionic acid, 3-Hydroxy-4-methoxyphenyllactic acid, Dihydroferulic acid 3-sulfate, 4-Hydroxyphenyl-2-propionic acid |
| Hydroxy-phenylpentanoic acids | 5-(3'-Methoxy-4'-hydroxyphenyl)-γ-valerolactone, 5-(3'-Methoxy-4'-hydroxyphenyl)-γ-valerolactone 4'-O-glucuronide, 4-Hydroxy-(3',4'-dihydroxyphenyl)valeric acid, 5-(3',4'-dihydroxyphenyl)-valeric acid, 5-(3',4',-dihydroxyphenyl)-γ-valerolactone, 5-(3',4',5'-trihydroxyphenyl)-γ-valerolactone, 5-(3',5'-dihydroxyphenyl)-γ-valerolactone, 5-Hydroxyphenyl-γ-valerolactone, 3-Hydroxyphenylvaleric acid, 5-(3',5'-dihydroxyphenyl)-γ-valerolactone 3-O-glucuronide |
| Stilbenes | Trans-Resveratrol, Trans-Resveratrol 3-O-glucoside, Piceatannol, Cis-Resveratrol, e-Viniferin, Pterostilbene, d-Viniferin, Cis-Resveratrol 3-O-glucoside, Pallidol, Piceatannol 3-O-glucoside, Pinosylvin, Resveratrol 5-O-glucoside, Resveratrol, Resveratrol 3-O-glucoside, 3,4,5,4'-Tetramethoxystilbene, 3'-Hydroxy-3,4,5,4'-tetramethoxystilbene, 3-Hydroxy-4,5,4'-trimethoxystilbene, 4,4'-Dihydroxy-3,5-dimethoxystilbene, 4'-Hydroxy-3,4,5-trimethoxystilbene, 4-Hydroxy-3,5,4'-trimethoxystilbene, cis-Resveratrol 3-O-glucuronide, cis-Resveratrol 3-sulfate, cis-Resveratrol 4'-O-glucuronide, cis-Resveratrol 4'-sulfate, Resveratrol 3-O-glucuronide, Resveratrol 3-sulfate, Resveratrol 4'-O-glucuronide, trans-Resveratrol 3,5-disulfate, trans-Resveratrol 3,4'-disulfate, trans-Resveratrol 3-O-glucuronide, trans-Resveratrol 3-sulfate, trans-Resveratrol 4'-O-glucuronide, trans-Resveratrol 4'-sulfate, Dihydroresveratrol |

EQUIVALENTS AND SCOPE

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

We claim:

1. A method of treating a human subject having a disease or disorder associated with elevated levels of trimethylamine N-oxide (TMAO) comprising administering to the subject a pharmaceutical composition comprising a glycan therapeutic preparation in an amount effective to treat the disease or disorder, wherein (i) the glycan therapeutic preparation comprises branched glycans that comprise glucose, galactose, arabinose, mannose, fructose, xylose, fucose, or rhamnose glycan units;
(ii) the average degree of branching (DB) of the branched glycans in the glycan therapeutic preparation is between 0.01 and 0.5;
(iii) at least 50% of the glycans in the glycan therapeutic preparation have a degree of polymerization (DP) of at least 3 and less than 30 glycan units;
(iv) the ratio of alpha- to beta-glycosidic bonds present in the glycans of the glycan therapeutic preparation is between about 0.8:1 to about 5:1;
(v) at least two of the glycosidic bonds independently comprise a 1→2 glycosidic bond, a 1→3 glycosidic bond, a 1→4 glycosidic bond, or a 1→6 glycosidic bond; and
(vi) the glycan therapeutic preparation has a final solubility limit in water of at least about 60 Brix at 23° C.

2. The method of claim 1, wherein the disease or disorder associated with elevated levels of TMAO is chronic kidney disease (CKD).

3. The method of claim 1, wherein the average DP of the glycan therapeutic preparation is between about DP6 and about DP12.

4. The method of claim 1, wherein at least 60% of the glycan therapeutic preparation has an average molecular weight of less than 2000 g/mol.

5. The method of claim 1, wherein the average degree of branching (DB) of the branched glycans in the glycan therapeutic preparation is between 0.05 and 0.25.

6. The method of claim 1, wherein the glycan therapeutic preparation comprises branched glycans consisting of glucose glycan units.

7. The method of claim 1, wherein the glycan therapeutic preparation comprises branched glycans consisting of glucose and mannose glycan units.

8. The method of claim 1, wherein the pharmaceutical composition is administered daily.

9. The method of claim 1, wherein the method further comprises administering a second drug or pharmaceutical composition.

10. The method of claim 1, wherein the glycan therapeutic preparation comprises branched glycans comprising glucose glycan units.

11. The method of claim 1, wherein the glycan therapeutic preparation comprises branched glycans comprising glucose and mannose glycan units.

* * * * *